(12) United States Patent
Choi

(10) Patent No.: US 11,931,332 B2
(45) Date of Patent: Mar. 19, 2024

(54) PHENYL ALKYL CARBAMATE COMPOUNDS FOR USE IN PREVENTING OR TREATING NEURODEGENERATIVE DISEASE

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd., Gyeonggi-do (KR)

(*) Notice: Subject to any disclaimer, the term of this patent is extended or adjusted under 35 U.S.C. 154(b) by 99 days.

(21) Appl. No.: 17/461,695

(22) Filed: Aug. 30, 2021

(65) Prior Publication Data

US 2022/0062220 A1    Mar. 3, 2022

Related U.S. Application Data

(60) Provisional application No. 63/072,855, filed on Aug. 31, 2020.

(51) Int. Cl.
| | | |
|---|---|---|
| *A61K 31/27* | (2006.01) | |
| *A61P 25/16* | (2006.01) | |
| *A61P 25/28* | (2006.01) | |

(52) U.S. Cl.
CPC .............. *A61K 31/27* (2013.01); *A61P 25/16* (2018.01); *A61P 25/28* (2018.01)

(58) Field of Classification Search
CPC ................................ A61K 31/27; A61P 25/28
See application file for complete search history.

(56) References Cited

U.S. PATENT DOCUMENTS

| | | | |
|---|---|---|---|
| 6,762,205 B1 | 7/2004 | Koizumi et al. | |
| 9,956,197 B2 * | 5/2018 | Choi ...................... | A61P 25/08 |
| 2003/0078213 A1 | 4/2003 | Ehrenberg et al. | |
| 2009/0247616 A1 | 10/2009 | Smith-Swintowsky | |
| 2016/0310461 A1 | 10/2016 | Choi | |
| 2018/0230090 A1 | 8/2018 | Choi | |

FOREIGN PATENT DOCUMENTS

| | | |
|---|---|---|
| WO | WO 2001/002349 | 1/2001 |
| WO | WO 2002/067925 | 9/2002 |
| WO | WO 2006/044472 | 4/2006 |
| WO | WO 2010/011548 | 1/2010 |
| WO | WO 2014/097137 | 6/2014 |
| WO | WO 2014/142547 | 9/2014 |
| WO | WO 2016/190638 | 12/2016 |
| WO | WO 2022/054987 | 3/2022 |

OTHER PUBLICATIONS

U.S. Appl. No. 16/980,822, filed Sep. 14, 2020, by Choi (copy not provided)..
Bourin et al., "The mouse light/dark box test," Eur J Pharm (2003) 463:55-65.
Bourwknecht et al., "Behavioral and physiological mouse assays for anxiety: a survey in nine mouse strains," Behavioural Brian Research (2002) 136:489-501.
Brummelte et al., "Chronic corticosterone during pregnancy and postpartum affects maternal care, cell proliferation and depressive-like behavior in the dam," Hormones and Behavior (2010) 58:769-779.
Heck et al., "Analysis of cerebellar function in Ube3a-deficient mice reveals novel genotype-specific behaviors," Hum Mol Genet. (2008) 17(14): 2181-2189.
Porsolt et al., "Depression: a new animal model sensitive to antidepressant treatements," Nature (1997) 266(5604):730-732.
Prut et al., "The open field as a paradigm to measure the effects of drugs on anxiety-like behaviors: a review," Eur J Pharm (2003) 463:3-33.
Shin et al., "Jowiseungchungtang Inhibits Amyloid-ß Aggregation and Amyloid-ß-Mediated Pathology in 5XFAD Mice," Int J Mol Sci. (2018) 19(12): 4026.
Shiotsuki et al.,. "A rotarod test for evaluation of motor skill learning," J Neurosci Methods. (2010) 189(2):180-5.
Vergara et al., "Amyloid-ß pathology enhances pathological fibrillary tau seeding induced by Alzheimer PHF in vivo," Acta Neuropathol. (2019) 137(3):397-412.

* cited by examiner

*Primary Examiner* — Paul V Ward
(74) *Attorney, Agent, or Firm* — MORRISON & FOERSTER LLP

(57) ABSTRACT

The present invention relates to a phenyl alkyl carbamate compound for use in preventing or treating neurodegenerative diseases. The phenyl alkyl carbamate compound of the present invention, prevented dopaminergic neuron loss, attenuated activation of astrocyte/microglia, repressed phosphorylated alpha-synuclein, and regulated phosphorylation levels of tau and acetylation levels of alpha-tubulin in the Parkinson's disease animal model. In addition, the phenyl alkyl carbamate compound of the present invention reduced the Amyloid-beta precursor protein and Amyloid-beta. Therefore, the phenyl alkyl carbamate compound of the present invention may be effectively used for preventing or treating neurodegenerative diseases.

14 Claims, 5 Drawing Sheets

[FIG. 1]
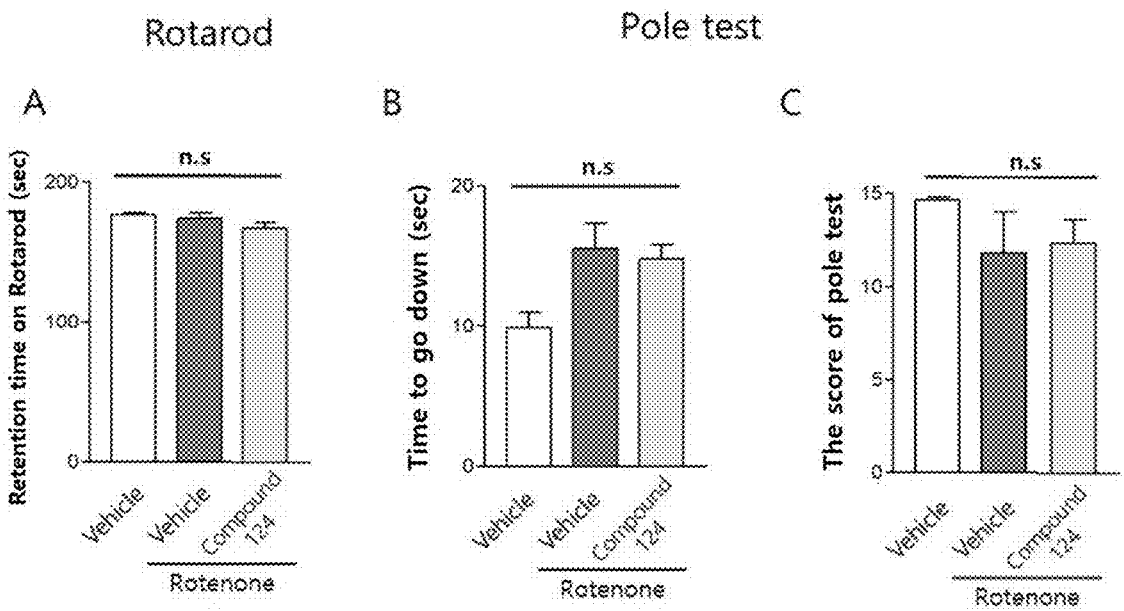
[FIG. 2]
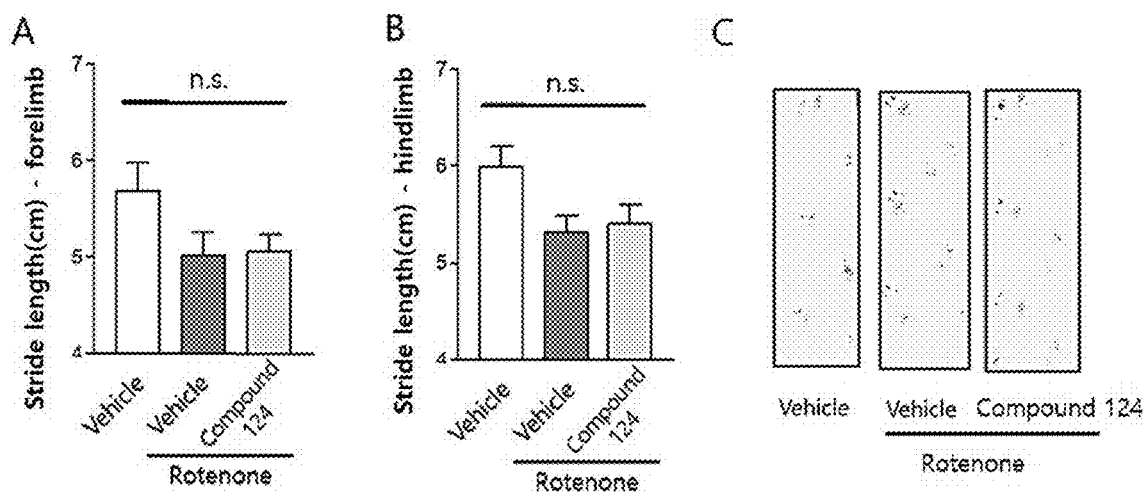

[FIG. 3]
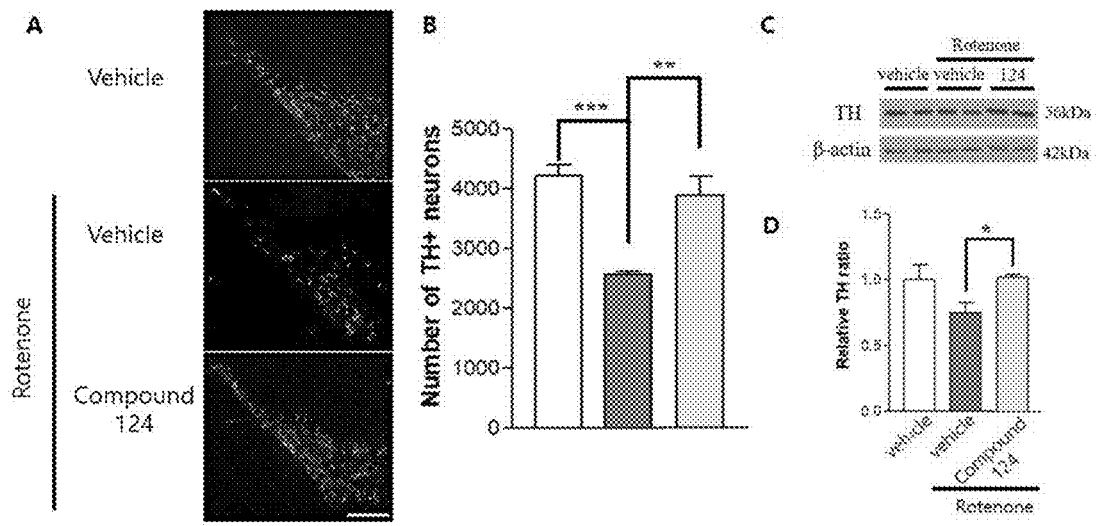
[FIG. 4]
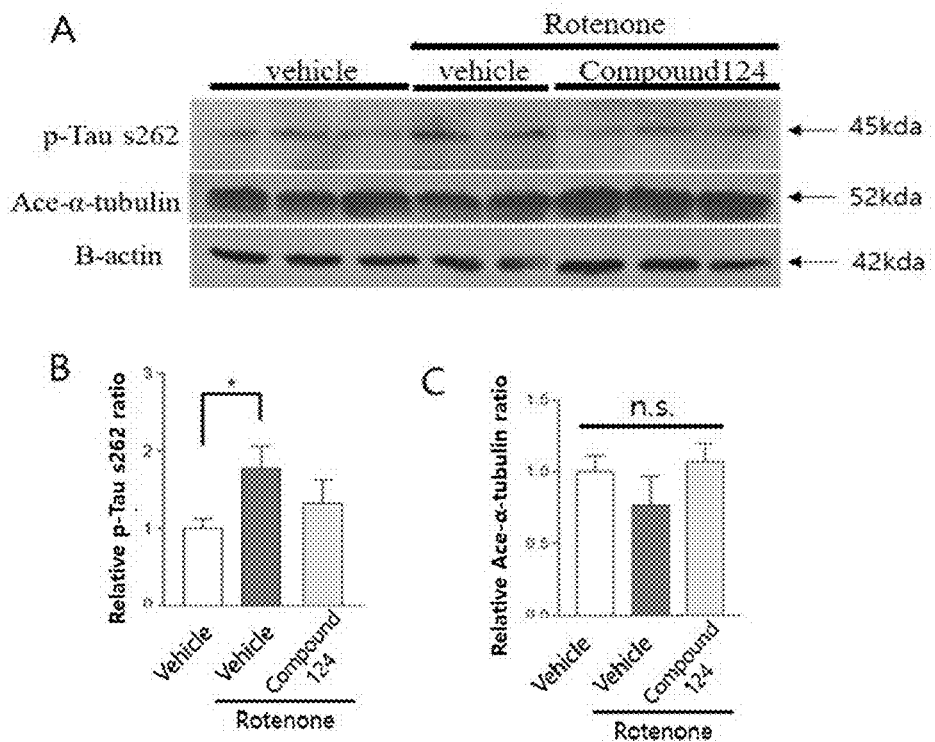

[FIG. 5]
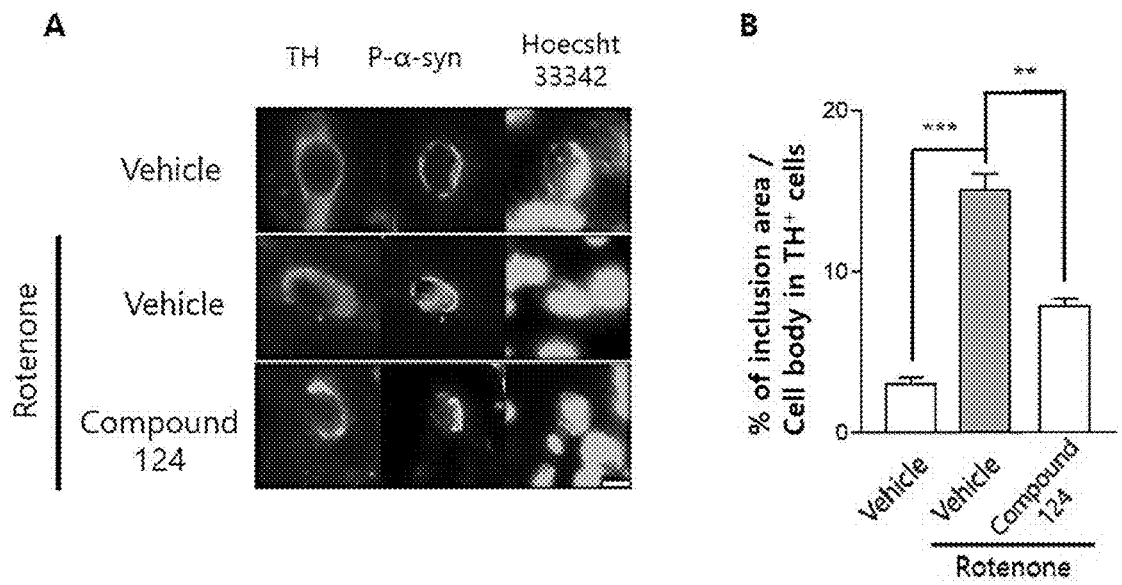
[FIG. 6]
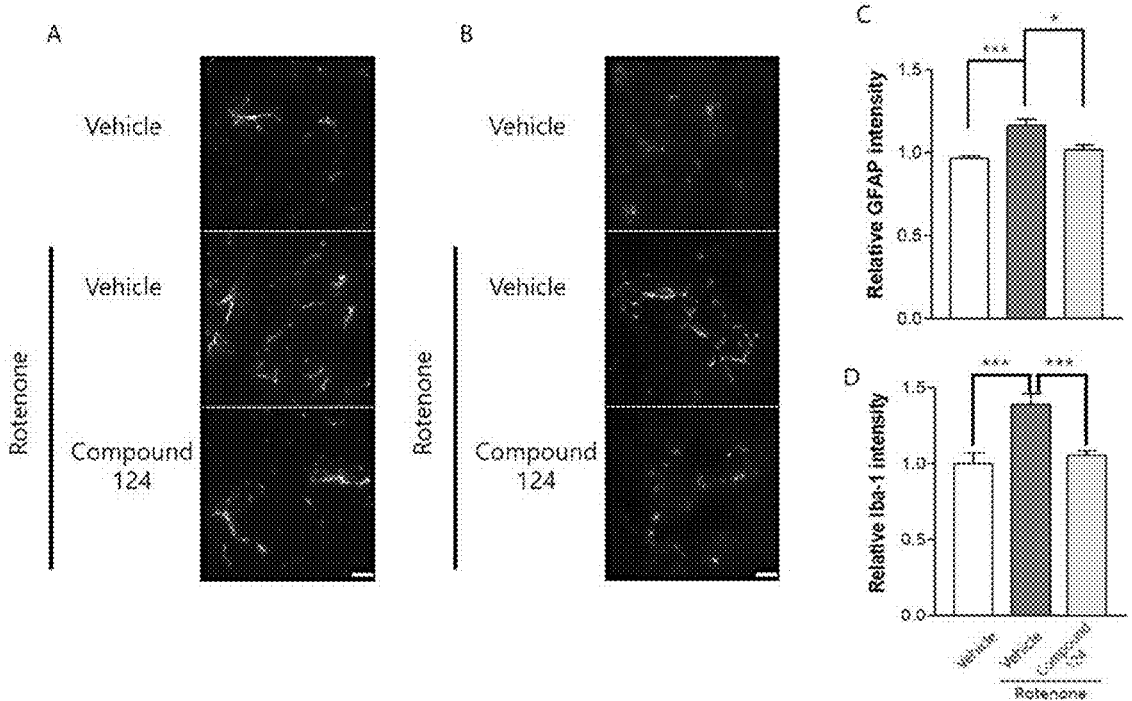

[FIG. 7]
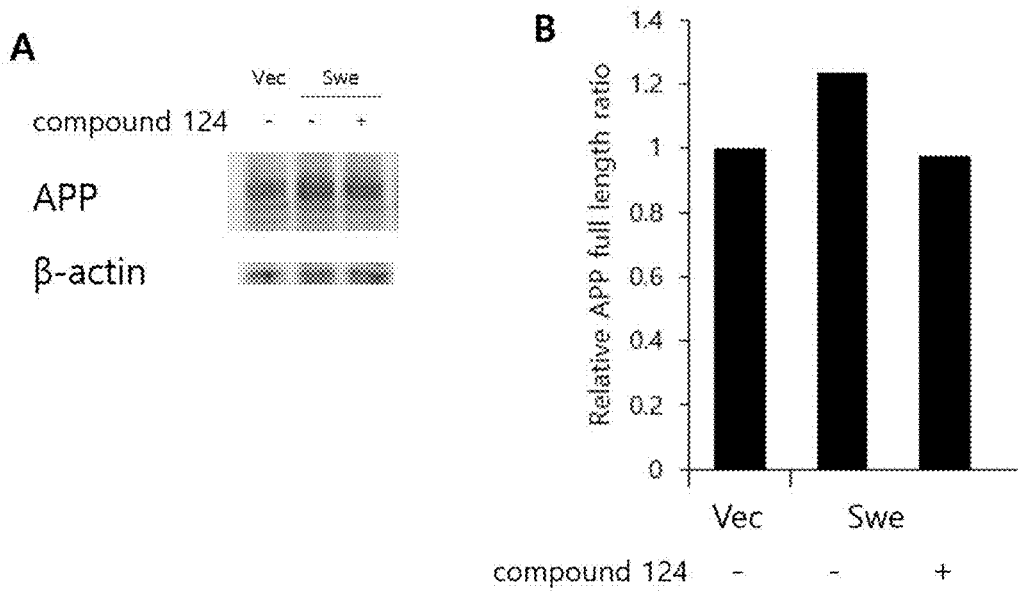
[FIG. 8]
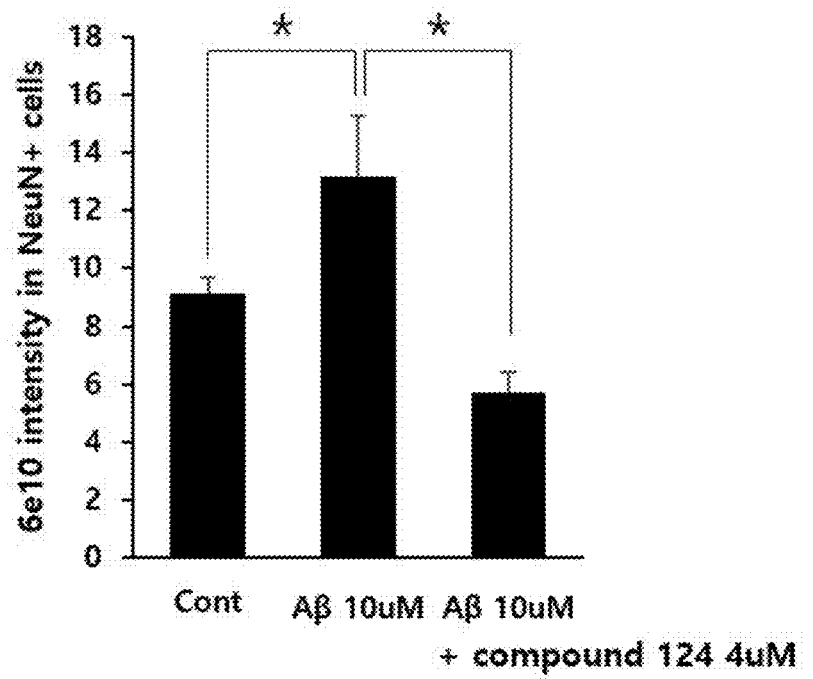

[FIG. 9]
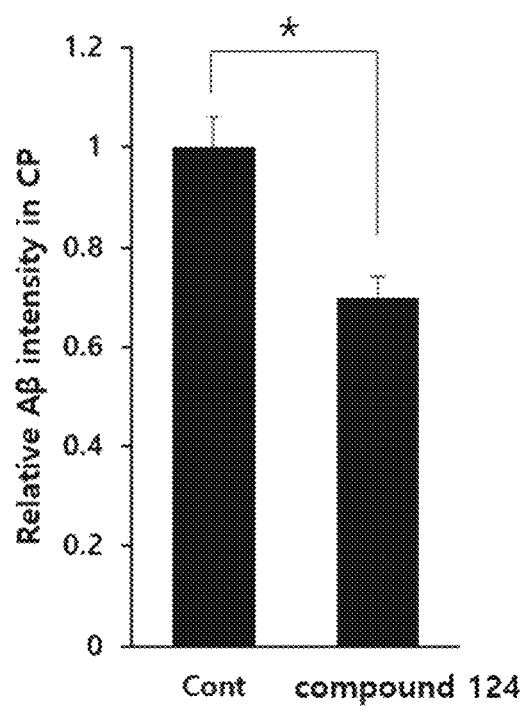

PHENYL ALKYL CARBAMATE COMPOUNDS FOR USE IN PREVENTING OR TREATING NEURODEGENERATIVE DISEASE

CROSS-REFERENCE TO RELATED APPLICATION

This application claims priority to and the benefit of the filing date of U.S. Provisional Application Ser. No. 63/072,855, filed Aug. 31, 2020, the disclosure of which is incorporated herein by reference in its entirety.

TECHNICAL FIELD

The present invention provides a pharmaceutical composition for preventing and/or treating a neurodegenerative disease comprising the phenyl alkyl carbamate compound as an active ingredient, and a use of the phenyl alkyl carbamate compound for preventing and/or treating a neurodegenerative disease.

BACKGROUND ART

Parkinson's disease is caused by a degenerative disease that affects a dopamine producing region of the brain. An individual with Parkinson's disease can experience uncontrollable tremors, stiffness of the extremities and general physical impairment that prevents easy motor coordination.

The cause of the disease is not fully understood although some surgical procedures and drug therapies have helped to reduce symptoms in certain patients.

SUMMARY OF THE INVENTION

An embodiment provides a pharmaceutical composition for the prevention and the treatment of a neurodegenerative disease, comprising a phenyl alkyl carbamate compound of the following Chemical Formula 1, an enantiomer or a diastereomer thereof, or a mixture of enantiomers or diastereomers; or a pharmaceutically acceptable salt thereof.

Another embodiment is to provide a method of preventing and/or treating a neurodegenerative disease in a subject comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to the subject in need.

Still other embodiment is to provide a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of a neurodegenerative disease or the manufacture of a pharmaceutical composition for preventing and/or treating a neurodegenerative disease.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is an image confirming the effect of improving Rotenone-induced motor dysfunctions by the compound of Example 124; Motor functions were assessed through rota-rod test and pole test. (A) The time mice stayed on accelerating rota-rod apparatus was used as the value. (B) The score of pole test among 3 groups (Wild type vehicle n=8, Rotenone vehicle n=5, Rotenone+compound 124 n=9) (n.s: not significant). Values are expressed as the means±SEMs. Statistical analyses were performed using one-way ANOVA;

FIG. 2 is an image confirming the effect of improving walking patterns of rotenone-induced Parkinson's disease model mice by the compound of Example 124; Footprint assay of gait abnormalities was analyzed in 3 groups of mice (Wild type vehicle n=8, Rotenone vehicle n=5, Rotenone+compound 124 n=9). (A) Stride length of forepaws (B) Stride length of hind paws (C) Representative images of footprinting assay (forepaws: green, hind paws: blue) (n.s: not significant) Values are expressed as the means±SEMs. Statistical analyses were performed using one-way ANOVA;

FIG. 3 is an image confirming the effect of blocking rotenone-induced dopaminergic neuronal cell death by the compound of Example 124; (A) Representative images of striatum stained with tyrosine hydroxylase (TH). (×10 TH(Red), scale bar:50 μm (B) Quantification of the effect of Rotenone, compound 124 by counting the number of TH positive cells from SN (Wild type vehicle n=4, Rotenone vehicle n=4, Rotenone+compound 124 n=3). Values are expressed as the means±SEMs. Statistical analyses were performed using one-way ANOVA ($p<0.01$, *$p<0.001$). (C) Western blot detection of Tyrosine hydroxylase (TH) expression in ventral midbrain protein. (D) Quantification of the relative ratio of TH/B-actin (Wild type vehicle n=5, Rotenone vehicle n=2, Rotenone+compound 124 n=3). Values are expressed as the means±SEMs. Statistical analyses were performed using a t-test. (*$p<0.05$);

FIG. 4 is an image confirming the effect of modulating the levels of Tau phosphorylation and Acetylation of α-tubulin by the compound of Example 124; (A) Representative western blot of phosphorylated tau(p-Tau s262) and Acetylated alpha-tubulin (Ace-α-tubulin) (B) Quantification of the relative ratio of p-Tau s262 compared with wild type vehicle group. (C) Quantification of the relative ratio of p-Tau s262 compared with wild type vehicle group (Wild type vehicle n=5, Rotenone vehicle n=4, Rotenone+compound 124 n=5). Values are expressed as the means±SEMs. Statistical analyses were performed using a t-test. (*$p<0.05$, n.s: not significant);

FIG. 5 is an image confirming the effect of reducing p-α-Synuclein aggregates formation in TH+ neurons by the compound of Example 124; (A) Double immunostaining for TH and p-α-syn in the substantial nigra (SN) of mice (×40; TH: red, P-α-syn: Green, Scale bar: 50 μm), Merged images show phosphorylated alpha-synuclein formed inclusions in cell bodies of TH positive neurons. (B) Quantitative analysis of phosphorylated α-synuclein-positive inclusions in TH+ neurons. Areas of phospho-alpha-synuclein immunopositive aggregates were measured in 5 randomly chosen tissues from each group (Wild type vehicle n=3, Rotenone vehicle n=4, Rotenone+compound 124 n=4). Values are expressed as the means±SEMs. Statistical analyses were performed using one-way ANOVA (***$p<0.001$);

FIG. 6 is an image confirming the effect of reducing activation of astrocytes and glial cells by rotenone by the compound of Example 124; Striatal glial fibrillary acidic protein (GFAP)-positive astrocytes and ionized calcium binding adaptor molecule-1(Iba-1)-positive microglia. (×40;

GFAP: Green, Iba-1: Red, Scale bar: 50 μm) (A) Representative images of GFAP (Green) positive cells (B) Representative images of Iba-1 (Red) positive cells (C) Relative GFAP intensity among 3 groups. (Wild type vehicle n=3, Rotenone vehicle n=3, Rotenone+compound 124 n=3) Values are expressed as the means±SEMs. Statistical analyses were performed using one-way ANOVA (*p<0.05, *p<0.001) (D) Relative Iba-1 intensity among 4 groups. Values are expressed as the means±SEMs. Statistical analyses were performed using one-way ANOVA (p<0.01, ***p<0.001);

FIG. 7 is an image confirming the effect of reducing the Amyloid-beta precursor protein (APP) in Alzheimer's disease In Vitro Model by the compound of Example 124;

(A) Western blot detection of Amyloid-beta precursor protein (APP) expression in Alzheimer's disease In Vitro Model (vec=vehicle group, swe=pcDNA3-APPswe transfected group). (B) Quantification of the relative ratio of APP/B-actin;

FIG. 8 is an image confirming the effect of reducing the Amyloid-beta (Aβ) in primary cultured neurons by the compound of Example 124 (cont=control group, Aβ=Aβ-treated group, Aβ+compound 124=Aβ+compound of Example 124-treated group); and FIG. 9 is an image confirming the effect of reducing the Amyloid-beta (Aβ) in brain tissue by the compound of Example 124 (cont=control group, compound 124=compound of Example 124-treated group).

DETAILED DESCRIPTION OF THE EMBODIMENTS

Continuing its research work in the field of a neurodegenerative disease, as results of studies on the development of the drugs useful for prevention and/or treatment of a neurodegenerative disease, found that a substituted phenyl alkyl carbamate compounds of the following Chemical Formula 1 exhibits remarkably excellent anti-neurodegeneration activity in various emulation models and simultaneously has very low toxicity, and completed the invention.

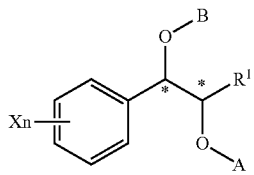

[Chemical Formula I]

wherein,
X is a halogen, for example, chlorine, fluorine, iodine, or bromine,
n, that means the number of substituent X, is an integer from 1 to 5, for example, 1 or 2, wherein X is the same or different each other, when n is 2 or larger,
$R^1$ is a hydrogen or linear or branched $C_1$-$C_4$ alkyl group, for example, methyl group, ethyl group, isopropyl group, or butyl group,
A is selected from the group consisting of an allyl, a $C_1$-$C_{19}$ linear or branched alkyl group (such as a methyl, t-butyl, benzyl, p-methoxybenzyl, 2-napthylmethyl, trityl group etc.), a $C_2$-$C_8$ alkoxy alky ether group (such as a methoxy methyl(MOM), methoxyethoxymethyl(MEM), tetrahydropyranyl(THP), benzyloxymethyl(BOM), methylthiomethyl(MTM), trimethylsilylethoxymethyl(SEM), ethoxyethyl(EE) group etc.), and a carbamoyl derivative represented by

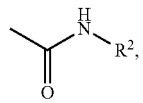

B is selected from the group consisting of an allyl, a $C_1$-$C_{19}$ linear or branched alkyl group (such as a methyl, t-butyl, benzyl, p-methoxybenzyl, 2-napthylmethyl, trityl group etc.), a $C_2$-$C_8$ alkoxy alky ether group (such as a methoxy methyl(MOM), methoxyethoxymethyl(MEM), tetrahydropyranyl(THP), benzyloxymethyl(BOM), methylthiomethyl(MTM), trimethylsilylethoxymethyl(SEM), ethoxyethyl(EE) group etc.), and a carbamoyl derivative represented by

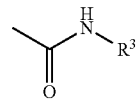

and
$R^2$ and $R^3$ may be the same as or different from each other, and independently selected from the group consisting of hydrogen, a linear or branched lower alkyl group of $C_1$-$C_4$, for example $C_1$-$C_3$, a cycloalkyl group of $C_3$-$C_8$, for example $C_3$-$C_7$, and benzyl group, and more specifically, $R^2$ and $R^3$ may be the same as or different from each other, and independently selected from the group consisting of hydrogen, methyl group, propyl group, isopropyl group, cyclopropyl group, cyclohexyl group, bicycloheptane group, and benzyl group.

In a concrete embodiment, if IV is hydrogen and one of A and B is the carbamoyl derivative, the other is not the carbamoyl derivative.

In an embodiment, when A is a carbamoyl group, B is an allyl, a linear or branched $C_1$-$C_{19}$ alkyl group or a $C_2$-$C_8$ alkoxy alky ether group; when B is a carbamoyl group, A is an allyl, a linear or branched $C_1$-$C_{19}$ alkyl group or a $C_2$-$C_8$ alkoxy alky ether group; or A and B are carbamoyl derivative at the same time.

In an embodiment of Chemical Formula 1, the $C_1$-$C_{19}$ linear or branched alkyl group is independently linear or branched $C_1$-$C_6$ lower aliphatic alkyl such as methyl, ethyl, t-butyl and the like; a substituted or unsubstituted $C_3$-$C_{19}$ cycloaliphatic and substituted or unsubstituted $C_6$-$C_{18}$ aromatic group such as benzyl, naphtyl, trityl and the like. The cycloaliphatic group and the aromatic group may be substituted with at least one selected from the group consisting of hydrogen, $C_1$-$C_6$ lower alkyl and $C_1$-$C_6$ alkoxy group.

The examples of $C_1$-$C_6$ lower aliphatic alkyl include methyl, ethyl, propyl, t-butyl, pantyl, hexyl and the like. The examples of $C_6$-$C_{18}$ aromatic group is benzyl such as benzyl, methylbenzyl, methoxybenzyl and the like, naphtyl such as 2-naphtylmethyl, trityl group and the like.

Another embodiment provides a pharmaceutical composition containing a phenyl alkyl carbamate derivative compound represented by Chemical Formula I; a racemate, an enantiomer, a diastereomer, a mixture of enantiomers, or a mixture of diastereomers thereof; or a pharmaceutically acceptable salt thereof, as an active ingredient.

Since the compound has two chiral carbons at the 1$^{st}$ and 2$^{nd}$ positions from the X substituted phenyl alkyl carbamate derivative group, they may be in the form of a racemate, an enantiomer, a diastereomer, a mixture of enantiomers, or a mixture of diastereomers.

In a concrete embodiment, the compound may be selected from the group consisting of:
- 1-(2-chlorophenyl)-1-carbamoyloxypropyl-2-carbamate,
- 1-(2-chlorophenyl)-1-carbamoyloxypropyl-2-N-methylcarbamate,
- 1-(2-chlorophenyl)-1-carbamoyloxypropyl-2-N-propylcarbamate
- 1-(2-chlorophenyl)-1-carbamoyloxybutyl-2-carbamate,
- 1-(2-chlorophenyl)-1-carbamoyloxy-3-methyl-butyl-2-carbamate,
- 1-(2-chlorophenyl)-1-carbamoyloxyhexyl-2-carbamate,
- 1-(2-iodophenyl)-1-carbamoyloxypropyl-2-carbamate,
- 1-(2-iodophenyl)-1-carbamoyloxybutyl-2-carbamate,
- 1-(2-iodophenyl)-1-carbamoyloxy-3-methyl-butyl-2-carbamate,
- 1-(2-iodophenyl)-1-carbamoyloxyhexyl-2-carbamate,
- 1-(2-fluorophenyl)-1-carbamoyloxypropyl-2-carbamate,
- 1-(2-fluorophenyl)-1-carbamoyloxybutyl-2-carbamate,
- 1-(2-fluorophenyl)-1-carbamoyloxy-3-methyl-butyl-2-carbamate,
- 1-(2-fluorophenyl)-1-carbamoyloxyhexyl-2-carbamate,
- 1-(2,4-dichlorophenyl)-1-carbamoyloxypropyl-2-carbamate,
- 1-(2,4-dichlorophenyl)-1-carbamoyloxybutyl-2-carbamate,
- 1-(2,4-dichlorophenyl)-1-carbamoyloxy-3-methyl-butyl-2-carbamate,
- 1-(2,4-dichlorophenyl)-1-carbamoyloxyhexyl-2-carbamate,
- 1-(2,6-dichlorophenyl)-1-carbamoyloxypropyl-2-carbamate,
- 1-(2,6-dichlorophenyl)-1-carbamoyloxybutyl-2-carbamate,
- 1-(2,6-dichlorophenyl)-1-carbamoyloxy-3-methyl-butyl-2-carbamate,
- 1-(2,6-dichlorophenyl)-1-carbamoyloxyhexyl-2-carbamate,
- 1-(2,4-difluorophenyl)-1-carbamoyloxypropyl-2-carbamate
- 1-(2,5-difluorophenyl)-1-carbamoyloxypropyl-2-carbamate
- 1-(2,6-difluorophenyl)-1-carbamoyloxypropyl-2-carbamate
- 1-(2-chloro-6-fluorophenyl)-1-carbamoyloxypropyl-2-carbamate
- 1-(2-chlorophenyl)-1-(methoxy)-ethyl-2-carbamate,
- 1-(2-fluorophenyl)-1-(methoxy)-ethyl-2-carbamate,
- 1-(2-iodophenyl)-1-(methoxy)-ethyl-2-carbamate,
- 1-(2-iodophenyl)-1-(methoxy)-propyl-2-carbamate,
- 1-(2-iodophenyl)-1-(methoxy)-propyl-2-N-methylcarbamate,
- 1-(2-iodophenyl)-1-(methoxy)-propyl-2-N-propylcarbamate,
- 1-(2-iodophenyl)-1-(methoxy)-propyl-2-N-isopropylcarbamate,
- 1-(2-iodophenyl)-1-(methoxy)-propyl-2-N-cyclopropylcarbamate,
- 1-(2-iodophenyl)-1-(methoxy)-propyl-2-N-cyclohexylcarbamate,
- 1-(2-iodophenyl)-1-(methoxy)-propyl-2-N-benzylcarbamate,
- 1-(2-iodophenyl)-1-(methoxy)-propyl-2-N-bicyclo[2,2,1]heptanecarbamate
- 1-(2-iodophenyl)-1-(methoxy)-butyl-2-carbamate,
- 1-(2-iodophenyl)-1-(methoxy)-butyl-2-N-methylcarbamate,
- 1-(2-iodophenyl)-1-(methoxy)-butyl-2-N-propylcarbamate,
- 1-(2-iodophenyl)-1-(methoxy)-butyl-2-N-isopropylcarbamate,
- 1-(2-iodophenyl)-1-(methoxy)-butyl-2-N-cyclopropylcarbamate,
- 1-(2-iodophenyl)-1-(methoxy)-butyl-2-N-cyclohexylcarbamate,
- 1-(2-iodophenyl)-1-(methoxy)-butyl-2-N-benzylcarbamate,
- 1-(2-iodophenyl)-1-(methoxy)-butyl-2-N-bicyclo[2,2,1]heptanecarbamate,
- 1-(2-iodophenyl)-1-(methoxy)3-methyl-butyl-2-carbamate,
- 1-(2-iodophenyl)-1-(methoxy)-3-methyl-butyl-2-N-methylcarbamate,
- 1-(2-iodophenyl)-1-(methoxy)-3-methyl-butyl-2-N-propylcarbamate,
- 1-(2-iodophenyl)-1-(methoxy)-3-methyl-butyl-2-N-isopropylcarbamate,
- 1-(2-iodophenyl)-1-(methoxy)-3-methyl-butyl-2-N-cyclopropylcarbamate,
- 1-(2-iodophenyl)-1-(methoxy)-3-methyl-butyl-2-N-cyclohexylcarbamate,
- 1-(2-iodophenyl)-1-(methoxy)-3-methyl-butyl-2-N-benzylcarbamate,
- 1-(2-iodophenyl)-1-(methoxy)-3-methyl-butyl-2-N-bicyclo[2,2,1]heptanecarbamate,
- 1-(2-iodophenyl)-1-(methoxy)-hexyl-2-carbamate,
- 1-(2-iodophenyl)-1-(methoxy)-hexyl-2-N-methylcarbamate,
- 1-(2-iodophenyl)-1-(methoxy)-hexyl-2-N-propylcarbamate,
- 1-(2-iodophenyl)-1-(methoxy)-hexyl-2-N-isopropylcarbamate,
- 1-(2-iodophenyl)-1-(methoxy)-hexyl-2-N-cyclopropylcarbamate,
- 1-(2-iodophenyl)-1-(methoxy)-hexyl-2-N-cyclohexylcarbamate,
- 1-(2-iodophenyl)-1-(methoxy)-hexyl-2-N-benzylcarbamate,
- 1-(2-iodophenyl)-1-(methoxy)-hexyl-2-N-bicyclo[2,2,1]heptanecarbamate,
- 1-(3-iodophenyl)-1-(methoxy)-propyl-2-carbamate,
- 1-(3-iodophenyl)-1-(methoxy)-butyl-2-carbamate,
- 1-(3-iodophenyl)-1-(methoxy)3-methyl-butyl-2-carbamate,
- 1-(3-iodophenyl)-1-(methoxy)-hexyl-2-carbamate,
- 1-(2-fluorophenyl)-1-(methoxy)-propyl-2-carbamate,
- 1-(2-fluorophenyl)-1-(methoxy)-propyl-2-N-methylcarbamate,
- 1-(2-fluorophenyl)-1-(methoxy)-propyl-2-N-propylcarbamate,
- 1-(2-fluorophenyl)-1-(methoxy)-propyl-2-N-isopropylcarbamate,
- 1-(2-fluorophenyl)-1-(methoxy)-propyl-2-N-cyclopropylcarbamate,
- 1-(2-fluorophenyl)-1-(methoxy)-propyl-2-N-cyclohexylcarbamate,
- 1-(2-fluorophenyl)-1-(methoxy)-propyl-2-N-benzylcarbamate, 1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-propyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate, 1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate,
1-(2-chlorophenyl)-2-(methoxy)-propyl-1-carbamate,
1-(2-fluorophenyl)-2-(methoxymethoxy)-propyl-1-carbamate,
1-(2-fluorophenyl)-2-(methoxy)-propyl-1-carbamate
1-(2-iodophenyl)-2-(methoxymethoxy)-propyl-1-carbamate,
1-(2-iodophenyl)-2-(methoxy)-propyl-1-carbamate and,
a racemate of the compound, an enantiomer of the compound, a diastereomer of the compound, a mixture of enantiomers of the compound, or a mixture of diastereomers of the compound.

In an embodiment, the phenyl alkyl carbamate compound is selected from the group consisting of:
1-(2-chlorophenyl)-(S)-1-carbamoyloxypropyl-(S)-2-carbamate,
1-(2-chlorophenyl)-(S)-1-carbamoyloxypropyl-(S)-2-N-methylcarbamate,
1-(2-chlorophenyl)-(S)-1-carbamoyloxypropyl-(S)-2-N-propylcarbamate
1-(2-chlorophenyl)-(S)-1-carbamoyloxybutyl-(S)-2-carbamate,
1-(2-chlorophenyl)-(S)-1-carbamoyloxy-3-methyl-butyl-(S)-2-carbamate,
1-(2-chlorophenyl)-(S)-1-carbamoyloxyhexyl-(S)-2-carbamate,
1-(2-iodophenyl)-(S)-1-carbamoyloxypropyl-(S)-2-carbamate,
1-(2-iodophenyl)-(S)-1-carbamoyloxybutyl-(S)-2-carbamate,
1-(2-iodophenyl)-(S)-1-carbamoyloxy-3-methyl-butyl-(S)-2-carbamate,
1-(2-iodophenyl)-(S)-1-carbamoyloxyhexyl-(S)-2-carbamate,
1-(2-fluorophenyl)-(S)-1-carbamoyloxypropyl-(S)-2-carbamate,
1-(2-fluorophenyl)-(S)-1-carbamoyloxybutyl-(S)-2-carbamate,
1-(2-fluorophenyl)-(S)-1-carbamoyloxy-3-methyl-butyl-(S)-2-carbamate,
1-(2-fluorophenyl)-(S)-1-carbamoyloxyhexyl-(S)-2-carbamate,
1-(2,4-dichlorophenyl)-(S)-1-carbamoyloxypropyl-(S)-2-carbamate,
1-(2,4-dichlorophenyl)-(S)-1-carbamoyloxybutyl-(S)-2-carbamate,
1-(2,4-dichlorophenyl)-(S)-1-carbamoyloxy-3-methyl-butyl-2-carbamate,
1-(2,4-dichlorophenyl)-(S)-1-carbamoyloxyhexyl-(S)-2-carbamate,
1-(2,6-dichlorophenyl)-(S)-1-carbamoyloxypropyl-(S)-2-carbamate,
1-(2,6-dichlorophenyl)-(S)-1-carbamoyloxybutyl-(S)-2-carbamate,
1-(2,6-dichlorophenyl)-(S)-1-carbamoyloxy-3-methyl-butyl-(S)-2-carbamate,
1-(2,6-dichlorophenyl)-(S)-1-carbamoyloxyhexyl-(S)-2-carbamate,
1-(2-chloro-6-fluorophenyl)-(S)-1-carbamoyloxypropyl-(S)-2-carbamate
1-(2-chlorophenyl)-(S)-1-(methoxy)-ethyl-2-carbamate,
1-(2-fluorophenyl)-(S)-1-(methoxy)-ethyl-2-carbamate,
1-(2-iodophenyl)-(S)-1-(methoxy)-ethyl-2-carbamate,
1-(2-iodophenyl)-(S)-1-(methoxy)-propyl-(S)-2-carbamate,
1-(2-iodophenyl)-(S)-1-(methoxy)-propyl-(S)-2-N-methylcarbamate,
1-(2-iodophenyl)-(S)-1-(methoxy)-propyl-(S)-2-N-propylcarbamate,
1-(2-iodophenyl)-(S)-1-(methoxy)-propyl-(S)-2-N-isopropylcarbamate, 1-(2-iodophenyl)-(S)-1-(methoxy)-propyl-(S)-2-N-cyclopropylcarbamate,
1-(2-iodophenyl)-(S)-1-(methoxy)-propyl-(S)-2-N-cyclohexylcarbamate,
1-(2-iodophenyl)-(S)-1-(methoxy)-propyl-(S)-2-N-benzylcarbamate,
1-(2-iodophenyl)-(S)-1-(methoxy)-propyl-(S)-2-N-bicyclo[2,2,1]heptanecarbamate
1-(2-iodophenyl)-(S)-1-(methoxy)-butyl(S)-2-carbamate,
1-(2-iodophenyl)-(S)-1-(methoxy)-butyl-(S)-2-N-methylcarbamate,
1-(2-iodophenyl)-(S)-1-(methoxy)-butyl-(S)-2-N-propylcarbamate,
1-(2-iodophenyl)-(S)-1-(methoxy)-butyl-(S)-2-N-isopropylcarbamate,
1-(2-iodophenyl)-(S)-1-(methoxy)-butyl-(S)-2-N-cyclopropylcarbamate,
1-(2-iodophenyl)-(S)-1-(methoxy)-butyl-(S)-2-N-cyclohexylcarbamate,
1-(2-iodophenyl)-(S)-1-(methoxy)-butyl-(S)-2-N-benzylcarbamate,
1-(2-iodophenyl)-(S)-1-(methoxy)-butyl-(S)-2-N-bicyclo[2,2,1]heptanecarbamate,
1-(2-iodophenyl)-(S)-1-(methoxy)3-methyl-butyl-(S)-2-carbamate,
1-(2-iodophenyl)-(S)-1-(methoxy)-3-methyl-butyl-(S)-2-N-methylcarbamate,
1-(2-iodophenyl)-(S)-1-(methoxy)-3-methyl-butyl-(S)-2-N-propylcarbamate,
1-(2-iodophenyl)-(S)-1-(methoxy)-3-methyl-butyl-(S)-2-N-isopropylcarbamate,
1-(2-iodophenyl)-(S)-1-(methoxy)-3-methyl-butyl-(S)-2-N-cyclopropylcarbamate,
1-(2-iodophenyl)-(S)-1-(methoxy)-3-methyl-butyl-(S)-2-N-cyclohexylcarbamate,
1-(2-iodophenyl)-(S)-1-(methoxy)-3-methyl-butyl-(S)-2-N-benzylcarbamate,
1-(2-iodophenyl)-(S)-1-(methoxy)-3-methyl-butyl-(S)-2-N-bicyclo[2,2,1]heptanecarbamate,
1-(2-iodophenyl)-(S)-1-(methoxy)-hexyl-(S)-2-carbamate,
1-(2-iodophenyl)-(S)-1-(methoxy)-hexyl-(S)-2-N-methylcarbamate,
1-(2-iodophenyl)-(S)-1-(methoxy)-hexyl-(S)-2-N-propylcarbamate,
1-(2-iodophenyl)-(S)-1-(methoxy)-hexyl-(S)-2-N-isopropylcarbamate,
1-(2-iodophenyl)-(S)-1-(methoxy)-hexyl-(S)-2-N-cyclopropylcarbamate,
1-(2-iodophenyl)-(S)-1-(methoxy)-hexyl-(S)-2-N-cyclohexylcarbamate,
1-(2-iodophenyl)-(S)-1-(methoxy)-hexyl-(S)-2-N-benzylcarbamate,
1-(2-iodophenyl)-(S)-1-(methoxy)-hexyl-(S)-2-N-bicyclo[2,2,1]heptanecarbamate,
1-(3-iodophenyl)-(S)-1-(methoxy)-propyl-(S)-2-carbamate,
1-(3-iodophenyl)-(S)-1-(methoxy)-butyl-(S)-2-carbamate,
1-(3-iodophenyl)-(S)-1-(methoxy)3-methyl-butyl-(S)-2-carbamate,
1-(3-iodophenyl)-(S)-1-(methoxy)-hexyl-(S)-2-carbamate,
1-(2-fluorophenyl)-(S)-1-(methoxy)-propyl-(S)-2-carbamate,
1-(2-fluorophenyl)-(S)-1-(methoxy)-propyl-(S)-2-N-methylcarbamate,
1-(2-fluorophenyl)-(S)-1-(methoxy)-propyl-(S)-2-N-propylcarbamate,
1-(2-fluorophenyl)-(S)-1-(methoxy)-propyl-(S)-2-N-isopropylcarbamate,
1-(2-fluorophenyl)-(S)-1-(methoxy)-propyl-(S)-2-N-cyclopropylcarbamate,
1-(2-fluorophenyl)-(S)-1-(methoxy)-propyl-(S)-2-N-cyclohexylcarbamate,
1-(2-fluorophenyl)-(S)-1-(methoxy)-propyl-(S)-2-N-benzylcarbamate,
1-(2-fluorophenyl)-(S)-1-(methoxy)-propyl-(S)-2-N-bicyclo[2,2,1]heptanecarbamate
1-(4-fluorophenyl)-(S)-1-(methoxy)-propyl-(S)-2-carbamate,
1-(4-fluorophenyl)-(S)-1-(methoxy)-butyl-(S)-2-carbamate,
1-(4-fluorophenyl)-(S)-1-(methoxy)-3-methyl-butyl-(S)-2-carbamate,
1-(4-fluorophenyl)-(S)-1-(methoxy)-hexyl-(S)-2-carbamate,
1-(2-chlorophenyl)-(S)-1-(methoxy)-propyl-(S)-2-carbamate,
1-(2-chlorophenyl)-(S)-1-(methoxy)-propyl-(S)-2-N-methylcarbamate,
1-(2-chlorophenyl)-(S)-1-(methoxy)-propyl-(S)-2-N-propylcarbamate,
1-(2-chlorophenyl)-(S)-1-(methoxy)-propyl-(S)-2-N-isopropylcarbamate,
1-(2-chlorophenyl)-(S)-1-(methoxy)-propyl-(S)-2-N-cyclopropylcarbamate,
1-(2-chlorophenyl)-(S)-1-(methoxy)-propyl-(S)-2-N-cyclohexylcarbamate,
1-(2-chlorophenyl)-(S)-1-(methoxy)-propyl-(S)-2-N-benzylcarbamate,
1-(2-chlorophenyl)-(S)-1-(methoxy)-propyl-(S)-2-N-bicyclo[2,2,1]heptanecarbamate
1-(2-chlorophenyl)-(S)-1-(methoxy)-butyl-(S)-2-carbamate,
1-(2-chlorophenyl)-(S)-1-(methoxy)-3-methyl-butyl-(S)-2-carbamate,
1-(2-chlorophenyl)-(S)-1-(methoxy)-hexyl-(S)-2-carbamate,
1-(2,3-dichlorophenyl)-(S)-1-(methoxy)-propyl-(S)-2-carbamate,
1-(2,4-dichlorophenyl)-(S)-1-(methoxy)-propyl-(S)-2-carbamate,
1-(2,4-dichlorophenyl)-(S)-1-(methoxy)-butyl-(S)-2-carbamate,
1-(2,4-dichlorophenyl)-(S)-1-(methoxy)-3-methyl-butyl-(S)-2-carbamate,
1-(2,4-dichlorophenyl)-(S)-1-(methoxy)-hexyl-(S)-2-carbamate,
1-(2,6-dichlorophenyl)-(S)-1-(methoxy)-propyl-(S)-2-carbamate,
1-(2,6-dichlorophenyl)-(S)-1-(methoxy)-butyl-(S)-2-carbamate,
1-(2,6-dichlorophenyl)-(S)-1-(methoxy)-3-methyl-butyl-(S)-2-carbamate,
1-(2,6-dichlorophenyl)-(S)-1-(methoxy)-hexyl-(S)-2-carbamate,
1-(2-chlorophenyl)-(S)-1-(methoxymethoxy)-ethyl-(S)-2-carbamate,
1-(2-fluorophenyl)-(S)-1-(methoxymethoxy)-ethyl-(S)-2-carbamate,
1-(2-iodophenyl)-(S)-1-(methoxymethoxy)-ethyl-(S)-2-carbamate, 1-(2-chlorophenyl)-(S)-1-(methoxymethoxy)-propyl-(S)-2-carbamate,
1-(2-chlorophenyl)-(S)-1-(methoxymethoxy)-propyl-(S)-2-N-methylcarbamate,
1-(2-chlorophenyl)-(S)-1-(methoxymethoxy)-propyl-(S)-2-N-propylcarbamate,
1-(2-chlorophenyl)-(S)-1-(methoxymethoxy)-propyl-(S)-2-N-isopropylcarbamate,
1-(2-chlorophenyl)-(S)-1-(methoxymethoxy)-propyl-(S)-2-N-cyclopropylcarbamate,
1-(2-chlorophenyl)-(S)-1-(methoxymethoxy)-propyl-(S)-2-N-cyclohexylcarbamate,
1-(2-chlorophenyl)-(S)-1-(methoxymethoxy)-propyl-2-N-benzylcarbamate,
1-(2-chlorophenyl)-(S)-1-(methoxymethoxy)-propyl-2-N-bicyclo[2,2,1]heptanecarbamate
1-(2-chlorophenyl)-(S)-1-(methoxymethoxy)-butyl-(S)-2-carbamate,
1-(2-chlorophenyl)-(S)-1-(methoxymethoxy)-3-methyl-butyl-(S)-2-carbamate,
1-(2-chlorophenyl)-(S)-1-(methoxymethoxy)-hexyl-(S)-2-carbamate,
1-(2,3-dichlorophenyl)-(S)-1-(methoxymethoxy)-propyl-(S)-2-carbamate,
1-(2,4-dichlorophenyl)-(S)-1-(methoxymethoxy)-propyl-(S)-2-carbamate,
1-(2,4-dichlorophenyl)-(S)-1-(methoxymethoxy)-butyl-(S)-2-carbamate,
1-(2,4-dichlorophenyl)-(S)-1-(methoxymethoxy)-3-methyl-butyl-(S)-2-carbamate,
1-(2,4-dichlorophenyl)-(S)-1-(methoxymethoxy)-hexyl-(S)-2-carbamate,
1-(2,5-dichlorophenyl)-(S)-1-(methoxymethoxy)-propyl-(S)-2-carbamate,
1-(2,6-dichlorophenyl)-(S)-1-(methoxymethoxy)-propyl-(S)-carbamate,
1-(2,6-dichlorophenyl)-(S)-1-(methoxymethoxy)-butyl-(S)-2-carbamate,
1-(2,6-dichlorophenyl)-(S)-1-(methoxymethoxy)-3-methyl-butyl-(S)-2-carbamate,
1-(2,6-dichlorophenyl)-(S)-1-(methoxymethoxy)-hexyl-(S)-2-carbamate,
1-(2-fluorophenyl)-(S)-1-(methoxymethoxy)-propyl-(S)-2-carbamate,
1-(2-fluorophenyl)-(S)-1-(methoxymethoxy)-propyl-(S)-2-N-methylcarbamate,
1-(2-fluorophenyl)-(S)-1-(methoxymethoxy)-propyl-(S)-2-N-propylcarbamate,
1-(2-fluorophenyl)-(S)-1-(methoxymethoxy)-propyl-(S)-2-N-isopropylcarbamate,
1-(2-fluorophenyl)-(S)-1-(methoxymethoxy)-propyl-(S)-2-N-cyclopropylcarbamate,
1-(2-fluorophenyl)-(S)-1-(methoxymethoxy)-propyl-(S)-2-N-cyclohexylcarbamate,
1-(2-fluorophenyl)-(S)-1-(methoxymethoxy)-propyl-(S)-2-N-benzylcarbamate,
1-(2-fluorophenyl)-(S)-1-(methoxymethoxy)-propyl-(S)-2-N-bicyclo[2,2,1]heptanecarbamate
1-(2-fluorophenyl)-(S)-1-(methoxymethoxy)-butyl-(S)-2-carbamate,
1-(2-fluorophenyl)-(S)-1-(methoxymethoxy)-3-methyl-butyl-(S)-2-carbamate,
1-(2-fluorophenyl)-(S)-1-(methoxymethoxy)-hexyl-(S)-2-carbamate,
1-(4-fluorophenyl)-(S)-1-(methoxymethoxy)-propyl-(S)-2-carbamate,
1-(4-fluorophenyl)-(S)-1-(methoxymethoxy)-butyl-(S)-2-carbamate,
1-(4-fluorophenyl)-(S)-1-(methoxymethoxy)-3-methyl-butyl-(S)-2-carbamate,
1-(4-fluorophenyl)-(S)-1-(methoxymethoxy)-hexyl-(S)-2-carbamate,
1-(2,6-difluorophenyl)-(S)-1-(methoxymethoxy)-propyl-(S)-2-carbamate,
1-(2-iodophenyl)-(S)-1-(methoxymethoxy)-propyl-(S)-2-carbamate,
1-(2-iodophenyl)-(S)-1-(methoxymethoxy)-propyl-(S)-2-N-methylcarbamate,
1-(2-iodophenyl)-(S)-1-(methoxymethoxy)-propyl-(S)-2-N-propylcarbamate,
1-(2-iodophenyl)-(S)-1-(methoxymethoxy)-propyl-(S)-2-N-isopropylcarbamate,
1-(2-iodophenyl)-(S)-1-(methoxymethoxy)-propyl-(S)-2-N-cyclopropylcarbamate,
1-(2-iodophenyl)-(S)-1-(methoxymethoxy)-propyl-(S)-2-N-cyclohexylcarbamate,
1-(2-iodophenyl)-(S)-1-(methoxymethoxy)-propyl-(S)-2-N-benzylcarbamate,
1-(2-iodophenyl)-(S)-1-(methoxymethoxy)-propyl-2-N-bicyclo[2,2,1]heptanecarbamate
1-(2-iodophenyl)-(S)-1-(methoxymethoxy)-butyl-(S)-2-carbamate,
1-(2-iodophenyl)-(S)-1-(methoxymethoxy)-butyl-(S)-2-N-methylcarbamate,
1-(2-iodophenyl)-(S)-1-(methoxymethoxy)-butyl-(S)-2-N-propylcarbamate,
1-(2-iodophenyl)-(S)-1-(methoxymethoxy)-butyl-(S)-2-N-isopropylcarbamate,
1-(2-iodophenyl)-(S)-1-(methoxymethoxy)-butyl-(S)-2-N-cyclopropylcarbamate,
1-(2-iodophenyl)-(S)-1-(methoxymethoxy)-butyl-(S)-2-N-cyclohexylcarbamate,
1-(2-iodophenyl)-(S)-1-(methoxymethoxy)-butyl-(S)-2-N-benzylcarbamate,
1-(2-iodophenyl)-(S)-1-(methoxymethoxy)-butyl-(S)-2-N-bicyclo[2,2,1]heptanecarbamate
1-(2-iodophenyl)-(S)-1-(methoxymethoxy)-3-methyl-butyl-(S)-2-carbamate,
1-(2-iodophenyl)-(S)-1-(methoxymethoxy)-3-methyl-butyl-(S)-2-N-methylcarbamate,
1-(2-iodophenyl)-(S)-1-(methoxymethoxy)-3-methyl-butyl-(S)-2-N-propylcarbamate,
1-(2-iodophenyl)-(S)-1-(methoxymethoxy)-3-methyl-butyl-(S)-2-N-isopropylcarbamate,
1-(2-iodophenyl)-(S)-1-(methoxymethoxy)-3-methyl-butyl-(S)-2-N-cyclopropylcarbamate,
1-(2-iodophenyl)-(S)-1-(methoxymethoxy)-3-methyl-butyl-(S)-2-N-cyclohexylcarbamate,
1-(2-iodophenyl)-(S)-1-(methoxymethoxy)-3-methyl-butyl-(S)-2-N-benzylcarbamate,
1-(2-iodophenyl)-(S)-1-(methoxymethoxy)-3-methyl-butyl-(S)-2-N-bicyclo[2,2,1]heptanecarbamate,
1-(2-iodophenyl)-(S)-1-(methoxymethoxy)-hexyl-2-carbamate,
1-(2-iodophenyl)-(S)-1-(methoxymethoxy)-hexyl-(S)-2-N-methylcarbamate,
1-(2-iodophenyl)-(S)-1-(methoxymethoxy)-hexyl-(S)-2-N-propylcarbamate,
1-(2-iodophenyl)-(S)-1-(methoxymethoxy)-hexyl-(S)-2-N-isopropylcarbamate,
1-(2-iodophenyl)-(S)-1-(methoxymethoxy)-hexyl-(S)-2-N-cyclopropylcarbamate, 1-(2-iodophenyl)-(S)-1-(methoxymethoxy)-hexyl-(S)-2-N-cyclohexylcarbamate,
1-(2-iodophenyl)-(S)-1-(methoxymethoxy)-hexyl-(S)-2-N-benzylcarbamate,
1-(2-iodophenyl)-(S)-1-(methoxymethoxy)-hexyl-(S)-2-N-bicyclo[2,2,1]heptanecarbamate
1-(3-iodophenyl)-(S)-1-(methoxymethoxy)-propyl-(S)-2-carbamate,
1-(3-iodophenyl)-(S)-1-(methoxymethoxy)-butyl-(S)-2-carbamate,
1-(3-iodophenyl)-(S)-1-(methoxymethoxy)-3-methyl-butyl-(S)-2-carbamate,
1-(3-iodophenyl)-(S)-1-(methoxymethoxy)-hexyl-(S)-2-carbamate,
1-(2-chlorophenyl)-(S)-2-(methoxymethoxy)-propyl-(S)-1-carbamate,
1-(2-chlorophenyl)-(S)-2-(methoxy)-propyl-(S)-1-carbamate,
1-(2-fluorophenyl)-(S)-2-(methoxymethoxy)-propyl-(S)-1-carbamate,
1-(2-fluorophenyl)-(S)-2-(methoxy)-propyl-(S)-1-carbamate
1-(2-iodophenyl)-(S)-2-(methoxymethoxy)-propyl-(S)-1-carbamate,
1-(2-iodophenyl)-(S)-2-(methoxy)-propyl-(S)-1-carbamate
1-(2-chlorophenyl)-(R)-1-carbamoyloxypropyl-(R)-2-carbamate,
1-(2-iodophenyl)-(R)-1-carbamoyloxypropyl-(R)-2-carbamate,
1-(2-fluorophenyl)-(R)-1-carbamoyloxypropyl-(R)-2-carbamate,
1-(2,4-dichlorophenyl)-(R)-1-carbamoyloxypropyl-(R)-2-carbamate,
1-(2,6-dichlorophenyl)-(R)-1-carbamoyloxypropyl-(R)-2-carbamate,
1-(2,4-difluorophenyl)-(R)-1-carbamoyloxypropyl(R)-2-carbamate
1-(2,5-difluorophenyl)-(R)-1-carbamoyloxypropyl-(R)-2-carbamate
1-(2,6-difluorophenyl)-(R)-1-carbamoyloxypropyl-(R)-2-carbamate
1-(2-chloro-6-fluorophenyl)-(R)-1-carbamoyloxypropyl-(R)-2-carbamate
1-(2-iodophenyl)-(R)-1-(methoxy)-propyl-(R)-2-carbamate,
1-(2-iodophenyl)-(R)-1-(methoxy)-butyl(R)-2-carbamate,
1-(2-iodophenyl)-(R)-1-(methoxy)3-methyl-butyl-(R)-2-carbamate,
1-(2-iodophenyl)-(R)-1-(methoxy)-hexyl-(R)-2-carbamate,
1-(3-iodophenyl)-(R)-1-(methoxy)-propyl-(R)-2-carbamate,
1-(3-iodophenyl)-(R)-1-(methoxy)-butyl-(R)-2-carbamate,
1-(3-iodophenyl)-(R)-1-(methoxy)3-methyl-butyl-(R)-2-carbamate,
1-(3-iodophenyl)-(R)-1-(methoxy)-hexyl-(R)-2-carbamate,
1-(2-fluorophenyl)-(R)-1-(methoxy)-propyl-(R)-2-carbamate,
1-(4-fluorophenyl)-(R)-1-(methoxy)-propyl-(R)-2-carbamate,
1-(4-fluorophenyl)-(R)-1-(methoxy)-butyl-(R)-2-carbamate,
1-(4-fluorophenyl)-(R)-1-(methoxy)-3-methyl-butyl-(R)-2-carbamate,
1-(4-fluorophenyl)-(R)-1-(methoxy)-hexyl-(R)-2-carbamate,
1-(2-chlorophenyl)-(R)-1-(methoxy)-propyl-(R)-2-carbamate,
1-(2-chlorophenyl)-(R)-1-(methoxy)-propyl-(R)-2-N-methylcarbamate,
1-(2-chlorophenyl)-(R)-1-(methoxy)-propyl-(R)-2-N-propylcarbamate,
1-(2-chlorophenyl)-(R)-1-(methoxy)-propyl-(R)-2-N-isopropylcarbamate,
1-(2-chlorophenyl)-(R)-1-(methoxy)-propyl-(R)-2-N-cyclopropylcarbamate,
1-(2-chlorophenyl)-(R)-1-(methoxy)-propyl-(R)-2-N-cyclohexylcarbamate,
1-(2-chlorophenyl)-(R)-1-(methoxy)-propyl-(R)-2-N-benzylcarbamate,
1-(2-chlorophenyl)-(R)-1-(methoxy)-propyl-(R)-2-N-bicyclo[2,2,1]heptanecarbamate
1-(2-chlorophenyl)-(R)-1-(methoxy)-butyl-(R)-2-carbamate,
1-(2-chlorophenyl)-(R)-1-(methoxy)-3-methyl-butyl-(R)-2-carbamate,
1-(2-chlorophenyl)-(R)-1-(methoxy)-hexyl-(R)-2-carbamate,
1-(2,3-dichlorophenyl)-(R)-1-(methoxy)-propyl-(R)-2-carbamate,
1-(2,4-dichlorophenyl)-(R)-1-(methoxy)-propyl-(R)-2-carbamate,
1-(2,4-dichlorophenyl)-(R)-1-(methoxy)-butyl(R)-2-carbamate,
1-(2,4-dichlorophenyl)-(R)-1-(methoxy)-3-methyl-butyl-(R)-2-carbamate,
1-(2,4-dichlorophenyl)-(R)-1-(methoxy)-hexyl-(R)-2-carbamate,
1-(2,6-dichlorophenyl)-(R)-1-(methoxy)-propyl-(R)-2-carbamate,
1-(2,6-dichlorophenyl)-(R)-1-(methoxy)-butyl-(R)-2-carbamate,
1-(2,6-dichlorophenyl)-(R)-1-(methoxy)-3-methyl-butyl-(R)-2-carbamate,
1-(2,6-dichlorophenyl)-(R)-1-(methoxy)-hexyl-(R)-2-carbamate,
1-(2-chlorophenyl)-(R)-1-(methoxymethoxy)-ethyl-(R)-2-carbamate,
1-(2-fluorophenyl)-(R)-1-(methoxymethoxy)-ethyl-(R)-2-carbamate,
1-(2-iodophenyl)-(R)-1-(methoxymethoxy)-ethyl-(R)-2-carbamate,
1-(2-chlorophenyl)-(R)-1-(methoxymethoxy)-propyl-(R)-2-carbamate,
1-(2-chlorophenyl)-(R)-1-(methoxymethoxy)-propyl-(R)-2-N-methylcarbamate,
1-(2-chlorophenyl)-(R)-1-(methoxymethoxy)-propyl-(R)-2-N-propylcarbamate,
1-(2-chlorophenyl)-(R)-1-(methoxymethoxy)-propyl-(R)-2-N-isopropylcarbamate,
1-(2-chlorophenyl)-(R)-1-(methoxymethoxy)-propyl-(R)-2-N-cyclopropylcarbamate,
1-(2-chlorophenyl)-(R)-1-(methoxymethoxy)-propyl-(R)-2-N-cyclohexylcarbamate,
1-(2-chlorophenyl)-(R)-1-(methoxymethoxy)-propyl-(R)-2-N-benzylcarbamate,
1-(2-chlorophenyl)-(R)-1-(methoxymethoxy)-propyl-(R)-2-N-bicyclo[2,2,1]heptanecarbamate 1-(2-chlorophenyl)-(R)-1-(methoxymethoxy)-butyl-(R)-2-carbamate,
1-(2-chlorophenyl)-(R)-1-(methoxymethoxy)-3-methyl-butyl-(R)-2-carbamate,
1-(2-chlorophenyl)-(R)-1-(methoxymethoxy)-hexyl-(R)-2-carbamate,
1-(2,3-dichlorophenyl)-(R)-1-(methoxymethoxy)-propyl-(R)-2-carbamate,
1-(2,4-dichlorophenyl)-(R)-1-(methoxymethoxy)-propyl-(R)-2-carbamate,
1-(2,4-dichlorophenyl)-(R)-1-(methoxymethoxy)-butyl-(R)-2-carbamate,
1-(2,4-dichlorophenyl)-(R)-1-(methoxymethoxy)-3-methyl-butyl-(R)-2-carbamate,
1-(2,4-dichlorophenyl)-(R)-1-(methoxymethoxy)-hexyl-(R)-2-carbamate,
1-(2,5-dichlorophenyl)-(R)-1-(methoxymethoxy)-propyl-(R)-2-carbamate,
1-(2,6-dichlorophenyl)-(R)-1-(methoxymethoxy)-propyl-(R)-carbamate,
1-(2,6-dichlorophenyl)-(R)-1-(methoxymethoxy)-butyl-(R)-2-carbamate,
1-(2,6-dichlorophenyl)-(R)-1-(methoxymethoxy)-3-methyl-butyl-(R)-2-carbamate,
1-(2,6-dichlorophenyl)-(R)-1-(methoxymethoxy)-hexyl-(R)-2-carbamate,
1-(2-fluorophenyl)-(R)-1-(methoxymethoxy)-propyl-(R)-2-carbamate,
1-(4-fluorophenyl)-(R)-1-(methoxymethoxy)-propyl-(R)-2-carbamate,
1-(4-fluorophenyl)-(R)-1-(methoxymethoxy)-butyl-(R)-2-carbamate,
1-(4-fluorophenyl)-(R)-1-(methoxymethoxy)-3-methyl-butyl-(R)-2-carbamate,
1-(4-fluorophenyl)-(R)-1-(methoxymethoxy)-hexyl-(R)-2-carbamate,
1-(2-iodophenyl)-(R)-1-(methoxymethoxy)-propyl-(R)-2-carbamate,
1-(2-iodophenyl)-(R)-1-(methoxymethoxy)-butyl-(R)-2-carbamate,
1-(2-iodophenyl)-(R)-1-(methoxymethoxy)-3-methyl-butyl-(R)-2-carbamate,
1-(2-iodophenyl)-(R)-1-(methoxymethoxy)-hexyl-(R)-2-carbamate,
1-(3-iodophenyl)-(R)-1-(methoxymethoxy)-propyl-(R)-2-carbamate,
1-(3-iodophenyl)-(R)-1-(methoxymethoxy)-butyl-(R)-2-carbamate,
1-(3-iodophenyl)-(R)-1-(methoxymethoxy)-3-methyl-butyl-(R)-2-carbamate,
1-(3-iodophenyl)-(R)-1-(methoxymethoxy)-hexyl-(R)-2-carbamate,
1-(2-chlorophenyl)-(S)-1-carbamoyloxypropyl-(R)-2-carbamate,
1-(2-chlorophenyl)-(R)-1-carbamoyloxypropyl-(S)-2-carbamate,
1-(2-chlorophenyl)-(S)-1-(methoxy)-propyl-(R)-2-carbamate,
1-(2-chlorophenyl)-(R)-1-(methoxy)-propyl-(S)-2-carbamate,
1-(2-chlorophenyl)-(S)-1-(methoxymethoxy)-propyl-(R)-2-carbamate, and
1-(2-chlorophenyl)-(R)-1-(methoxymethoxy)-propyl-(S)-2-carbamate.

Two substances in the form of regioisomers of a single carbamate of diol having halogen substituent at phenyl ring may be separated by flash column chromatography to obtain two kinds of single carbamate compounds.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

The carbamate compound of the present invention may prepared by the following reaction formula.

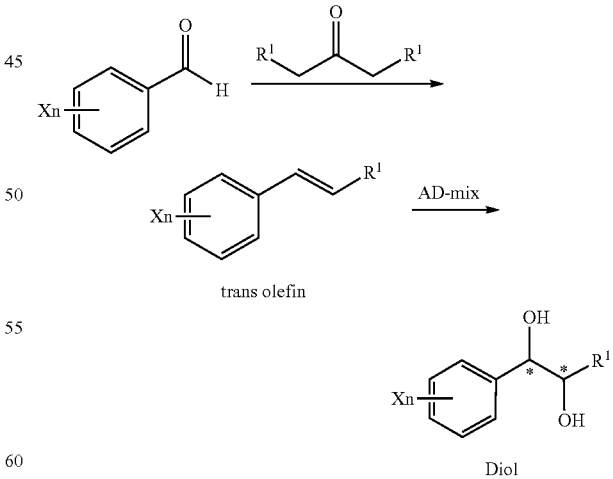

Reaction Formula I: Synthesis of Diol-1

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

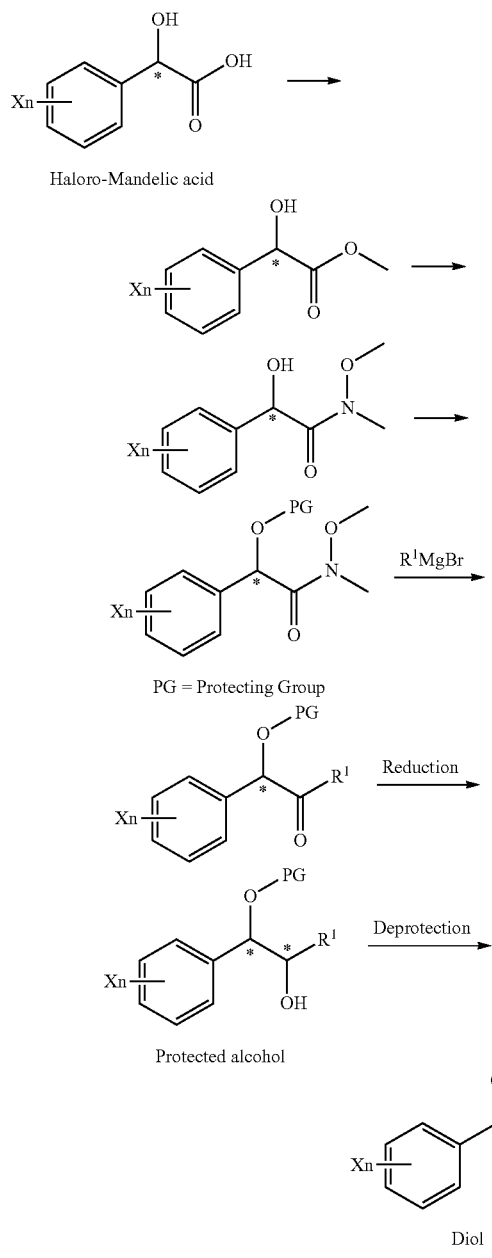

Diol

Reaction Formula III: Carbamation reaction-1

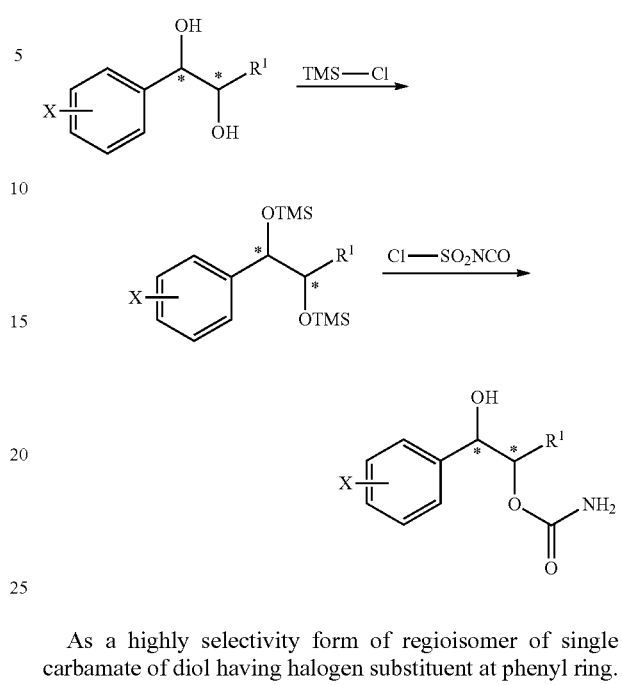

As a highly selectivity form of regioisomer of single carbamate of diol having halogen substituent at phenyl ring.

Reaction Formula IV: Carbamation reaction-2

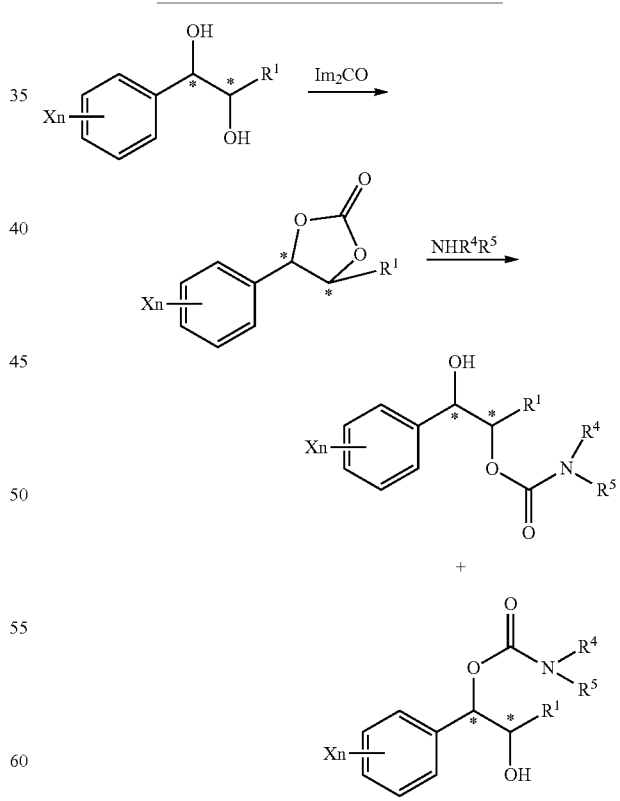

As indicated in the Reaction Formula II, the optically active substance of diol may also be synthesized using a reduction reagent after synthesizing a hydroxy-ketone compound using Haloro-Mandelic acid. In the Reaction Formula II, PG may be Trialkyl Silyl group(TMS, TES, TIPS, TBDMS, TBDPS), Ether group[MOM(Methoxymethyl ether), MEM(2-Methoxyethoxymethyl ether), BOM(Benzyloxymethyl ether). MTM(Methylthiomethyl ether), SEM(2-(Trimethylsilyl)ethoxymethyl ether), PMBM(p-Methoxybenzyl ether), THP(Tetrahydropyranyl ether), Allyl ether, Trityl ether, Ester group[Ac(acetate), Bz(Benzoate), Pv(Pivaloate), Cbz(Benzyl carbonate), BOC(t-Butyl carbonate), Fmoc(9-Fulorenylmethyl)carbaonate, Alloc(Allyl Carbonate), Troc(Trichloroehtyl carbonate), or p-Methoxybenzoate, Methyl carbonate, and so on.

Two substances in the form of regioisomers of a single carbamate of diol having halogen substituent at phenyl ring may be separated by flash column chromatography to obtain two kinds of single carbamate compounds.

Reaction Formula V: Substitution reaction

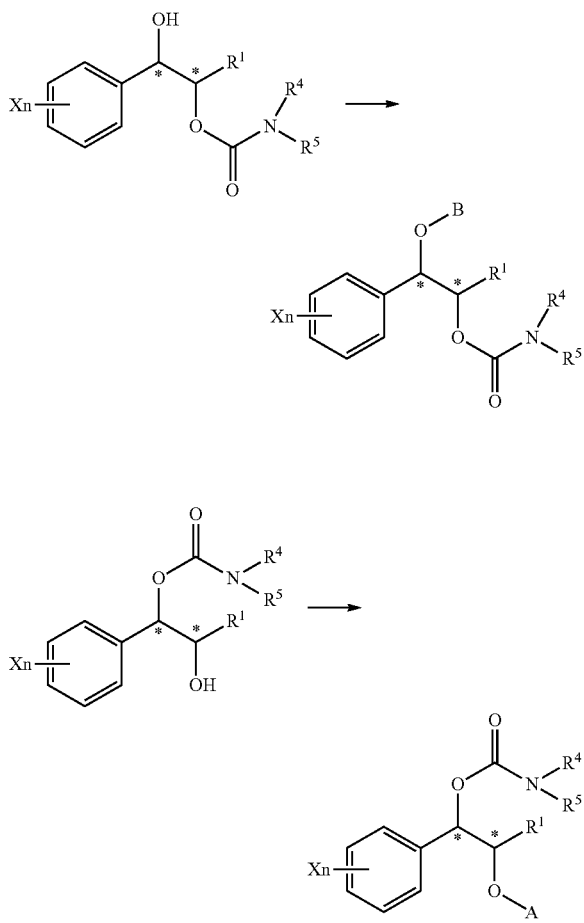

R$^1$ is a hydrogen or linear or branched C$_1$-C$_4$ alkyl group, for example, methyl group, ethyl group, isopropyl group, or butyl group, A is selected from the group consisting of an allyl, a C$_1$-C$_{19}$ linear or branched alkyl group (such as a methyl, t-butyl, benzyl, p-methoxybenzyl, 2-napthylmethyl, trityl group etc.), a C$_2$-C$_8$ alkoxy alky ether group (such as a methoxy methyl(MOM), methoxyethoxymethyl(MEM), tetrahydropyranyl(THP), benzyloxymethyl(BOM), methylthiomethyl(MTM), trimethylsilylethoxymethyl(SEM), ethoxyethyl(EE) group etc.), and a carbamoyl derivative represented by

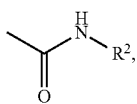

B is selected from the group consisting of an allyl, a C$_1$-C$_{19}$ linear or branched alkyl group (such as a methyl, t-butyl, benzyl, p-methoxybenzyl, 2-napthylmethyl, trityl group etc.), a C$_2$-C$_8$ alkoxy alky ether group (such as a methoxy methyl(MOM), methoxyethoxymethyl(MEM), tetrahydropyranyl(THP), benzyloxymethyl(BOM), methylthiomethyl(MTM), trimethylsilylethoxymethyl(SEM), ethoxyethyl(EE) group etc.), and a carbamoyl derivative represented by

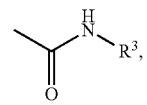

and

R$^2$ and R$^3$ may be the same as or different from each other, and independently selected from the group consisting of hydrogen, a linear or branched lower alkyl group of C$_1$-C$_4$, for example C$_1$-C$_3$, a cycloalkyl group of C$_3$-C$_8$, for example C$_3$-C$_7$, and benzyl group, and more specifically, R$^2$ and R$^3$ may be the same as or different from each other, and independently selected from the group consisting of hydrogen, methyl group, propyl group, isopropyl group, cyclopropyl group, cyclohexyl group, bicycloheptane group, and benzyl group.

In an embodiment, when A is a carbamoyl group, B is an allyl, linear or branched C$_1$-C$_{19}$ alkyl group or a C$_2$-C$_8$ alkoxy alky ether group; when B is a carbamoyl group, A is an allyl, a linear or branched C$_1$-C$_{19}$ alkyl group or a C$_2$-C$_8$ alkoxy alky ether group; or A and B are carbamoyl derivative at the same time.

In an embodiment of Chemical Formula 1, the C$_1$-C$_{19}$ linear or branched alkyl group is independently linear or branched C$_1$-C$_6$ lower aliphatic alkyl such as methyl, ethyl, t-butyl and the like; a substituted or unsubstituted C$_3$-C$_{19}$ cycloaliphatic and substituted or unsubstituted C$_6$-C$_{18}$ aromatic group such as benzyl, naphtyl, trityl and the like. The cycloaliphatic group and the aromatic group may be substituted with at least one selected from the group consisting of hydrogen, C$_1$-C$_6$ lower alkyl and C$_1$-C$_6$ alkoxy group.

The examples of C$_1$-C$_6$ lower aliphatic alkyl include methyl, ethyl, propyl, t-butyl, pantyl, hexyl and the like. The examples of C$_6$-C$_{18}$ aromatic group is benzyl such as benzyl, methylbenzyl, methoxybenzyl and the like, naphtyl such as 2-naphtylmethyl, trityl group and the like.

A and B is independently C$_2$-C$_8$ alkoxy alky ether group such as such as a methoxy methyl(MOM), methoxyethoxymethyl(MEM), tetrahydropyranyl(THP), benzyloxymethyl(BOM), methylthiomethyl(MTM), trimethylsilylethoxymethyl(SEM), ethoxyethyl(EE) group and the like.

R$^2$ and R$^3$ may be independently selected from the group consisting of hydrogen, a linear or branched alkyl group of C$_1$-C$_4$, for example C$_1$-C$_3$ alkyl, a cycloalkyl group of C$_3$-C$_8$, for example benzyl group, and more specifically, R$^2$ and R$^3$ may be selected from the group consisting of hydrogen, methyl group, propyl group, isopropyl group, cyclopropyl group, cyclohexyl group, bicycloheptane group, and benzyl group.

Another embodiment provides a method of prevention and/or treatment of a neurodegenerative disease, comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating a neurodegenerative disease.

The method may further comprise a step of identifying the subject in need of preventing and/or treating a neurodegenerative disease, prior to the step of administering. Another embodiment provides a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of a neurodegenerative disease.

Another embodiment provides a use of a phenyl alkyl carbamate compound represented by Chemical Formula 1; a racemate, an enantiomer, a diastereomer, a mixture of enantiomers, or a mixture of diastereomers thereof, or a pharmaceutically acceptable salt thereof for the manufacture of a pharmaceutical composition for preventing and/or treating a neurodegenerative disease.

By "neurodegenerative disease or disorder" is meant a disorder (including a neuropathy) associated with degeneration or dysfunction of neurons or other neural cells such as retinal ganglion cells. A neurodegenerative disease or disorder can be any disease or condition in which decreased function or dysfunction of neurons, or loss or neurons or other neural cells, can occur.

Such conditions include, without limitation, Parkinson's disease, Alzheimer's disease, Huntington's disease, Pick's disease, diffuse Lewy body disease, drug intoxication or withdrawal, Steel-Richardson syndrome, Shy-Drager syndrome, cortical basal degeneration, subacute sclerosing panencephalitis, synucleinopathies, primary progressive aphasia, striatonigral degeneration, Machado-Joseph disease, spinocerebellar ataxia, olivopontocerebellar degenerations, macular degeneration, bulbar and pseudobulbar palsy, spinal and spinobulbar muscular atrophy, systemic lupus erythematosus, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leuko-encephalopathy and familial dysautonomia, autism spectrum disease (such as autism, Asperger syndrome and pervasive developmental disorder not otherwise specified (PDD-NOS)) and prion disease (Creutzfeldt-Jakob disease, Gerstmann-Sträussler-Scheinker disease, Kuru disease and fatal familial insomnia).

Another embodiment provides a method for preventing and/or treating dopamine neurons loss or a disease caused by dopamine neurons loss, comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof, or a pharmaceutically acceptable salt thereof, to a subject in need of preventing and/or treating dopamine neurons loss or a disease caused by dopamine neurons loss.

Another embodiment provides a use of a phenyl alkyl carbamate compound represented by Chemical Formula 1; a racemate, an enantiomer, a diastereomer, a mixture of enantiomers, or a mixture of diastereomers thereof, or a pharmaceutically acceptable salt thereof for the manufacture of a pharmaceutical composition for preventing and/or treating dopamine neurons loss or a disease caused by dopamine neurons loss.

Another embodiment provides a method for preventing and/or alleviating an activation of astrocytes and glial, or alleviating a neurotoxicity occurred by immune process, comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or alleviating an activation of astrocytes and glial, or alleviating a neurotoxicity occurred by immune process.

Another embodiment provides a use a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof for the manufacture of a pharmaceutical composition for preventing and/or alleviating an activation of astrocytes and glial, or alleviating a neurotoxicity occurred by immune process.

Another embodiment provides a method for preventing and/or treating α-synucleinopathy or a disease associated with α-synuclein aggregates, comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating α-synucleinopathy.

Another embodiment provides a use a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof for the manufacture of a pharmaceutical composition for preventing and/or treating α-synucleinopathy or a disease associated with α-synuclein aggregates.

The term "α-synucleinopathy" includes all neurodegenerative disorders characterized by pathological synuclein aggregates. Parkinson's disease, Parkinson's disease dementia (PDD), Dementia with Lewy body (DLB), Lewy body disease, Dementia accompanied with Lewy bodies, Parkinson's syndrome with Dementia, Multiple system atrophy (MSA), multiple nervous system atrophy, and neurodegeneration type I with brain iron accumulation (NBIA Type I), are collectively grouped as synucleinopathy. In addition, the aggregations of α-synucleins have been also found secondary in Alzheimer's disease.

Herein "a disease associated with alpha-synuclein aggregates" is a group of neurodegenerative diseases called as synucleinopathy, in which alpha-synuclein aggregates are found in lesions including neurons and glia, and has characteristics such as dopamine system degeneration, mobility change, cognitive impairment, and formation of Lewy bodies and/or Lewy Neurites. These diseases include Parkinson's disease, Parkinson's disease dementia, Lewy body dementia, Lewy body variant of Alzheimer's disease, combined Alzheimer's and Parkinson's disease, multiple system atrophy, and many other neuroaxonal diseases, but are not limited to.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like. In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like. Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the pharmaceutically effective amount of 0.01 to 750 mg/kg (body weight), preferably 0.1 to 500 mg/kg (body weight) per one day, based on the active ingredient. The pharmaceutically effective amount may refers to an amount capable of exhibiting a desired effect, i.e., an effect of treating and/or preventing neurodegenerative diseases The pharmaceutically effective amount may be administered through oral or parenteral pathway (e.g., an intravenous injection, an intramuscular injection, etc.), one or two or more times per one day.

The pharmaceutically effective amount and the administration pathway of the present pharmaceutical composition may be properly adjusted by a person skilled in the relevant field considering the conditions of the subject (patient), desired effects, and the like. The subject may be a mammal including human or cells and/or tissues obtained therefrom.

EXAMPLE

The present invention is further explained in more detail with reference to the following examples. These examples, however, should not be interpreted as limiting the scope of the present invention in any manner.

Preparation Example 1: Synthesis of 1-(2-chlorophenyl)-trans-1-propene

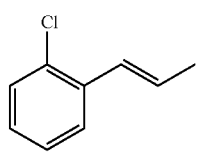

48 mL of 2-chlorobenzenaldehyde (0.42 mol) and 49.7 mL of 3-pentanone (0.47 mol) were dissolved in 600 mL of hexane in flask, and then stirred with raising the temperature. 53.6 mL of Boron trifluoride etherate ($BF_3OEt_2$, 0.42 mol) was added to the resultant under reflux conditions. When the reaction was completed, water was added thereto. After layer separation, the obtained organic layer was washed twice with 1 M sodium hydroxide solution (1 M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38.0 g, yield 58%).

$^1$H NMR (400 MHz, $CDCl_3$) δ 1.94 (d, J=4.8 Hz, 3H), 6.24 (m, 1H), 6.78 (d, J=14.0 Hz, 1H), 7.11~7.51 (m, 4H).

Preparation Example 2: Synthesis of 1-(2-chlorophenyl)-trans-1-butene

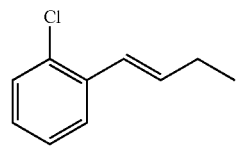

The substantially same method as described in Preparation Example 1 was conducted, except that 3-heptanone was used instead of 3-pentanone, to obtain the title compound (2.9 g, yield 83%).

$^1$H NMR (400 MHz, $CDCl_3$) δ 1.14 (d, J=7.6 Hz, 3H), 2.29~2.33 (m, 2H), 6.28 (dt, J=6.4, 16.0 Hz, 1H), 6.78 (d, J=15.6 Hz, 1H), 7.13~7.54 (m, 4H).

Preparation Example 3: Synthesis of 1-(2-chlorophenyl)-3-methyl-trans-1-butene

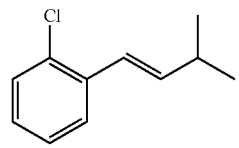

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400 MHz, $CDCl_3$) δ 1.14 (d, J=6.8 Hz, 6H), 2.25~2.57 (m, 1H), 6.20 (dd, J=7.2, 16.0 Hz, 1H), 7.64 (d, J=16.0 Hz, 1H), 7.12~7.54 (m, 4H).

Preparation Example 4: Synthesis of 1-(2-chlorophenyl)-trans-1-hexene

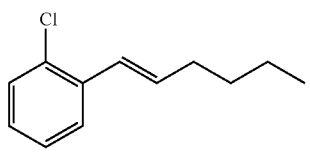

The substantially same method as described in Preparation Example 1 was conducted, except that 6-undecanone was used instead of 3-pentanone, to obtain the title compound (10.0 g, yield 85%).

$^1$H NMR (400 MHz, $CDCl_3$) δ 0.96 (t, J=7.2 Hz, 3H), 1.33~1.56 (m, 4H), 2.26~2.32 (m, 4H), 6.24 (dt, J=7.0, 15.6 Hz, 1H), 6.78 (d, J=16.0 Hz, 1H), 7.13~7.54 (m, 4H).

Preparation Example 5: Synthesis of 1-(2,4-dichlorophenyl)-trans-1-propene

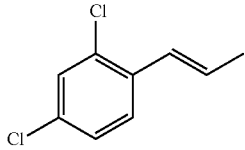

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ 1.95 (dd, J=1.6, 6.8 Hz, 3H), 6.24 (m, 1H), 6.72 (d, J=15.6 Hz, 1H), 7.18~7.44 (m, 3H).

Preparation Example 6: Synthesis of 1-(2,4-dichlorophenyl)-trans-1-butene

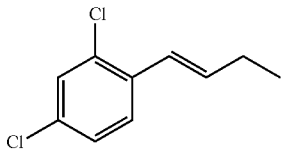

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ 1.14 (d, J=7.6 Hz, 3H), 2.20~2.33 (m, 2H), 6.26 (dt, J=6.8, 16.0 Hz, 1H), 6.70 (d, J=15.6 Hz, 1H), 7.18~7.46 (m, 3H).

Preparation Example 7: Synthesis of 1-(2,6-dichlorophenyl)-3-methyl-trans-1-butene

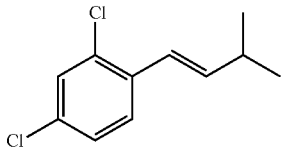

The substantially same method as described in Preparation Example 5 was conducted, except that 2,6-dimethylheptan-4-one was used instead of 3-pentanone, to obtain the title compound (0.23 g, yield 10~40%).

$^1$H NMR (400 MHz, CDCl$_3$) δ 1.15 (d, J=6.8 Hz, 6H), 2.53~2.58 (m, 1H), 6.19 (dd, J=6.8, 16.4 Hz, 1H), 6.31 (d, J=16.4 Hz, 1H), 7.18~7.46 (m, 3H).

Preparation Example 8: Synthesis of 1-(2,4-dichlorophenyl)-trans-1-hexene

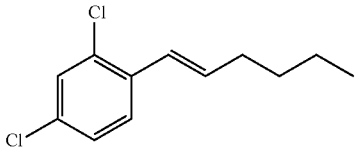

The substantially same method as described in Preparation Example 5 was conducted, except that 6-undecanone was used instead of 3-pentanone, to obtain the title compound (3.2 g, yield 40~80%).

$^1$H NMR (400 MHz, CDCl$_3$) δ 0.96 (t, J=7.2 Hz, 3H), 1.38~1.52 (m, 4H), 2.25~2.31 (m, 2H), 6.22 (dt, J=6.8, 15.6 Hz, 1H), 6.70 (d, J=15.6 Hz, 1H), 7.18~7.46 (m, 3H).

Preparation Example 9: Synthesis of 1-(2,6-dichlorophenyl)-trans-1-propene

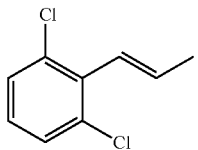

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR (400 MHz, CDCl$_3$) δ 1.98 (d, J=8.0 Hz, 3H), 6.23~6.31 (m, 1H), 6.40 (d, J=16.0 Hz, 1H), 7.05~7.32 (m, 3H).

Preparation Example 10: Synthesis of 1-(2,6-dichlorophenyl)-trans-1-butene

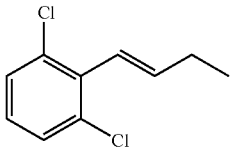

The substantially same method as described in Preparation Example 9 was conducted, except that 3-heptanone was used instead of 3-pentanone, to obtain the title compound (1.2 g, yield 10~40%).

$^1$H NMR (400 MHz, CDCl$_3$) δ 1.17 (t, J=7.6 Hz, 3H), 2.30~2.37 (m, 2H), 6.29 (dt, J=6.0, 16.4 Hz, 1H), 6.37 (d, J=16.4 Hz, 1H), 7.05~7.32 (m, 3H).

Preparation Example 11: Synthesis of 1-(2,6-dichlorophenyl)-3-methyl-trans-1-butene

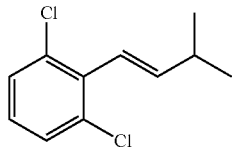

The substantially same method as described in Preparation Example 9 was conducted, except that 2,6-dimethyl-heptan-4-one was used instead of 3-pentanone, to obtain the title compound (0.23 g, yield 10~40%).

$^1$H NMR (400 MHz, CDCl$_3$) δ 1.15 (d, J=6.8 Hz, 6H), 2.53~2.58 (m, 1H), 6.19 (dd, J=6.8, 16.4 Hz, 1H), 6.31 (d, J=16.4 Hz, 1H), 7.05~7.32 (m, 3H).

Preparation Example 12: Synthesis of 1-(2,6-dichlorophenyl)-trans-1-hexene

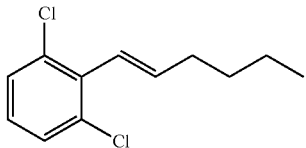

The substantially same method as described in Preparation Example 9 was conducted, except that 6-undecanone was used instead of 3-pentanone, to obtain the title compound (0.2 g, yield 10~40%).

$^1$H NMR (400 MHz, CDCl$_3$) δ 0.99 (t, J=7.2 Hz, 3H), 1.14~1.59 (m, 4H), 2.30~2.36 (m, 2H), 6.24 (dt, J=6.6, 16.0 Hz, 1H), 6.38 (d, J=16.4 Hz, 1H), 7.05~7.33 (m, 3H).

Preparation Example 13: Synthesis of 1-(2,3-dichlorophenyl)-trans-1-propene

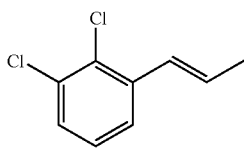

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR (400 MHz, CDCl$_3$) δ 1.94 (d, J=4.8 Hz, 3H), 6.24 (m, 1H), 6.78 (d, J=14.0 Hz, 1H), 7.11~7.51 (m, 3H).

Preparation Example 14: Synthesis of 1-(2-chlorophenyl)-(S,S)-1,2-propanediol

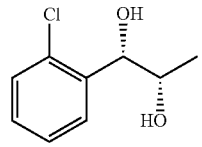

1-(2-chlorophenyl)-trans-1-propene (1.5 g, Preparation Example 1) was dissolved in 30 mL of the mixture of t-BuOH/H$_2$O (1:1(V/V)). At 0° C., AD-mix-α (Aldrich, U.S.A.) (13.7 g) and methane sulfone amide (CH$_3$SO$_2$NH$_2$, 0.76 g, 0.008 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (1.65 g, yield 90%).

$^1$H NMR (400 MHz, CDCl$_3$) δ 1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H).

$^{13}$C NMR (100 MHz, CDCl$_3$) δ 18.8, 71.5, 74.4, 127.1, 128.1, 128.9, 129.5, 132.6, 138.9

Preparation Example 15: Synthesis of 1-(2-chlorophenyl)-(R,R)-1,2-propanediol

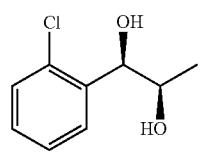

1-(2-chlorophenyl)-trans-1-propene (2.5 g, Preparation Example 1) was dissolved in 50 mL of the mixture of t-BuOH/H$_2$O (1:1(V/V)). At 0° C., AD-mix-α (Aldrich, U.S.A.) (23.5 g) and methane sulfone amide (CH$_3$SO$_2$NH$_2$, 1.27 g, 0.013 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (2.96 g, yield 90%).

$^1$H NMR (400 MHz, CDCl$_3$) δ 1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H).

Preparation Example 16: Synthesis of the Mixture of 1-(2-chlorophenyl)-(S,S)-1,2-propanediol and 1-(2-chlorophenyl)-(R,R)-1,2-propanediol

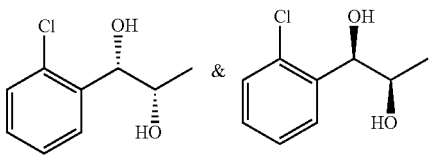

1-(2-chlorophenyl)-trans-1-propene (6.53 g, Preparation Example 1) was dissolved in 45 mL of the mixture of acetone/t-BuOH/H₂O (5:1:1(V/V)). At the room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concentrated under reduced pressure. The concentrated residue was purified by a silica gel column chromatography to produce the title compound (6.42 g, yield 80%).

¹H NMR (400 MHz, CDCl₃) δ 1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H).

Preparation Example 17: Synthesis of 1-(2-chlorophenyl)-(S,S)-1,2-butanediol

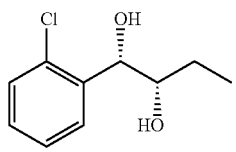

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

¹H NMR (400 MHz, CDCl₃) δ 1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H).

Preparation Example 18: Synthesis of 1-(2-chlorophenyl)-(R,R)-1,2-butanediol

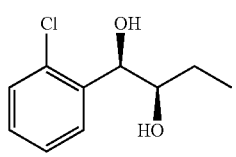

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

¹H NMR (400 MHz, CDCl₃) δ 1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H).

Preparation Example 19: Synthesis of the Mixture of 1-(2-chlorophenyl)-(S,S)-1,2-butanediol and 1-(2-chlorophenyl)-(R,R)-1,2-butanediol

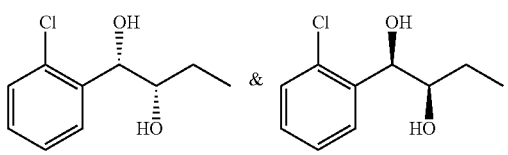

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

¹H NMR (400 MHz, CDCl₃) δ 1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H).

Preparation Example 20: Synthesis of 1-(2-chlorophenyl)-3-methyl-(S,S)-1,2-butanediol

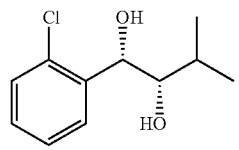

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

¹H NMR (400 MHz, CDCl₃) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H).

Preparation Example 21: Synthesis of 1-(2-chlorophenyl)-3-methyl-(R,R)-1,2-butanediol

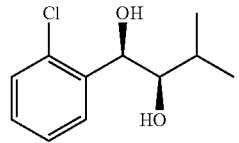

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR (400 MHz, CDCl$_3$) δ 1.07 (t, J=7.2 Hz, 6H), 1.82~1.90 (m, 1H), 1.93 (d, J=5.6 Hz, 1H), 2.79 (d, J=6.0 Hz, 1H), 3.53~3.57 (m, 1H), 5.23~5.25 (m, 1H), 7.23~7.54 (m, 4H).

Preparation Example 22: Synthesis of the Mixture of 1-(2-chlorophenyl)-3-methyl-(S,S)-1,2-butanediol and 1-(2-chlorophenyl)-3-methyl-(R,R)-1,2-butanediol

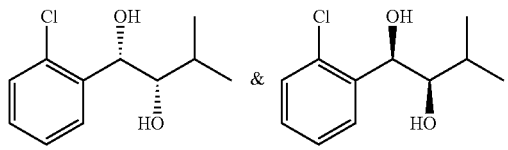

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

$^1$H NMR (400 MHz, CDCl$_3$) δ 1.07 (t, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H).

Preparation Example 23: Synthesis of 1-(2-chlorophenyl)-(S,S)-1,2-hexanediol

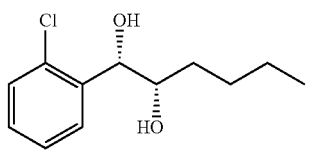

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

$^1$H NMR (400 MHz, CDCl$_3$) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H).

Preparation Example 24: Synthesis of 1-(2-chlorophenyl)-(R,R)-1,2-hexanediol

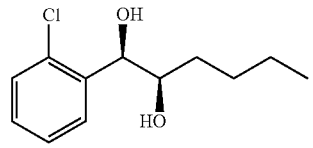

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).

$^1$H NMR (400 MHz, CDCl$_3$) δ 0.91 (t, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H).

Preparation Example 25: Synthesis of the Mixture of 1-(2-chlorophenyl)-(S,S)-1,2-hexanediol and 1-(2-chlorophenyl)-(R,R)-1,2-hexanediol

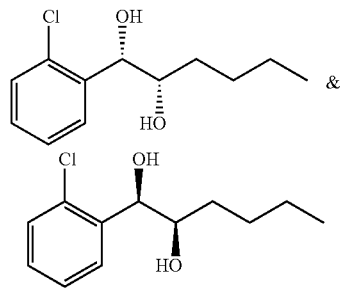

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

$^1$H NMR (400 MHz, CDCl$_3$) δ 0.90 (t, J=7.2 Hz, 3H), 1.26~1.55 (m, 6H), 2.08 (d, J=4.4 Hz, 1H), 2.71 (d, J=5.6 Hz, 1H), 3.78~3.84 (m, 1H), 5.04 (t, J=3.2 Hz, 1H), 7.24~7.55 (m, 4H).

Preparation Example 26: Synthesis of 1-(2,4-dichlorophenyl)-(S,S)-1,2-propanediol

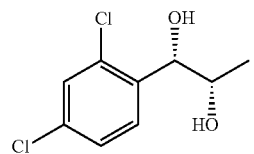

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

$^{1}$H NMR (400 MHz, CDCl$_{3}$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0, 8.0 Hz, 1H), 7.40 (d, J=2.0 Hz, 1H), 7.49 (d, J=8.4 Hz, 1H).

Preparation Example 27: Synthesis of 1-(2,4-dichlorophenyl)-(R,R)-1,2-propanediol

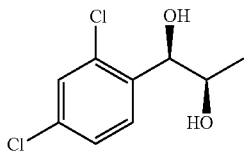

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^{1}$H NMR (400 MHz, CDCl$_{3}$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H).

Preparation Example 28: Synthesis of the Mixture of 1-(2,4-dichlorophenyl)-(S,S)-1,2-propanediol and 1-(2,4-dichlorophenyl)-(R,R)-1,2-propanediol

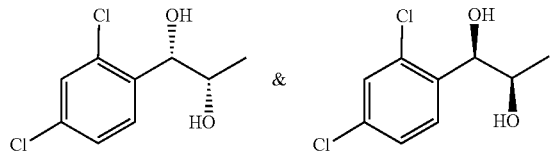

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^{1}$H NMR (400 MHz, CDCl$_{3}$) δ 1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H).

Preparation Example 29: Synthesis of 1-(2,4-dichlorophenyl)-(S,S)-1,2-butanediol

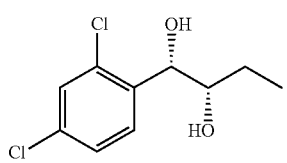

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^{1}$H NMR (400 MHz, CDCl$_{3}$) δ 1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H).

Preparation Example 30: Synthesis of 1-(2,4-dichlorophenyl)-(R,R)-1,2-butanediol

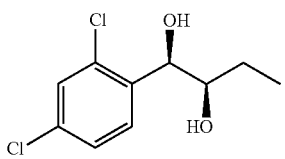

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^{1}$H NMR (400 MHz, CDCl$_{3}$) δ 1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H).

Preparation Example 31: Synthesis of the Mixture of 1-(2,4-dichlorophenyl)-(S,S)-1,2-butanediol and 1-(2,4-dichlorophenyl)-(R,R)-1,2-butanediol

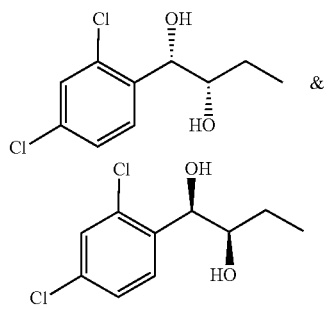

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^{1}$H NMR (400 MHz, CDCl$_{3}$) δ 1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H).

Preparation Example 32: Synthesis of 1-(2,4-dichlorophenyl)-3-methyl-(S,S)-1,2-butanediol

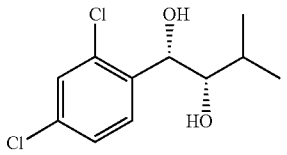

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).
$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 33: Synthesis of 1-(2,4-dichlorophenyl)-3-methyl-(R,R)-1,2-butanediol

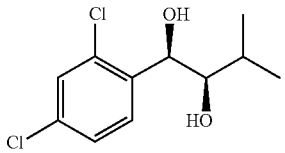

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).
$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 34: Synthesis of the Mixture of 1-(2,4-dichlorophenyl)-3-methyl-(S,S)-1,2-butanediol and 1-(2,4-dichlorophenyl)-3-methyl-(R,R)-1,2-butanediol

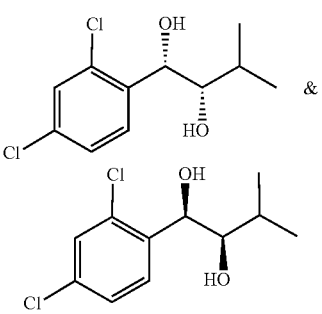

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).
$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 35: Synthesis of 1-(2,4-dichlorophenyl)-(S,S)-1,2-hexanediol

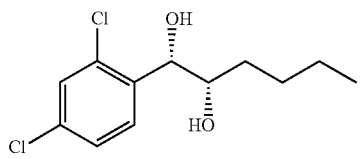 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.1 g, yield 60~90%).
$^1$H NMR (400 MHz, CDCl$_3$) δ 0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H).

Preparation Example 36: Synthesis of 1-(2,4-dichlorophenyl)-(R,R)-1,2-hexanediol

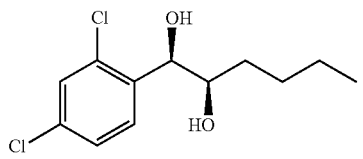 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.2 g, yield 60~95%).
$^1$H NMR (400 MHz, CDCl$_3$) δ 0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H).

Preparation Example 37: Synthesis of the Mixture of 1-(2,4-dichlorophenyl)-(S,S)-1,2-hexanediol and 1-(2,4-dichlorophenyl)-(R,R)-1,2-hexanediol

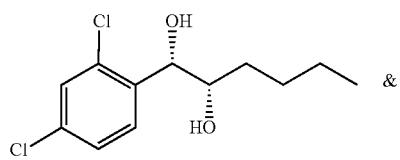

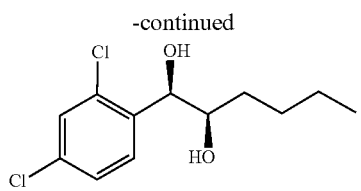

The substantially same method as described in Preparation Example 16 was conducted, except that 1-(2,4-dichlorophenyl)-trans-1-propene (Preparation Example 8) was used instead of 1-(2-chlorophenyl)-trans-1-propene (Preparation Example 1), to obtain the title compound (0.67 g, yield 60~95%).

$^1$H NMR (400 MHz, CDCl$_3$) δ 0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H).

Preparation Example 38: Synthesis of 1-(2,6-dichlorophenyl)-(S,S)-1,2-propanediol

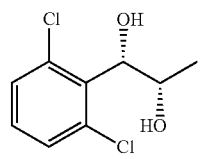

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H).

Preparation Example 39: Synthesis of 1-(2,6-dichlorophenyl)-(R,R)-1,2-propanediol

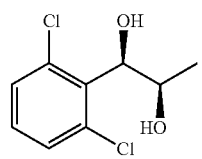

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H).

Preparation Example 40: Synthesis of the Mixture of 1-(2,6-dichlorophenyl)-(S,S)-1,2-propanediol and 1-(2,6-dichlorophenyl)-(R,R)-1,2-propanediol

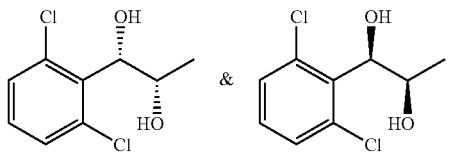

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H).

Preparation Example 41: Synthesis of 1-(2,6-dichlorophenyl)-(S,S)-1,2-butanediol

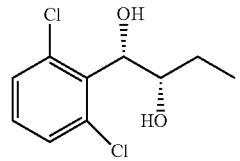

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR (400 MHz, CDCl$_3$) δ 0.97 (t, J=7.6 Hz, 3H), 1.26~1.53 (m, 2H), 2.64 (dd, J=0.8, 4.0 Hz, 1H), 3.14 (d, J=8.4 Hz, 1H), 4.22~4.26 (m, 1H), 5.26 (t, J=8.4 Hz, 1H), 7.17~7.35 (m, 3H).

Preparation Example 42: Synthesis of 1-(2,6-dichlorophenyl)-(R,R)-1,2-butanediol

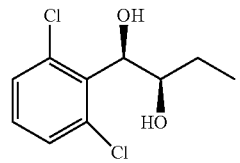

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR (400 MHz, CDCl$_3$) δ 0.97 (t, J=7.6 Hz, 3H), 1.26~1.53 (m, 2H), 2.64 (dd, J=0.8, 4.0 Hz, 1H), 3.14 (d, J=8.4 Hz, 1H), 4.22~4.26 (m, 1H), 5.26 (t, J=8.4 Hz, 1H), 7.17~7.35 (m, 3H).

Preparation Example 43: Synthesis of the Mixture of 1-(2,6-dichlorophenyl)-(S,S)-1,2-butanediol and 1-(2,6-dichlorophenyl)-(R,R)-1,2-butanediol

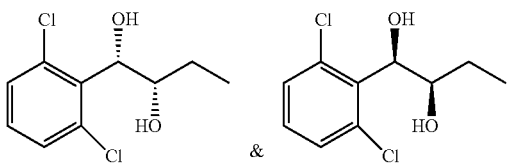

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR (400 MHz, CDCl$_3$) δ 0.97 (t, J=7.6 Hz, 3H), 1.26~1.53 (m, 2H), 2.64 (dd, J=0.8, 4.0 Hz, 1H), 3.14 (d, J=8.4 Hz, 1H), 4.22~4.26 (m, 1H), 5.26 (t, J=8.4 Hz, 1H), 7.17~7.35 (m, 3H).

Preparation Example 44: Synthesis of 1-(2,6-dichlorophenyl)-3-methyl-(S,S)-1,2-butanediol

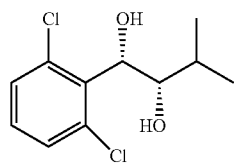

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 45: Synthesis of 1-(2,6-dichlorophenyl)-3-methyl-(R,R)-1,2-butanediol

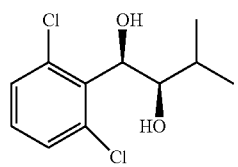

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 46: Synthesis of the Mixture of 1-(2,6-dichlorophenyl)-3-methyl-(S,S)-1,2-butanediol and 1-(2,6-dichlorophenyl)-3-methyl-(R,R)-1,2-butanediol

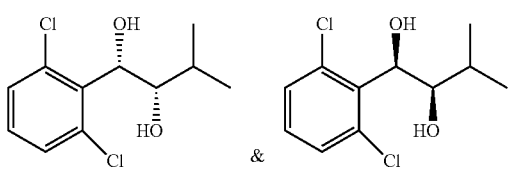

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR (400 MHz, CDCl$_3$) δ 1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H).

Preparation Example 47: Synthesis of 1-(2,6-dichlorophenyl)-(S,S)-1,2-hexanediol

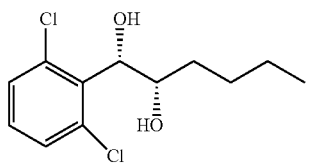 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR (400 MHz, CDCl$_3$) δ 0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H).

Preparation Example 48: Synthesis of 1-(2,6-dichlorophenyl)-(R,R)-1,2-hexanediol

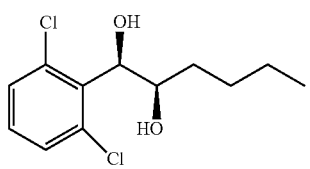 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR (400 MHz, CDCl$_3$) δ 0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H).

Preparation Example 49: Synthesis of the Mixture of 1-(2,6-dichlorophenyl)-(S,S)-1,2-hexanediol and 1-(2,6-dichlorophenyl)-(R,R)-1,2-hexanediol

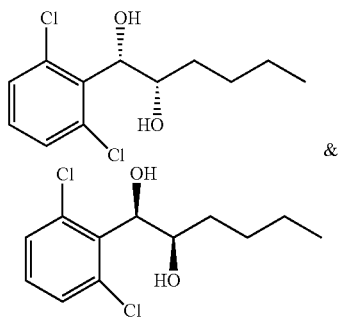

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR (400 MHz, CDCl$_3$) δ 0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H).

Preparation Example 50: Synthesis of methyl 2-(2-chlorophenyl)-(R)-2-hydroxyacetate

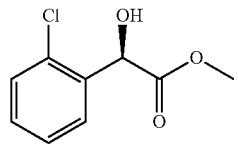

15.0 g of (R)-2-chloromandelic acid was mixed with methanol (CH$_3$OH, 150 mL) and phosphorus chloride oxide (POCl$_3$, 0.76 mL) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR (400 MHz, CDCl$_3$) δ 3.59 (d, J=5.2 Hz, 1H), 3.79 (t, J=6.0 Hz, 3H), 5.59 (d, J=5.2 Hz, 1H), 7.28~7.43 (m, 4H).

Preparation Example 51: Synthesis of 2-(2-chlorophenyl)-(R)-2-hydroxy-N-methoxy-N-methylacetamide

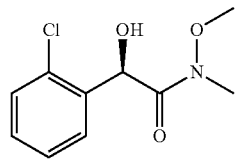

N,O-dimethylhydroxylamine hydrochloride (N,O-dimethylhydroxylamine.HCl, 15.2 g) was dissolved in dichloromethane (DCM, 150 mL), and cooled to 0° C. using an ice-bath. Then, 77.7 mL of 2 M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 mL) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 mL). The obtained organic layer was washed with distilled water and brine, dehydrated with anhydrous magnesium sulfate (MgSO$_4$), filtrated, and concentrated under reduced pressure. The concentrated residue was purified by a silica gel column chromatography to produce the title compound (14.68 g, yield 82%).

$^1$H NMR (400 MHz, CDCl$_3$) δ 3.23 (s, 3H), 3.28 (s, 3H), 4.33 (d, J=6.0 Hz, 1H), 5.81 (d, J=5.6 Hz, 1H), 7.23~7.42 (m, 4H).

Preparation Example 52: Synthesis of 2-(2-chlorophenyl)-N-methoxy-(R)-2-(methoxymethoxy)-N-methylacetamide

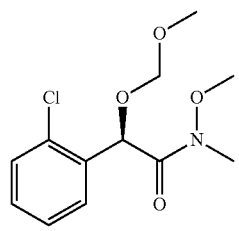 [SMILES: COCO[C@@H](C(=O)N(C)OC)c1ccccc1Cl]

2-(2-chlorophenyl)-(R)-2-hydroxy-N-methoxy-N-methylacetamide (14.68 g) obtained in Preparation Example 51 was dissolved in dichloromethane (DCM, 140 mL), and cooled to 0° C. Diisopropylethylamine (55.67 mL) was slowly added thereto in drop-wise manner, and stirred for 10 minutes. Chloro methyl methyl ether (25.25 mL) was slowly added thereto in drop-wise manner for 30 minutes. After 30 minutes, the ice-bath was removed and the obtained product was stirred for 30 at room temperature. When the reaction was completed, the obtained product was cooled to 0° C. And then, to the obtained product, 1 M sodium hydroxide solution (1 M NaOH, 20 mL) was added in drop-wise manner, and dichloromethane (DMC) was injected. Then the obtained product was washed with water. The obtained organic layer was dehydrated with anhydrous magnesium sulfate (MgSO₄), filtrated, and concentrated under reduced pressure. The concentrated residue was purified by a silica gel column chromatography to produce the title compound (15.57 g, yield 89%).

¹H NMR (400 MHz, CDCl₃) δ 3.19 (s, 3H), 3.42 (s, 3H), 3.47 (s, 3H), 4.75 (d, J=6.8 Hz, 1H), 4.81 (d, J=6.8 Hz, 1H), 6.07 (s, 1H), 7.27~7.58 (m, 4H).

Preparation Example 53: Synthesis of 1-(2-chlorophenyl)-(R)-1-(methoxymethoxy)propane-2-on

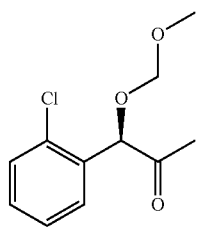

2-(2-chlorophenyl)-N-methoxy-(R)-2-(methoxymethoxy)-N-methylacetamide (15.57 g) obtained in Preparation Example 52 was dissolved in tetrahydrofuran (THF, 150 mL), and cooled to 0° C. 3 M methyl magnesium bromide (MeMgBr) solution in ether was added thereto in drop-wise manner for 30 minutes, and the obtained product was stirred for 1 hour at 0° C. When the reaction was completed, diethylether (100 mL) was added thereto. The obtained product was washed with 10% (w/v) potassium hydrogen sulfate (KHSO₄, 100 mL) and then, washed again with brine. The obtained organic layer was dehydrated with anhydrous magnesium sulfate (MgSO₄), filtrated, and concentrated under reduced pressure. The concentrated residue was purified by a silica gel column chromatography to produce the title compound (11.83 g, yield 90%).

¹H NMR (400 MHz, CDCl₃) δ 2.18 (s, 3H), 3.39 (s, 3H), 4.65 (d, J=6.8 Hz, 1H), 4.74 (d, J=6.8 Hz, 1H), 5.63 (s, 1H), 7.30~7.45 (m, 4H).

Preparation Example 54: Synthesis of 1-(2-chlorophenyl)-(R)-1-(methoxymethoxy)-(S)-2-propanol

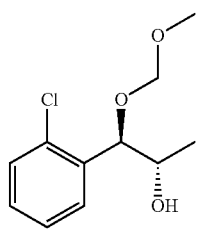

1-(2-chlorophenyl)-(R)-1-(methoxymethoxy)propane-2-on (11.83 g) obtained in Preparation Example 53 was dissolved in toluene (110 mL), and cooled to −40° C. Sodium bis(2-methoxyethoxy)aluminumhydride solution (15.7 mL) in toluene was slowly added thereto for 30 minutes, and then, the obtained product was stirred for 1 hour. When the reaction was completed, the obtained product was washed by slow drop-wise addition of sodium potassium tartrate (100 mL). The obtained organic layer was dehydrated with anhydrous magnesium sulfate (MgSO₄), filtrated, and concentrated under reduced pressure. The concentrated residue was purified by a silica gel column chromatography to produce the title compound (10.38 g, yield 87%).

¹H NMR (400 MHz, CDCl₃) δ 1.13 (d, J=6.4 Hz, 3H), 2.33 (d, J=7.2 Hz, 1H), 3.44 (s, 3H), 4.10~4.18 (m, 1H), 4.61 (d, J=6.4 Hz, 1H), 4.69 (d, J=6.8 Hz, 1H), 5.14 (d, J=3.6 Hz, 1H), 7.22~7.55 (m, 4H).

Preparation Example 55: Synthesis of 1-(2-chlorophenyl)-(R,S)-1,2-propanediol

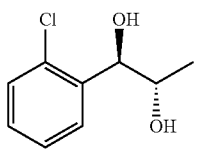

1-(2-chlorophenyl)-(R)-1-(methoxymethoxy)-(S)-2-propanol (10.38 g) obtained in Preparation Example 54 was dissolved in methanol (CH₃₀H, 100 mL), and then, cooled to 0° C. 8 M hydrochloric acid (HCl, 56.2 mL) was slowly added in drop-wise manner to the obtained product, and then, the obtained product was warmed to the room temperature, and stirred for 15 hours. When the reaction was completed, the obtained product was cooled to 0° C. 5 N sodium hydroxide (NaOH, 30 mL) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concentrated under reduced pressure. The concentrated residue was purified by a silica gel column chromatography to produce the title compound (7.05 g, yield 60~90%).

¹H NMR (400 MHz, CDCl₃) δ 1.07 (d, J=6.8 Hz, 3H), 2.01 (d, J=5.6 Hz, 1H), 2.61 (s, 1H), 4.21~4.27 (m, 1H), 5.24 (d, J=3.6 Hz, 1H), 7.22~7.64 (m, 4H).

Preparation Example 56: Synthesis of 1-(2-chlorophenyl)-(S,R)-1,2-propanediol

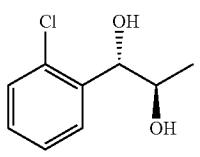

The substantially same method as described in Preparation Example 50~55 was conducted, except that (S)-2-chloromandelic acid was used instead of (R)-2-chloromandelic acid, to obtain the title compound (5.04 g, yield 84%).

¹H NMR (400 MHz, CDCl₃) δ 1.07 (d, J=6.8 Hz, 3H), 2.00 (d, J=5.6 Hz, 1H), 2.54 (d, J=3.6 Hz, 1H), 4.22~4.26 (m, 1H), 5.25 (t, J=3.2 Hz, 1H), 7.22~7.65 (m, 4H).

Preparation Example 57: Synthesis of 1-(2,3-dichlorophenyl)-(S,S)-1,2-propanediol

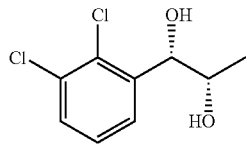

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~ (m, 3H).

Preparation Example 58: Synthesis of 1-(2,3-dichlorophenyl)-(R,R)-1,2-propanediol

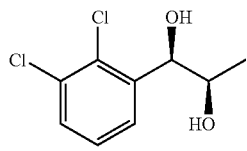

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H).

Preparation Example 59: Synthesis of the Mixture of 1-(2,3-dichlorophenyl)-(S,S)-1,2-propanediol and 1-(2,3-dichlorophenyl)-(R,R)-1,2-propanediol

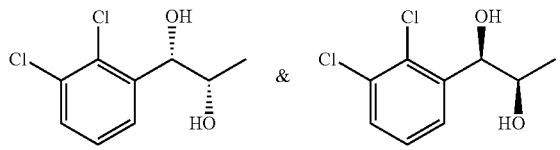

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H).

Preparation Example 60: Synthesis of 1-(2-fluorophenyl)-trans-1-propene

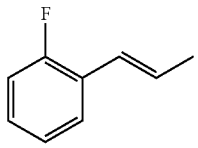

The substantially same method as described in Preparation Example 1 was conducted, except that 2-fluorobenzenaldehyde was used instead of 2-chlorobenzenealdehyde, to obtain the title compound (6.67 g, yield 61%).

$^1$H NMR (400 MHz, CDCl$_3$) δ 1.94 (d, J=6.8 Hz, 3H), 6.30~6.38 (m, 1H), 6.57 (d, J=16.0 Hz, 1H), 7.00~7.41 (m, 4H).

Preparation Example 61: Synthesis of 1-(2-fluorophenyl)-(S,S)-1,2-propanediol

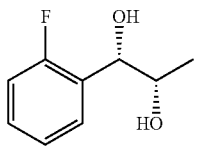

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

$^1$H NMR (400 MHz, CDCl$_3$) δ 1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H).

Preparation Example 62: Synthesis of 1-(2-fluorophenyl)-(R,R)-1,2-propanediol

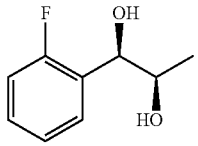

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

$^1$H NMR (400 MHz, CDCl$_3$) δ 1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H).

Preparation Example 63: Synthesis of 2-iodobenzenealdehyde

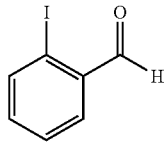

In a flask, 2-iodobenzyl alcohol (4.0 g, 17.09 mmol) was dissolved in dichloromethane (MC, 85 mL), and then, manganese oxide ($MnO_2$, 14.86 g, 170.92 mmol) was added thereto. The obtained reaction product was stirred under the reflux condition. When the reaction was completed, the obtained reaction product was cooled to the room temperature, and then, filtrated and concentrated using celite, to obtain the title compound (3.6 g, yield 91%).

$^1$H NMR (400 MHz, $CDCl_3$) δ 7.30~7.99 (m, 4H), 10.10 (s, 1H).

Preparation Example 64: Synthesis of 1-(2-iodophenyl)-trans-1-propene

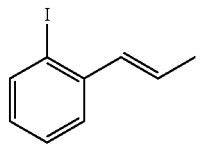

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR (400 MHz, $CDCl_3$) δ 1.95 (dd, J=1.6, 6.8 Hz, 3H), 6.09~6.18 (m, 1H), 6.60 (dd, J=1.8, 15.7 Hz, 1H), 6.89~7.84 (m, 4H).

Preparation Example 65: Synthesis of 1-(2-iodophenyl)-trans-1-butene

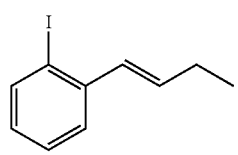

The substantially same method as described in Preparation Example 64 was conducted, except that 3-heptanone was used instead of 3-pentanone, to obtain the title compound (8.5 g, yield 75%).

$^1$H NMR (400 MHz, $CDCl_3$) δ 1.46 (t, J=7.6 Hz, 3H), 2.26~2.34 (m, 2H), 6.17 (dt, J=6.6, 15.6 Hz, 1H), 6.57 (d, J=15.6 Hz, 1H), 6.89~7.85 (m, 4H).

Preparation Example 66: Synthesis of 1-(2-iodophenyl)-(S,S)-1,2-propanediol

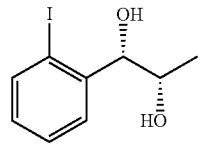

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400 MHz, $CDCl_3$) δ 1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H).

Preparation Example 67: Synthesis of 1-(2-iodorophenyl)-(R,R)-1,2-propanediol

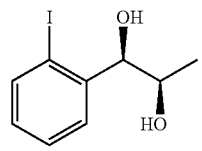

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR (400 MHz, $CDCl_3$) δ 1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=4.4, 5.0 Hz, 1H), 7.00~7.87 (m, 4H).

Preparation Example 68: Synthesis of 1-(2-iodophenyl)-(S,S)-1,2-butanediol

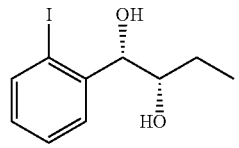

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR (400 MHz, $CDCl_3$) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H).

Preparation Example 69: Synthesis of 1-(2-iodophenyl)-(R,R)-1,2-butanediol

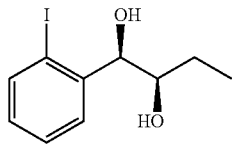

The substantially same method as described in Preparation Example 15 was conducted, except that 1-(2-iodophenyl)-trans-1-butene (Preparation Example 65) was used instead of 1-(2-chlorophenyl)-trans-1-propene (Preparation Example 1), to obtain the title compound (1.9 g, yield 70~90%).

$^1$H NMR (400 MHz, CDCl$_3$) δ 1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.03~7.84 (m, 4H).

Preparation Example 70: Synthesis of 1-(2-iodophenyl)-3-methyl-trans-1-butene

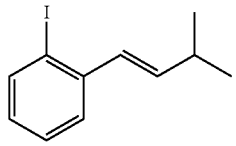

The substantially same method as described in Preparation Example 3 was conducted, except that 2-iodobenzenaldehyde was used instead of 2-chlorobenzenaldehyde, to obtain the title compound (0.37 g, yield 10~40%).

$^1$H NMR (400 MHz, CDCl$_3$) δ 1.14 (d, J=6.8 Hz, 6H), 2.25~2.57 (m, 1H), 6.20 (dd, J=7.2, 16.0 Hz, 1H), 7.64 (d, J=16.0 Hz, 1H), 7.04~7.82 (m, 4H).

Preparation Example 71: Synthesis of 1-(2-iodophenyl)-trans-1-hexene

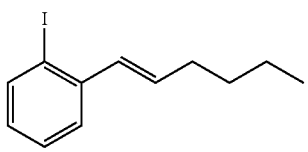

The substantially same method as described in Preparation Example 4 was conducted, except that 2-iodobenzenaldehyde was used instead of 2-chlorobenzenaldehyde, to obtain the title compound (1.21 g, yield 10~40%).

$^1$H NMR (400 MHz, CDCl$_3$) δ 0.96 (t, J=7.2 Hz, 3H), 1.33~1.56 (m, 4H), 2.26~2.32 (m, 4H), 6.24 (dt, J=7.0, 15.6 Hz, 1H), 6.78 (d, J=16.0 Hz, 1H), 7.12~7.51 (m, 4H).

Preparation Example 72: Synthesis of 1-(2-fluorophenyl)-trans-1-butene

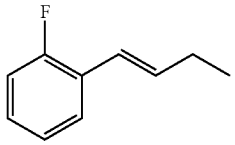

The substantially same method as described in Preparation Example 2 was conducted, except that 2-fluorobenzenaldehyde was used instead of 2-chlorobenzenaldehyde, to obtain the title compound (0.72 g, yield 10~40%).

$^1$H NMR (400 MHz, CDCl$_3$) δ 1.14 (d, J=7.6 Hz, 3H), 2.29~2.33 (m, 2H), 6.28 (dt, J=6.4, 16.0 Hz, 1H), 6.78 (d, J=15.6 Hz, 1H), 7.15~7.55 (m, 4H).

Preparation Example 73: Synthesis of 1-(2-fluorophenyl)-3-methyl-trans-1-butene

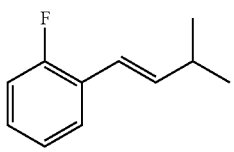

The substantially same method as described in Preparation Example 3 was conducted, except that 2-fluorobenzenaldehyde was used instead of 2-chlorobenzenaldehyde, to obtain the title compound (1.31 g, yield 10~40%).

$^1$H NMR (400 MHz, CDCl$_3$) δ 1.14 (d, J=6.8 Hz, 6H), 2.25~2.57 (m, 1H), 6.20 (dd, J=7.2, 16.0 Hz, 1H), 7.64 (d, J=16.0 Hz, 1H), 7.11~7.55 (m, 4H).

Preparation Example 74: Synthesis of 1-(2-fluorophenyl)-trans-1-hexene

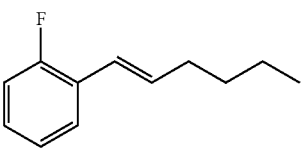

The substantially same method as described in Preparation Example 4 was conducted, except that 2-fluorobenzenaldehyde was used instead of 2-chlorobenzenaldehyde, to obtain the title compound (1.02 g, yield 10~40%).

$^1$H NMR (400 MHz, CDCl$_3$) δ 0.96 (t, J=7.2 Hz, 3H), 1.33~1.56 (m, 4H), 2.26~2.32 (m, 4H), 6.24 (dt, J=7.0, 15.6 Hz, 1H), 6.78 (d, J=16.0 Hz, 1H), 7.14~7.52 (m, 4H).

Preparation Example 75: Synthesis of 1-(3-iodophenyl)-trans-1-propene

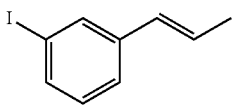

The substantially same method as described in Preparation Example 64 was conducted, except that 3-iodobenzenaldehyde was used instead of 2-iodobenzenaldehyde, to obtain the title compound (1.22 g, yield 10~40%).

$^1$H NMR (400 MHz, CDCl$_3$) δ 1.95 (dd, J=1.6, 6.8 Hz, 3H), 6.09~6.18 (m, 1H), 6.60 (dd, J=1.8, 15.7 Hz, 1H), 6.87~7.80 (m, 4H).

Preparation Example 76: Synthesis of 1-(3-iodophenyl)-trans-1-butene

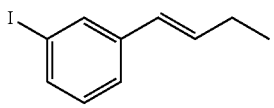

The substantially same method as described in Preparation Example 65 was conducted, except that 3-iodobenzenaldehyde was used instead of 2-iodobenzenaldehyde, to obtain the title compound (1.12 g, yield 10~40%).

$^1$H NMR (400 MHz, CDCl$_3$) δ 1.46 (t, J=7.6 Hz, 3H), 2.26~2.34 (m, 2H), 6.17 (dt, J=6.6, 15.6 Hz, 1H), 6.57 (d, J=15.6 Hz, 1H), 6.86~7.81 (m, 4H).

Preparation Example 77: Synthesis of 1-(3-iodophenyl)-3-methyl-trans-1-butene

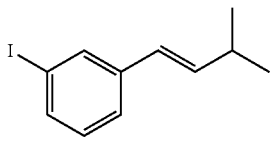

The substantially same method as described in Preparation Example 70 was conducted, except that 3-iodobenzenaldehyde was used instead of 2-iodobenzenaldehyde, to obtain the title compound (0.62 g, yield 10~40%).

$^1$H NMR (400 MHz, CDCl$_3$) δ 1.14 (d, J=6.8 Hz, 6H), 2.25~2.57 (m, 1H), 6.20 (dd, J=7.2, 16.0 Hz, 1H), 7.64 (d, J=16.0 Hz, 1H), 6.88~7.64 (m, 4H).

Preparation Example 78: Synthesis of 1-(3-iodophenyl)-trans-1-hexene

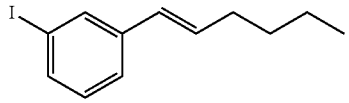

The substantially same method as described in Preparation Example 71 was conducted, except that 3-iodobenzenaldehyde was used instead of 2-iodobenzenaldehyde, to obtain the title compound (0.42 g, yield 10~40%).

$^1$H NMR (400 MHz, CDCl$_3$) δ 0.96 (t, J=7.2 Hz, 3H), 1.33~1.56 (m, 4H), 2.26~2.32 (m, 4H), 6.24 (dt, J=7.0, 15.6 Hz, 1H), 6.78 (d, J=16.0 Hz, 1H), 6.88~7.59 (m, 4H).

Preparation Example 79: Synthesis of 1-(4-fluorophenyl)-trans-1-propene

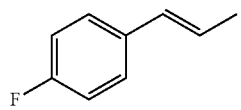

The substantially same method as described in Preparation Example 60 was conducted, except that 4-fluorobenzenaldehyde was used instead of 2-fluorobenzenaldehyde, to obtain the title compound (0.29 g, yield 10~40%).

$^1$H NMR (400 MHz, CDCl$_3$) δ 1.94 (d, J=6.8 Hz, 3H), 6.30~6.38 (m, 1H), 6.57 (d, J=16.0 Hz, 1H), 6.85~7.04 (m, 4H).

Preparation Example 80: Synthesis of 1-(4-fluorophenyl)-trans-1-butene

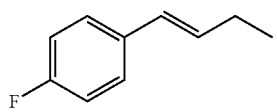

The substantially same method as described in Preparation Example 72 was conducted, except that 4-fluorobenzenaldehyde was used instead of 2-fluorobenzenaldehyde, to obtain the title compound (1.03 g, yield 10~40%).

$^1$H NMR (400 MHz, CDCl$_3$) δ 1.14 (d, J=7.6 Hz, 3H), 2.29~2.33 (m, 2H), 6.28 (dt, J=6.4, 16.0 Hz, 1H), 6.78 (d, J=15.6 Hz, 1H), 6.88~7.05 (m, 4H).

Preparation Example 81: Synthesis of 1-(4-fluorophenyl)-3-methyl-trans-1-butene

The substantially same method as described in Preparation Example 73 was conducted, except that 4-fluorobenzenaldehyde was used instead of 2-fluorobenzenaldehyde, to obtain the title compound (1.41 g, yield 10~40%).

$^1$H NMR (400 MHz, CDCl$_3$) δ 1.14 (d, J=6.8 Hz, 6H), 2.25~2.57 (m, 1H), 6.20 (dd, J=7.2, 16.0 Hz, 1H), 7.64 (d, J=16.0 Hz, 1H), 6.83~7.09 (m, 4H).

Preparation Example 82: Synthesis of 1-(4-fluorophenyl)-trans-1-hexene

The substantially same method as described in Preparation Example 74 was conducted, except that 4-fluorobenzenaldehyde was used instead of 2-fluorobenzenaldehyde, to obtain the title compound (0.43 g, yield 10~40%).

$^{1}$H NMR (400 MHz, CDCl$_{3}$) δ 0.96 (t, J=7.2 Hz, 3H), 1.33~1.56 (m, 4H), 2.26~2.32 (m, 4H), 6.24 (dt, J=7.0, 15.6 Hz, 1H), 6.78 (d, J=16.0 Hz, 1H), 6.84~7.07 (m, 4H).

Preparation Example 83: Synthesis of 1-(2-iodophenyl)-3-methyl-(S,S)-1,2-butanediol

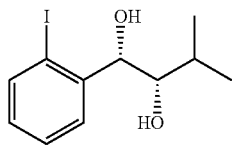

The substantially same method as described in Preparation Example 14 was conducted, except that 1-(2-iodophenyl)-3-methyl-trans-1-butene (Preparation Example 70) was used instead of 1-(2-chlorophenyl)-trans-1-propene (Preparation Example 1), to obtain the title compound (0.52 g, yield 60~90%).

$^{1}$H NMR (400 MHz, CDCl$_{3}$) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.04~7.85 (m, 4H).

Preparation Example 84: Synthesis of 1-(2-iodophenyl)-3-methyl-(R,R)-1,2-butanediol

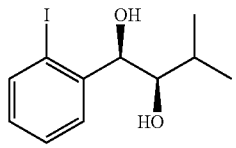

The substantially same method as described in Preparation Example 15 was conducted, except that 1-(2-iodophenyl)-trans-1-butene (Preparation Example 65) was used instead of 1-(2-chlorophenyl)-trans-1-propene (Preparation Example 1), to obtain the title compound (0.52 g, yield 60~90%).

$^{1}$H NMR (400 MHz, CDCl$_{3}$) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H).

Preparation Example 85: Synthesis of 1-(2-iodophenyl)-(S,S)-1,2-hexanediol

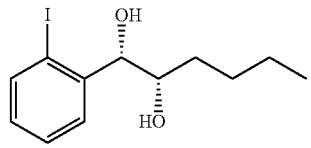

The substantially same method as described in Preparation Example 14 was conducted, except that 1-(2-iodophenyl)-trans-1-hexene (Preparation Example 71) was used instead of 1-(2-chlorophenyl)-trans-1-propene (Preparation Example 1), to obtain the title compound (1.21 g, yield 60~90%).

$^{1}$H NMR (400 MHz, CDCl$_{3}$) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H).

Preparation Example 86: Synthesis of 1-(2-iodophenyl)-(R,R)-1,2-hexanediol

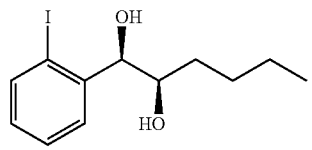

The substantially same method as described in Preparation Example 15 was conducted, except that 1-(2-iodophenyl)-trans-1-hexene (Preparation Example 71) was used instead of 1-(2-chlorophenyl)-trans-1-propene (Preparation Example 1), to obtain the title compound (0.74 g, yield 60~90%).

$^{1}$H NMR (400 MHz, CDCl$_{3}$) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H).

Preparation Example 87: Synthesis of 1-(3-iodophenyl)-(S,S)-1,2-propanediol

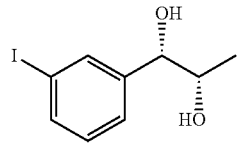

The substantially same method as described in Preparation Example 66 was conducted, except that 1-(3-iodophenyl)-trans-1-propene (Preparation Example 75) was used instead of 1-(2-iodophenyl)-trans-1-propene (Preparation Example 64), to obtain the title compound (2.03 g, yield 60~90%).

$^{1}$H NMR (400 MHz, CDCl$_{3}$) δ 1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H).

Preparation Example 88: Synthesis of 1-(3-iodophenyl)-(R,R)-1,2-propanediol

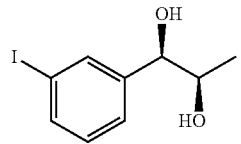

The substantially same method as described in Preparation Example 67 was conducted, except that 1-(3-iodophenyl)-trans-1-propene (Preparation Example 75) was used instead of 1-(2-iodophenyl)-trans-1-propene (Preparation Example 64), to obtain the title compound (1.12 g, yield 60~90%).

¹H NMR (400 MHz, CDCl₃) δ 1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H).

Preparation Example 89: Synthesis of 1-(3-iodophenyl)-(S,S)-1,2-butanediol

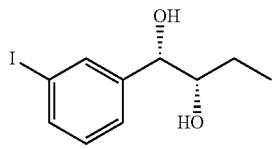

The substantially same method as described in Preparation Example 68 was conducted, except that 1-(3-iodophenyl)-trans-1-butene (Preparation Example 76) was used instead of 1-(2-iodophenyl)-trans-1-propene (Preparation Example 64), to obtain the title compound (2.03 g, yield 60~90%).

¹H NMR (400 MHz, CDCl₃) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H).

Preparation Example 90: Synthesis of 1-(3-iodophenyl)-(R,R)-1,2-butanediol

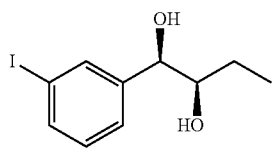

The substantially same method as described in Preparation Example 84 was conducted, except that 1-(3-iodophenyl)-trans-1-butene (Preparation Example 76) was used instead of 1-(2-iodophenyl)-trans-1-propene (Preparation Example 64), to obtain the title compound (1.18 g, yield 60~90%).

¹H NMR (400 MHz, CDCl₃) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H).

Preparation Example 91: Synthesis of 1-(3-iodophenyl)-3-methyl-(S,S)-1,2-butanediol

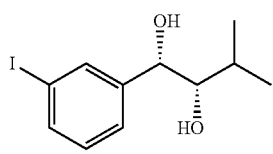

The substantially same method as described in Preparation Example 83 was conducted, except that 1-(3-iodophenyl)-3-methyl-trans-1-butene (Preparation Example 77) was used instead of 1-(2-iodophenyl)-3-methyl-trans-1-butene (Preparation Example 70), to obtain the title compound (0.51 g, yield 60~90%).

¹H NMR (400 MHz, CDCl₃) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H).

Preparation Example 92: Synthesis of 1-(3-iodophenyl)-3-methyl-(R,R)-1,2-butanediol

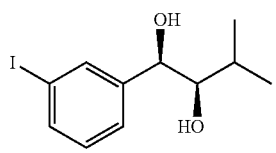

The substantially same method as described in Preparation Example 90 was conducted, except that 1-(3-iodophenyl)-3-methyl-trans-1-butene (Preparation Example 77) was used instead of 1-(3-iodophenyl)-trans-1-butene (Preparation Example 76), to obtain the title compound (1.10 g, yield 60~90%).

¹H NMR (400 MHz, CDCl₃) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H).

Preparation Example 93: Synthesis of 1-(3-iodophenyl)-(S,S)-1,2-hexanediol

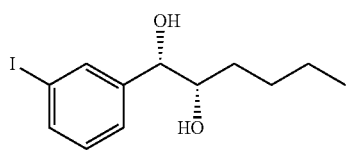

The substantially same method as described in Preparation Example 85 was conducted, except that 1-(3-iodophenyl)-trans-1-hexene (Preparation Example 78) was used instead of 1-(2-iodophenyl)-trans-1-hexene (Preparation Example 71), to obtain the title compound (0.95 g, yield 60~90%).

¹H NMR (400 MHz, CDCl₃) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H).

Preparation Example 94: Synthesis of 1-(3-iodophenyl)-(R,R)-1,2-hexanediol

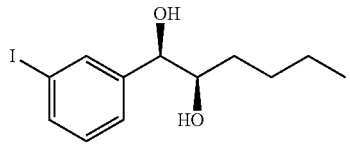

The substantially same method as described in Preparation Example 86 was conducted, except that 1-(3-iodophenyl)-trans-1-hexene (Preparation Example 78) was used instead of 1-(2-iodophenyl)-trans-1-hexene (Preparation Example 71), to obtain the title compound (0.41 g, yield 60~90%).

$^1$H NMR (400 MHz, CDCl$_3$) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H).

Preparation Example 95: Synthesis of 1-(4-fluorophenyl)-(S,S)-1,2-propanediol

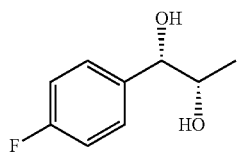

The substantially same method as described in Preparation Example 87 was conducted, except that 1-(4-fluorophenyl)-trans-1-propene (Preparation Example 79) was used instead of 1-(3-iodophenyl)-trans-1-propene (Preparation Example 75), to obtain the title compound (2.01 g, yield 60~90%).

$^1$H NMR (400 MHz, CDCl$_3$) δ 1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H).

Preparation Example 96: Synthesis of 1-(3-fluorophenyl)-(R,R)-1,2-propanediol

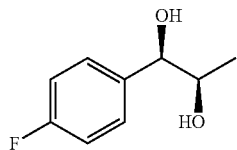

The substantially same method as described in Preparation Example 88 was conducted, except that 1-(4-fluorophenyl)-trans-1-propene (Preparation Example 79) was used instead of 1-(3-iodophenyl)-trans-1-propene (Preparation Example 75), to obtain the title compound (1.27 g, yield 60~90%).

$^1$H NMR (400 MHz, CDCl$_3$) δ 1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H).

Preparation Example 97: Synthesis of 1-(4-fluorophenyl)-(S,S)-1,2-butanediol

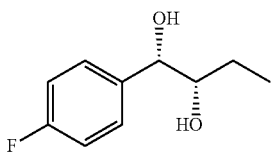

The substantially same method as described in Preparation Example 89 was conducted, except that 1-(4-fluorophenyl)-trans-1-butene (Preparation Example 80) was used instead of 1-(3-iodophenyl)-trans-1-butene (Preparation Example 76), to obtain the title compound (0.43 g, yield 60~90%).

$^1$H NMR (400 MHz, CDCl$_3$) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H).

Preparation Example 98: Synthesis of 1-(3-fluorophenyl)-(R,R)-1,2-butanediol

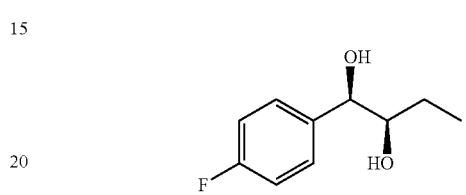

The substantially same method as described in Preparation Example 90 was conducted, except that 1-(4-fluorophenyl)-trans-1-butene (Preparation Example 80) was used instead of 1-(3-iodophenyl)-trans-1-butene (Preparation Example 76), to obtain the title compound (1.13 g, yield 60~90%).

$^1$H NMR (400 MHz, CDCl$_3$) δ 1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H).

Preparation Example 99: Synthesis of 1-(4-fluorophenyl)-3-methyl-(S,S)-1,2-butanediol

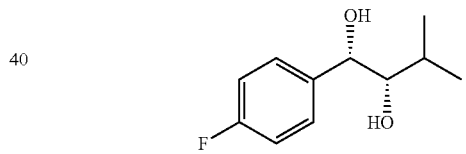

The substantially same method as described in Preparation Example 91 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (0.71 g, yield 60~90%).

$^1$H NMR (400 MHz, CDCl$_3$) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H).

Preparation Example 100: Synthesis of 1-(3-fluorophenyl)-3-methyl-(R,R)-1,2-butanediol

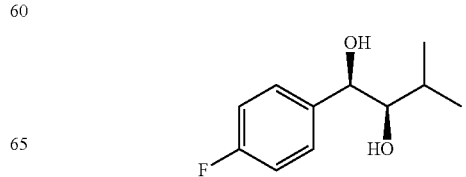

The substantially same method as described in Preparation Example 92 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (1.21 g, yield 60~90%).

¹H NMR (400 MHz, CDCl₃) δ 1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H).

Preparation Example 101: Synthesis of 1-(4-fluorophenyl)-(S,S)-1,2-hexanediol

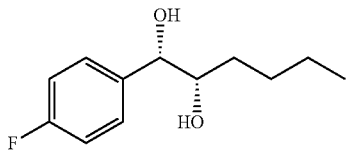

The substantially same method as described in Preparation Example 93 was conducted, except that 1-(4-fluorophenyl)-trans-1-hexene (Preparation Example 82) was used instead of 1-(3-iodophenyl)-trans-1-hexene (Preparation Example 78), to obtain the title compound (1.13 g, yield 60~90%).

¹H NMR (400 MHz, CDCl₃) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H).

Preparation Example 102: Synthesis of 1-(3-fluorophenyl)-(R,R)-1,2-hexanediol

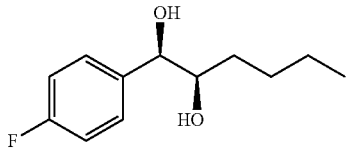

The substantially same method as described in Preparation Example 94 was conducted, except that 1-(4-fluorophenyl)-trans-1-hexene (Preparation Example 82) was used instead of 1-(3-iodophenyl)-trans-1-hexene (Preparation Example 78), to obtain the title compound (1.42 g, yield 60~90%).

¹H NMR (400 MHz, CDCl₃) δ 0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H).

Preparation Example 103: Synthesis of 1-(2-chlorophenyl)-(S)-1-hydroxypropyl-(S)-2-carbamate

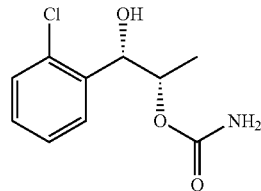

1-(2-chlorophenyl)-(S,S)-1,2-propanediol (2.33 g) obtained in Preparation Example 14, tetrahydrofuran (THF, 12 mL), and carbonyldiimidazole (CDI, 3.04 g) were put into a flask and stirred at the room temperature. After approximately 3 hours, ammonia solution (NH₄OH, 4 mL) was added thereto. When the reaction was completed, the obtained product was washed with 1 M HCl solution and ethylacetate (EA). The separated organic layer was dehydrated with anhydrous magnesium sulfate (MgSO₄), filtrated, and concentrated under reduced pressure. The concentrated residue was purified by a silica gel column chromatography, to obtain the title compound (1.40 g, yield 49%).

M.P. 83~84° C.

¹H NMR (400 MHz, CDCl₃) δ 1.24 (d, J=6.4 Hz, 3H), 2.91 (d, J=4.8 Hz, 1H), 4.68 (br s, 2H), 5.06~5.09 (m, 1H), 5.18~5.21 (m, 1H), 7.23~7.55 (m, 4H). ¹³C NMR (100 MHz, CDCl₃) δ 16.4, 73.1, 75.0, 127.0, 128.4, 129.1, 129.5, 132.7, 138.0, 156.6.

Preparation Example 104: Synthesis of 1-(2-chlorophenyl)-(R)-1-hydroxypropyl-(R)-2-carbamate

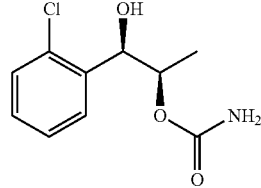

The substantially same method as described in Preparation Example 103 was conducted, except that 1-(2-chlorophenyl)-(R,R)-1,2-propanediol obtained in Preparation Example 15 was used instead of 1-(2-chlorophenyl)-(S,S)-1,2-propanediol, to obtain the title compound (1.74 g, yield 50%).

M.P. 85~86° C.

¹H NMR (400 MHz, CDCl₃) δ 1.24 (d, J=6.4 Hz, 3H), 2.98 (d, J=4.0 Hz, 1H), 4.73 (br s, 2H), 5.04~5.10 (m, 1H), 5.18~5.20 (m, 1H), 7.24~7.55 (m, 4H).

Preparation Example 105: Synthesis of 1-(2-chlorophenyl)-1-hydroxypropyl-2-carbamate

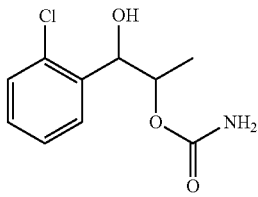

The substantially same method as described in Preparation Example 103 was conducted, except that the mixture of 1-(2-chlorophenyl)-(S,S)-1,2-propanediol and 1-(2-chlorophenyl)-(R,R)-1,2-propanediol obtained in Preparation Example 16 was used instead of 1-(2-chlorophenyl)-(S,S)-1,2-propanediol, to obtain the title compound (0.41 g, yield 38%).

$^1$H NMR (400 MHz, CDCl$_3$) δ 1.14 (d, J=6.8 Hz, 3H), 3.34 (d, J=3.2 Hz, 1H), 5.06 (brs, 2H), 5.09~5.15 (m, 1H), 5.31 (br t, J=2.4 Hz, 1H), 7.18~7.59 (m, 4H).

Preparation Example 106: Synthesis of 1-(2-chlorophenyl)-(R)-1-hydroxypropyl-(S)-2-carbamate

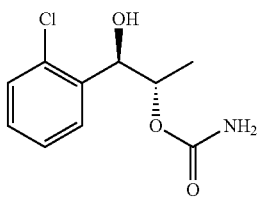

The substantially same method as described in Preparation Example 103 was conducted, except that 1-(2-chlorophenyl)-(R,S)-1,2-propanediol obtained in Preparation Example 55 was used instead of 1-(2-chlorophenyl)-(S,S)-1,2-propanediol, to obtain the title compound (1.7 g, yield 50%).

$^1$H NMR (400 MHz, CDCl$_3$) δ 1.20 (d, J=6.8 Hz, 3H), 2.68 (s, 1H), 4.67 (s, 2H), 5.16~5.22 (m, 1H), 5.36 (t, J=3.2 Hz, 1H), 7.23~7.61 (m, 4H).

Preparation Example 107: Synthesis of 1-(2-chlorophenyl)-(S)-1-hydroxypropyl-(R)-2-carbamate

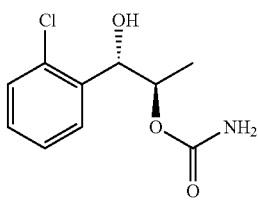

The substantially same method as described in Preparation Example 103 was conducted, except that 1-(2-chlorophenyl)-(S,R)-1,2-propanediol obtained in Preparation Example 56 was used instead of 1-(2-chlorophenyl)-(S,S)-1,2-propanediol, to obtain the title compound (1.74 g, yield 50%).

$^1$H NMR (400 MHz, CDCl$_3$) δ 1.20 (d, J=6.4 Hz, 3H), 2.83 (d, J=3.6 Hz, 1H), 4.78 (s, 2H), 5.15~5.21 (m, 1H), 5.36 (t, J=3.2 Hz, 1H), 7.23~7.63 (m, 4H).

Preparation Example 108: Synthesis of 1-(2-chlorophenyl)-(S)-1-hydroxybutyl-(S)-2-carbamate

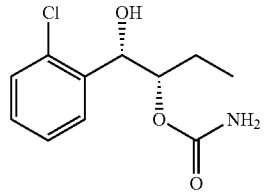 [SMILES: CC[C@H](OC(N)=O)[C@@H](O)c1ccccc1Cl]

The substantially same method as described in Preparation Example 103 was conducted, except that 1-(2-chlorophenyl)-(S,S)-1,2-butanediol obtained in Preparation Example 17 was used instead of 1-(2-chlorophenyl)-(S,S)-1,2-propanediol, to obtain the title compound (1.0 g, yield 45%).

$^1$H NMR (400 MHz, CDCl$_3$) δ 0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H).

Preparation Example 109: Synthesis of 1-(2-chlorophenyl)-(R)-1-hydroxybutyl-(R)-2-carbamate

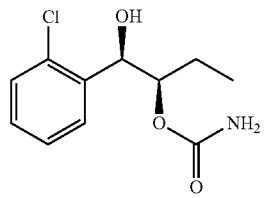 [SMILES: CC[C@@H](OC(N)=O)[C@H](O)c1ccccc1Cl]

The substantially same method as described in Preparation Example 103 was conducted, except that 1-(2-chlorophenyl)-(R,R)-1,2-butanediol obtained in Preparation Example 18 was used instead of 1-(2-chlorophenyl)-(S,S)-1,2-propanediol, to obtain the title compound (1.5 g, yield 25%).

$^1$H NMR (400 MHz, CDCl$_3$) δ 0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H).

Preparation Example 110: Synthesis of 1-(2-chlorophenyl)-1-hydroxybutyl-2-carbamate

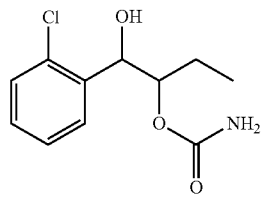 [SMILES: CCC(OC(N)=O)C(O)c1ccccc1Cl]

The substantially same method as described in Preparation Example 103 was conducted, except that 1-(2-chlorophenyl)-1,2-butanediol obtained in Preparation Example 19 was used instead of 1-(2-chlorophenyl)-(S,S)-1,2-propanediol, to obtain the title compound (1.8 g, yield 30%).

¹H NMR (400 MHz, CDCl₃) δ 0.97 (t, J=7.0 Hz, 3H), 1.58~1.74 (m, 2H), 2.94 (d, J=6.0 Hz, 1H), 4.69 (br s, 2H), 4.94~4.99 (m, 1H), 5.24 (t, J=6.0 Hz, 1H), 7.23~7.56 (m, 4H).

Preparation Example 111: Synthesis of 1-(2-chlorophenyl)-(S)-1-hydroxy-3-methyl-butyl-(S)-2-carbamate

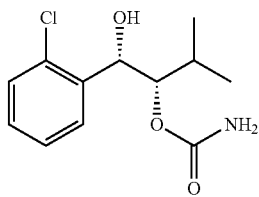 [SMILES: CC(C)[C@H](OC(N)=O)[C@@H](O)c1ccccc1Cl]

The substantially same method as described in Preparation Example 103 was conducted, except that 1-(2-chlorophenyl)-3-methyl-(S,S)-1,2-butanediol obtained in Preparation Example 20 was used instead of 1-(2-chlorophenyl)-(S,S)-1,2-propanediol, to obtain the title compound (0.72 g, yield 48%).

¹H NMR (400 MHz, CDCl₃) δ 1.01 (d, J=6.4 Hz, 3H), 1.09 (d, J=6.8 Hz, 3H), 2.06 (m, 1H), 2.75 (d, J=6.8 Hz, 1H), 4.58 (br s, 2H), 4.85~4.88 (m, 1H), 5.34~5.37 (m, 1H), 7.22~7.33 (m, 2H), 7.35~7.37 (m, 1H), 7.51~7.53 (m, 1H).

Preparation Example 112: Synthesis of 1-(2-chlorophenyl)-(R)-1-hydroxy-3-methyl-butyl-(R)-2-carbamate

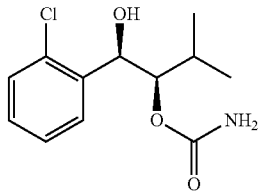 [SMILES: CC(C)[C@@H](OC(N)=O)[C@H](O)c1ccccc1Cl]

The substantially same method as described in Preparation Example 103 was conducted, except that 1-(2-chlorophenyl)-3-methyl-(R,R)-1,2-butanediol obtained in Preparation Example 21 was used instead of 1-(2-chlorophenyl)-(S,S)-1,2-propanediol, to obtain the title compound (0.56 g, yield 43%).

¹H NMR (400 MHz, CDCl₃) δ 1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H).

Preparation Example 113: Synthesis of 1-(2-chlorophenyl)-1-hydroxy-3-methyl-butyl-2-carbamate

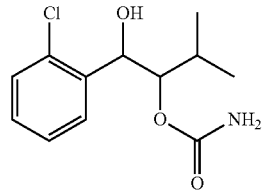 [SMILES: CC(C)C(OC(N)=O)C(O)c1ccccc1Cl]

The substantially same method as described in Preparation Example 103 was conducted, except that 1-(2-chlorophenyl)-3-methyl-1,2-butanediol obtained in Preparation Example 22 was used instead of 1-(2-chlorophenyl)-(S,S)-1,2-propanediol, to obtain the title compound (1.5 g, yield 23%).

¹H NMR (400 MHz, CDCl₃) δ 1.00 (d, J=6.4 Hz, 3H), 1.09 (d, J=6.4 Hz, 3H), 2.08 (m, 1H), 2.76 (d, J=6.0 Hz, 1H), 4.59 (br s, 2H), 4.87 (dd, J=4.4, 7.2 Hz, 1H), 5.36 (t, J=4.6 Hz, 1H), 7.23~7.54 (m, 4H).

Preparation Example 114: Synthesis of 1-(2-chlorophenyl)-(S)-1-hydroxyhexyl-(S)-2-carbamate

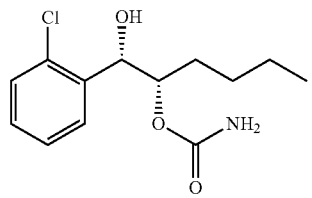 [SMILES: CCCC[C@H](OC(N)=O)[C@@H](O)c1ccccc1Cl]

The substantially same method as described in Preparation Example 103 was conducted, except that 1-(2-chlorophenyl)-(S,S)-1,2-hexanediol obtained in Preparation Example 23 was used instead of 1-(2-chlorophenyl)-(S,S)-1,2-propanediol, to obtain the title compound (0.24 g, yield 49%).

¹H NMR (400 MHz, CDCl₃) δ 0.88 (t, J=7.0 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H).

Preparation Example 115: Synthesis of 1-(2-chlorophenyl)-(R)-1-hydroxyhexyl-(R)-2-carbamate

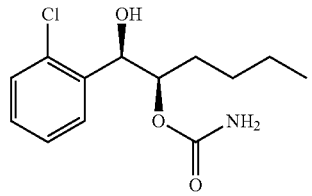 [SMILES: CCCC[C@@H](OC(N)=O)[C@H](O)c1ccccc1Cl]

The substantially same method as described in Preparation Example 103 was conducted, except that 1-(2-chlorophenyl)-(R,R)-1,2-hexanediol obtained in Preparation Example 24 was used instead of 1-(2-chlorophenyl)-(S,S)-1,2-propanediol, to obtain the title compound (2.2 g, yield 44%).

$^1$H NMR (400 MHz, CDCl$_3$) δ 0.89 (dd, J=5.0 Hz, 3H), 1.28~1.43 (m, 4H), 1.52~1.58 (m, 1H), 1.65~1.72 (m, 1H), 2.90 (d, J=6.0 Hz, 1H), 4.64 (br s, 2H), 5.01~5.06 (m, 1H), 5.22 (t, J=6.0 Hz, 1H), 7.22~7.56 (m, 4H).

Preparation Example 116: Synthesis of 1-(2-chlorophenyl)-1-hydroxyhexyl-2-carbamate

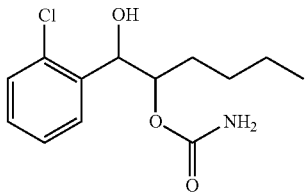 [SMILES: CCCCC(OC(N)=O)C(O)c1ccccc1Cl]

The substantially same method as described in Preparation Example 103 was conducted, except that 1-(2-chlorophenyl)-1,2-hexanediol obtained in Preparation Example 25 was used instead of 1-(2-chlorophenyl)-(S,S)-1,2-propanediol, to obtain the title compound (1.6 g, yield 34%).

$^1$H NMR (400 MHz, CDCl$_3$) δ 0.88 (dd, J=5.0 Hz, 3H), 1.31~1.43 (m, 4H), 1.63~1.70 (m, 1H), 1.52~1.60 (m, 1H), 3.06 (d, J=6.0 Hz, 1H), 4.75 (br s, 2H), 5.00~5.05 (m, 1H), 5.21 (t, J=6.0 Hz, 1H), 7.22~7.55 (m, 4H).

Preparation Example 117: Synthesis of 1-(2-chlorophenyl)-(S)-1-hydroxypropyl-(S)-2-methylcarbamate

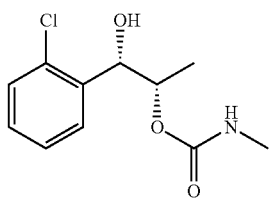 [SMILES: CNC(=O)O[C@@H](C)[C@@H](O)c1ccccc1Cl]

The substantially same method as described in Preparation Example 103 was conducted, except that methylamine was used instead of ammonia solution (NH$_4$OH), to obtain the title compound (1.6 g, yield 51%).

$^1$H NMR (400 MHz, CDCl$_3$) δ 1.03~1.25 (m, 3H), 2.76 (s, 3H), 3.34 (s, 1H), 4.80 (br s 1H), 5.04 (t, J=12.5 Hz, 1H), 5.14 (s, 1H), 7.20~7.53 (m, 4H).

Preparation Example 118: Synthesis of 1-(2-chlorophenyl)-(S)-1-hydroxypropyl-(S)-2-propylcarbamate

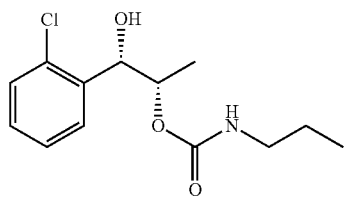 [SMILES: CCCNC(=O)O[C@@H](C)[C@@H](O)c1ccccc1Cl]

The substantially same method as described in Preparation Example 103 was conducted, except that propylamine was used instead of ammonia solution (NH$_4$OH), to obtain the title compound (0.79 g, yield 25%).

$^1$H NMR (400 MHz, CDCl$_3$) δ 0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.9 Hz, 1H), 5.14 (s, 1H), 7.22~7.53 (m, 4H).

Preparation Example 119: Synthesis of 1-(2-chlorophenyl)-(S)-1-hydroxypropyl-(R)-2-isopropylcarbamate

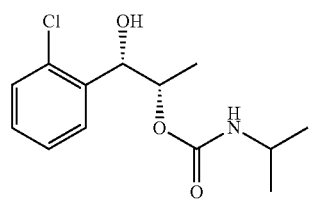

The substantially same method as described in Preparation Example 103 was conducted, except that isopropylamine was used instead of ammonia solution (NH$_4$OH), to obtain the title compound (1.5 g, yield 41%).

$^1$H NMR (400 MHz, CDCl$_3$) δ 1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.20~7.53 (m, 4H).

Preparation Example 120: Synthesis of 1-(2-chlorophenyl)-(S)-1-hydroxypropyl-(R)-2-cyclopropylcarbamate

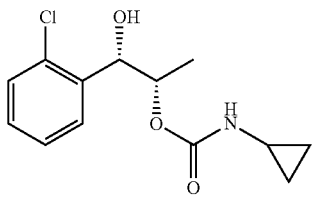 [SMILES: C[C@H](OC(=O)NC1CC1)[C@@H](O)c1ccccc1Cl]

The substantially same method as described in Preparation Example 103 was conducted, except that cyclopropylamine was used instead of ammonia solution (NH$_4$OH), to obtain the title compound (2.2 g, yield 43%).

$^1$H NMR (400 MHz, CDCl$_3$) δ 0.50~0.56 (m, 2H), 0.74 (d, J=7.2 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H).

Preparation Example 121: Synthesis of 1-(2-chlorophenyl)-(S)-1-hydroxypropyl-(R)-2-cyclohexyl carbamate

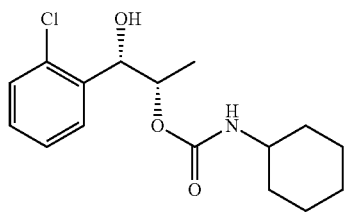 [SMILES: C[C@H](OC(=O)NC1CCCCC1)[C@@H](O)c1ccccc1Cl]

The substantially same method as described in Preparation Example 103 was conducted, except that cyclohexylamine was used instead of ammonia solution (NH$_4$OH), to obtain the title compound (1.1 g, yield 26%).

$^1$H NMR (400 MHz, CDCl$_3$) δ 1.06~1.40 (m, 7H), 1.56~1.61 (m, 2H), 1.69~1.71 (m, 2H), 1.87~1.94 (m, 2H), 3.19 (d, J=4.3 Hz, 1H), 3.45 (s, 1H), 4.64 (br s 1H), 5.02~5.07 (m, 1H), 5.14 (t, J=6.1 Hz, 1H) 7.20~7.53 (m, 4H).

Preparation Example 122: Synthesis of 1-(2-chlorophenyl)-(S)-1-hydroxypropyl-(S)-2-benzyl carbamate

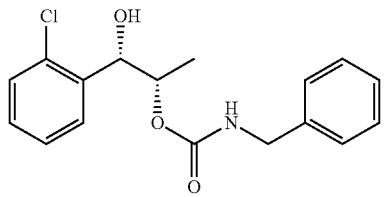 [SMILES: C[C@H](OC(=O)NCc1ccccc1)[C@@H](O)c1ccccc1Cl]

The substantially same method as described in Preparation Example 103 was conducted, except that benzylamine was used instead of ammonia solution (NH$_4$OH), to obtain the title compound (1.2 g, yield 18%).

$^1$H NMR (400 MHz, CDCl$_3$) δ 1.27 (d, J=10.0 Hz, 3H), 3.12 (d, J=5.0 Hz, 1H), 4.37 (d, J=6.0 Hz, 2H), 5.12~5.19 (m, 3H), 7.15~7.56 (m, 9H).

Preparation Example 123: Synthesis of 1-(2-chlorophenyl)-(S)-1-hydroxypropyl-(S)-2-bicyclo[2,2,1]heptanescarbamate

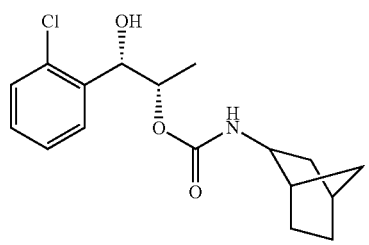 [SMILES: C[C@H](OC(=O)NC1CC2CCC1C2)[C@@H](O)c1ccccc1Cl]

The substantially same method as described in Preparation Example 103 was conducted, except that 2-aminonorbornane was used instead of ammonia solution (NH$_4$OH), to obtain the title compound (1.7 g, yield 32%).

$^1$H NMR (400 MHz, CDCl$_3$) δ 1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H).

Preparation Example 124: Synthesis of 1-(2-chlorophenyl)-(R)-1-hydroxypropyl-(R)-2-methylcarbamate

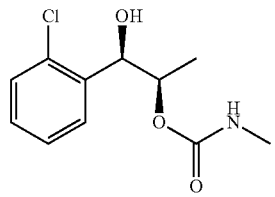 [SMILES: CNC(=O)O[C@H](C)[C@H](O)c1ccccc1Cl]

The substantially same method as described in Example 2 was conducted, except that methylamine was used instead of ammonia solution (NH$_4$OH), to obtain the title compound (3.36 g, yield 60%).

$^1$H NMR (400 MHz, CDCl$_3$) δ 1.20 (d, J=6.8 Hz, 3H), 2.80 (d, J=4.8 Hz, 3H), 3.20 (d, J=4.4 Hz, 1H), 4.75 (br s, 1H), 5.03~5.09 (m, 1H), 5.14~5.17 (m, 1H), 7.22~7.55 (m, 4H).

Preparation Example 125: Synthesis of 1-(2-chlorophenyl)-(R)-1-hydroxypropyl-(R)-2-propylcarbamate

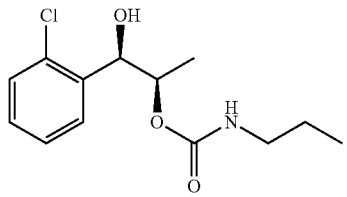 [SMILES: CCCNC(=O)O[C@H](C)[C@H](O)c1ccccc1Cl]

The substantially same method as described in Preparation Example 104 was conducted, except that propylamine was used instead of ammonia solution (NH$_4$OH), to obtain the title compound (3.1 g, yield 53%).

$^1$H NMR (400 MHz, CDCl$_3$) δ 0.92 (t, J=7.6 Hz, 3H), 1.21 (d, J=6.4 Hz, 3H), 1.51 (m, 2H), 3.09~3.14 (m, 2H), 3.28 (d, J=4.4 Hz, 1H), 4.82 (br s, 1H), 5.03~5.09 (m, 1H), 5.14~5.17 (m, 1H), 7.22~7.55 (m. 4H).

Preparation Example 126: Synthesis of 1-(2-chlorophenyl)-(R)-1-hydroxypropyl-(R)-2-isopropylcarbamate

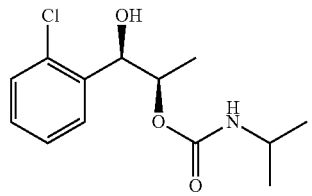 [SMILES: CC(C)NC(=O)O[C@H](C)[C@H](O)c1ccccc1Cl]

The substantially same method as described in Preparation Example 104 was conducted, except that isopropylamine was used instead of ammonia solution (NH₄OH), to obtain the title compound (0.16 g, yield 27%).

¹H NMR (400 MHz, CDCl₃) δ 0.88~1.16 (m, 6H), 1.19~1.26 (m, 3H), 3.34 (s, 1H), 3.71~3.78 (m, 1H), 4.62 (br s, 1H), 5.03 (t, J=5.8 Hz, 1H), 5.13 (d, J=4.9 Hz, 1H), 7.20~7.53 (m, 4H).

Preparation Example 127: Synthesis of 1-(2-chlorophenyl)-(R)-1-hydroxypropyl-(R)-2-cyclopropylcarbamate

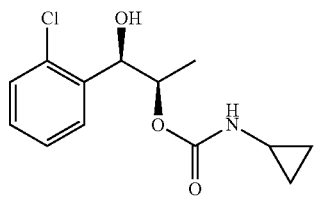 [SMILES: C[C@@H](OC(=O)NC1CC1)[C@H](O)c1ccccc1Cl]

The substantially same method as described in Preparation Example 104 was conducted, except that cyclopropylamine was used instead of ammonia solution (NH₄OH), to obtain the title compound (3.7 g, yield 60%).

¹H NMR (400 MHz, CDCl₃) δ 0.49~0.54 (m, 2H), 0.74 (d, J=7.2 Hz, 2H), 1.22 (s, 3H), 2.55~2.60 (m, 1H), 3.16 (s, 1H), 5.00 (s, 1H), 5.04~5.11 (m, 1H), 5.16 (s, 1H), 7.23~7.54 (m, 4H).

Preparation Example 128: Synthesis of 1-(2-chlorophenyl)-(R)-1-hydroxypropyl-(R)-2-cyclohexyl carbamate

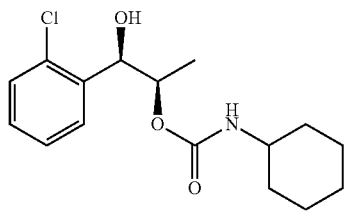 [SMILES: C[C@@H](OC(=O)NC1CCCCC1)[C@H](O)c1ccccc1Cl]

The substantially same method as described in Preparation Example 104 was conducted, except that cyclohexylamine was used instead of ammonia solution (NH₄OH), to obtain the title compound (1.9 g, yield 28%).

¹H NMR (400 MHz, CDCl₃) δ 1.05~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2 Hz, 1H), 7.20~7.54 (m, 4H).

Preparation Example 129: Synthesis of 1-(2-chlorophenyl)-(R)-1-hydroxypropyl-(R)-2-benzylcarbamate

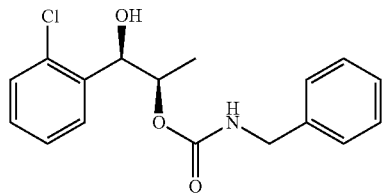 [SMILES: C[C@@H](OC(=O)NCc1ccccc1)[C@H](O)c1ccccc1Cl]

The substantially same method as described in Preparation Example 104 was conducted, except that benzylamine was used instead of ammonia solution (NH₄OH), to obtain the title compound (0.52 g, yield 19%).

¹H NMR (400 MHz, CDCl₃) δ 1.25 (d, J=6.0 Hz, 3H), 1.64 (s, 1H), 3.13 (d, J=4.4 Hz, 1H), 4.37 (d, J=5.6 Hz, 2H), 5.12~5.19 (m, 2H), 7.23~7.55 (m, 9H).

Preparation Example 130: Synthesis of 1-(2-chlorophenyl)-(R)-1-hydroxypropyl-(R)-2-bicyclo[2,2,1]heptanecarbamate

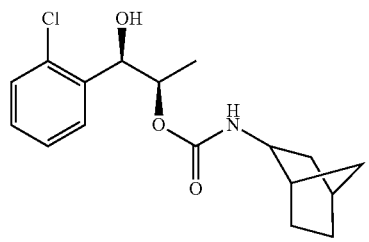 [SMILES: C[C@@H](OC(=O)NC1CC2CCC1C2)[C@H](O)c1ccccc1Cl]

The substantially same method as described in Preparation Example 104 was conducted, except that 2-aminonorbornane was used instead of ammonia solution (NH₄OH), to obtain the title compound (1.7 g, yield 20~50%).

¹H NMR (400 MHz, CDCl₃) δ 1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H).

Preparation Example 131: Synthesis of 1-(2-chlorophenyl)-1-hydroxypropyl-2-methylcarbamate

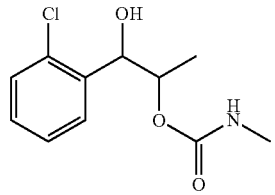 [SMILES: CNC(=O)OC(C)C(O)c1ccccc1Cl]

The substantially same method as described in Preparation Example 105 was conducted, except that methylamine was used instead of ammonia solution (NH₄OH), to obtain the title compound (2.6 g, yield 45%).

¹H NMR (400 MHz, CDCl₃) δ 1.21 (d, J=6.0 Hz, 3H), 2.81 (d, J=5.0 Hz, 3H), 3.14 (d, J=4.0 Hz, 1H), 4.72 (br s, 1H), 5.07 (dd, J=6.0 Hz, 1H), 5.16 (t, J=6.0 Hz, 1H), 7.22~7.56 (m, 4H).

Preparation Example 132: Synthesis of 1-(2-chlorophenyl)-1-hydroxypropyl-2-propylcarbamate

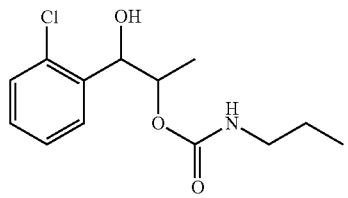 [SMILES: CCCNC(=O)OC(C)C(O)c1ccccc1Cl]

The substantially same method as described in Preparation Example 105 was conducted, except that propylamine was used instead of ammonia solution (NH₄OH), to obtain the title compound (1.0 g, yield 17%).
¹H NMR (400 MHz, CDCl₃) δ 0.92 (t, J=7.0 Hz, 3H), 1.21 (d, J=6.0 Hz, 3H), 1.53 (dd, J=7.0 Hz, 2H), 3.13 (dd, J=7.0 Hz, 2H), 3.28 (d, 1H), 4.82 (S, 1H), 5.06 (dd, J=7.0 Hz, 1H), 5.16 (t, J=5.0 Hz, 1H), 7.21~7.56 (m, 4H).

Preparation Example 133: Synthesis of 1-(2-chlorophenyl)-1-hydroxypropyl-2-isopropylcarbamate

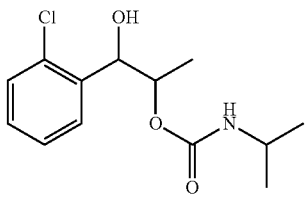

The substantially same method as described in Preparation Example 105 was conducted, except that isopropylamine was used instead of ammonia solution (NH₄OH), to obtain the title compound (0.54 g, yield 16%).
¹H NMR (400 MHz, CDCl₃) δ 1.16 (dd, J=6.0 Hz, 6H), 1.21 (d, J=6.0 Hz, 3H), 3.23 (d, J=6.0 Hz, 1H), 3.75~3.84 (m, 1H), 4.61 (br s, 1H), 5.06 (t, J=6.0 Hz, 1H), 5.16 (t, J=6.0 Hz, 1H), 7.22~7.56 (m, 4H).

Preparation Example 134: Synthesis of 1-(2-chlorophenyl)-1-hydroxypropyl-2-cyclopropylcarbamate

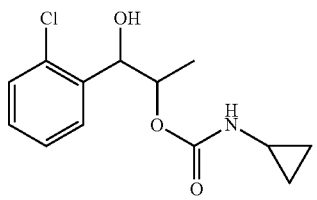 [SMILES: CC(OC(=O)NC1CC1)C(O)c1ccccc1Cl]

The substantially same method as described in Preparation Example 105 was conducted, except that cyclopropylamine was used instead of ammonia solution (NH₄OH), to obtain the title compound (1.0 g, yield 17%).
¹H NMR (400 MHz, CDCl₃) δ 0.50 (t, J=6.0 Hz, 2H), 0.77 (t, J=3.0 Hz, 2H), 1.12 (d, J=7.0 Hz, 3H), 2.53~2.59 (m, 1H), 3.22 (d, J=4.0 Hz, 1H), 5.08 (dd, J=6.0 Hz, 1H), 5.15 (S, 1H), 7.22~7.55 (m, 4H).

Preparation Example 135: Synthesis of 1-(2-chlorophenyl)-1-hydroxypropyl-2-cyclohexylcarbamate

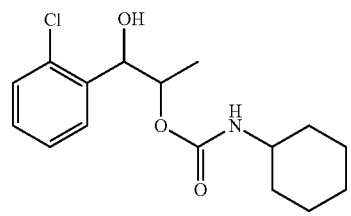 [SMILES: CC(OC(=O)NC1CCCCC1)C(O)c1ccccc1Cl]

The substantially same method as described in Preparation Example 105 was conducted, except that cyclohexylamine was used instead of ammonia solution (NH₄OH), to obtain the title compound (2.2 g, yield 33%).
¹H NMR (400 MHz, CDCl₃) δ 1.07~1.17 (m, 3H), 1.21 (d, J=6.0 Hz, 3H), 1.29~1.42 (m, 3H), 1.72 (dd, J=6.0 Hz, 2H), 1.92 (dd, J=6.0 Hz, 2H), 3.26 (d, J=4.0 Hz, 1H), 3.46 (t, J=4.0 Hz, 1H), 4.68 (d, J=6.0 Hz, 1H), 5.07 (dd, J=6.0 Hz, 1H), 5.16 (t, J=6.0 Hz, 1H), 7.22~7.55 (m, 4H).

Preparation Example 136: Synthesis of 1-(2-chlorophenyl)-1-hydroxypropyl-2-benzylcarbamate

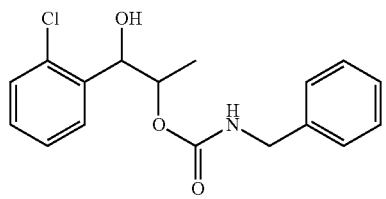

The substantially same method as described in Preparation Example 105 was conducted, except that benzylamine was used instead of ammonia solution (NH₄OH), to obtain the title compound (1.3 g, yield 19%).
¹H NMR (400 MHz, CDCl₃) δ 1.25 (d, J=6.0 Hz, 3H), 3.16 (d, J=4.0 Hz, 1H), 4.36 (d, J=6.0 Hz, 2H), 5.14 (dd, J=6.0 Hz, 3H), 7.23~7.56 (m, 9H)

Preparation Example 137: Synthesis of 1-(2-chlorophenyl)-1-hydroxypropyl-2-bicyclo[2,2,1]heptanecarbamate

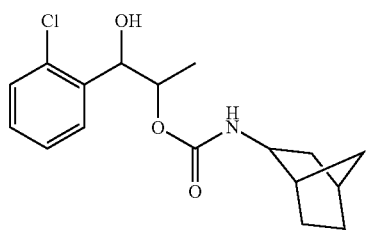 [SMILES: CC(OC(=O)NC1CC2CCC1C2)C(O)c1ccccc1Cl]

The substantially same method as described in Preparation Example 105 was conducted, except that 2-aminonorbornane was used instead of ammonia solution (NH₄OH), to obtain the title compound (1.7 g, yield 20~50%).

¹H NMR (400 MHz, CDCl₃) δ 1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H).

Preparation Example 138: Synthesis of 1-(2,4-dichlorophenyl)-(S)-1-hydroxypropyl-(S)-2-carbamate

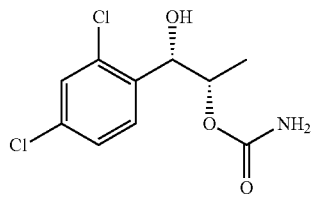 [SMILES: C[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-propanediol obtained in Preparation Example 26 was used instead of 1-(2-chlorophenyl)-(S,S)-1,2-propanediol, to obtain the title compound (0.14 g, yield 34%).

¹H NMR (400 MHz, CDCl₃) δ 1.22 (d, J=6.4 Hz, 3H), 4.16 (br t, 1H) 4.96 (br t, 3H), 5.07 (t, J=4.8 Hz, 1H), 7.23~7.52 (m, 3H).

Preparation Example 139: Synthesis of 1-(2,6-dichlorophenyl)-(S)-1-hydroxypropyl-(S)-2-carbamate

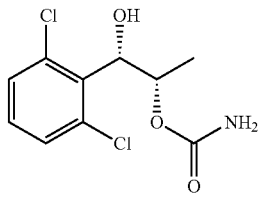

The substantially same method as described in Preparation Example 103 was conducted, except that 1-(2,6-dichlorophenyl)-(S,S)-1,2-propanediol obtained in Preparation Example 38 was used instead of 1-(2-chlorophenyl)-(S,S)-1,2-propanediol, to obtain the title compound (0.22 g, yield 49%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 140: Synthesis of 1-(2,3-dichlorophenyl)-(S)-1-hydroxypropyl-(S)-2-carbamate

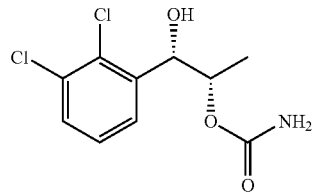 [SMILES: C[C@H](OC(N)=O)[C@@H](O)c1cccc(Cl)c1Cl]

The substantially same method as described in Preparation Example 103 was conducted, except that 1-(2,3-dichlorophenyl)-(S,S)-1,2-propanediol obtained in Preparation Example 57 was used instead of 1-(2-chlorophenyl)-(S,S)-1,2-propanediol, to obtain the title compound (0.21 g, yield 20~60%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 141: Synthesis of 1-(2,4-dichlorophenyl)-(S)-1-hydroxybutyl-(S)-2-carbamate

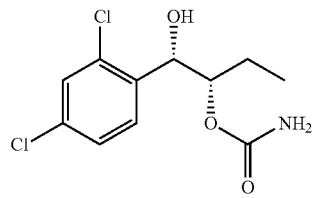 [SMILES: CC[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-butanediol obtained in Preparation Example 29 was used instead of 1-(2-chlorophenyl)-(S,S)-1,2-propanediol, to obtain the title compound (0.23 g, yield 52%).

¹H NMR (400 MHz, CDCl₃) δ 0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H).

Preparation Example 142: Synthesis of 1-(2,6-dichlorophenyl)-(S)-1-hydroxybutyl-(S)-2-carbamate

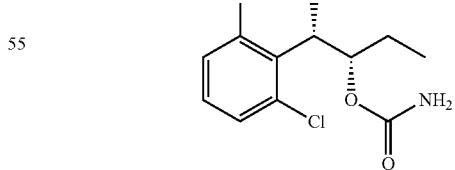

The substantially same method as described in Preparation Example 103 was conducted, except that 1-(2,6-dichlorophenyl)-(S,S)-1,2-butanediol obtained in Preparation Example 41 was used instead of 1-(2-chlorophenyl)-(S,S)-1,2-propanediol, to obtain the title compound (0.49 g, yield 34%).

¹H NMR (400 MHz, CDCl₃) δ 0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H).

Preparation Example 143: Synthesis of 1-(2,4-dichlorophenyl)-(S)-1-hydroxy-3-methyl-butyl-(S)-2-carbamate

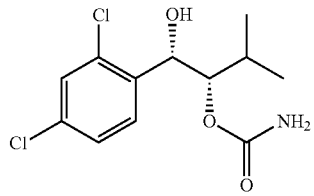

The substantially same method as described in Preparation Example 103 was conducted, except that 1-(2,4-dichlorophenyl)-3-methyl-(S,S)-1,2-butanediol obtained in Preparation Example 32 was used instead of 1-(2-chlorophenyl)-(S,S)-1,2-propanediol, to obtain the title compound (0.13 g, yield 20~60%).
¹H NMR (400 MHz, CDCl₃) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H).

Preparation Example 144: Synthesis of 1-(2,6-dichlorophenyl)-(S)-1-hydroxy-3-methyl-butyl-(S)-2-carbamate

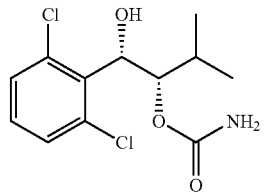

The substantially same method as described in Preparation Example 103 was conducted, except that 1-(2,6-dichlorophenyl)-3-methyl-(S,S)-1,2-butanediol obtained in Preparation Example 44 was used instead of 1-(2-chlorophenyl)-(S,S)-1,2-propanediol, to obtain the title compound (0.12 g, yield 20%).
¹H NMR (400 MHz, CDCl₃) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H).

Preparation Example 145: Synthesis of 1-(2,4-dichlorophenyl)-(S)-1-hydroxyhexyl-(S)-2-carbamate

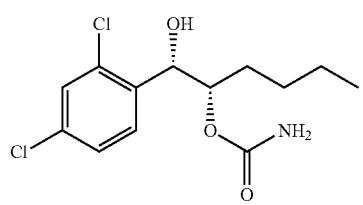

The substantially same method as described in Preparation Example 103 was conducted, except that 1-(2,4-dichlorophenyl)-(S,S)-1,2-hexanediol obtained in Preparation Example 35 was used instead of 1-(2-chlorophenyl)-(S,S)-1,2-propanediol, to obtain the title compound (0.94 g, yield 81%).
¹H NMR (400 MHz, CDCl₃) δ 0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m 3H).

Preparation Example 146: Synthesis of 1-(2,6-dichlorophenyl)-(S)-1-hydroxyhexyl-(S)-2-carbamate

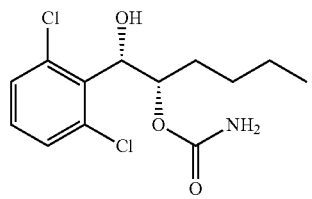

The substantially same method as described in Preparation Example 103 was conducted, except that 1-(2,6-dichlorophenyl)-(S,S)-1,2-hexanediol obtained in Preparation Example 47 was used instead of 1-(2-chlorophenyl)-(S,S)-1,2-propanediol, to obtain the title compound (0.15 g, yield 31%).
¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H).

Preparation Example 147: Synthesis of 1-(2,4-dichlorophenyl)-(R)-1-hydroxypropyl-(R)-2-carbamate

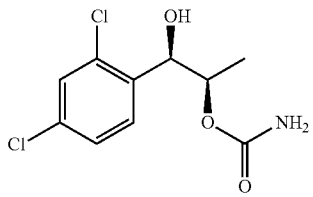 [SMILES: C[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-propanediol obtained in Preparation Example 27 was used instead of 1-(2-chlorophenyl)-(S,S)-1,2-propanediol, to obtain the title compound (0.14 g, yield 20~60%).
¹H NMR (400 MHz, CDCl₃) δ 1.22 (d, J=6.4 Hz, 3H), 4.16 (br t, 1H) 4.96 (br t, 3H), 5.07 (t, J=4.8 Hz, 1H), 7.23~7.52 (m, 3H).

Preparation Example 148: Synthesis of 1-(2,6-di-chlorophenyl)-(R)-1-hydroxypropyl-(R)-2-carbamate

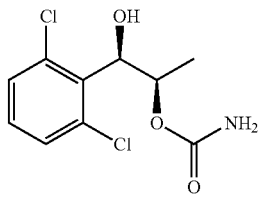 [SMILES: C[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-propanediol obtained in Preparation Example 39 was used instead of 1-(2-chlorophenyl)-(S,S)-1,2-propanediol, to obtain the title compound (0.21 g, yield 20~60%).
$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 149: Synthesis of 1-(2,3-di-chlorophenyl)-(R)-1-hydroxypropyl-(R)-2-carbamate

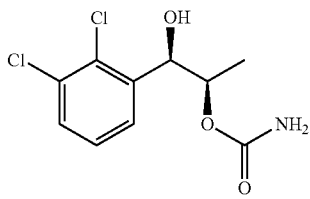 [SMILES: C[C@@H](OC(N)=O)[C@H](O)c1cccc(Cl)c1Cl]

The substantially same method as described in Preparation Example 103 was conducted, except that 1-(2,3-dichlorophenyl)-(R,R)-1,2-propanediol obtained in Preparation Example 58 was used instead of 1-(2-chlorophenyl)-(S,S)-1,2-propanediol, to obtain the title compound (0.08 g, yield 20~60%).
$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 150: Synthesis of 1-(2,4-di-chlorophenyl)-(R)-1-hydroxybutyl-(R)-2-carbamate

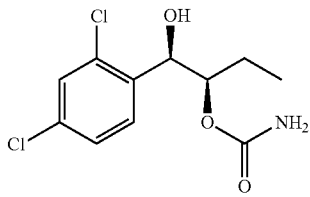 [SMILES: CC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-butanediol obtained in Preparation Example 30 was used instead of 1-(2-chlorophenyl)-(S,S)-1,2-propanediol, to obtain the title compound (0.23 g, yield 20~60%).
$^1$H NMR (400 MHz, CDCl$_3$) δ 0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H).

Preparation Example 151: Synthesis of 1-(2,6-di-chlorophenyl)-(R)-1-hydroxybutyl-(R)-2-carbamate

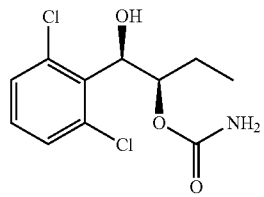 [SMILES: CC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-butanediol obtained in Preparation Example 42 was used instead of 1-(2-chlorophenyl)-(S,S)-1,2-propanediol, to obtain the title compound (0.49 g, yield 20~60%).
$^1$H NMR (400 MHz, CDCl$_3$) δ 0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H).

Preparation Example 152: Synthesis of 1-(2,4-di-chlorophenyl)-(R)-1-hydroxy-3-methyl-butyl-(R)-2-carbamate

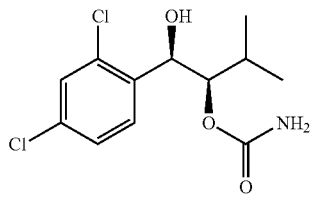 [SMILES: CC(C)[C@@H](OC(N)=O)[C@H](O)c1ccc(Cl)cc1Cl]

The substantially same method as described in Preparation Example 103 was conducted, except that 1-(2,4-dichlorophenyl)-3-methyl-(R,R)-1,2-butanediol obtained in Preparation Example 33 was used instead of 1-(2-chlorophenyl)-(S,S)-1,2-propanediol, to obtain the title compound (0.23 g, yield 20~60%).
$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H).

Preparation Example 153: Synthesis of 1-(2,6-di-chlorophenyl)-(R)-1-hydroxy-3-methyl-butyl-(R)-2-carbamate

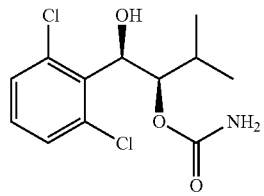 [SMILES: CC(C)[C@@H](OC(N)=O)[C@H](O)c1c(Cl)cccc1Cl]

The substantially same method as described in Preparation Example 103 was conducted, except that 1-(2,6-dichlorophenyl)-3-methyl-(R,R)-1,2-butanediol obtained in Preparation Example 45 was used instead of 1-(2-chlorophenyl)-(S,S)-1,2-propanediol, to obtain the title compound (0.14 g, yield 20~60%).

$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H).

Preparation Example 154: Synthesis of 1-(2,4-dichlorophenyl)-(R)-1-hydroxyhexyl-(R)-2-carbamate

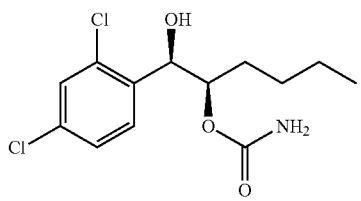 [SMILES: CCCC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-hexanediol obtained in Preparation Example 36 was used instead of 1-(2-chlorophenyl)-(S,S)-1,2-propanediol, to obtain the title compound (0.84 g, yield 20~60%).

$^1$H NMR (400 MHz, CDCl$_3$) δ 0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H).

Preparation Example 155: Synthesis of 1-(2,6-dichlorophenyl)-(R)-1-hydroxyhexyl-(R)-2-carbamate

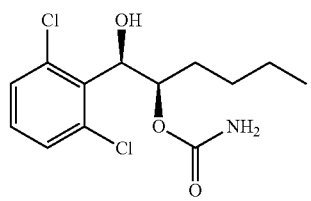 [SMILES: CCCC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-hexanediol obtained in Preparation Example 48 was used instead of 1-(2-chlorophenyl)-(S,S)-1,2-propanediol, to obtain the title compound (0.15 g, yield 20~60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H).

Preparation Example 156: Synthesis of 1-(2,4-dichlorophenyl)-1-hydroxypropyl-2-carbamate

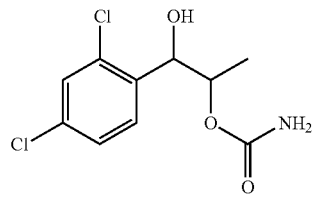

The substantially same method as described in Preparation Example 103 was conducted, except that 1-(2,4-dichlorophenyl)-1,2-propanediol obtained in Preparation Example 28 was used instead of 1-(2-chlorophenyl)-(S,S)-1,2-propanediol, to obtain the title compound (0.14 g, yield 60%).

$^1$H NMR (400 MHz, CDCl$_3$) δ 1.22 (d, J=6.4 Hz, 3H), 4.16 (br t, 1H), 4.96 (br t, 3H), 5.07 (t, J=4.8 Hz, 1H), 7.23~7.52 (m, 3H).

Preparation Example 157: Synthesis of 1-(2,6-dichlorophenyl)-1-hydroxypropyl-2-carbamate

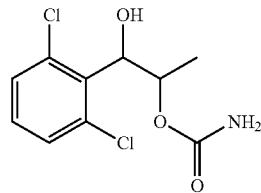 [SMILES: CC(OC(N)=O)C(O)c1c(Cl)cccc1Cl]

The substantially same method as described in Preparation Example 103 was conducted, except that 1-(2,6-dichlorophenyl)-1,2-propanediol obtained in Preparation Example 40 was used instead of 1-(2-chlorophenyl)-(S,S)-1,2-propanediol, to obtain the title compound (0.19 g, yield 60%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 158: Synthesis of 1-(2,3-dichlorophenyl)-1-hydroxypropyl-2-carbamate

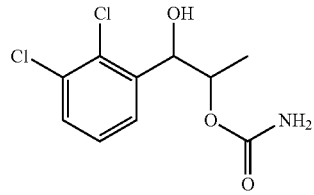

The substantially same method as described in Preparation Example 103 was conducted, except that 1-(2,3-dichlorophenyl)-1,2-propanediol obtained in Preparation Example 59 was used instead of 1-(2-chlorophenyl)-(S,S)-1,2-propanediol, to obtain the title compound (0.21 g, yield 60%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 159: Synthesis of 1-(2,4-dichlorophenyl)-1-hydroxybutyl-2-carbamate

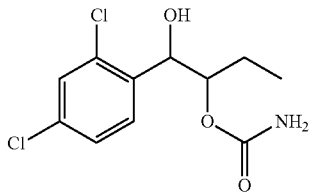 [SMILES: CCC(OC(N)=O)C(O)c1ccc(Cl)cc1Cl]

The substantially same method as described in Preparation Example 103 was conducted, except that 1-(2,4-dichlorophenyl)-1,2-butanediol obtained in Preparation Example 31 was used instead of 1-(2-chlorophenyl)-(S,S)-1,2-propanediol, to obtain the title compound (0.23 g, yield 20~60%).
$^1$H NMR (400 MHz, CDCl$_3$) δ 0.96 (t, J=7.4 Hz, 3H), 1.58~1.74 (m, 2H), 2.98 (d, J=5.6 Hz, 1H), 4.68 (br s, 2H), 5.59 (dt, J=5.2, 8.8 Hz, 1H), 5.19 (t, J=5.4 Hz, 1H), 7.30~7.50 (m, 3H).

Preparation Example 160: Synthesis of 1-(2,6-dichlorophenyl)-1-hydroxybutyl-2-carbamate

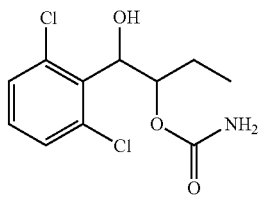 [SMILES: CCC(OC(N)=O)C(O)c1c(Cl)cccc1Cl]

The substantially same method as described in Preparation Example 103 was conducted, except that 1-(2,6-dichlorophenyl)-1,2-butanediol obtained in Preparation Example 43 was used instead of 1-(2-chlorophenyl)-(S,S)-1,2-propanediol, to obtain the title compound (0.49 g, yield 60%).
$^1$H NMR (400 MHz, CDCl$_3$) δ 0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H).

Preparation Example 161: Synthesis of 1-(2,4-dichlorophenyl)-1-hydroxy-3-methyl-butyl-2-carbamate

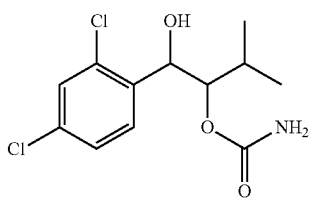 [SMILES: CC(C)C(OC(N)=O)C(O)c1ccc(Cl)cc1Cl]

The substantially same method as described in Preparation Example 103 was conducted, except that 1-(2,4-dichlorophenyl)-3-methyl-1,2-butanediol obtained in Preparation Example 34 was used instead of 1-(2-chlorophenyl)-(S,S)-1,2-propanediol, to obtain the title compound (0.13 g, yield 20~60%).
$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H).

Preparation Example 162: Synthesis of 1-(2,6-dichlorophenyl)-1-hydroxy-3-methyl-butyl-2-carbamate

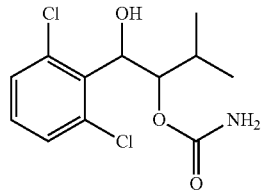 [SMILES: CC(C)C(OC(N)=O)C(O)c1c(Cl)cccc1Cl]

The substantially same method as described in Preparation Example 103 was conducted, except that 1-(2,6-dichlorophenyl)-3-methyl-1,2-butanediol obtained in Preparation Example 46 was used instead of 1-(2-chlorophenyl)-(S,S)-1,2-propanediol, to obtain the title compound (0.13 g, yield 20~60%).
$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H).

Preparation Example 163: Synthesis of 1-(2,4-dichlorophenyl)-1-hydroxyhexyl-2-carbamate

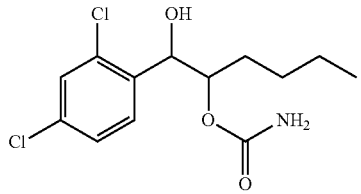 [SMILES: CCCCC(OC(N)=O)C(O)c1ccc(Cl)cc1Cl]

The substantially same method as described in Preparation Example 103 was conducted, except that 1-(2,4-dichlorophenyl)-1,2-hexanediol obtained in Preparation Example 37 was used instead of 1-(2-chlorophenyl)-(S,S)-1,2-propanediol, to obtain the title compound (0.94 g, yield 60%).
$^1$H NMR (400 MHz, CDCl$_3$) δ 0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H).

Preparation Example 164: Synthesis of 1-(2,6-dichlorophenyl)-1-hydroxyhexyl-2-carbamate

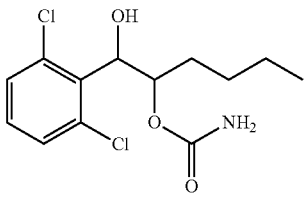 [SMILES: CCCCC(OC(N)=O)C(O)c1c(Cl)cccc1Cl]

The substantially same method as described in Preparation Example 103 was conducted, except that 1-(2,6-dichlororophenyl)-1,2-hexanediol obtained in Preparation Example 49 was used instead of 1-(2-chlorophenyl)-(S,S)-1,2-propanediol, to obtain the title compound (0.15 g, yield 60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H).

Preparation Example 165: Synthesis of 1-(2-fluorophenyl)-(S)-1-hydroxypropyl-(S)-2-carbamate

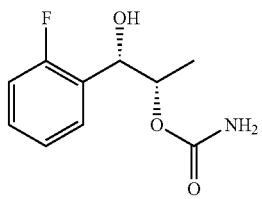

The substantially same method as described in Preparation Example 103 was conducted, except that 1-(2-fluorophenyl)-(S,S)-1,2-propanediol (12.23 g) obtained in Preparation Example 61 was used instead of 1-(2-chlorophenyl)-(S,S)-1,2-propanediol, to obtain the title compound (6.11 g, yield 40%).

$^1$H NMR (400 MHz, CDCl$_3$) δ 1.19 (d, J=5.2 Hz, 3H), 2.93 (d, J=4.4 Hz, 1H), 4.71 (br s, 2H), 4.99~5.06 (m, H), 7.04~7.48 (m, 4H).

Preparation Example 166: Synthesis of 1-(2-fluorophenyl)-(R)-1-hydroxypropyl-(R)-2-carbamate

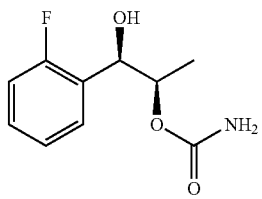

The substantially same method as described in Preparation Example 103 was conducted, except that 1-(2-fluorophenyl)-(R,R)-1,2-propanediol (6.26 g) obtained in Preparation Example 62 was used instead of 1-(2-chlorophenyl)-(S,S)-1,2-propanediol, to obtain the title compound (3.13 g, yield 40%).

$^1$H NMR (400 MHz, CDCl$_3$) δ 1.19 (d, J=5.2 Hz, 3H), 2.93 (d, J=4.4 Hz, 1H), 4.71 (br s, 2H), 4.99~5.06 (m, H), 7.04~7.48 (m, 4H).

Preparation Example 167: Synthesis of 1-(2-iodophenyl)-(S)-1-hydroxypropyl-(S)-2-carbamate

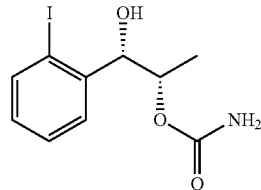

The substantially same method as described in Preparation Example 103 was conducted, except that 1-(2-iodophenyl)-(S,S)-1,2-propanediol obtained in Preparation Example 66 was used instead of 1-(2-chlorophenyl)-(S,S)-1,2-propanediol, to obtain the title compound (2.2 g, yield 30~60%).

$^1$H NMR (400 MHz, CDCl$_3$) δ 1.27 (d, J=6.4 Hz, 3H), 3.09 (br s, 1H), 4.83 (br s, 2H), 5.00~5.10 (m, 2H), 7.00~7.76 (m, 4H).

Preparation Example 168: Synthesis of 1-(2-iodophenyl)-(R)-1-hydroxypropyl-(R)-2-carbamate

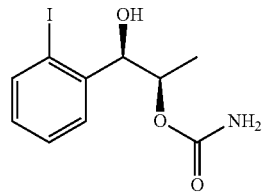

The substantially same method as described in Preparation Example 103 was conducted, except that 1-(2-iodophenyl)-(R,R)-1,2-propanediol obtained in Preparation Example 67 was used instead of 1-(2-chlorophenyl)-(S,S)-1,2-propanediol, to obtain the title compound (3.13 g, yield 30~60%).

$^1$H NMR (400 MHz, CDCl$_3$) δ 1.27 (d, J=6.4 Hz, 3H), 2.95 (d, J=3.6 Hz, 1H), 4.73 (br s, 2H), 5.01~5.11 (m, 2H), 7.01~7.86 (m, 4H).

Preparation Example 169: Synthesis of 1-(2-iodophenyl)-(S)-1-hydroxybutyl-(S)-2-carbamate

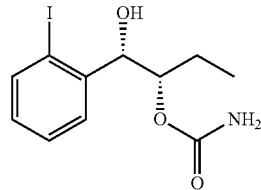 [SMILES: CC[C@H](OC(N)=O)[C@@H](O)c1ccccc1I]

The substantially same method as described in Preparation Example 103 was conducted, except that 1-(2-iodophenyl)-(S,S)-1,2-butanediol obtained in Preparation Example 68 was used instead of 1-(2-chlorophenyl)-(S,S)-1,2-propanediol, to obtain the title compound (3.6 g, yield 30~60%).

¹H NMR (400 MHz, CDCl₃) δ 1.27 (d, J=6.4 Hz, 3H), 3.09 (br s, 1H), 4.83 (br s, 2H), 5.00~5.10 (m, 2H), 7.00~7.76 (m, 4H).

Preparation Example 170: Synthesis of 1-(2-chlorophenyl)-(S)-2-hydroxypropyl-(S)-1-carbamate

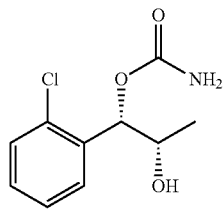

A regioisomer of monocarbamate was separated and purified by conducting the silica gel column chromatography as described in Preparation Example 103, to obtain the title compound (0.34 g, yield 10%).
¹H NMR (400 MHz, CDCl₃) δ 1.24 (d, J=6.8 Hz, 3H), 2.13 (d, J=4.4 Hz, 1H), 4.12~4.16 (m, 1H), 4.85 (br s, 2H), 5.98 (d, J=5.6 Hz, 1H), 7.24~7.43 (m, 4H).

Preparation Example 171: Synthesis of 1-(2-chlorophenyl)-(R)-2-hydroxypropyl-(R)-1-carbamate

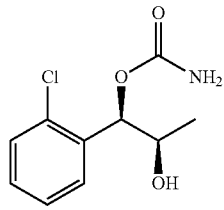

A regioisomer of monocarbamate was separated and purified by conducting the silica gel column chromatography as described in Preparation Example 104, to obtain the title compound (0.77 g, yield 16%).
¹H NMR (400 MHz, CDCl₃) δ 1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H).

Preparation Example 172: Synthesis of 1-(2-chlorophenyl)-2-hydroxypropyl-1-carbamate

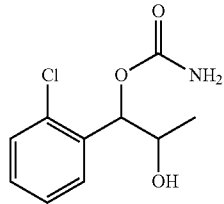

A regioisomer of monocarbamate was separated and purified by conducting the silica gel column chromatography as described in Preparation Example 105, to obtain the title compound (0.16 g, yield 10~30%).

¹H NMR (400 MHz, CDCl₃) δ 1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H).

Preparation Example 173: Synthesis of 1-(2-chlorophenyl)-(S)-2-hydroxypropyl-(S)-1-methylcarbamate

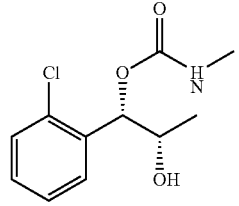 [SMILES: CNC(=O)O[C@@H](c1ccccc1Cl)[C@H](C)O]

A regioisomer of monocarbamate was separated and purified by conducting the silica gel column chromatography as described in Preparation Example 117, to obtain the title compound (0.70 g, yield 10~30%).
¹H NMR (400 MHz, CDCl₃) δ 1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H).

Preparation Example 174: Synthesis of 1-(2-chlorophenyl)-(R)-2-hydroxypropyl-(R)-1-methylcarbamate

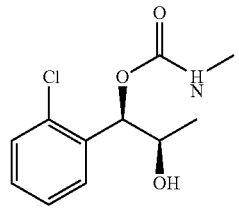 [SMILES: CNC(=O)O[C@H](c1ccccc1Cl)[C@@H](C)O]

A regioisomer of monocarbamate was separated and purified by conducting the silica gel column chromatography as described in Preparation Example 124, to obtain the title compound (0.69 g, yield 10~30%).
¹H NMR (400 MHz, CDCl₃) δ 1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H).

Preparation Example 175: Synthesis of 1-(2-chlorophenyl)-2-hydroxypropyl-1-methylcarbamate

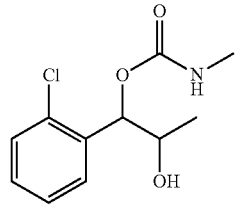 [SMILES: CNC(=O)OC(c1ccccc1Cl)C(C)O]

A regioisomer of monocarbamate was separated and purified by conducting the silica gel column chromatography as described in Preparation Example 131, to obtain the title compound (0.73 g, yield 10%).

¹H NMR (400 MHz, CDCl₃) δ 1.22 (d, J=6.0 Hz, 3H), 2.15 (d, J=4.0 Hz, 1H), 2.81 (d, J=5.0 Hz, 3H), 4.12 (dd, J=6.0 Hz, 1H), 4.83 (br s, 1H), 6.00 (d, J=6.0 Hz, 1H), 7.23~7.41 (m, 4H).

Preparation Example 176: Synthesis of 1-(2-chlorophenyl)-(S)-2-hydroxypropyl-(S)-1-propylcarbamate

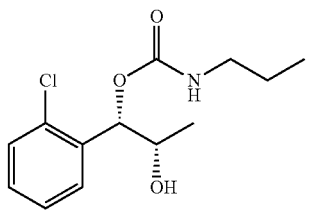 [SMILES: CCCNC(=O)O[C@@H](c1ccccc1Cl)[C@H](C)O]

A regioisomer of monocarbamate was separated and purified by conducting the silica gel column chromatography as described in Preparation Example 118, to obtain the title compound (0.15 g, yield 10~30%).
¹H NMR (400 MHz, CDCl₃) δ 0.91 (t, J=7.0 Hz, 3H), 1.22 (d, J=6.0 Hz, 3H), 1.52 (dd, J=7.0 Hz, 2H), 2.23 (d, J=4.0 Hz, 1H), 3.09~3.21 (m, 2H), 4.09~4.17 (m, 1H), 4.93 (s, 1H), 5.99 (d, J=6.0 Hz, 1H), 7.23~7.47 (m, 4H).

Preparation Example 177: Synthesis of 1-(2-chlorophenyl)-(R)-2-hydroxypropyl-(R)-1-propylcarbamate

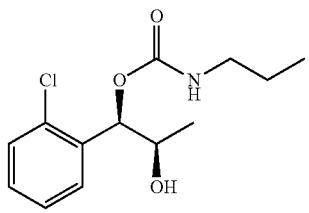 [SMILES: CCCNC(=O)O[C@H](c1ccccc1Cl)[C@@H](C)O]

A regioisomer of monocarbamate was separated and purified by conducting the silica gel column chromatography as described in Preparation Example 125, to obtain the title compound (0.04 g, yield 10~30%).
¹H NMR (400 MHz, CDCl₃) δ 0.91 (t, J=7.0 Hz, 3H), 1.22 (d, J=6.0 Hz, 3H), 1.52 (dd, J=7.0 Hz, 2H), 2.23 (d, J=4.0 Hz, 1H), 3.09~3.21 (m, 2H), 4.09~4.17 (m, 1H), 4.93 (s, 1H), 5.99 (d, J=6.0 Hz, 1H), 7.23~7.47 (m, 4H).

Preparation Example 178: Synthesis of 1-(2-chlorophenyl)-2-hydroxypropyl-1-propylcarbamate

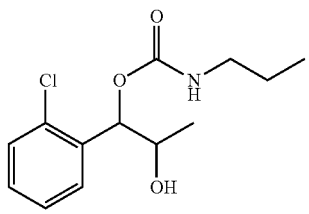 [SMILES: CCCNC(=O)OC(c1ccccc1Cl)C(C)O]

A regioisomer of monocarbamate was separated and purified by conducting the silica gel column chromatography as described in Preparation Example 132, to obtain the title compound (0.15 g, yield 10%).
¹H NMR (400 MHz, CDCl₃) δ 0.91 (t, J=7.0 Hz, 3H), 1.22 (d, J=6.0 Hz, 3H), 1.52 (dd, J=7.0 Hz, 2H), 2.23 (d, J=4.0 Hz, 1H), 3.09~3.21 (m, 2H), 4.09~4.17 (m, 1H), 4.93 (s, 1H), 5.99 (d, J=6.0 Hz, 1H), 7.23~7.47 (m, 4H).

Preparation Example 179: Synthesis of 1-(2-chlorophenyl)-(S)-2-hydroxypropyl-(S)-1-isopropylcarbamate

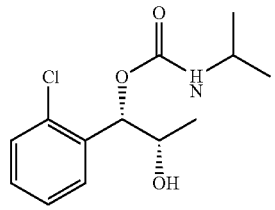 [SMILES: CC(C)NC(=O)O[C@@H](c1ccccc1Cl)[C@H](C)O]

A regioisomer of monocarbamate was separated and purified by conducting the silica gel column chromatography as described in Preparation Example 119, to obtain the title compound (0.42 g, yield 28%).
¹H NMR (400 MHz, CDCl₃) δ 1.10 (d, J=6.0 Hz, 3H), 1.15~1.19 (m, 6H), 2.41 (s, 1H), 3.76~4.08 (m, 1H), 4.34 (s, 1H), 4.83 (br s 1H), 5.95 (d, J=5.3 Hz, 1H), 7.19~7.39 (m, 4H).

Preparation Example 180: Synthesis of 1-(2-chlorophenyl)-(R)-2-hydroxypropyl-(R)-1-isopropylcarbamate

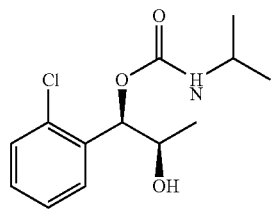 [SMILES: CC(C)NC(=O)O[C@H](c1ccccc1Cl)[C@@H](C)O]

A regioisomer of monocarbamate was separated and purified by conducting the silica gel column chromatography as described in Preparation Example 126, to obtain the title compound (0.5 g, yield 10%).
¹H NMR (400 MHz, CDCl₃) δ 1.13 (d, J=6.0 Hz, 3H), 1.20 (dd, J=9.2 Hz, 6H), 2.23 (s, 1H), 3.77~3.82 (m, 1H), 4.10 (s, 1H), 4.76 (br s, 1H), 5.98 (d, J=5.6 Hz, 1H), 7.23~7.41 (m, 4H).

Preparation Example 181: Synthesis of 1-(2-chlorophenyl)-2-hydroxypropyl-1-isopropylcarbamate

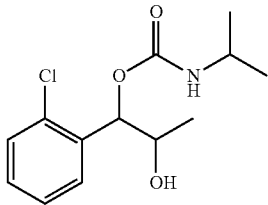 [SMILES: CC(C)NC(=O)OC(c1ccccc1Cl)C(C)O]

A regioisomer of monocarbamate was separated and purified by conducting the silica gel column chromatography as described in Preparation Example 133, to obtain the title compound (0.09 g, yield 40%).

$^1$H NMR (400 MHz, CDCl$_3$) δ 1.14 (d, J=6.0 Hz, 3H), 1.21 (dd, J=6.0 Hz, 6H), 2.16 (d, J=5.0 Hz, 1H), 3.81 (t, J=6.0 Hz, 1H), 4.11 (d, J=5.0 Hz, 1H), 4.73 (br s, 1H), 5.98 (d, J=5.0 Hz, 1H), 7.24~741 (m, 4H).

Preparation Example 182: Synthesis of 1-(2-chlorophenyl)-(S)-2-hydroxypropyl-(S)-1-cyclopropylcarbamate

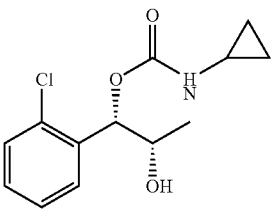 [SMILES: C[C@H](O)[C@@H](OC(=O)NC1CC1)c1ccccc1Cl]

A regioisomer of monocarbamate was separated and purified by conducting the silica gel column chromatography as described in Preparation Example 120, to obtain the title compound (0.53 g, yield 10~30%).

$^1$H NMR (400 MHz, CDCl$_3$) δ 0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.2 Hz, 1H), 7.23~7.40 (m, 4H).

Preparation Example 183: Synthesis of 1-(2-chlorophenyl)-(R)-2-hydroxypropyl-(R)-1-cyclopropylcarbamate

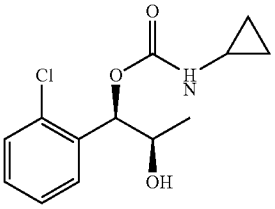 [SMILES: C[C@@H](O)[C@H](OC(=O)NC1CC1)c1ccccc1Cl]

A regioisomer of monocarbamate was separated and purified by conducting the silica gel column chromatography as described in Preparation Example 127, to obtain the title compound (0.58 g, yield 10%).

$^1$H NMR (400 MHz, CDCl$_3$) δ 0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.2 Hz, 1H), 7.23~7.40 (m, 4H).

Preparation Example 184: Synthesis of 1-(2-chlorophenyl)-2-hydroxypropyl-1-cyclopropylcarbamate

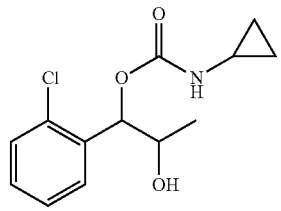 [SMILES: CC(O)C(OC(=O)NC1CC1)c1ccccc1Cl]

A regioisomer of monocarbamate was separated and purified by conducting the silica gel column chromatography as described in Preparation Example 134, to obtain the title compound (0.38 g, yield 14%).

$^1$H NMR (400 MHz, CDCl$_3$) δ 0.71 (s, 2H), 1.19 (d, J=6.0 Hz, 3H), 2.45 (S, 1H), 2.57 (S, 1H), 4.08~4.12 (m, 1H), 5.26 (s, 1H), 5.97 (d, J=4.0 Hz, 1H), 7.22~7.54 (m, 4H).

Preparation Example 185: Synthesis of 1-(2-chlorophenyl)-(S)-2-hydroxypropyl-(S)-1-cyclohexylcarbamate

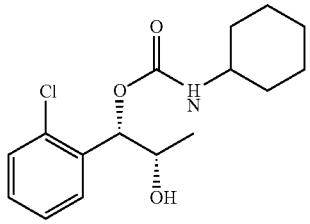 [SMILES: C[C@H](O)[C@@H](OC(=O)NC1CCCCC1)c1ccccc1Cl]

A regioisomer of monocarbamate was separated and purified by conducting the silica gel column chromatography as described in Preparation Example 121, to obtain the title compound (0.24 g, yield 10~30%).

$^1$H NMR (400 MHz, CDCl$_3$) δ 1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4.0 Hz, 1H), 4.10~4.11 (m, 1H), 4.80 (br s 1H), 5.97 (d, J=5.6 Hz, 1H), 7.23~7.41 (m, 4H).

Preparation Example 186: Synthesis of 1-(2-chlorophenyl)-(R)-2-hydroxypropyl-(R)-1-cyclohexylcarbamate

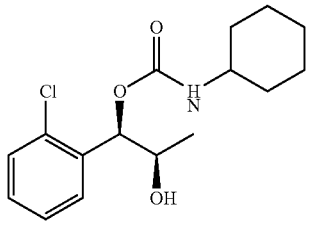 [SMILES: C[C@@H](O)[C@H](OC(=O)NC1CCCCC1)c1ccccc1Cl]

A regioisomer of monocarbamate was separated and purified by conducting the silica gel column chromatography as described in Preparation Example 128, to obtain the title compound (0.35 g, yield 10%).

¹H NMR (400 MHz, CDCl₃) δ 1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4.0 Hz, 1H), 4.10~4.11 (m, 1H), 4.80 (br s 1H), 5.97 (d, J=5.6 Hz, 1H), 7.23~7.41 (m, 4H).

Preparation Example 187: Synthesis of 1-(2-chlorophenyl)-2-hydroxypropyl-1-cyclohexylcarbamate

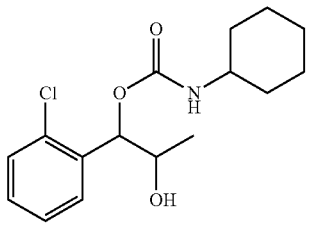 [SMILES: CC(O)C(OC(=O)NC1CCCCC1)c1ccccc1Cl]

A regioisomer of monocarbamate was separated and purified by conducting the silica gel column chromatography as described in Preparation Example 135, to obtain the title compound (0.26 g, yield 10%).

¹H NMR (400 MHz, CDCl₃) δ 1.12~1.19 (m, 3H), 1.22 (d, J=6.0 Hz, 3H), 1.27~1.37 (m, 1H), 1.71 (t, J=6.0 Hz, 2H), 1.86~1.88 (m, 1H), 1.97~2.00 (m, 1H), 2.18 (d, J=4.0 Hz, 1H), 3.47 (S, 1H), 4.12 (t, J=6.0 Hz, 1H), 4.78 (S, 1H), 5.97 (d, J=6.0 Hz, 1H), 7.23~7.40 (m, 4H).

Preparation Example 188: Synthesis of 1-(2-chlorophenyl)-(S)-2-hydroxypropyl-(S)-1-benzylcarbamate

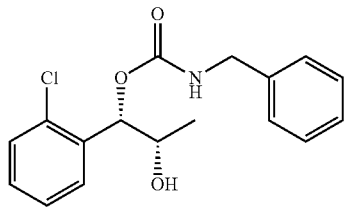

A regioisomer of monocarbamate was separated and purified by conducting the silica gel column chromatography as described in Preparation Example 122, to obtain the title compound (0.19 g, yield 10~30%).

¹H NMR (400 MHz, CDCl₃) δ 1.23 (d, J=6.0 Hz, 3H), 2.16 (d, J=4.0 Hz, 1H), 4.12 (t, J=6.0 Hz, 1H), 4.31~4.44 (m, 2H), 5.22 (br S, 1H), 6.04 (d, J=6.0 Hz, 1H), 7.27~7.42 (m, 9H).

Preparation Example 189: Synthesis of 1-(2-chlorophenyl)-(R)-2-hydroxypropyl-(R)-1-benzylcarbamate

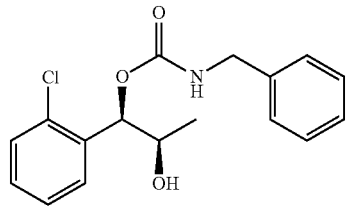 [SMILES: C[C@@H](O)[C@H](OC(=O)NCc1ccccc1)c1ccccc1Cl]

A regioisomer of monocarbamate was separated and purified by conducting the silica gel column chromatography as described in Preparation Example 129, to obtain the title compound (0.07 g, yield 10~30%).

¹H NMR (400 MHz, CDCl₃) δ 1.23 (d, J=6.0 Hz, 3H), 2.16 (d, J=4.0 Hz, 1H), 4.12 (t, J=6.0 Hz, 1H), 4.31~4.44 (m, 2H), 5.22 (br S, 1H), 6.04 (d, J=6.0 Hz, 1H), 7.27~7.42 (m, 9H).

Preparation Example 190: Synthesis of 1-(2-chlorophenyl)-2-hydroxypropyl-1-benzylcarbamate

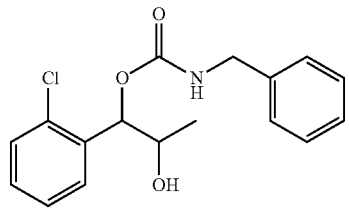 [SMILES: CC(O)C(OC(=O)NCc1ccccc1)c1ccccc1Cl]

A regioisomer of monocarbamate was separated and purified by conducting the silica gel column chromatography as described in Preparation Example 136, to obtain the title compound (0.21 g, yield 14%).

¹H NMR (400 MHz, CDCl₃) δ 1.23 (d, J=6.0 Hz, 3H), 2.16 (d, J=4.0 Hz, 1H), 4.12 (t, J=6.0 Hz, 1H), 4.31~4.44 (m, 2H), 5.22 (br S, 1H), 6.04 (d, J=6.0 Hz, 1H), 7.27~7.42 (m, 9H).

Preparation Example 191: Synthesis of 1-(2,4-dichlorophenyl)-(S)-2-hydroxypropyl-(S)-1-carbamate

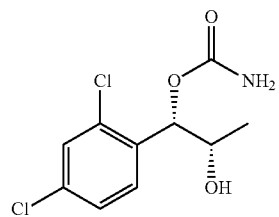 [SMILES: C[C@H](O)[C@@H](OC(N)=O)c1ccc(Cl)cc1Cl]

A regioisomer of monocarbamate was separated and purified by conducting the silica gel column chromatography as described in Preparation Example 138, to obtain the title compound (0.05 g, yield 10~30%).

¹H NMR (400 MHz, CDCl₃) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30 (d, J=8.4 Hz, 1H), 7.39 (d, J=2.0 Hz, 2H), 7.50 (dd, J=2.0, 8.4 Hz, 1H).

Preparation Example 192: Synthesis of 1-(2,6-dichlorophenyl)-(S)-2-hydroxypropyl-(S)-1-carbamate

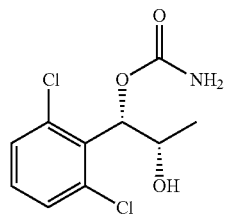

A regioisomer of monocarbamate was separated and purified by conducting the silica gel column chromatography as described in Preparation Example 139, to obtain the title compound (0.07 g, yield 24%).

$^1$H NMR (400 MHz, CDCl$_3$) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H).

Preparation Example 193: Synthesis of 1-(2,3-dichlorophenyl)-(S)-2-hydroxypropyl-(S)-carbamate

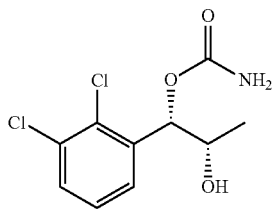 [SMILES: C[C@H](O)[C@@H](OC(N)=O)c1cccc(Cl)c1Cl]

A regioisomer of monocarbamate was separated and purified by conducting the silica gel column chromatography as described in Preparation Example 140, to obtain the title compound (0.08 g, yield 10~30%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 194: Synthesis of 1-(2,4-dichlorophenyl)-(S)-2-hydroxybutyl-(S)-1-carbamate

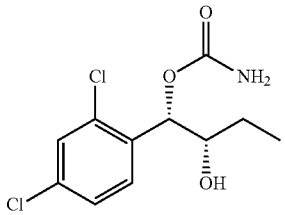

A regioisomer of monocarbamate was separated and purified by conducting the silica gel column chromatography as described in Preparation Example 141, to obtain the title compound (0.07 g, yield 10~30%).

$^1$H NMR (400 MHz, CDCl$_3$) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H).

Preparation Example 195: Synthesis of 1-(2,6-dichlorophenyl)-(S)-2-hydroxybutyl-(S)-1-carbamate

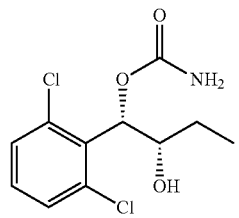 [SMILES: CC[C@H](O)[C@@H](OC(N)=O)c1c(Cl)cccc1Cl]

A regioisomer of monocarbamate was separated and purified by conducting the silica gel column chromatography as described in Preparation Example 142, to obtain the title compound (0.11 g, yield 29%).

$^1$H NMR (400 MHz, CDCl$_3$) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H).

Preparation Example 196: Synthesis of 1-(2,4-dichlorophenyl)-(S)-2-hydroxy-3-methyl-butyl-(S)-1-carbamate

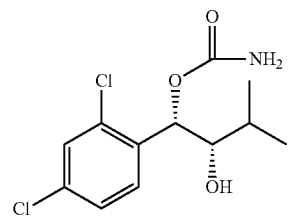 [SMILES: CC(C)[C@H](O)[C@@H](OC(N)=O)c1ccc(Cl)cc1Cl]

A regioisomer of monocarbamate was separated and purified by conducting the silica gel column chromatography as described in Preparation Example 143, to obtain the title compound (0.01 g, yield 10~30%).

$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H).

Preparation Example 197: Synthesis of 1-(2,6-dichlorophenyl)-(S)-2-hydroxy-3-methyl-butyl-(S)-1-carbamate

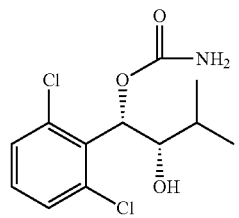 [SMILES: CC(C)[C@H](O)[C@@H](OC(N)=O)c1c(Cl)cccc1Cl]

A regioisomer of monocarbamate was separated and purified by conducting the silica gel column chromatography as described in Preparation Example 144, to obtain the title compound (0.03 g, yield 10~30%).

$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H).

Preparation Example 198: Synthesis of 1-(2,4-dichlorophenyl)-(S)-2-hydroxyhexyl-(S)-1-carbamate

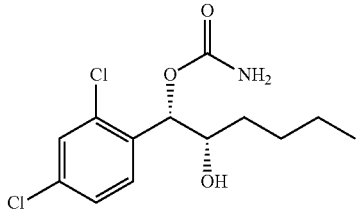 [SMILES: CCCC[C@H](O)[C@@H](OC(N)=O)c1ccc(Cl)cc1Cl]

A regioisomer of monocarbamate was separated and purified by conducting the silica gel column chromatography as described in Preparation Example 145, to obtain the title compound (0.21 g, yield 10~30%).

$^1$H NMR (400 MHz, CDCl$_3$) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H).

Preparation Example 199: Synthesis of 1-(2,6-dichlorophenyl)-(S)-2-hydroxyhexyl-(S)-1-carbamate

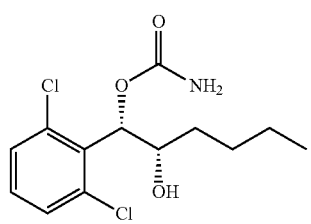

A regioisomer of monocarbamate was separated and purified by conducting the silica gel column chromatography as described in Preparation Example 146, to obtain the title compound (0.06 g, yield 29%).

$^1$H NMR (400 MHz, CDCl$_3$) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H).

Preparation Example 200: Synthesis of 1-(2,4-dichlorophenyl)-(R)-2-hydroxypropyl-(R)-1-carbamate

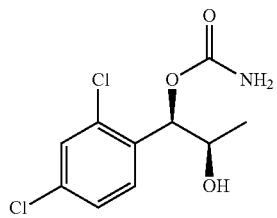 [SMILES: C[C@@H](O)[C@H](OC(N)=O)c1ccc(Cl)cc1Cl]

A regioisomer of monocarbamate was separated and purified by conducting the silica gel column chromatography as described in Preparation Example 147, to obtain the title compound (0.04 g, yield 10~30%).

$^1$H NMR (400 MHz, CDCl$_3$) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H).

Preparation Example 201: Synthesis of 1-(2,6-dichlorophenyl)-(R)-2-hydroxypropyl-(R)-1-carbamate

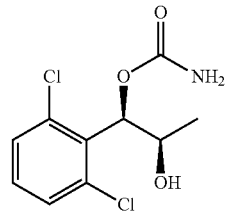 [SMILES: C[C@@H](O)[C@H](OC(N)=O)c1c(Cl)cccc1Cl]

A regioisomer of monocarbamate was separated and purified by conducting the silica gel column chromatography as described in Preparation Example 148, to obtain the title compound (0.09 g, yield 10~30%).

$^1$H NMR (400 MHz, CDCl$_3$) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H).

Preparation Example 202: Synthesis of 1-(2,3-dichlorophenyl)-(R)-2-hydroxypropyl-(R)-1-carbamate

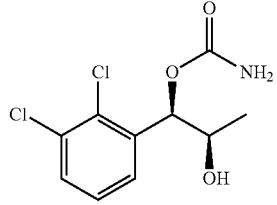 [SMILES: C[C@@H](O)[C@H](OC(N)=O)c1cccc(Cl)c1Cl]

A regioisomer of monocarbamate was separated and purified by conducting the silica gel column chromatography as described in Preparation Example 149, to obtain the title compound (0.25 g, yield 10~30%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 203: Synthesis of 1-(2,4-dichlorophenyl)-(R)-2-hydroxybutyl-(R)-1-carbamate

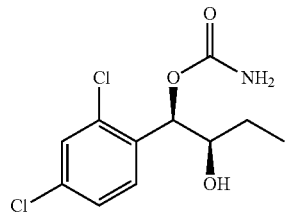 [SMILES: CC[C@@H](O)[C@H](OC(N)=O)c1ccc(Cl)cc1Cl]

A regioisomer of monocarbamate was separated and purified by conducting the silica gel column chromatography as described in Preparation Example 150, to obtain the title compound (0.08 g, yield 10~30%).

$^1$H NMR (400 MHz, CDCl$_3$) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H).

Preparation Example 204: Synthesis of 1-(2,6-dichlorophenyl)-(R)-2-hydroxybutyl-(R)-1-carbamate

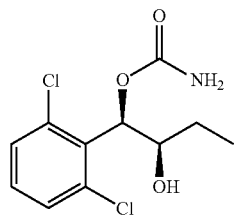 [SMILES: CC[C@@H](O)[C@H](OC(N)=O)c1c(Cl)cccc1Cl]

A regioisomer of monocarbamate was separated and purified by conducting the silica gel column chromatography as described in Preparation Example 151, to obtain the title compound (0.09 g, yield 10~30%).

$^1$H NMR (400 MHz, CDCl$_3$) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H).

Preparation Example 205: Synthesis of 1-(2,4-dichlorophenyl)-(R)-2-hydroxy-3-methyl-butyl-(R)-1-carbamate

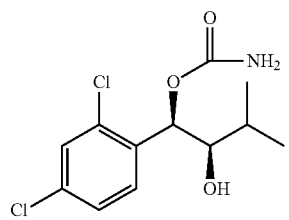 [SMILES: CC(C)[C@@H](O)[C@H](OC(N)=O)c1ccc(Cl)cc1Cl]

A regioisomer of monocarbamate was separated and purified by conducting the silica gel column chromatography as described in Preparation Example 152, to obtain the title compound (0.01 g, yield 10~30%).

$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H).

Preparation Example 206: Synthesis of 1-(2,6-dichlorophenyl)-(R)-2-hydroxy-3-methyl-butyl-(R)-1-carbamate

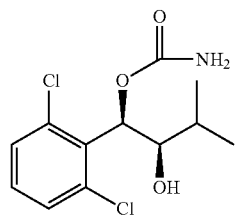 [SMILES: CC(C)[C@@H](O)[C@H](OC(N)=O)c1c(Cl)cccc1Cl]

A regioisomer of monocarbamate was separated and purified by conducting the silica gel column chromatography as described in Preparation Example 153, to obtain the title compound (0.01 g, yield 10~30%).

$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H).

Preparation Example 207: Synthesis of 1-(2,4-dichlorophenyl)-(R)-2-hydroxyhexyl-(R)-1-carbamate

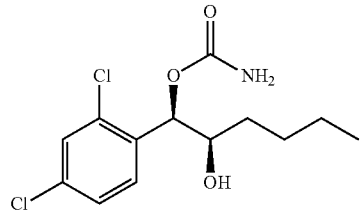 [SMILES: CCCC[C@@H](O)[C@H](OC(N)=O)c1ccc(Cl)cc1Cl]

A regioisomer of monocarbamate was separated and purified by conducting the silica gel column chromatography as described in Preparation Example 154, to obtain the title compound (0.21 g, yield 10~30%).

$^1$H NMR (400 MHz, CDCl$_3$) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H).

Preparation Example 208: Synthesis of 1-(2,6-dichlorophenyl)-(R)-2-hydroxyhexyl-(R)-1-carbamate

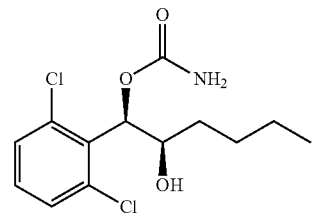 [SMILES: CCCC[C@@H](O)[C@H](OC(N)=O)c1c(Cl)cccc1Cl]

A regioisomer of monocarbamate was separated and purified by conducting the silica gel column chromatography as described in Preparation Example 155, to obtain the title compound (0.12 g, yield 10~30%).

¹H NMR (400 MHz, CDCl₃) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H).

Preparation Example 209: Synthesis of 1-(2,4-dichlorophenyl)-2-hydroxypropyl-1-carbamate

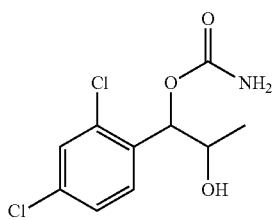 [SMILES: CC(O)C(OC(N)=O)c1ccc(Cl)cc1Cl]

A regioisomer of monocarbamate was separated and purified by conducting the silica gel column chromatography as described in Preparation Example 156, to obtain the title compound (0.05 g, yield 10~30%).

¹H NMR (400 MHz, CDCl₃) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H).

Preparation Example 210: Synthesis of 1-(2,6-dichlorophenyl)-2-hydroxypropyl-1-carbamate

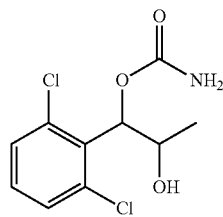 [SMILES: CC(O)C(OC(N)=O)c1c(Cl)cccc1Cl]

A regioisomer of monocarbamate was separated and purified by conducting the silica gel column chromatography as described in Preparation Example 157, to obtain the title compound (0.06 g, yield 10~30%).

¹H NMR (400 MHz, CDCl₃) δ 1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H).

Preparation Example 211: Synthesis of 1-(2,3-dichlorophenyl)-(R)-2-hydroxypropyl-(R)-1-carbamate

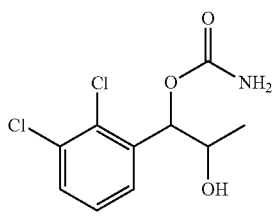 [SMILES: CC(O)C(OC(N)=O)c1cccc(Cl)c1Cl]

A regioisomer of monocarbamate was separated and purified by conducting the silica gel column chromatography as described in Preparation Example 158, to obtain the title compound (0.02 g, yield 10~30%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 212: Synthesis of 1-(2,4-dichlorophenyl)-2-hydroxybutyl-1-carbamate

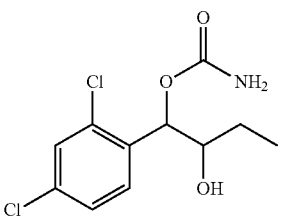

A regioisomer of monocarbamate was separated and purified by conducting the silica gel column chromatography as described in Preparation Example 159, to obtain the title compound (0.07 g, yield 10~30%).

¹H NMR (400 MHz, CDCl₃) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H).

Preparation Example 213: Synthesis of 1-(2,6-dichlorophenyl)-2-hydroxybutyl-1-carbamate

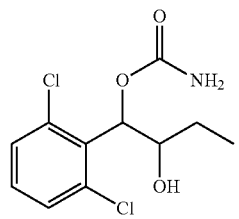 [SMILES: CCC(O)C(OC(N)=O)c1c(Cl)cccc1Cl]

A regioisomer of monocarbamate was separated and purified by conducting the silica gel column chromatography as described in Preparation Example 160, to obtain the title compound (0.10 g, yield 10~30%).

¹H NMR (400 MHz, CDCl₃) δ 0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H).

Preparation Example 214: Synthesis of 1-(2,4-dichlorophenyl)-2-hydroxy-3-methyl-butyl-1-carbamate

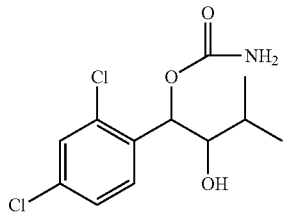

A regioisomer of monocarbamate was separated and purified by conducting the silica gel column chromatography as described in Preparation Example 161, to obtain the title compound (0.04 g, yield 10~30%).
$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H).

Preparation Example 215: Synthesis of 1-(2,6-dichlorophenyl)-2-hydroxy-3-methyl-butyl-1-carbamate

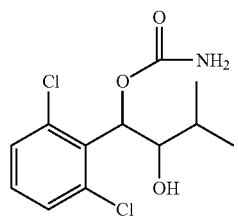 [SMILES: CC(C)C(O)C(OC(N)=O)c1c(Cl)cccc1Cl]

A regioisomer of monocarbamate was separated and purified by conducting the silica gel column chromatography as described in Preparation Example 162, to obtain the title compound (0.01 g, yield 10~30%).
$^1$H NMR (400 MHz, CDCl$_3$) δ 1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H).

Preparation Example 216: Synthesis of 1-(2,4-dichlorophenyl)-2-hydroxyhexyl-1-carbamate

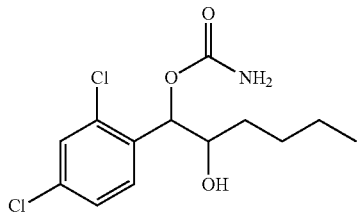 [SMILES: CCCCC(O)C(OC(N)=O)c1ccc(Cl)cc1Cl]

A regioisomer of monocarbamate was separated and purified by conducting the silica gel column chromatography as described in Preparation Example 163, to obtain the title compound (0.21 g, yield 10~30%).
$^1$H NMR (400 MHz, CDCl$_3$) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H).

Preparation Example 217: Synthesis of 1-(2,6-dichlorophenyl)-2-hydroxyhexyl-1-carbamate

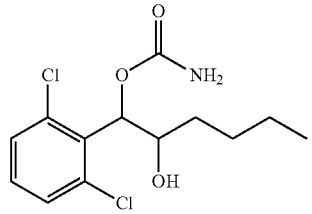 [SMILES: CCCCC(O)C(OC(N)=O)c1c(Cl)cccc1Cl]

A regioisomer of monocarbamate was separated and purified by conducting the silica gel column chromatography as described in Preparation Example 164, to obtain the title compound (0.12 g, yield 10~30%).
$^1$H NMR (400 MHz, CDCl$_3$) δ 0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H).

Preparation Example 218: Synthesis of 1-(2-iodophenyl)-(S)-1-hydroxy-3-methyl-butyl-(S)-2-carbamate

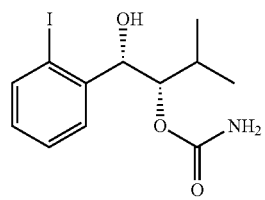 [SMILES: CC(C)[C@H](OC(N)=O)[C@@H](O)c1ccccc1I]

The substantially same method as described in Example 169 was conducted, except that 1-(2-iodophenyl)-3-methyl-(S,S)-1,2-butanediol (Preparation example 83) was used instead of 1-(2-iodophenyl)-(S,S)-1,2-butanediol (Preparation Example 68), to obtain the title compound (1.92 g, yield 20~50%).
$^1$H NMR (400 MHz, CDCl$_3$) δ 0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H).

Preparation Example 219: Synthesis of 1-(2-iodophenyl)-(S)-1-hydroxyhexyl-(S)-2-carbamate

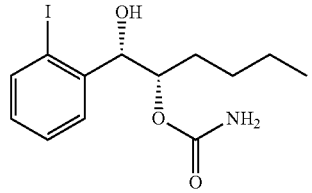 [SMILES: CCCC[C@H](OC(N)=O)[C@@H](O)c1ccccc1I]

The substantially same method as described in Preparation Example 103 was conducted, except that 1-(2-iodophenyl)-(S,S)-1,2-hexanediol obtained in Preparation Example 85 was used instead of 1-(2-chlorophenyl)-(S,S)-1,2-propanediol, to obtain the title compound (1.68 g, yield 60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.96~7.57 (m, 4H).

Preparation Example 220: Synthesis of 1-(2-iodophenyl)-(S)-1-hydroxypropyl-(S)-2-methylcarbamate

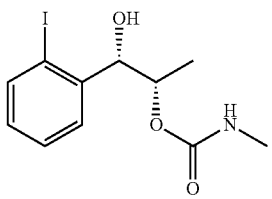

The substantially same method as described in Example 117 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.01 g, yield 20~50%).

$^1$H NMR (400 MHz, CDCl$_3$) δ 1.03~1.25 (m, 3H), 2.76 (s, 3H), 3.34 (s, 1H), 4.80 (br s 1H), 5.04 (t, J=12.5 Hz, 1H), 5.14 (s, 1H), 7.01~7.63 (m, 4H).

Preparation Example 221: Synthesis of 1-(2-iodophenyl)-(S)-1-hydroxypropyl-(S)-2-propylcarbamate

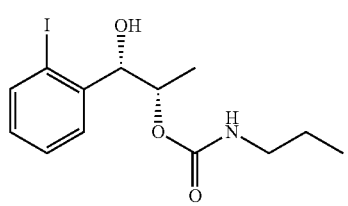

The substantially same method as described in Example 118 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.72 g, yield 20~50%).

$^1$H NMR (400 MHz, CDCl$_3$) δ 0.90 (t, J=6.8 Hz, 3H), 1.20 (d, J=6.0 Hz, 3H), 1.49 (dd, J=14.2 Hz, 2H), 3.11 (d, J=6.3 Hz, 2H), 3.34 (s, 1H), 4.84 (br s, 1H), 5.05 (t, J=5.9 Hz, 1H), 5.14 (s, 1H), 7.02~7.63 (m, 4H).

Preparation Example 222: Synthesis of 1-(2-iodophenyl)-(S)-1-hydroxypropyl-(S)-2-isopropylcarbamate

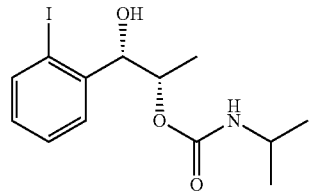 [SMILES: CC(C)NC(=O)O[C@@H](C)[C@@H](O)c1ccccc1I]

The substantially same method as described in Example 119 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ 1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H).

Preparation Example 223: Synthesis of 1-(2-iodophenyl)-(S)-1-hydroxypropyl-(S)-2-cyclopropylcarbamate

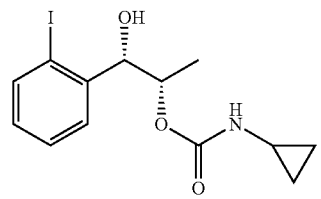 [SMILES: C[C@H](OC(=O)NC1CC1)[C@@H](O)c1ccccc1I]

The substantially same method as described in Example 120 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.02 g, yield 20~50%).

$^1$H NMR (400 MHz, CDCl$_3$) δ 0.50~0.56 (m, 2H), 0.74 (d, J=7.2 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.03~7.64 (m, 4H).

Preparation Example 224: Synthesis of 1-(2-iodophenyl)-(S)-1-hydroxypropyl-(S)-2-cyclohexyl carbamate

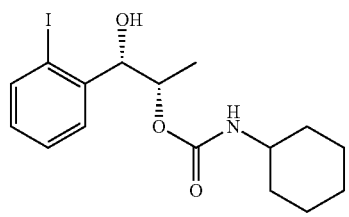 [SMILES: C[C@H](OC(=O)NC1CCCCC1)[C@@H](O)c1ccccc1I]

The substantially same method as described in Example 121 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.84 g, yield 20~50%).

$^1$H NMR (400 MHz, CDCl$_3$) δ 1.06~1.40 (m, 7H), 1.56~1.61 (m, 2H), 1.69~1.71 (m, 2H), 1.87~1.94 (m, 2H), 3.19 (d, J=4.3 Hz, 1H), 3.45 (s, 1H), 4.64 (br s 1H), 5.02~5.07 (m, 1H), 5.14 (t, J=6.1 Hz, 1H) 7.02~7.63 (m, 4H).

Preparation Example 225: Synthesis of 1-(2-iodo-phenyl)-(S)-1-hydroxypropyl-(S)-2-benzyl carbamate

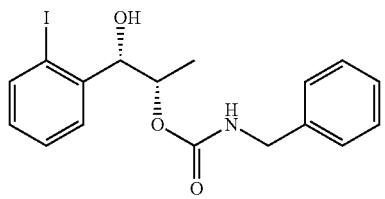 [SMILES: C[C@H](OC(=O)NCc1ccccc1)[C@@H](O)c1ccccc1I]

The substantially same method as described in Example 122 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.72 g, yield 20~50%).

$^1$H NMR (400 MHz, CDCl$_3$) δ 1.27 (d, J=10.0 Hz, 3H), 3.12 (d, J=5.0 Hz, 1H), 4.37 (d, J=6.0 Hz, 2H), 5.12~5.19 (m, 3H), 7.05~7.66 (m, 9H).

Preparation Example 226: Synthesis of 1-(2-chloro-phenyl)-(S)-1-hydroxypropyl-(S)-2-bicyclo[2,2,1] heptanescarbamate

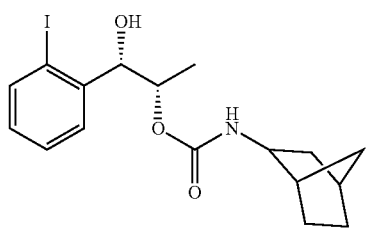 [SMILES: C[C@H](OC(=O)NC1CC2CCC1C2)[C@@H](O)c1ccccc1I]

The substantially same method as described in Example 123 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.82 g, yield 20~50%).

$^1$H NMR (400 MHz, CDCl$_3$) δ 1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H).

Preparation Example 227: Synthesis of 1-(2-fluoro-phenyl)-(S)-1-hydroxypropyl-(S)-2-methylcarbamate

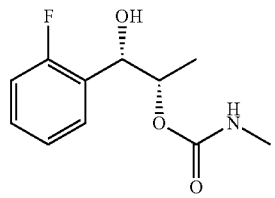

The substantially same method as described in Example 220 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (1.19 g, yield 20~50%).

$^1$H NMR (400 MHz, CDCl$_3$) δ 1.03~1.25 (m, 3H), 2.76 (s, 3H), 3.34 (s, 1H), 4.80 (br s 1H), 5.04 (t, J=12.5 Hz, 1H), 5.14 (s, 1H), 6.90~7.50 (m, 4H).

Preparation Example 228: Synthesis of 1-(2-fluoro-phenyl)-(S)-1-hydroxypropyl-(S)-2-propylcarbamate

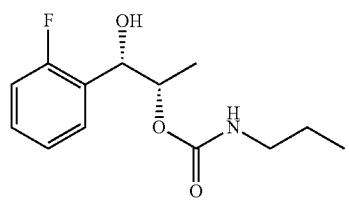

The substantially same method as described in Example 221 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.86 g, yield 20~50%).

$^1$H NMR (400 MHz, CDCl$_3$) δ 0.90 (t, J=6.8 Hz, 3H), 1.20 (d, J=6.0 Hz, 3H), 1.49 (dd, J=14.2 Hz, 2H), 3.11 (d, J=6.3 Hz, 2H), 3.34 (s, 1H), 4.84 (br s, 1H), 5.05 (t, J=5.9 Hz, 1H), 5.14 (s, 1H), 6.99~7.53 (m, 4H).

Preparation Example 229: Synthesis of 1-(2-fluoro-phenyl)-(S)-1-hydroxypropyl-(S)-2-isopropylcarbamate

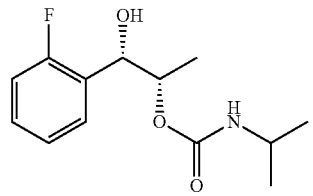 [SMILES: CC(C)NC(=O)O[C@@H](C)[C@@H](O)c1ccccc1F]

The substantially same method as described in Example 222 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.48 g, yield 20~50%).

¹H NMR (400 MHz, CDCl₃) δ 1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.62 (m, 4H).

Preparation Example 230: Synthesis of 1-(2-fluorophenyl)-(S)-1-hydroxypropyl-(S)-2-cyclopropylcarbamate

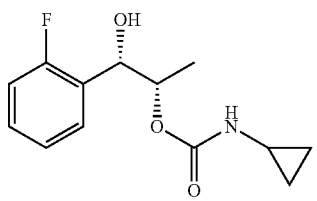

The substantially same method as described in Example 223 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%).

¹H NMR (400 MHz, CDCl₃) δ 0.50~0.56 (m, 2H), 0.74 (d, J=7.2 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.01~7.65 (m, 4H).

Preparation Example 231: Synthesis of 1-(2-fluorophenyl)-(S)-1-hydroxypropyl-(S)-2-cyclohexyl carbamate

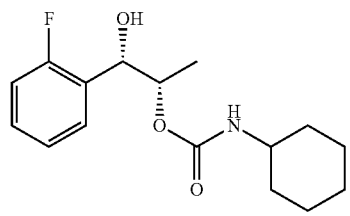 [SMILES: C[C@H](OC(=O)NC1CCCCC1)[C@@H](O)c1ccccc1F]

The substantially same method as described in Example 225 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.54 g, yield 20~50%).

¹H NMR (400 MHz, CDCl₃) δ 1.06~1.40 (m, 7H), 1.56~1.61 (m, 2H), 1.69~1.71 (m, 2H), 1.87~1.94 (m, 2H), 3.19 (d, J=4.3 Hz, 1H), 3.45 (s, 1H), 4.64 (br s 1H), 5.02~5.07 (m, 1H), 5.14 (t, J=6.1 Hz, 1H) 7.00~7.65 (m, 4H).

Preparation Example 232: Synthesis of 1-(2-fluorophenyl)-(S)-1-hydroxypropyl-(S)-2-benzyl carbamate

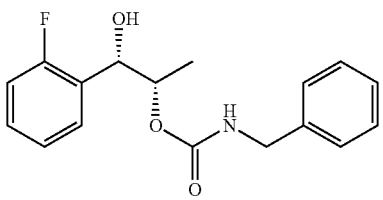 [SMILES: C[C@H](OC(=O)NCc1ccccc1)[C@@H](O)c1ccccc1F]

The substantially same method as described in Example 226 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%).

¹H NMR (400 MHz, CDCl₃) δ 1.27 (d, J=10.0 Hz, 3H), 3.12 (d, J=5.0 Hz, 1H), 4.37 (d, J=6.0 Hz, 2H), 5.12~5.19 (m, 3H), 7.01~7.67 (m, 9H).

Preparation Example 233: Synthesis of 1-(2-fluorophenyl)-(S)-1-hydroxypropyl-(S)-2-bicyclo[2,2,1]heptanescarbamate

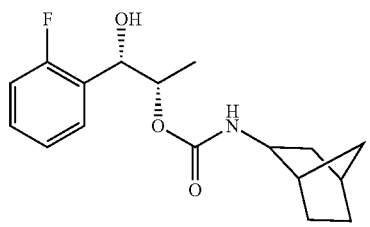 [SMILES: C[C@H](OC(=O)NC1CC2CCC1C2)[C@@H](O)c1ccccc1F]

The substantially same method as described in Example 227 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.57 g, yield 20~50%).

¹H NMR (400 MHz, CDCl₃) δ 1.08~1.35 (m, 9H), 1.65 (br s, 1H), 1.71~1.75 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.01~7.66 (m, 4H).

Preparation Example 234: Synthesis of 1-(2-iodophenyl)-(S)-1-hydroxybutyl-(S)-2-methylcarbamate

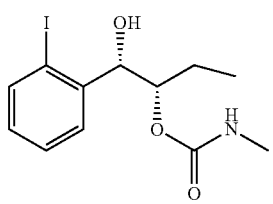 [SMILES: CC[C@H](OC(=O)NC)[C@@H](O)c1ccccc1I]

The substantially same method as described in Example 117 was conducted, except that 1-(2-iodophenyl)-(S,S)-1,2- butanediol (Preparation example 68) was used instead of 1-(2-iodophenyl)-(S,S)-1,2-propandiol (Preparation example 66), to obtain the title compound (1.81 g, yield 20~50%).

¹H NMR (400 MHz, CDCl₃) δ 0.97 (d, J=6.4 Hz, 3H), 1.56 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H).

Preparation Example 235: Synthesis of 1-(2-iodo-phenyl)-(S)-1-hydroxybutyl-(S)-2-propylcarbamate

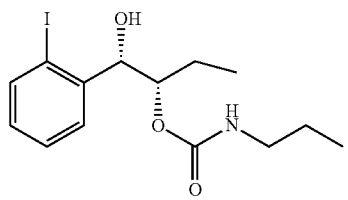 [SMILES: CCCNC(=O)O[C@@H](CC)[C@@H](O)c1ccccc1I]

The substantially same method as described in Example 118 was conducted, except that 1-(2-iodophenyl)-(S,S)-1,2-butanediol (Preparation example 68) was used instead of 1-(2-iodophenyl)-(S,S)-1,2-propandiol (Preparation example 66), to obtain the title compound (0.92 g, yield 20~50%).

¹H NMR (400 MHz, CDCl₃) δ 0.90 (t, J=6.8 Hz, 3H), 1.20 (d, J=6.0 Hz, 3H), 1.49 (dd, J=14.2 Hz, 2H), 1.57 (m, 2H), 3.11 (d, J=6.3 Hz, 2H), 3.34 (s, 1H), 4.84 (br s, 1H), 5.05 (t, J=5.9 Hz, 1H), 5.14 (s, 1H), 7.02~7.63 (m, 4H).

Preparation Example 236: Synthesis of 1-(2-iodo-phenyl)-(S)-1-hydroxybutyl-(S)-2-isopropylcarbamate

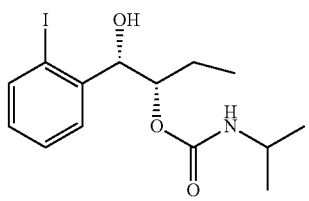 [SMILES: CC[C@H](OC(=O)NC(C)C)[C@@H](O)c1ccccc1I]

The substantially same method as described in Example 119 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.28 g, yield 20~50%).

¹H NMR (400 MHz, CDCl₃) δ 0.96 (t, J=6.8 Hz, 3H), 1.14 (dd, J=6.5 Hz, 6H), 1.57 (m, 2H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H).

Preparation Example 237: Synthesis of 1-(2-iodo-phenyl)-(S)-1-hydroxybutyl-(S)-2-cyclopropylcarbamate

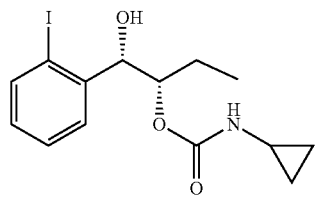 [SMILES: CC[C@H](OC(=O)NC1CC1)[C@@H](O)c1ccccc1I]

The substantially same method as described in Example 120 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.51 g, yield 20~50%).

¹H NMR (400 MHz, CDCl₃) δ 0.50~0.56 (m, 2H), 0.74 (d, J=7.2 Hz, 2H), 0.96 (t, J=6.8 Hz, 3H), 1.25 (m, 2H), 2.56~2.61 (m, 1H), 3.72 (s, 1H), 4.98 (br s, 1H), 5.05~5.11 (m, 1H), 7.16 (s, 1H), 6.96~7.57 (m, 4H).

Preparation Example 238: Synthesis of 1-(2-iodo-phenyl)-(S)-1-hydroxybutyl-(S)-2-cyclohexyl carbamate

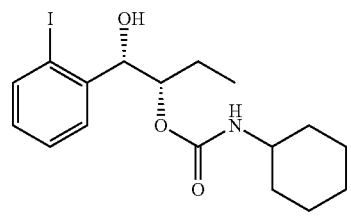 [SMILES: CC[C@H](OC(=O)NC1CCCCC1)[C@@H](O)c1ccccc1I]

The substantially same method as described in Example 121 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.92 g, yield 20~50%).

¹H NMR (400 MHz, CDCl₃) δ 0.96 (t, J=6.8 Hz, 3H), 1.06~1.40 (m, 7H), 1.56~1.61 (m, 2H), 1.69~1.71 (m, 2H), 1.87~1.94 (m, 2H), 3.19 (d, J=4.3 Hz, 1H), 3.45 (s, 1H), 4.64 (br s 1H), 5.02~5.07 (m, 1H), 5.14 (t, J=6.1 Hz, 1H), 7.02~7.63 (m, 4H).

Preparation Example 239: Synthesis of 1-(2-iodo-phenyl)-(S)-1-hydroxybutyl-(S)-2-benzyl carbamate

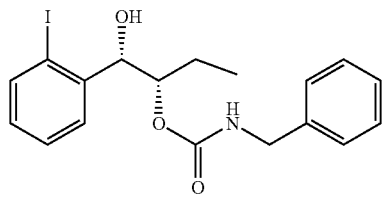 [SMILES: CC[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.52 g, yield 20~50%).

$^1$H NMR (400 MHz, CDCl$_3$) δ 0.96 (t, J=6.8 Hz, 3H), 1.55~1.62 (m, 2H), 3.12 (d, J=5.0 Hz, 1H), 4.37 (d, J=6.0 Hz, 2H), 5.12~5.19 (m, 3H), 7.05~7.66 (m, 9H).

Preparation Example 240: Synthesis of 1-(2-chlorophenyl)-(S)-1-hydroxybutyl-(S)-2-bicyclo[2,2,1]heptanescarbamate

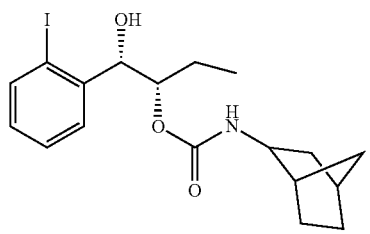 [SMILES: CC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ 0.96 (t, J=6.8 Hz, 3H), 1.08~1.35 (m, 6H), 1.55~1.62 (m, 2H), 1.65 (br s, 1H), 1.71~1.75 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H).

Preparation Example 241: Synthesis of 1-(2-iodophenyl)-(S)-1-hydroxy-3-methyl-butyl-(S)-2-methylcarbamate

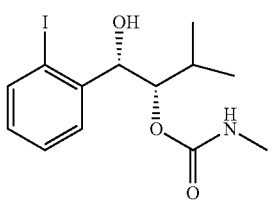 [SMILES: CNC(=O)O[C@@H](C(C)C)[C@@H](O)c1ccccc1I]

The substantially same method as described in Example 117 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.92 g, yield 20~50%).

$^1$H NMR (400 MHz, CDCl$_3$) δ 0.97 (d, J=6.4 Hz, 6H), 2.36~2.52 (m, 1H), 2.76 (s, 3H), 3.34 (s, 1H), 4.80 (br s 1H), 5.04 (t, J=12.5 Hz, 1H), 5.14 (s, 1H), 7.01~7.63 (m, 4H).

Preparation Example 242: Synthesis of 1-(2-iodophenyl)-(S)-1-hydroxy-3-methyl-butyl-(S)-2-propylcarbamate

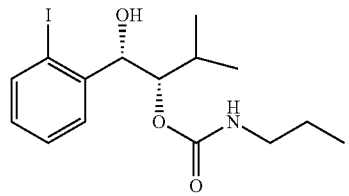 [SMILES: CCCNC(=O)O[C@@H](C(C)C)[C@@H](O)c1ccccc1I]

The substantially same method as described in Example 118 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.82 g, yield 20~50%).

$^1$H NMR (400 MHz, CDCl$_3$) δ 0.96 (t, J=6.8 Hz, 3H), 1.10 (d, J=6.4 Hz, 6H), 1.49 (dd, J=14.2 Hz, 2H), 2.38~2.42 (m, 1H), 3.11 (d, J=6.3 Hz, 2H), 3.34 (s, 1H), 4.84 (br s, 1H), 5.05 (t, J=5.9 Hz, 1H), 5.14 (s, 1H), 7.02~7.63 (m, 4H).

Preparation Example 243: Synthesis of 1-(2-iodophenyl)-(S)-1-hydroxy-3-methyl-butyl-(S)-2-isopropylcarbamate

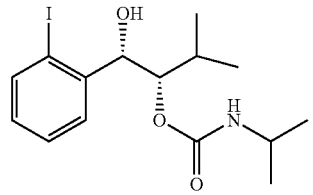 [SMILES: CC(C)NC(=O)O[C@@H](C(C)C)[C@@H](O)c1ccccc1I]

The substantially same method as described in Example 119 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.77 g, yield 20~50%).

$^1$H NMR (400 MHz, CDCl$_3$) δ 1.01 (d, J=6.8 Hz, 6H), 1.14 (d, J=6.5 Hz, 6H), 2.39~2.47 (m, 1H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H).

Preparation Example 244: Synthesis of 1-(2-iodophenyl)-(S)-1-hydroxy-3-methyl-butyl-(S)-2-cyclopropylcarbamate

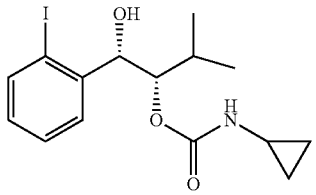 [SMILES: CC(C)[C@H](OC(=O)NC1CC1)[C@@H](O)c1ccccc1I]

The substantially same method as described in Example 120 was conducted, except that 1-(2-iodophenyl)-3-methyl- (S,S)-1,2-butanediol (Preparation example 83) was used instead of 1-(2-chlorophenyl)-(S,S)-1,2-propandiol (Preparation example 14), to obtain the title compound (1.81 g, yield 20~50%).

¹H NMR (400 MHz, CDCl₃) δ 0.50~0.56 (m, 2H), 0.74 (d, J=7.2 Hz, 2H), 1.01 (d, J=6.8 Hz, 6H), 2.38~2.44 (m, 1H), 2.56~2.61 (m, 1H), 3.72 (s, 1H), 4.98 (br s, 1H), 5.05~5.11 (m, 1H), 7.16 (s, 1H), 6.96~7.57 (m, 4H).

Preparation Example 245: Synthesis of 1-(2-iodophenyl)-(S)-1-hydroxy-3-methyl-butyl-(S)-2-cyclohexyl carbamate

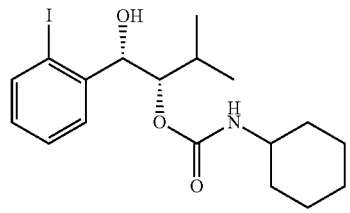 [SMILES: CC(C)[C@H](OC(=O)NC1CCCCC1)[C@@H](O)c1ccccc1I]

The substantially same method as described in Example 121 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.29 g, yield 20~50%).

¹H NMR (400 MHz, CDCl₃) δ 1.01 (d, J=6.8 Hz, 6H), 1.11~1.21 (m, 4H), 1.47~1.49 (m, 4H), 1.69~1.71 (m, 2H), 2.38~2.44 (m, 1H), 3.19 (d, J=4.3 Hz, 1H), 3.45 (s, 1H), 4.64 (br s 1H), 5.02~5.07 (m, 1H), 5.14 (t, J=6.1 Hz, 1H) 7.02~7.63 (m, 4H).

Preparation Example 246: Synthesis of 1-(2-iodophenyl)-(S)-1-hydroxy-3-methyl-butyl-(S)-2-benzyl carbamate

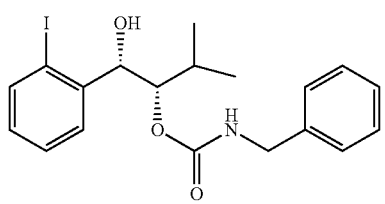 [SMILES: CC(C)[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.91 g, yield 20~50%).

¹H NMR (400 MHz, CDCl₃) δ 1.10 (d, J=6.8 Hz, 3H), 2.42 (m, 1H), 3.12 (d, J=5.0 Hz, 1H), 4.37 (d, J=6.0 Hz, 2H), 5.12~5.19 (m, 3H), 7.05~7.66 (m, 9H).

Preparation Example 247: Synthesis of 1-(2-chlorophenyl)-(S)-1-hydroxy-3-methyl-butyl-(S)-2-bicyclo[2,2,1]heptanescarbamate

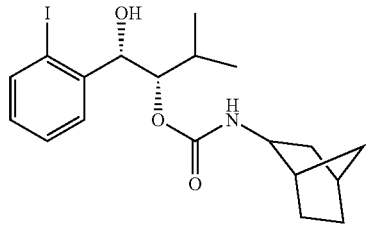 [SMILES: CC(C)[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

¹H NMR (400 MHz, CDCl₃) δ 1.01 (d, J=6.8 Hz, 6H), 1.08~1.35 (m, 6H), 1.55~1.62 (m, 2H), 1.65 (br s, 1H), 1.71~1.75 (m, 1H), 2.14~2.24 (m, 1H), 2.42 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H).

Preparation Example 248: Synthesis of 1-(2-iodophenyl)-(S)-1-hydroxyhexyl-(S)-2-methylcarbamate

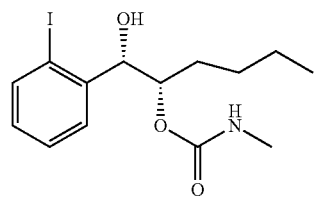 [SMILES: CCCC[C@H](OC(=O)NC)[C@@H](O)c1ccccc1I]

The substantially same method as described in Example 117 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.58 g, yield 20~50%).

¹H NMR (400 MHz, CDCl₃) δ 0.97 (t, J=6.4 Hz, 3H), 1.29~1.33 (m, 4H), 1.53 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H).

Preparation Example 249: Synthesis of 1-(2-iodophenyl)-(S)-1-hydroxyhexyl-(S)-2-propylcarbamate

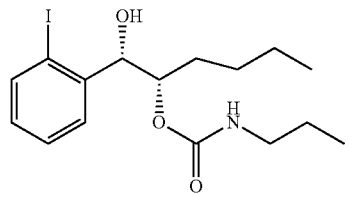 [SMILES: CCCC[C@H](OC(=O)NCCC)[C@@H](O)c1ccccc1I]

The substantially same method as described in Example 118 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.38 g, yield 20~50%).

¹H NMR (400 MHz, CDCl₃) δ 0.96 (t, J=6.8 Hz, 3H), 0.97 (t, J=6.4 Hz, 3H), 1.29~1.33 (m, 4H), 1.53 (m, 2H), 1.55~1.60 (m, 2H), 2.96 (t, J=6.0 Hz, 2H), 3.34 (s, 1H), 4.84 (br s, 1H), 5.05 (t, J=5.9 Hz, 1H), 5.14 (s, 1H), 7.02~7.63 (m, 4H).

Preparation Example 250: Synthesis of 1-(2-iodophenyl)-(S)-1-hydroxyhexyl-(S)-2-isopropylcarbamate

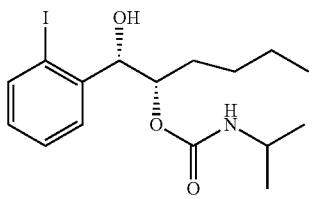 [SMILES: CCCC[C@H](OC(=O)NC(C)C)[C@@H](O)c1ccccc1I]

The substantially same method as described in Example 119 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.73 g, yield 20~50%).

¹H NMR (400 MHz, CDCl₃) δ 0.97 (t, J=6.4 Hz, 3H), 1.14 (d, J=6.5 Hz, 6H), 1.29~1.33 (m, 4H), 1.53 (m, 2H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H).

Preparation Example 251: Synthesis of 1-(2-iodophenyl)-(S)-1-hydroxyhexyl-(S)-2-cyclopropylcarbamate

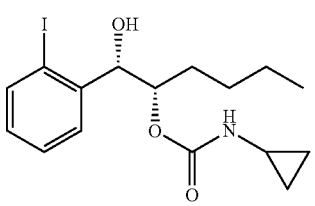 [SMILES: CCCC[C@H](OC(=O)NC1CC1)[C@@H](O)c1ccccc1I]

The substantially same method as described in Example 120 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.81 g, yield 20~50%).

¹H NMR (400 MHz, CDCl₃) δ 0.50~0.56 (m, 2H), 0.74 (d, J=7.2 Hz, 2H), 0.97 (t, J=6.4 Hz, 3H), 1.29~1.33 (m, 4H), 1.53 (m, 2H), 2.38~2.44 (m, 1H), 3.72 (s, 1H), 4.98 (br s, 1H), 5.05~5.11 (m, 1H), 7.16 (s, 1H), 6.96~7.57 (m, 4H).

Preparation Example 252: Synthesis of 1-(2-iodophenyl)-(S)-1-hydroxyhexyl-(S)-2-cyclohexyl carbamate

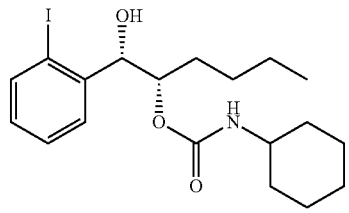 [SMILES: CCCC[C@H](OC(=O)NC1CCCCC1)[C@@H](O)c1ccccc1I]

The substantially same method as described in Example 121 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.79 g, yield 20~50%).

¹H NMR (400 MHz, CDCl₃) δ 0.97 (t, J=6.4 Hz, 3H), 1.11~1.21 (m, 4H), 1.29~1.33 (m, 4H), 1.47~1.49 (m, 4H), 1.53 (m, 2H), 1.69~1.71 (m, 2H), 3.19 (d, J=4.3 Hz, 1H), 3.45 (s, 1H), 4.64 (br s 1H), 5.02~5.07 (m, 1H), 5.14 (t, J=6.1 Hz, 1H) 7.02~7.63 (m, 4H).

Preparation Example 253: Synthesis of 1-(2-iodophenyl)-(S)-1-hydroxyhexyl-(S)-2-benzyl carbamate

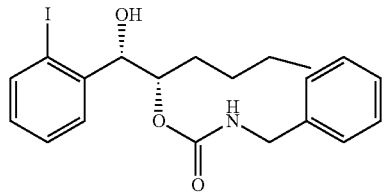 [SMILES: CCCC[C@H](OC(=O)NCc1ccccc1)[C@@H](O)c1ccccc1I]

The substantially same method as described in Example 122 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.51 g, yield 20~50%).

¹H NMR (400 MHz, CDCl₃) δ 0.97 (t, J=6.4 Hz, 3H), 1.29~1.33 (m, 4H), 1.53 (m, 2H), 3.12 (d, J=5.0 Hz, 1H), 4.37 (d, J=6.0 Hz, 2H), 5.12~5.19 (m, 3H), 7.05~7.66 (m, 9H).

Preparation Example 254: Synthesis of 1-(2-chlorophenyl)-(S)-1-hydroxyhexyl-(S)-2-bicyclo[2,2,1]heptanescarbamate

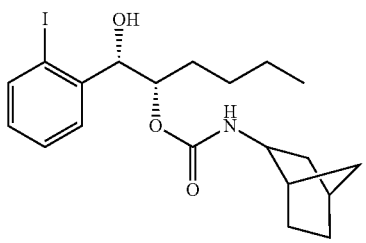 [SMILES: CCCC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

$^1$H NMR (400 MHz, CDCl$_3$) δ 0.97 (t, J=6.4 Hz, 3H), 1.08~1.35 (m, 6H), 1.29~1.33 (m, 4H), 1.53 (m, 2H), 1.55~1.62 (m, 2H), 1.65 (br s, 1H), 1.71~1.75 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H).

Preparation Example 255: Synthesis of 1-(3-iodophenyl)-(S)-1-hydroxypropyl-(S)-2-carbamate

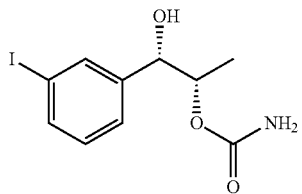

The substantially same method as described in Preparation Example 103 was conducted, except that 1-(3-iodophenyl)-(S,S)-1,2-butanediol obtained in Preparation Example 87 was used instead of 1-(2-chlorophenyl)-(S,S)-1,2-propanediol, to obtain the title compound (2.04 g, yield 60%).

$^1$H NMR (400 MHz, CDCl$_3$) δ 0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H).

Preparation Example 256: Synthesis of 1-(3-iodophenyl)-(S)-1-hydroxybutyl-(S)-2-carbamate

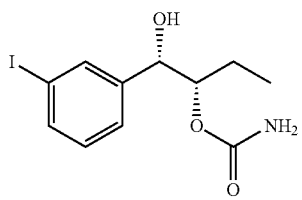 [SMILES: CC[C@H](OC(N)=O)[C@@H](O)c1cccc(I)c1]

The substantially same method as described in Preparation Example 103 was conducted, except that 1-(3-iodophenyl)-(S,S)-1,2-butanediol obtained in Preparation Example 89 was used instead of 1-(2-chlorophenyl)-(S,S)-1,2-propanediol, to obtain the title compound (1.49 g, yield 60%).

$^1$H NMR (400 MHz, CDCl$_3$) δ 0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H).

Preparation Example 257: Synthesis of 1-(3-iodophenyl)-(S)-1-hydroxy-3-methyl-butyl-(S)-2-carbamate

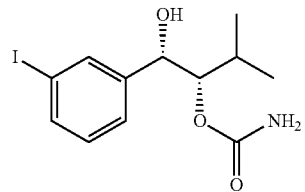 [SMILES: CC(C)[C@H](OC(N)=O)[C@@H](O)c1cccc(I)c1]

The substantially same method as described in Preparation Example 103 was conducted, except that 1-(3-iodophenyl)-3-methyl-(S,S)-1,2-butanediol obtained in Preparation Example 91 was used instead of 1-(2-chlorophenyl)-(S,S)-1,2-propanediol, to obtain the title compound (1.82 g, yield 30~60%).

$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H).

Preparation Example 258: Synthesis of 1-(3-iodophenyl)-(S)-1-hydroxyhexyl-(S)-2-carbamate

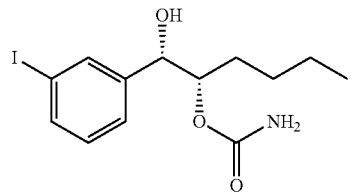 [SMILES: CCCC[C@H](OC(N)=O)[C@@H](O)c1cccc(I)c1]

The substantially same method as described in Preparation Example 103 was conducted, except that 1-(3-iodophenyl)-(S,S)-1,2-hexanediol obtained in Preparation Example 93 was used instead of 1-(2-chlorophenyl)-(S,S)-1,2-propanediol, to obtain the title compound (1.92 g, yield 30~60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H).

Preparation Example 259: Synthesis of 1-(4-fluorophenyl)-(S)-1-hydroxypropyl-(S)-2-carbamate

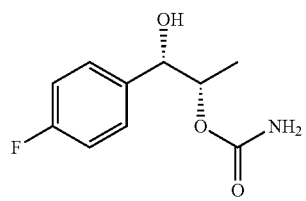

The substantially same method as described in Preparation Example 103 was conducted, except that 1-(4-fluorophenyl)-(S,S)-1,2-propanediol obtained in Preparation Example 95 was used instead of 1-(2-chlorophenyl)-(S,S)-1,2-propanediol, to obtain the title compound (1.61 g, yield 30~60%).

¹H NMR (400 MHz, CDCl₃) δ 1.27 (d, J=6.4 Hz, 3H), 3.09 (br s, 1H), 4.83 (br s, 2H), 5.00~5.10 (m, 2H), 6.89~7.05 (m, 4H).

Preparation Example 260: Synthesis of 1-(4-fluorophenyl)-(S)-1-hydroxybutyl-(S)-2-carbamate

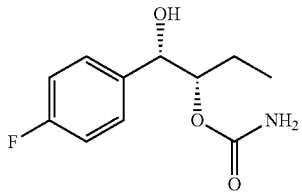 [SMILES: CC[C@H](OC(N)=O)[C@@H](O)c1ccc(F)cc1]

The substantially same method as described in Preparation Example 103 was conducted, except that 1-(4-fluorophenyl)-(S,S)-1,2-butanediol obtained in Preparation Example 97 was used instead of 1-(2-chlorophenyl)-(S,S)-1,2-propanediol, to obtain the title compound (1.55 g, yield 30~60%).

¹H NMR (400 MHz, CDCl₃) δ 0.96 (t. J=7.4 Hz, 3H), 1.53~1.73 (m, 2H), 3.09 (br s, 1H), 4.83 (br s, 2H), 5.00~5.10 (m, 2H), 6.92~7.09 (m, 4H).

Preparation Example 261: Synthesis of 1-(4-fluorophenyl)-(S)-1-hydroxy-3-methyl-butyl-(S)-2-carbamate

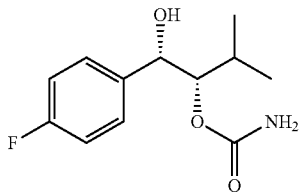 [SMILES: CC(C)[C@H](OC(N)=O)[C@@H](O)c1ccc(F)cc1]

The substantially same method as described in Preparation Example 103 was conducted, except that 1-(4-fluorophenyl)-3-methyl-(S,S)-1,2-butanediol obtained in Preparation Example 99 was used instead of 1-(2-chlorophenyl)-(S,S)-1,2-propanediol, to obtain the title compound (1.97 g, yield 30~60%).

¹H NMR (400 MHz, CDCl₃) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.94~7.03 (m, 4H).

Preparation Example 262: Synthesis of 1-(4-fluorophenyl)-(S)-1-hydroxyhexyl-(S)-2-carbamate

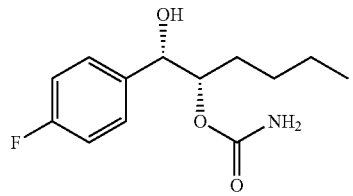 [SMILES: CCCC[C@H](OC(N)=O)[C@@H](O)c1ccc(F)cc1]

The substantially same method as described in Preparation Example 103 was conducted, except that 1-(4-fluorophenyl)-(S,S)-1,2-hexanediol obtained in Preparation Example 101 was used instead of 1-(2-chlorophenyl)-(S,S)-1,2-propanediol, to obtain the title compound (1.86 g, yield 30~60%).

¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.17 (m, 4H).

Preparation Example 263: Synthesis of 1-(2-iodophenyl)-(R)-1-hydroxybutyl-(R)-2-carbamate

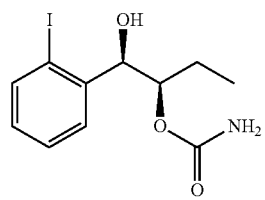 [SMILES: CC[C@@H](OC(N)=O)[C@H](O)c1ccccc1I]

The substantially same method as described in Preparation Example 103 was conducted, except that 1-(2-iodophenyl)-(R,R)-1,2-butanediol obtained in Preparation Example 69 was used instead of 1-(2-chlorophenyl)-(S,S)-1,2-propanediol, to obtain the title compound (1.98 g, yield 30~60%).

¹H NMR (400 MHz, CDCl₃) δ 1.27 (d, J=6.4 Hz, 3H), 3.09 (br s, 1H), 4.83 (br s, 2H), 5.00~5.10 (m, 2H), 7.00~7.76 (m, 4H).

Preparation Example 264: Synthesis of 1-(2-iodophenyl)-(R)-1-hydroxy-3-methyl-butyl-(R)-2-carbamate

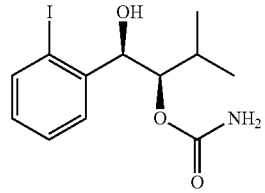 [SMILES: CC(C)[C@@H](OC(N)=O)[C@H](O)c1ccccc1I]

The substantially same method as described in Example 169 was conducted, except that 1-(2-iodophenyl)-3-methyl-(R,R)-1,2-butanediol (Preparation example 84) was used instead of 1-(2-iodophenyl)-(S,S)-1,2-butanediol (Preparation Example 68), to obtain the title compound (1.88 g, yield 20~50%).

¹H NMR (400 MHz, CDCl₃) δ 0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H).

Preparation Example 265: Synthesis of 1-(2-iodo-phenyl)-(R)-1-hydroxyhexyl-(R)-2-carbamate

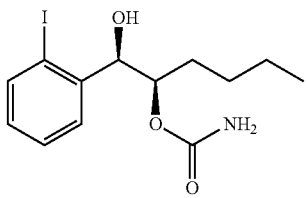 [SMILES: CCCC[C@@H](OC(N)=O)[C@H](O)c1ccccc1I]

The substantially same method as described in Preparation Example 103 was conducted, except that 1-(2-iodophenyl)-(R,R)-1,2-hexanediol obtained in Preparation Example 86 was used instead of 1-(2-chlorophenyl)-(S,S)-1,2-propanediol, to obtain the title compound (1.68 g, yield 60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.99~7.55 (m, 4H).

Preparation Example 266: Synthesis of 1-(4-fluoro-phenyl)-(R)-1-hydroxypropyl-(R)-2-carbamate

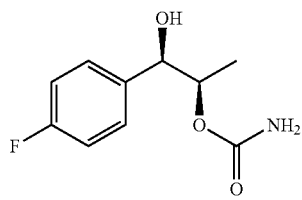

The substantially same method as described in Preparation Example 103 was conducted, except that 1-(4-fluorophenyl)-(R,R)-1,2-propanediol obtained in Preparation Example 96 was used instead of 1-(2-chlorophenyl)-(S,S)-1,2-propanediol, to obtain the title compound (1.49 g, yield 30~60%).

$^1$H NMR (400 MHz, CDCl$_3$) δ 1.27 (d, J=6.4 Hz, 3H), 3.09 (br s, 1H), 4.83 (br s, 2H), 5.00~5.10 (m, 2H), 7.00~7.22 (m, 4H).

Preparation Example 267: Synthesis of 1-(4-fluoro-phenyl)-(R)-1-hydroxybutyl-(R)-2-carbamate

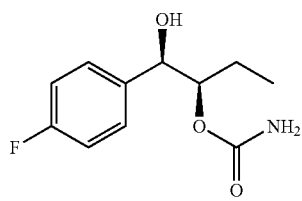 [SMILES: CC[C@@H](OC(N)=O)[C@H](O)c1ccc(F)cc1]

The substantially same method as described in Preparation Example 103 was conducted, except that 1-(4-fluorophenyl)-(R,R)-1,2-butanediol obtained in Preparation Example 98 was used instead of 1-(2-chlorophenyl)-(S,S)-1,2-propanediol, to obtain the title compound (2.25 g, yield 30~60%).

$^1$H NMR (400 MHz, CDCl$_3$) δ 0.96 (t, J=7.4 Hz, 3H), 1.53~1.73 (m, 2H), 3.09 (br s, 1H), 4.83 (br s, 2H), 5.00~5.10 (m, 2H), 6.92~7.20 (m, 4H).

Preparation Example 268: Synthesis of 1-(4-fluoro-phenyl)-(R)-1-hydroxy-3-methyl-butyl-(R)-2-carbamate

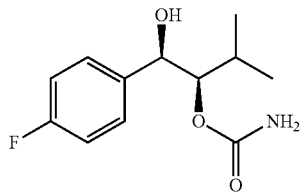 [SMILES: CC(C)[C@@H](OC(N)=O)[C@H](O)c1ccc(F)cc1]

The substantially same method as described in Preparation Example 103 was conducted, except that 1-(4-fluorophenyl)-3-methyl-(R,R)-1,2-butanediol obtained in Preparation Example 100 was used instead of 1-(2-chlorophenyl)-(S,S)-1,2-propanediol, to obtain the title compound (1.74 g, yield 30~60%).

$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.92~7.20 (m, 4H).

Preparation Example 269: Synthesis of 1-(4-fluoro-phenyl)-(R)-1-hydroxyhexyl-(R)-2-carbamate

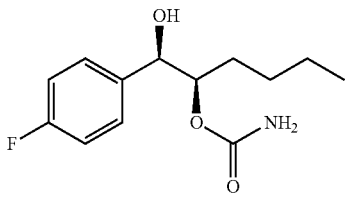 [SMILES: CCCC[C@@H](OC(N)=O)[C@H](O)c1ccc(F)cc1]

The substantially same method as described in Preparation Example 103 was conducted, except that 1-(4-fluorophenyl)-(R,R)-1,2-hexanediol obtained in Preparation Example 102 was used instead of 1-(2-chlorophenyl)-(S,S)-1,2-propanediol, to obtain the title compound (1.59 g, yield 30~60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.21 (m, 4H).

Preparation Example 270: Synthesis of 1-(3-iodo-phenyl)-(R)-1-hydroxypropyl-(R)-2-carbamate

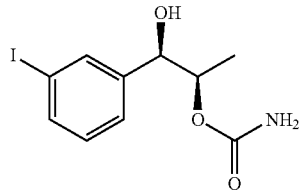

The substantially same method as described in Preparation Example 103 was conducted, except that 1-(3-iodophenyl)-(R,R)-1,2-butanediol obtained in Preparation Example 88 was used instead of 1-(2-chlorophenyl)-(S,S)-1,2-propanediol, to obtain the title compound (1.54 g, yield 30~60%).

$^1$H NMR (400 MHz, CDCl$_3$) δ 0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H).

Preparation Example 271: Synthesis of 1-(3-iodophenyl)-(R)-1-hydroxybutyl-(R)-2-carbamate

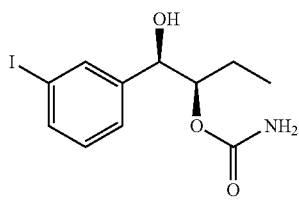 [SMILES: CC[C@@H](OC(N)=O)[C@H](O)c1cccc(I)c1]

The substantially same method as described in Preparation Example 103 was conducted, except that 1-(3-iodophenyl)-(R,R)-1,2-butanediol obtained in Preparation Example 90 was used instead of 1-(2-chlorophenyl)-(S,S)-1,2-propanediol, to obtain the title compound (1.44 g, yield 30~60%).

$^1$H NMR (400 MHz, CDCl$_3$) δ 0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H).

Preparation Example 272: Synthesis of 1-(3-iodophenyl)-(R)-1-hydroxy-3-methyl-butyl-(R)-2-carbamate

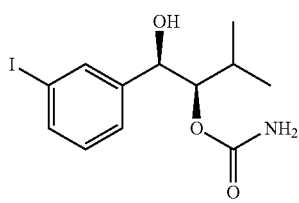 [SMILES: CC(C)[C@@H](OC(N)=O)[C@H](O)c1cccc(I)c1]

The substantially same method as described in Preparation Example 103 was conducted, except that 1-(3-iodophenyl)-3-methyl-(R,R)-1,2-butanediol obtained in Preparation Example 92 was used instead of 1-(2-chlorophenyl)-(S,S)-1,2-propanediol, to obtain the title compound (1.65 g, yield 30~60%).

$^1$H NMR (400 MHz, CDCl$_3$) δ 1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H).

Preparation Example 273: Synthesis of 1-(3-iodophenyl)-(R)-1-hydroxyhexyl-(R)-2-carbamate

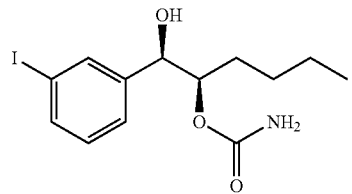 [SMILES: CCCC[C@@H](OC(N)=O)[C@H](O)c1cccc(I)c1]

The substantially same method as described in Preparation Example 103 was conducted, except that 1-(3-iodophenyl)-(R,R)-1,2-hexanediol obtained in Preparation Example 94 was used instead of 1-(2-chlorophenyl)-(S,S)-1,2-propanediol, to obtain the title compound (1.71 g, yield 60%).

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H).

Preparation Example 274: Synthesis of 1-(2,6-difluorophenyl)-trans-1-propene

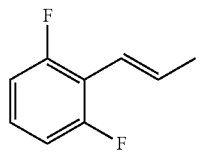

The substantially same method as described in Preparation Example 1 was conducted, except that 2,6-difluorobenzenaldehyde was used instead of 2-chlorobenzenaldehyde, to obtain the title compound (3.4 g, yield 52%).

$^1$H NMR (400 MHz, CDCl$_3$) δ 1.95 (dd, J=1.6, 6.8 Hz, 3H), 6.24 (m, 1H), 6.72 (d, J=15.6 Hz, 1H), 7.18~7.44 (m, 3H).

Preparation Example 275: Synthesis of 1-(2,6-difluorophenyl)-(S,S)-1,2-propanediol

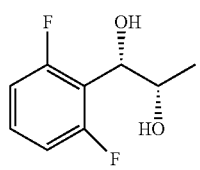

The substantially same method as described in Preparation Example 14 was conducted, except that 1-(2,6-difluorophenyl)-trans-1-propene (Preparation Example 275) was used instead of 1-(2-chlorophenyl)-trans-1-propene (Preparation Example 1), to obtain the title compound (1.5 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H).

Preparation Example 276: Synthesis of 1-(2,6-difluorophenyl)-(S)-1-hydroxypropyl-(S)-2-carbamate

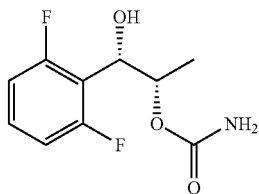 [SMILES: C[C@H](OC(N)=O)[C@@H](O)c1c(F)cccc1F]

The substantially same method as described in Preparation Example 103 was conducted, except that 1-(2,6-difluorophenyl)-1,2-propanediol (Preparation Example 275) was used instead of 1-(2-chlorophenyl)-(S,S)-1,2-propanediol, to obtain the title compound (2.4 g, yield 20~60%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 277: Synthesis of 1-(2,5-dichlorophenyl)-trans-1-propene

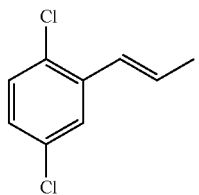

The substantially same method as described in Preparation Example 1 was conducted, except that 2,5-dichlorobenzenaldehyde was used instead of 2-chlorobenzenaldehyde, to obtain the title compound (3.1 g, yield 52%).

$^1$H NMR (400 MHz, CDCl$_3$) δ 1.95 (dd, J=1.6, 6.8 Hz, 3H), 6.24 (m, 1H), 6.72 (d, J=15.6 Hz, 1H), 7.09~7.25 (m, 3H).

Preparation Example 278: Synthesis of 1-(2,5-dichlorophenyl)-(S,S)-1,2-propanediol

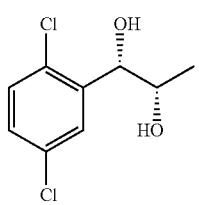

The substantially same method as described in Preparation Example 14 was conducted, except that 1-(2,5-dichlorophenyl)-trans-1-propene (Preparation Example 277) was used instead of 1-(2-chlorophenyl)-trans-1-propene (Preparation Example 1), to obtain the title compound (1.9 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H).

Preparation Example 279: Synthesis of 1-(2,5-dichlorophenyl)-1-hydroxypropyl-2-carbamate

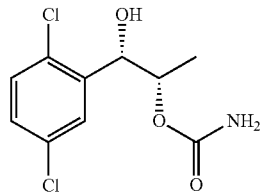 [SMILES: C[C@H](OC(N)=O)[C@@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.29 g, yield 20~60%).

$^1$H NMR (400 MHz, CDCl$_3$) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H).

Preparation Example 280: Synthesis of 1-(2,5-dichlorophenyl)-(R,R)-1,2-propanediol

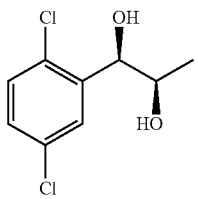

The substantially same method as described in Preparation Example 15 was conducted, except that 1-(2,5-dichlorophenyl)-trans-1-propene (Preparation Example 277) was used instead of 1-(2-chlorophenyl)-trans-1-propene (Preparation Example 1), to obtain the title compound (2.3 g, yield 60~90%).

$^1$H NMR (400 MHz, CDCl$_3$) δ 1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H).

Preparation Example 281: Synthesis of 1-(2,5-dichlorophenyl)-(R)-1-hydroxypropyl-(R)-2-carbamate

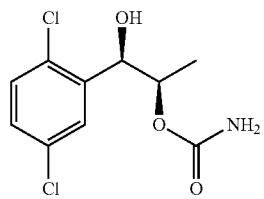 [SMILES: C[C@@H](OC(N)=O)[C@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.25 g, yield 20~60%).

¹H NMR (400 MHz, CDCl₃) δ 1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.13~7.25 (m, 3H).

Preparation Example 282: Synthesis of 1-(2-chlorophenyl)-1-(S)-1,2-ethanediol

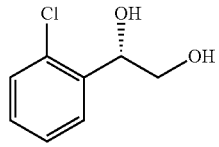 [SMILES: OC[C@@H](O)c1ccccc1Cl]

The substantially same method as described in Preparation Example 14 was conducted, except that 2-chlorostyrene (Aldrich No. 160679) was used instead of 1-(2-chlorophenyl)-trans-1-propene (Preparation Example 1), to obtain the title compound (2.29 g, yield 60~90%).

¹H NMR (400 MHz, CDCl₃) δ 2.72 (d, J=2.4 Hz, 1H), 3.10 (d, J=8.4 Hz, 1H), 4.47~4.54 (m, 1H), 4.91 (t, J=8.8 Hz, 1H), 7.09~7.26 (m, 4H).

Preparation Example 283: Synthesis of 1-(2-chlorophenyl)-(S)-1-hydroxyethyl-2-carbamate

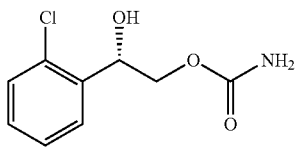

The substantially same method as described in Preparation Example 103 was conducted, except that 1-(2-chlorophenyl)-1-(S)-1,2-ethanediol (Preparation Example 282) was used instead of 1-(2-chlorophenyl)-(S,S)-1,2-propanediol, to obtain the title compound (1.92 g, yield 20~60%).

¹H NMR (400 MHz, CDCl₃) δ 1.72 (br s, 1H), 4.26 (dd, J=7.8, 12.0 Hz, 1H), 4.39 (dd, J=2.7, 12.0 Hz, 1H), 4.41 (dd, J=2.7, 7.8 Hz, 1H), 4.77 (br 2H), 7.26~7.68 (m, 4H).

Preparation Example 284: Synthesis of 2-iodostyrene

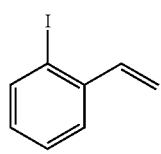

The substantially same method as described in Preparation Example 64 was conducted, except that 2-propanone was used instead of 3-pentanone, to obtain the title compound (2.1 g, yield 40%).

¹H NMR (400 MHz, CDCl₃) δ 5.34 (dd, J=0.8, 10.8 Hz, 1H), 5.65 (dd, J=0.8, 17.2 Hz, 1H), 6.89~7.92 (m, 5H).

Preparation Example 285: Synthesis of 1-(2-iodophenyl)-1-(S)-1,2-ethanediol

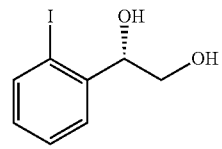 [SMILES: OC[C@@H](O)c1ccccc1I]

The substantially same method as described in Preparation Example 14 was conducted, except that 2-iodostyrene (Preparation Example 284) was used instead of 1-(2-chlorophenyl)-trans-1-propene (Preparation Example 1), to obtain the title compound (2.52 g, yield 60~90%).

¹H NMR (400 MHz, CDCl₃) δ 2.07~2.13 (m, 1H), 3.52~3.58 (m, 1H), 3.89~3.94 (m, 1H), 5.04~5.08 (m, 1H), 7.01~7.85 (m, 4H).

Preparation Example 286: Synthesis of 1-(2-iodophenyl)-(S)-1-hydroxyethyl-2-carbamate

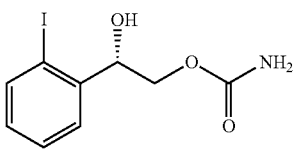 [SMILES: NC(=O)OC[C@@H](O)c1ccccc1I]

The substantially same method as described in Preparation Example 103 was conducted, except that 1-(2-chlorophenyl)-1-(S)-1,2-ethanediol (Preparation Example 282) was used instead of 1-(2-chlorophenyl)-(S,S)-1,2-propanediol, to obtain the title compound (1.92 g, yield 20~60%).

¹H NMR (400 MHz, CDCl₃) δ 1.72 (br s, 1H), 4.26 (dd, J=7.8, 12.0 Hz, 1H), 4.39 (dd, J=2.7, 12.0 Hz, 1H), 4.41 (dd, J=2.7, 7.8 Hz, 1H), 4.77 (br 2H), 7.06~7.29 (m, 4H).

Preparation Example 287: Synthesis of 2-fluorostyrene

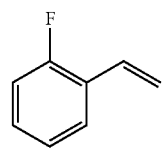

The substantially same method as described in Preparation Example 284 was conducted, except that 2-fluorobenzaldehyde (Aldrich No. F4807) was used instead of 2-iodobenzaldehyde (Preparation Example 63) to obtain the title compound (1.82 g, yield 20~40%).

¹H NMR (400 MHz, CDCl₃) δ 5.34 (dd, J=0.8, 10.8 Hz, 1H), 5.65 (dd, J=0.8, 17.2 Hz, 1H), 6.92~7.89 (m, 5H).

Preparation Example 288: Synthesis of 1-(2-fluorophenyl)-1-(S)-1,2-ethanediol

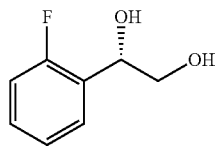 [SMILES: OC[C@@H](O)c1ccccc1F]

The substantially same method as described in Preparation Example 14 was conducted, except that 2-fluorostyrene (Preparation Example 287) was used instead of 1-(2-chlorophenyl)-trans-1-propene (Preparation Example 1), to obtain the title compound (2.32 g, yield 60~90%).

$^1$H NMR (400 MHz, CDCl$_3$) δ 2.07~2.13 (m, 1H), 3.52~3.58 (m, 1H), 3.89~3.94 (m, 1H), 5.04~5.08 (m, 1H), 6.90~7.17 (m, 4H).

Preparation Example 289: Synthesis of 1-(2-fluorophenyl)-(S)-1-hydroxyethyl-2-carbamate

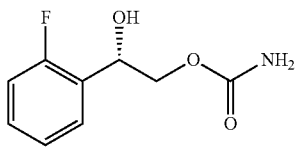 [SMILES: NC(=O)OC[C@@H](O)c1ccccc1F]

The substantially same method as described in Preparation Example 103 was conducted, except that 1-(2-fluorophenyl)-1-(S)-1,2-ethanediol (Preparation Example 288) was used instead of 1-(2-chlorophenyl)-(S,S)-1,2-propanediol, to obtain the title compound (1.59 g, yield 20~60%).

$^1$H NMR (400 MHz, CDCl$_3$) δ 1.72 (br s, 1H), 4.26 (dd, J=7.8, 12.0 Hz, 1H), 4.39 (dd, J=2.7, 12.0 Hz, 1H), 4.41 (dd, J=2.7, 7.8 Hz, 1H), 4.77 (br 2H), 7.01~7.27 (m, 4H).

Preparation Example 290: Synthesis of 1-(2-chloro-6-fluorophenyl)-trans-1-propene

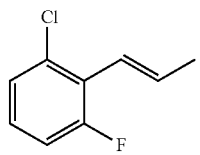

The substantially same method as described in Preparation Example 1 was conducted, except that 2-chloro-6-fluorobenzaldehyde was used instead of 2-chlorobenzaldehyde, to obtain the title compound (2.7 g, yield 40~80%).

$^1$H NMR (400 MHz, CDCl$_3$) δ 1.65 (d, J=7.2 Hz, 3H), 6.03~6.11 (m, 1H), 6.24 (d, J=11.2 Hz, 1H), 6.97~7.23 (m, 3H).

Preparation Example 291: Synthesis of 1-(2-chloro-6-fluorophenyl)-(S,S)-1,2-propanediol

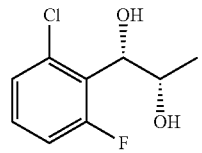

The substantially same method as described in Preparation Example 14 was conducted, except that 1-(2-chloro-6-fluorophenyl)-trans-1-propene (Preparation Example 290) was used instead of 1-(2-chlorophenyl)-trans-1-propene (Preparation Example 1), to obtain the title compound (1.6 g, yield 70~90%).

$^1$H NMR (400 MHz, CDCl$_3$) δ 1.13 (d, J=5.6 Hz, 3H), 2.78 (s, 1H), 2.92 (s, 1H), 4.17 (s, 1H), 5.01 (s, 1H) 6.03~6.11 (m, 1H), 6.24 (d, J=11.2 Hz, 1H), 6.97~7.23 (m, 3H).

Preparation Example 292: Synthesis of 1-(2-chloro-6-fluorophenyl)-(R,R)-1,2-propanediol

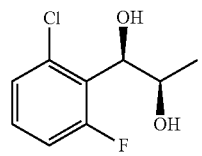

The substantially same method as described in Preparation Example 15 was conducted, except that 1-(2-chloro-6-fluorophenyl)-trans-1-propene (Preparation Example 290) was used instead of 1-(2-chlorophenyl)-trans-1-propene (Preparation Example 1), to obtain the title compound (1.9 g, yield 70~90%).

$^1$H NMR (400 MHz, CDCl$_3$) δ 1.13 (d, J=5.6 Hz, 3H), 2.78 (s, 1H), 2.92 (s, 1H), 4.17 (s, 1H), 5.01 (s, 1H) 6.03~6.11 (m, 1H), 6.24 (d, J=11.2 Hz, 1H), 6.97~7.23 (m, 3H).

Preparation Example 293: Synthesis of 1-(2-chloro-6-fluorophenyl)-(S)-1-hydroxypropyl-(S)-2-carbamate

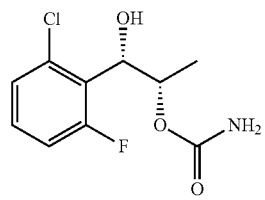 [SMILES: C[C@H](OC(N)=O)[C@@H](O)c1c(F)cccc1Cl]

The substantially same method as described in Preparation Example 103 was conducted, except that 1-(2-chloro-6-fluorophenyl)-(S,S)-1,2-propanediol (Preparation Example 291) was used instead of 1-(2-chlorophenyl)-(S,S)-1,2-propanediol (Preparation Example 14), to obtain the title compound (0.8 g, yield 30~60%).

¹H NMR (400 MHz, DMSO-d₆) δ 0.99 (d, J=6.4 Hz, 3H), 5.06 (d, J=8.8 Hz, 1H), 5.14~5.18 (m, 1H), 5.70 (s, 1H), 6.46 (brs, 2H), 7.19~7.40 (m, 3H).

Preparation Example 294: Synthesis of 1-(2-chloro-6-fluorophenyl)-(R)-1-hydroxypropyl-(R)-2-carbamate

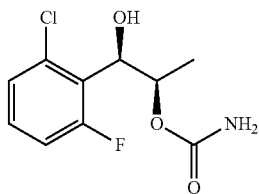 [SMILES: C[C@@H](OC(N)=O)[C@H](O)c1c(F)cccc1Cl]

The substantially same method as described in Preparation Example 103 was conducted, except that 1-(2-chloro-6-fluorophenyl)-(R,R)-1,2-propanediol (Preparation Example 292) was used instead of 1-(2-chlorophenyl)-(S,S)-1,2-propanediol (Preparation Example 14), to obtain the title compound (0.6 g, yield 30~60%).

¹H NMR (400 MHz, DMSO-d₆) δ 0.99 (d, J=6.4 Hz, 3H), 5.06 (d, J=8.8 Hz, 1H), 5.14~5.18 (m, 1H), 5.70 (s, 1H), 6.46 (brs, 2H), 7.19~7.40 (m, 3H).

Preparation Example 295: Synthesis of 1-(2-fluorophenyl)-(S)-2-hydroxypropyl-(S)-1-carbamate

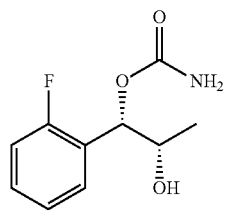

A regioisomer of monocarbamate was separated and purified by conducting the silica gel column chromatography as described in Preparation Example 165, to obtain the title compound (0.25 g, yield 10~30%).

¹H NMR (400 MHz, CDCl₃) δ 1.12 (d, J=6.8 Hz, 3H), 2.46 (d, J=4.0 Hz, 1H), 4.61~4.70 (m, 1H), 4.74 (br s, 2H), 6.19 (d, J=8.8 Hz, 1H), 7.28~7.49 (m, 4H).

Preparation Example 296: Synthesis of 1-(2-iodophenyl)-(S)-2-hydroxypropyl-(S)-1-carbamate

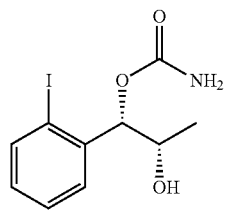

A regioisomer of monocarbamate was separated and purified by conducting the silica gel column chromatography as described in Preparation Example 167, to obtain the title compound (0.17 g, yield 10~30%).

¹H NMR (400 MHz, CDCl₃) δ 1.28 (d, J=8.4 Hz, 3H), 2.10 (d, J=5.2 Hz, 1H), 4.12~4.16 (m, 1H), 4.84 (brs, 2H), 5.79 (s, J=5.2 Hz, 1H), 7.0~7.39 (m, 3H), 7.87 (d, J=8.4 Hz, 1H).

Example Scheme I: Synthesis of 1-(n-halophenyl)-1-methoxymethoxyalkyl-2-alkylcarbamate (Examples 1 to 123, 271 to 274, 276 to 278 and 282, 284)

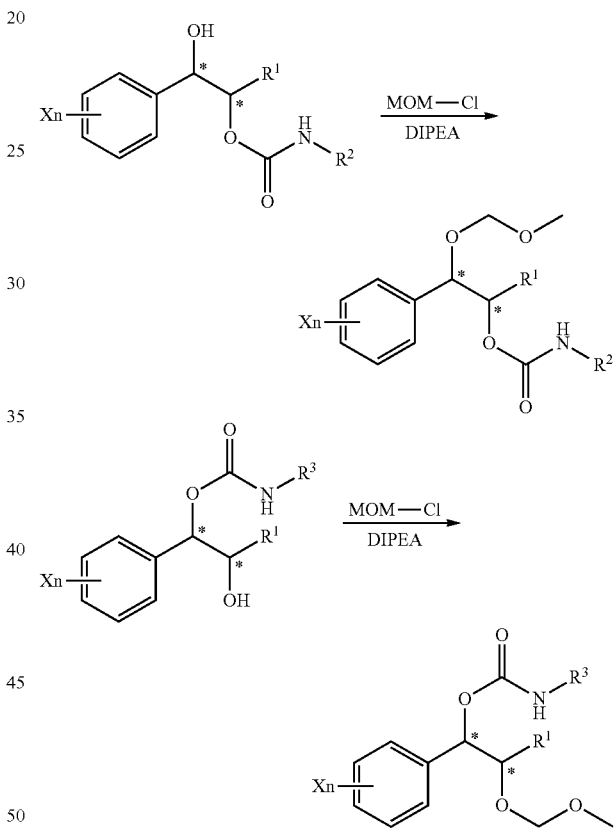

To a stirred solution of 1-(n-halophenyl)-1-hydorxyalkyl-2-alkylcarbamate in MC (Methylenechloloride) was added DIPEA(Diisopropylethylamine) at 0° C. under N₂ condition.

The mixture was added MOM-Cl (MOM-chloride) at 0° C. then slowly warm to R.T. When the reaction was completed, the obtained product was washed with H₂O and MC. The separated organic layer was dehydrated with anhydrous MgSO₄ (Magnesium sulfate), filtrated, and concentrated under reduced pressure. The concentrated residue was purified by a silica gel column chromatography, to obtain title compound (yield 40~60%).

Example scheme II: Synthesis of 1-(n-halophenyl)-1-methoxyalkyl-2-alkylcarbamate (Examples 124 to 246, 275, 279 to 281 and 283, 285)

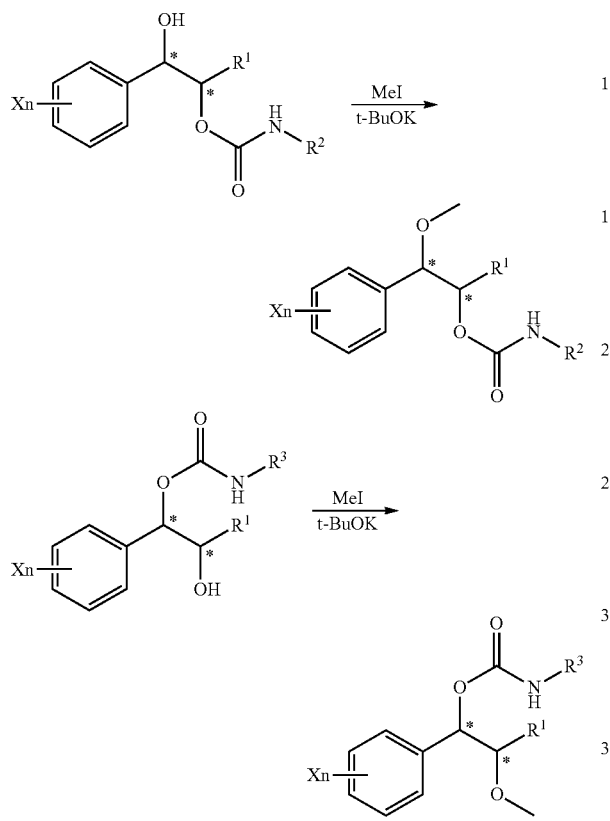

1-(n-halophenyl)-1-hydorxyalkyl-2-alkylcarbamate, THF (Tetrahydrofuran), MeI (Methyliodide) and t-BuOH (Potassium tert-butoxide) were put into a flask and stirred at the 0° C. When the reaction was completed, the obtained product was washed with 1 M HCl solution and EA (Ethylacetate). The separated organic layer was dehydrated with anhydrous MgSO$_4$ (Magnesium sulfate), filtrated, and concentrated under reduced pressure. The concentrated residue was purified by a silica gel column chromatography, to obtain title compound (yield 20~40%).

Example scheme III: Synthesis of 1-(n-halophenyl)-1-carbamoyloxyalkyl-2-alkylcarbamate (Examples 247 to 270 and 286 to 295)

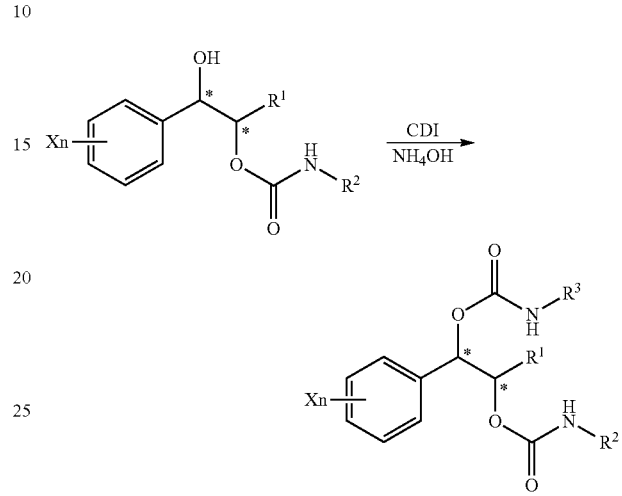

1-(n-halophenyl)-1-hydroxypropyl-1-carbamate, tetrahydrofuran (THF), and carbonyldiimidazole (CDI) were put into a flask and stirred at the room temperature. After approximately 3 hours, ammonia solution (NH$_4$OH) was added thereto. When the reaction was completed, the obtained product was washed with 1 M HCl solution and ethylacetate (EA). The separated organic layer was dehydrated with anhydrous MgSO$_4$(Magnesium sulfate), filtrated, and concentrated under reduced pressure. The concentrated residue was purified by a silica gel column chromatography, to obtain the title compound (yield 75~95%).

According to the above described methods, the compounds as defined in following Tables 1 and 2 were prepared.

TABLE 1

Carbamate derivatives (B is not a carbamoyl derivative)

| Example | X | Position | A | B | R$^1$ | R$^2$ | Chiral-1 | Chiral-2 |
|---|---|---|---|---|---|---|---|---|
| 1 | Cl | 2 | Carbamoyl | MOM | Me | H | S | S |
| 2 | Cl | 2 | Carbamoyl | MOM | Me | Me | S | S |
| 3 | Cl | 2 | Carbamoyl | MOM | Me | Propyl | S | S |
| 4 | Cl | 2 | Carbamoyl | MOM | Me | Isopropyl | S | S |
| 5 | Cl | 2 | Carbamoyl | MOM | Me | Cyclopropyl | S | S |
| 6 | Cl | 2 | Carbamoyl | MOM | Me | Cyclohexyl | S | S |
| 7 | Cl | 2 | Carbamoyl | MOM | Me | Benzyl | S | S |
| 8 | Cl | 2 | Carbamoyl | MOM | Me | Bicycloheptyl | S | S |
| 9 | Cl | 2 | Carbamoyl | MOM | Et | H | S | S |
| 10 | Cl | 2 | Carbamoyl | MOM | Isopropyl | H | S | S |
| 11 | Cl | 2 | Carbamoyl | MOM | Butyl | H | S | S |
| 12 | F | 2 | Carbamoyl | MOM | Me | H | S | S |
| 13 | F | 2 | Carbamoyl | MOM | Me | Me | S | S |
| 14 | F | 2 | Carbamoyl | MOM | Me | Propyl | S | S |
| 15 | F | 2 | Carbamoyl | MOM | Me | Isopropyl | S | S |
| 16 | F | 2 | Carbamoyl | MOM | Me | Cyclopropyl | S | S |
| 17 | F | 2 | Carbamoyl | MOM | Me | Cyclohexyl | S | S |
| 18 | F | 2 | Carbamoyl | MOM | Me | Benzyl | S | S |

TABLE 1-continued

Carbamate derivatives (B is not a carbamoyl derivative)

| Example | X | Position | A | B | R¹ | R² | Chiral-1 | Chiral-2 |
|---|---|---|---|---|---|---|---|---|
| 19 | F | 2 | Carbamoyl | MOM | Me | Bicycloheptyl | S | S |
| 20 | I | 2 | Carbamoyl | MOM | Me | H | S | S |
| 21 | I | 2 | Carbamoyl | MOM | Me | Me | S | S |
| 22 | I | 2 | Carbamoyl | MOM | Me | Propyl | S | S |
| 23 | I | 2 | Carbamoyl | MOM | Me | Isopropyl | S | S |
| 24 | I | 2 | Carbamoyl | MOM | Me | Cyclopropyl | S | S |
| 25 | I | 2 | Carbamoyl | MOM | Me | Cyclohexyl | S | S |
| 26 | I | 2 | Carbamoyl | MOM | Me | Benzyl | S | S |
| 27 | I | 2 | Carbamoyl | MOM | Me | Bicycloheptyl | S | S |
| 28 | I | 2 | Carbamoyl | MOM | Et | H | S | S |
| 29 | I | 2 | Carbamoyl | MOM | Et | Me | S | S |
| 30 | I | 2 | Carbamoyl | MOM | Et | Propyl | S | S |
| 31 | I | 2 | Carbamoyl | MOM | Et | Isopropyl | S | S |
| 32 | I | 2 | Carbamoyl | MOM | Et | Cyclopropyl | S | S |
| 33 | I | 2 | Carbamoyl | MOM | Et | Cyclohexyl | S | S |
| 34 | I | 2 | Carbamoyl | MOM | Et | Benzyl | S | S |
| 35 | I | 2 | Carbamoyl | MOM | Et | Bicycloheptyl | S | S |
| 36 | I | 2 | Carbamoyl | MOM | Isopropyl | H | S | S |
| 37 | I | 2 | Carbamoyl | MOM | Isopropyl | Me | S | S |
| 38 | I | 2 | Carbamoyl | MOM | Isopropyl | Propyl | S | S |
| 39 | I | 2 | Carbamoyl | MOM | Isopropyl | Isopropyl | S | S |
| 40 | I | 2 | Carbamoyl | MOM | Isopropyl | Cyclopropyl | S | S |
| 41 | I | 2 | Carbamoyl | MOM | Isopropyl | Cyclohexyl | S | S |
| 42 | I | 2 | Carbamoyl | MOM | Isopropyl | Benzyl | S | S |
| 43 | I | 2 | Carbamoyl | MOM | Isopropyl | Bicycloheptyl | S | S |
| 44 | I | 2 | Carbamoyl | MOM | Butyl | H | S | S |
| 45 | I | 2 | Carbamoyl | MOM | Butyl | Me | S | S |
| 46 | I | 2 | Carbamoyl | MOM | Butyl | Propyl | S | S |
| 47 | I | 2 | Carbamoyl | MOM | Butyl | Isopropyl | S | S |
| 48 | I | 2 | Carbamoyl | MOM | Butyl | Cuclopropyl | S | S |
| 49 | I | 2 | Carbamoyl | MOM | Butyl | Cyclohexyl | S | S |
| 50 | I | 2 | Carbamoyl | MOM | Butyl | Benzyl | S | S |
| 51 | I | 2 | Carbamoyl | MOM | Butyl | Bicycloheptyl | S | S |
| 52 | I | 3 | Carbamoyl | MOM | Me | H | S | S |
| 53 | I | 3 | Carbamoyl | MOM | Et | H | S | S |
| 54 | I | 3 | Carbamoyl | MOM | Isopropyl | H | S | S |
| 55 | I | 3 | Carbamoyl | MOM | Butyl | H | S | S |
| 56 | F | 4 | Carbamoyl | MOM | Me | H | S | S |
| 57 | F | 4 | Carbamoyl | MOM | Et | H | S | S |
| 58 | F | 4 | Carbamoyl | MOM | Isopropyl | H | S | S |
| 59 | F | 4 | Carbamoyl | MOM | Butyl | H | S | S |
| 60 | Cl | 2.4 | Carbamoyl | MOM | Me | H | S | S |
| 61 | Cl | 2.4 | Carbamoyl | MOM | Et | H | S | S |
| 62 | Cl | 2.4 | Carbamoyl | MOM | Isopropyl | H | S | S |
| 63 | Cl | 2.4 | Carbamoyl | MOM | Butyl | H | S | S |
| 64 | Cl | 2.6 | Carbamoyl | MOM | Me | H | S | S |
| 65 | Cl | 2.6 | Carbamoyl | MOM | Et | H | S | S |
| 66 | Cl | 2.6 | Carbamoyl | MOM | Isopropyl | H | S | S |
| 67 | Cl | 2.6 | Carbamoyl | MOM | Butyl | H | S | S |
| 68 | Cl | 2.3 | Carbamoyl | MOM | Me | H | S | S |
| 69 | Cl | 2 | Carbamoyl | MOM | Me | H | R | R |
| 70 | Cl | 2 | Carbamoyl | MOM | Me | H | rac | rac |
| 71 | Cl | 2 | Carbamoyl | MOM | Me | H | R | S |
| 72 | Cl | 2 | Carbamoyl | MOM | Me | H | S | R |
| 73 | Cl | 2 | Carbamoyl | MOM | Et | H | R | R |
| 74 | Cl | 2 | Carbamoyl | MOM | Et | H | rac | rac |
| 75 | Cl | 2 | Carbamoyl | MOM | Isopropyl | H | R | R |
| 76 | Cl | 2 | Carbamoyl | MOM | Isopropyl | H | rac | rac |
| 77 | Cl | 2 | Carbamoyl | MOM | Butyl | H | R | R |
| 78 | Cl | 2 | Carbamoyl | MOM | Butyl | H | rac | rac |
| 79 | Cl | 2 | Carbamoyl | MOM | Me | Me | R | R |
| 80 | Cl | 2 | Carbamoyl | MOM | Me | Propyl | R | R |
| 81 | Cl | 2 | Carbamoyl | MOM | Me | Isopropyl | R | R |
| 82 | Cl | 2 | Carbamoyl | MOM | Me | Cyclopropyl | R | R |
| 83 | Cl | 2 | Carbamoyl | MOM | Me | Cyclohexyl | R | R |
| 84 | Cl | 2 | Carbamoyl | MOM | Me | Benzyl | R | R |
| 85 | Cl | 2 | Carbamoyl | MOM | Me | Bicycloheptyl | R | R |
| 86 | F | 2 | Carbamoyl | MOM | Me | H | R | R |
| 87 | F | 4 | Carbamoyl | MOM | Me | H | R | R |
| 88 | F | 4 | Carbamoyl | MOM | Et | H | R | R |
| 89 | F | 4 | Carbamoyl | MOM | Isopropyl | H | R | R |
| 90 | F | 4 | Carbamoyl | MOM | Butyl | H | R | R |
| 91 | I | 2 | Carbamoyl | MOM | Me | H | R | R |
| 92 | I | 2 | Carbamoyl | MOM | Et | H | R | R |
| 93 | I | 2 | Carbamoyl | MOM | Isopropyl | H | R | R |
| 94 | I | 2 | Carbamoyl | MOM | Butyl | H | R | R |

TABLE 1-continued

Carbamate derivatives (B is not a carbamoyl derivative)

| Example | X | Position | A | B | R¹ | R² | Chiral-1 | Chiral-2 |
|---|---|---|---|---|---|---|---|---|
| 95 | I | 3 | Carbamoyl | MOM | Me | H | R | R |
| 96 | I | 3 | Carbamoyl | MOM | Et | H | R | R |
| 97 | I | 3 | Carbamoyl | MOM | Isopropyl | H | R | R |
| 98 | I | 3 | Carbamoyl | MOM | Butyl | H | R | R |
| 99 | Cl | 2 | Carbamoyl | MOM | Me | Me | rac | rac |
| 100 | Cl | 2 | Carbamoyl | MOM | Me | Propyl | rac | rac |
| 101 | Cl | 2 | Carbamoyl | MOM | Me | Isopropyl | rac | rac |
| 102 | Cl | 2 | Carbamoyl | MOM | Me | Cyclopropyl | rac | rac |
| 103 | Cl | 2 | Carbamoyl | MOM | Me | Cyclohexyl | rac | rac |
| 104 | Cl | 2 | Carbamoyl | MOM | Me | Benzyl | rac | rac |
| 105 | Cl | 2 | Carbamoyl | MOM | Me | Bicycloheptyl | rac | rac |
| 106 | Cl | 2.4 | Carbamoyl | MOM | Me | H | R | R |
| 107 | Cl | 2.6 | Carbamoyl | MOM | Me | H | R | R |
| 108 | Cl | 2.3 | Carbamoyl | MOM | Me | H | R | R |
| 109 | Cl | 2.4 | Carbamoyl | MOM | Et | H | R | R |
| 110 | Cl | 2.6 | Carbamoyl | MOM | Et | H | R | R |
| 111 | Cl | 2.4 | Carbamoyl | MOM | Isopropyl | H | R | R |
| 112 | Cl | 2.6 | Carbamoyl | MOM | Isopropyl | H | R | R |
| 113 | Cl | 2.4 | Carbamoyl | MOM | Butyl | H | R | R |
| 114 | Cl | 2.6 | Carbamoyl | MOM | Butyl | H | R | R |
| 115 | Cl | 2.4 | Carbamoyl | MOM | Me | H | rac | rac |
| 116 | Cl | 2.6 | Carbamoyl | MOM | Me | H | rac | rac |
| 117 | Cl | 2.3 | Carbamoyl | MOM | Me | H | rac | rac |
| 118 | Cl | 2.4 | Carbamoyl | MOM | Et | H | rac | rac |
| 119 | Cl | 2.6 | Carbamoyl | MOM | Et | H | rac | rac |
| 120 | Cl | 2.4 | Carbamoyl | MOM | Isopropyl | H | rac | rac |
| 121 | Cl | 2.6 | Carbamoyl | MOM | Isopropyl | H | rac | rac |
| 122 | Cl | 2.4 | Carbamoyl | MOM | Butyl | H | rac | rac |
| 123 | Cl | 2.6 | Carbamoyl | MOM | Butyl | H | rac | rac |
| 124 | Cl | 2 | Carbamoyl | Methyl | Me | H | S | S |
| 125 | Cl | 2 | Carbamoyl | Methyl | Me | Me | S | S |
| 126 | Cl | 2 | Carbamoyl | Methyl | Me | Propyl | S | S |
| 127 | Cl | 2 | Carbamoyl | Methyl | Me | Isopropyl | S | S |
| 128 | Cl | 2 | Carbamoyl | Methyl | Me | Cuclopropyl | S | S |
| 129 | Cl | 2 | Carbamoyl | Methyl | Me | Cyclohexyl | S | S |
| 130 | Cl | 2 | Carbamoyl | Methyl | Me | Benzyl | S | S |
| 131 | Cl | 2 | Carbamoyl | Methyl | Me | Bicycloheptyl | S | S |
| 132 | Cl | 2 | Carbamoyl | Methyl | Et | H | S | S |
| 133 | Cl | 2 | Carbamoyl | Methyl | Isopropyl | H | S | S |
| 134 | Cl | 2 | Carbamoyl | Methyl | Butyl | H | S | S |
| 135 | F | 2 | Carbamoyl | Methyl | Me | H | S | S |
| 136 | F | 2 | Carbamoyl | Methyl | Me | Me | S | S |
| 137 | F | 2 | Carbamoyl | Methyl | Me | Propyl | S | S |
| 138 | F | 2 | Carbamoyl | Methyl | Me | Isopropyl | S | S |
| 139 | F | 2 | Carbamoyl | Methyl | Me | Cuclopropyl | S | S |
| 140 | F | 2 | Carbamoyl | Methyl | Me | Cyclohexyl | S | S |
| 141 | F | 2 | Carbamoyl | Methyl | Me | Benzyl | S | S |
| 142 | F | 2 | Carbamoyl | Methyl | Me | Bicycloheptyl | S | S |
| 143 | I | 2 | Carbamoyl | Methyl | Me | H | S | S |
| 144 | I | 2 | Carbamoyl | Methyl | Me | Me | S | S |
| 145 | I | 2 | Carbamoyl | Methyl | Me | Propyl | S | S |
| 146 | I | 2 | Carbamoyl | Methyl | Me | Isopropyl | S | S |
| 147 | I | 2 | Carbamoyl | Methyl | Me | Cuclopropyl | S | S |
| 148 | I | 2 | Carbamoyl | Methyl | Me | Cyclohexyl | S | S |
| 149 | I | 2 | Carbamoyl | Methyl | Me | Benzyl | S | S |
| 150 | I | 2 | Carbamoyl | Methyl | Me | Bicycloheptyl | S | S |
| 151 | I | 2 | Carbamoyl | Methyl | Et | H | S | S |
| 152 | I | 2 | Carbamoyl | Methyl | Et | Me | S | S |
| 153 | I | 2 | Carbamoyl | Methyl | Et | Propyl | S | S |
| 154 | I | 2 | Carbamoyl | Methyl | Et | Isopropyl | S | S |
| 155 | I | 2 | Carbamoyl | Methyl | Et | Cyclopropyl | S | S |
| 156 | I | 2 | Carbamoyl | Methyl | Et | Cyclohexyl | S | S |
| 157 | I | 2 | Carbamoyl | Methyl | Et | Benzyl | S | S |
| 158 | I | 2 | Carbamoyl | Methyl | Et | Bicycloheptyl | S | S |
| 159 | I | 2 | Carbamoyl | Methyl | Isopropyl | H | S | S |
| 160 | I | 2 | Carbamoyl | Methyl | Isopropyl | Me | S | S |
| 161 | I | 2 | Carbamoyl | Methyl | Isopropyl | Propyl | S | S |
| 162 | I | 2 | Carbamoyl | Methyl | Isopropyl | Isopropyl | S | S |
| 163 | I | 2 | Carbamoyl | Methyl | Isopropyl | Cyclopropyl | S | S |
| 164 | I | 2 | Carbamoyl | Methyl | Isopropyl | Cyclohexyl | S | S |
| 165 | I | 2 | Carbamoyl | Methyl | Isopropyl | Benzyl | S | S |
| 166 | I | 2 | Carbamoyl | Methyl | Isopropyl | Bicycloheptyl | S | S |
| 167 | I | 2 | Carbamoyl | Methyl | Butyl | H | S | S |
| 168 | I | 2 | Carbamoyl | Methyl | Butyl | Me | S | S |
| 169 | I | 2 | Carbamoyl | Methyl | Butyl | Propyl | S | S |
| 170 | I | 2 | Carbamoyl | Methyl | Butyl | Isopropyl | S | S |

TABLE 1-continued

| Carbamate derivatives (B is not a carbamoyl derivative) | | | | | | | | |
|---|---|---|---|---|---|---|---|---|
| Example | X | Position | A | B | R¹ | R² | Chiral-1 | Chiral-2 |
| 171 | I | 2 | Carbamoyl | Methyl | Butyl | Cuclopropyl | S | S |
| 172 | I | 2 | Carbamoyl | Methyl | Butyl | Cyclohexyl | S | S |
| 173 | I | 2 | Carbamoyl | Methyl | Butyl | Benzyl | S | S |
| 174 | I | 2 | Carbamoyl | Methyl | Butyl | Bicycloheptyl | S | S |
| 175 | I | 3 | Carbamoyl | Methyl | Me | H | S | S |
| 176 | I | 3 | Carbamoyl | Methyl | Et | H | S | S |
| 177 | I | 3 | Carbamoyl | Methyl | Isopropyl | H | S | S |
| 178 | I | 3 | Carbamoyl | Methyl | Butyl | H | S | S |
| 179 | F | 4 | Carbamoyl | Methyl | Me | H | S | S |
| 180 | F | 4 | Carbamoyl | Methyl | Et | H | S | S |
| 181 | F | 4 | Carbamoyl | Methyl | Isopropyl | H | S | S |
| 182 | F | 4 | Carbamoyl | Methyl | Butyl | H | S | S |
| 183 | Cl | 2,4 | Carbamoyl | Methyl | Me | H | S | S |
| 184 | Cl | 2,4 | Carbamoyl | Methyl | Et | H | S | S |
| 185 | Cl | 2,4 | Carbamoyl | Methyl | Isopropyl | H | S | S |
| 186 | Cl | 2,4 | Carbamoyl | Methyl | Butyl | H | S | S |
| 187 | Cl | 2,6 | Carbamoyl | Methyl | Me | H | S | S |
| 188 | Cl | 2,6 | Carbamoyl | Methyl | Et | H | S | S |
| 189 | Cl | 2,6 | Carbamoyl | Methyl | Isopropyl | H | S | S |
| 190 | Cl | 2,6 | Carbamoyl | Methyl | Butyl | H | S | S |
| 191 | Cl | 2,3 | Carbamoyl | Methyl | Me | H | S | S |
| 192 | Cl | 2 | Carbamoyl | Methyl | Me | H | R | R |
| 193 | Cl | 2 | Carbamoyl | Methyl | Me | H | rac | rac |
| 194 | Cl | 2 | Carbamoyl | Methyl | Me | H | R | S |
| 195 | Cl | 2 | Carbamoyl | Methyl | Me | H | S | R |
| 196 | Cl | 2 | Carbamoyl | Methyl | Et | H | R | R |
| 197 | Cl | 2 | Carbamoyl | Methyl | Et | H | rac | rac |
| 198 | Cl | 2 | Carbamoyl | Methyl | Isopropyl | H | R | R |
| 199 | Cl | 2 | Carbamoyl | Methyl | Isopropyl | H | rac | rac |
| 200 | Cl | 2 | Carbamoyl | Methyl | Butyl | H | R | R |
| 201 | Cl | 2 | Carbamoyl | Methyl | Butyl | H | rac | rac |
| 202 | Cl | 2 | Carbamoyl | Methyl | Me | Me | R | R |
| 203 | Cl | 2 | Carbamoyl | Methyl | Me | Propyl | R | R |
| 204 | Cl | 2 | Carbamoyl | Methyl | Me | Isopropyl | R | R |
| 205 | Cl | 2 | Carbamoyl | Methyl | Me | Cyclopropyl | R | R |
| 206 | Cl | 2 | Carbamoyl | Methyl | Me | Cyclohexyl | R | R |
| 207 | Cl | 2 | Carbamoyl | Methyl | Me | Benzyl | R | R |
| 208 | Cl | 2 | Carbamoyl | Methyl | Me | Bicycloheptyl | R | R |
| 209 | F | 2 | Carbamoyl | Methyl | Me | H | R | R |
| 210 | F | 4 | Carbamoyl | Methyl | Me | H | R | R |
| 211 | F | 4 | Carbamoyl | Methyl | Et | H | R | R |
| 212 | F | 4 | Carbamoyl | Methyl | Isopropyl | H | R | R |
| 213 | F | 4 | Carbamoyl | Methyl | Butyl | H | R | R |
| 214 | I | 2 | Carbamoyl | Methyl | Me | H | R | R |
| 215 | I | 2 | Carbamoyl | Methyl | Et | H | R | R |
| 216 | I | 2 | Carbamoyl | Methyl | Isopropyl | H | R | R |
| 217 | I | 2 | Carbamoyl | Methyl | Butyl | H | R | R |
| 218 | I | 3 | Carbamoyl | Methyl | Me | H | R | R |
| 219 | I | 3 | Carbamoyl | Methyl | Et | H | R | R |
| 220 | I | 3 | Carbamoyl | Methyl | Isopropyl | H | R | R |
| 221 | I | 3 | Carbamoyl | Methyl | Butyl | H | R | R |
| 222 | Cl | 2 | Carbamoyl | Methyl | Me | Me | rac | rac |
| 223 | Cl | 2 | Carbamoyl | Methyl | Me | Propyl | rac | rac |
| 224 | Cl | 2 | Carbamoyl | Methyl | Me | Isopropyl | rac | rac |
| 225 | Cl | 2 | Carbamoyl | Methyl | Me | Cyclopropyl | rac | rac |
| 226 | Cl | 2 | Carbamoyl | Methyl | Me | Cyclohexyl | rac | rac |
| 227 | Cl | 2 | Carbamoyl | Methyl | Me | Benzyl | rac | rac |
| 228 | Cl | 2 | Carbamoyl | Methyl | Me | Bicycloheptyl | rac | rac |
| 229 | Cl | 2,4 | Carbamoyl | Methyl | Me | H | R | R |
| 230 | Cl | 2,6 | Carbamoyl | Methyl | Me | H | R | R |
| 231 | Cl | 2,3 | Carbamoyl | Methyl | Me | H | R | R |
| 232 | Cl | 2,4 | Carbamoyl | Methyl | Et | H | R | R |
| 233 | Cl | 2,6 | Carbamoyl | Methyl | Et | H | R | R |
| 234 | Cl | 2,4 | Carbamoyl | Methyl | Isopropyl | H | R | R |
| 235 | Cl | 2,6 | Carbamoyl | Methyl | Isopropyl | H | R | R |
| 236 | Cl | 2,4 | Carbamoyl | Methyl | Butyl | H | R | R |
| 237 | Cl | 2,6 | Carbamoyl | Methyl | Butyl | H | R | R |
| 238 | Cl | 2,4 | Carbamoyl | Methyl | Me | H | rac | rac |
| 239 | Cl | 2,6 | Carbamoyl | Methyl | Me | H | rac | rac |
| 240 | Cl | 2,3 | Carbamoyl | Methyl | Me | H | rac | rac |

TABLE 1-continued

Carbamate derivatives (B is not a carbamoyl derivative)

| Example | X | Position | A | B | R¹ | R² | Chiral-1 | Chiral-2 |
|---|---|---|---|---|---|---|---|---|
| 241 | Cl | 2.4 | Carbamoyl | Methyl | Et | H | rac | rac |
| 242 | Cl | 2.6 | Carbamoyl | Methyl | Et | H | rac | rac |
| 243 | Cl | 2.4 | Carbamoyl | Methyl | Isopropyl | H | rac | rac |
| 244 | Cl | 2.6 | Carbamoyl | Methyl | Isopropyl | H | rac | rac |
| 245 | Cl | 2.4 | Carbamoyl | Methyl | Butyl | H | rac | rac |
| 246 | Cl | 2.6 | Carbamoyl | Methyl | Butyl | H | rac | rac |
| 271 | F | 2.6 | Carbamoyl | MOM | Me | H | S | S |
| 272 | Cl | 2.5 | Carbamoyl | MOM | Me | H | S | S |
| 273 | Cl | 2.5 | Carbamoyl | MOM | Me | H | R | R |
| 276 | Cl | 2 | Carbamoyl | MOM | H | H | S | — |
| 277 | F | 2 | Carbamoyl | MOM | H | H | S | — |
| 278 | I | 2 | Carbamoyl | MOM | H | H | S | — |
| 279 | Cl | 2 | Carbamoyl | Methyl | H | H | S | — |
| 280 | F | 2 | Carbamoyl | Methyl | H | H | S | — |
| 281 | I | 2 | Carbamoyl | Methyl | H | H | S | — |

TABLE 2

Carbamate derivatives (B is a carbamoyl derivative)

| Example | X | Position | A | B — | B R³ | R¹ | R² | Chiral-1 | Chiral-2 |
|---|---|---|---|---|---|---|---|---|---|
| 247 | Cl | 2 | Carbamoyl | Carbamoyl | H | Me | H | S | S |
| 248 | Cl | 2 | Carbamoyl | Carbamoyl | H | Me | Me | S | S |
| 249 | Cl | 2 | Carbamoyl | Carbamoyl | H | Me | Propyl | S | S |
| 250 | Cl | 2 | Carbamoyl | Carbamoyl | H | Me | H | R | R |
| 251 | Cl | 2 | Carbamoyl | Carbamoyl | H | Me | H | rac | rac |
| 252 | Cl | 2 | Carbamoyl | Carbamoyl | H | Et | H | S | S |
| 253 | Cl | 2 | Carbamoyl | Carbamoyl | H | Isopropyl | H | S | S |
| 254 | Cl | 2 | Carbamoyl | Carbamoyl | H | Butyl | H | S | S |
| 255 | F | 2 | Carbamoyl | Carbamoyl | H | Me | H | S | S |
| 256 | F | 2 | Carbamoyl | Carbamoyl | H | Et | H | S | S |
| 257 | F | 2 | Carbamoyl | Carbamoyl | H | Isopropyl | H | S | S |
| 258 | F | 2 | Carbamoyl | Carbamoyl | H | Butyl | H | S | S |
| 259 | I | 2 | Carbamoyl | Carbamoyl | H | Me | H | S | S |
| 260 | I | 2 | Carbamoyl | Carbamoyl | H | Et | H | S | S |
| 261 | I | 2 | Carbamoyl | Carbamoyl | H | Isopropyl | H | S | S |
| 262 | I | 2 | Carbamoyl | Carbamoyl | H | Butyl | H | S | S |
| 263 | Cl | 2.4 | Carbamoyl | Carbamoyl | H | Me | H | S | S |
| 264 | Cl | 2.4 | Carbamoyl | Carbamoyl | H | Et | H | S | S |
| 265 | Cl | 2.4 | Carbamoyl | Carbamoyl | H | Isopropyl | H | S | S |
| 266 | Cl | 2.4 | Carbamoyl | Carbamoyl | H | Butyl | H | S | S |
| 267 | Cl | 2.6 | Carbamoyl | Carbamoyl | H | Me | H | S | S |
| 268 | Cl | 2.6 | Carbamoyl | Carbamoyl | H | Et | H | S | S |
| 269 | Cl | 2.6 | Carbamoyl | Carbamoyl | H | Isopropyl | H | S | S |
| 270 | Cl | 2.6 | Carbamoyl | Carbamoyl | H | Butyl | H | S | S |
| 274 | Cl | 2 | MOM | Carbamoyl | H | Me | H | S | S |
| 275 | Cl | 2 | Methyl | Carbamoyl | H | Me | H | S | S |
| 282 | I | 2 | MOM | Carbamoyl | H | Me | H | S | S |
| 283 | I | 2 | Methyl | Carbamoyl | H | Me | H | S | S |
| 284 | F | 2 | MOM | Carbamoyl | H | Me | H | S | S |
| 285 | F | 2 | Methyl | Carbamoyl | H | Me | H | S | S |
| 286 | Cl, F | 2.6 | Carbamoyl | Carbamoyl | H | Me | H | S | S |
| 287 | Cl, F | 2.6 | Carbamoyl | Carbamoyl | H | Me | H | R | R |
| 288 | I | 2 | Carbamoyl | Carbamoyl | H | Me | H | R | R |
| 289 | F | 2 | Carbamoyl | Carbamoyl | H | Me | H | R | R |
| 290 | Cl | 2.6 | Carbamoyl | Carbamoyl | H | Me | H | R | R |
| 291 | F | 2.4 | Carbamoyl | Carbamoyl | H | Me | H | R | R |
| 292 | F | 2.6 | Carbamoyl | Carbamoyl | H | Me | H | R | R |
| 293 | F | 2.5 | Carbamoyl | Carbamoyl | H | Me | H | R | R |
| 294 | Cl | 2 | Carbamoyl | Carbamoyl | H | Me | H | S | R |
| 295 | Cl | 2 | Carbamoyl | Carbamoyl | H | Me | H | R | S |

Example 1: Synthesis of 1-(2-chlorophenyl)-(S)-1-methoxymethoxypropyl-(S)-2-carbamate

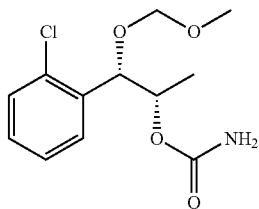 [SMILES: COCO[C@@H](c1ccccc1Cl)[C@H](C)OC(N)=O]

To a stirred solution of 1-(2-chlorophenyl)-1-hydorxyalkyl-2-carbamate (Preparation Example 103, 1.7 g) in MC (Methylenechloloride) was added DIPEA (Diisopropylethylamine, 5 eq, 5.1 mL) at 0° C. under N₂ condition. The mixture was added MOM-Cl (MOM-chloride, 5 eq, 2.3 mL) at 0° C. then slowly warm to R.T. When the reaction was completed, the obtained product was washed with H₂O and MC. The separated organic layer was dehydrated with anhydrous MgSO₄ (Magnesium sulfate), filtrated, and concentrated under reduced pressure. The concentrated residue was purified by a silica gel column chromatography, to obtain title compound.

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.26~7.70 (m, 4H).

According to the method described in Example 1, the following compounds of Examples 2 to 123 were prepared:

Example 2: Synthesis of 1-(2-chlorophenyl)-(S)-1-methoxymethoxypropyl-(S)-2-methylcarbamate

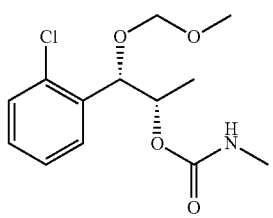 [SMILES: CNC(=O)O[C@@H](C)[C@@H](OCOC)c1ccccc1Cl]

The substantially same method as described in Example 1 was conducted, except that 1-(2-chlorophenyl)-(S)-1-hydroxypropyl-(S)-2-methylcarbamate (Preparation example 117) was used instead of 1-(2-chlorophenyl)-(S)-1-hydroxypropyl-(S)-2-carbamate (Preparation example 103), to obtain the title compound (0.86 g, yield 20~50%).

$^1$H NMR (400 MHz, CDCl$_3$) δ 1.37 (d, J=6.8 Hz, 3H), 2.58 (s, 3H), 3.30 (s, 3H), 4.71 (d, J=6.8 Hz, 1H), 4.82~4.88 (m, 1H), 5.45 (s, 2H), 7.26~7.70 (m, 4H).

Example 3: Synthesis of 1-(2-chlorophenyl)-(S)-1-methoxymethoxypropyl-(S)-2-propylcarbamate

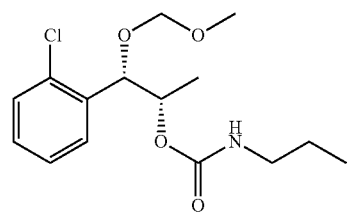 [SMILES: CCCNC(=O)O[C@@H](C)[C@@H](OCOC)c1ccccc1Cl]

$^1$H NMR (400 MHz, CDCl$_3$) δ 0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8 Hz, 1H), 4.82~4.88 (m, 1H), 5.45 (s, 2H), 7.26~7.70 (m, 4H).

Example 4: Synthesis of 1-(2-chlorophenyl)-(S)-1-methoxymethoxypropyl-(S)-2-isopropylcarbamate

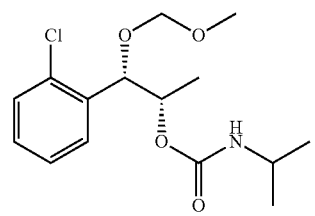 [SMILES: COCO[C@@H](c1ccccc1Cl)[C@H](C)OC(=O)NC(C)C]

$^1$H NMR (400 MHz, CDCl$_3$) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.26~7.70 (m, 4H).

Example 5: Synthesis of 1-(2-chlorophenyl)-(S)-1-methoxymethoxypropyl-(S)-2-cyclopropylcarbamate

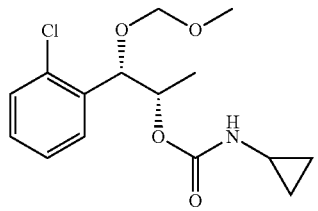

$^1$H NMR (400 MHz, CDCl$_3$) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 6: Synthesis of 1-(2-chlorophenyl)-(S)-1-methoxymethoxypropyl-(S)-2-cyclohexylcarbamate

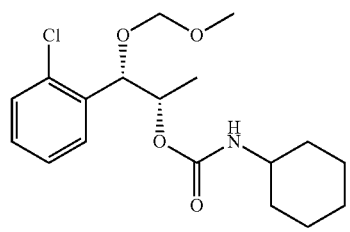

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.26~7.70 (m, 4H).

Example 7: Synthesis of 1-(2-chlorophenyl)-(S)-1-methoxymethoxypropyl-(S)-2-cyclohexylcarbamate

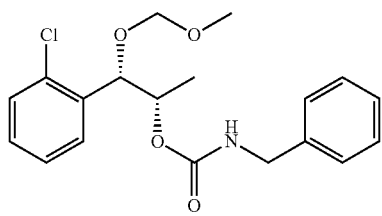

¹H NMR (400 MHz, CDCl₃) δ 1.37 (d, J=6.8 Hz, 3H), 3.30 (s, 3H), 4.20 (m, 2H), 4.71 (d, J=6.8 Hz, 1H), 4.82~4.88 (m, 1H), 5.45 (s, 2H), 7.13~7.19 (m, 4H), 7.37~7.88 (m, 5H).

Example 8: Synthesis of 1-(2-chlorophenyl)-(S)-1-methoxymethoxypropyl-(S)-2-bicyclo[2,2,1]heptan-escarbamate

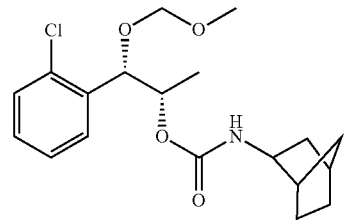 [SMILES: COCO[C@@H](c1ccccc1Cl)[C@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.13~7.19 (m, 4H), 7.37~7.88 (m, 5H).

Example 9: Synthesis of 1-(2-chlorophenyl)-(S)-1-methoxymethoxybutyl-(S)-2-carbamate

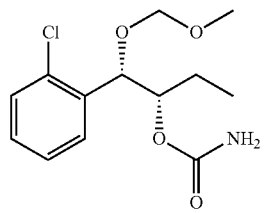 [SMILES: CC[C@H](OC(N)=O)[C@@H](OCOC)c1ccccc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 10: Synthesis of 1-(2-chlorophenyl)-(S)-1-methoxymethoxy-3-methyl-butyl-(S)-2-carbamate

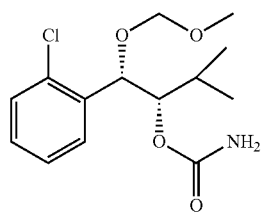 [SMILES: COCO[C@@H](c1ccccc1Cl)[C@@H](OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 11: Synthesis of 1-(2-chlorophenyl)-(S)-1-methoxymethoxyhexyl-(S)-2-carbamate

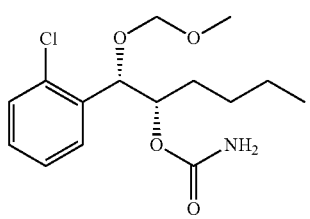 [SMILES: CCCC[C@H](OC(N)=O)[C@@H](OCOC)c1ccccc1Cl]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 12: Synthesis of 1-(2-fluorophenyl)-(S)-1-methoxymethoxypropyl-(S)-2-carbamate

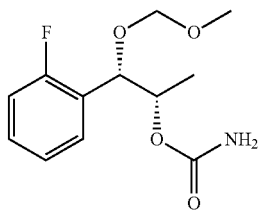

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.15~7.68 (m, 4H).

Example 13: Synthesis of 1-(2-fluorophenyl)-(S)-1-methoxymethoxypropyl-(S)-2-methylcarbamate

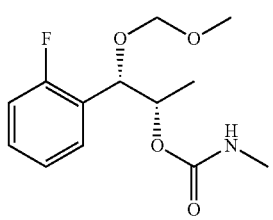 [SMILES: CNC(=O)O[C@@H](C)[C@@H](OCOC)c1ccccc1F]

¹H NMR (400 MHz, CDCl₃) δ 1.37 (d, J=6.8 Hz, 3H), 2.58 (s, 3H), 3.30 (s, 3H), 4.71 (d, J=6.8 Hz, 1H), 4.82~4.88 (m, 1H), 5.45 (s, 2H), 7.15~7.68 (m, 4H).

Example 14: Synthesis of 1-(2-fluorophenyl)-(S)-1-methoxymethoxypropyl-(S)-2-propylcarbamate

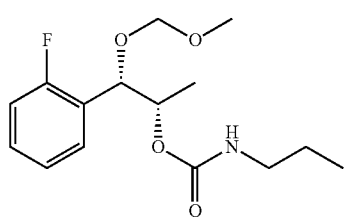 [SMILES: CCCNC(=O)O[C@@H](C)[C@@H](OCOC)c1ccccc1F]

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8 Hz, 1H), 4.82~4.88 (m, 1H), 5.45 (s, 2H), 7.15~7.68 (m, 4H).

Example 15: Synthesis of 1-(2-fluorophenyl)-(S)-1-methoxymethoxypropyl-(S)-2-isopropylcarbamate

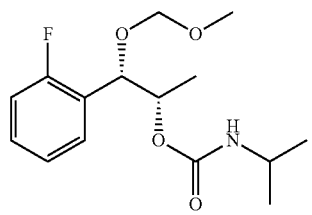 [SMILES: COCO[C@@H](c1ccccc1F)[C@H](C)OC(=O)NC(C)C]

¹H NMR (400 MHz, CDCl₃) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.15~7.69 (m, 4H).

Example 16: Synthesis of 1-(2-fluorophenyl)-(S)-1-methoxymethoxypropyl-(S)-2-cyclopropylcarbamate

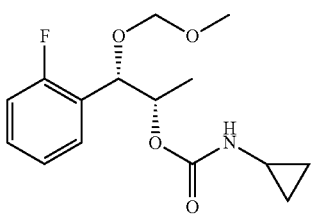 [SMILES: COCO[C@@H](c1ccccc1F)[C@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.16~7.70 (m, 4H).

Example 17: Synthesis of 1-(2-fluorophenyl)-(S)-1-methoxymethoxypropyl-(S)-2-cyclohexylcarbamate

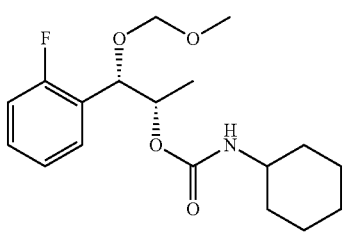

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.15~7.66 (m, 4H).

Example 18: Synthesis of 1-(2-fluorophenyl)-(S)-1-methoxymethoxypropyl-(S)-2-cyclohexylcarbamate

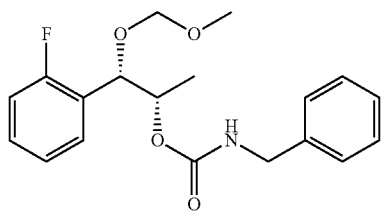

¹H NMR (400 MHz, CDCl₃) δ 1.37 (d, J=6.8 Hz, 3H), 3.30 (s, 3H), 4.20 (m, 2H), 4.71 (d, J=6.8 Hz, 1H), 4.82~4.88 (m, 1H), 5.45 (s, 2H), 7.15~7.68 (m, 4H), 7.72~7.88 (m, 5H).

Example 19: Synthesis of 1-(2fluorophenyl)-(S)-1-methoxymethoxypropyl-(S)-2-bicyclo[2,2,1]heptan-escarbamate

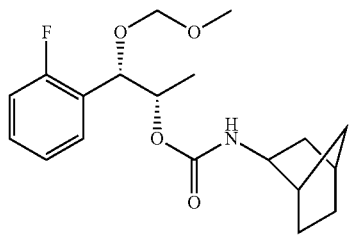 [SMILES: COCO[C@@H](c1ccccc1F)[C@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.15~7.68 (m, 4H), 7.37~7.88 (m, 5H).

Example 20: Synthesis of 1-(2-iodophenyl)-(S)-1-methoxymethoxypropyl-(S)-2-carbamate

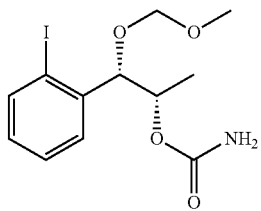 [SMILES: COCO[C@@H](c1ccccc1I)[C@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.13~7.88 (m, 4H).

Example 21: Synthesis of 1-(2-iodophenyl)-(S)-1-methoxymethoxypropyl-(S)-2-methylcarbamate

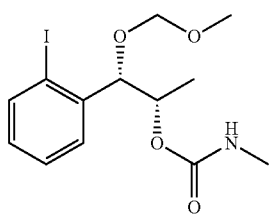 [SMILES: CNC(=O)O[C@@H](C)[C@@H](OCOC)c1ccccc1I]

¹H NMR (400 MHz, CDCl₃) δ 1.37 (d, J=6.8 Hz, 3H), 2.58 (s, 3H), 3.30 (s, 3H), 4.71 (d, J=6.8 Hz, 1H), 4.82~4.88 (m, 1H), 5.45 (s, 2H), 7.13~7.90 (m, 4H).

Example 22: Synthesis of 1-(2-iodophenyl)-(S)-1-methoxymethoxypropyl-(S)-2-propylcarbamate

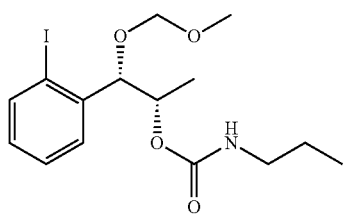

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8 Hz, 1H), 4.82~4.88 (m, 1H), 5.45 (s, 2H), 7.14~7.87 (m, 4H).

Example 23: Synthesis of 1-(2-iodophenyl)-(S)-1-methoxymethoxypropyl-(S)-2-isopropylcarbamate

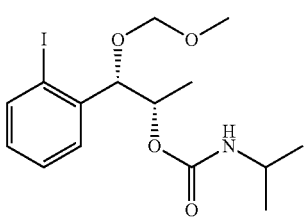 [SMILES: COCO[C@@H](c1ccccc1I)[C@H](C)OC(=O)NC(C)C]

¹H NMR (400 MHz, CDCl₃) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.15~7.89 (m, 4H).

Example 24: Synthesis of 1-(2-iodophenyl)-(S)-1-methoxymethoxypropyl-(S)-2-cyclopropylcarbamate

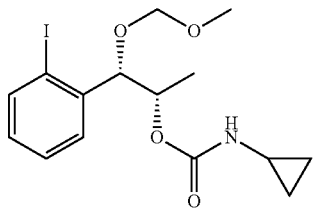 [SMILES: COCO[C@@H](c1ccccc1I)[C@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.16~7.87 (m, 4H).

Example 25: Synthesis of 1-(2-iodophenyl)-(S)-1-methoxymethoxypropyl-(S)-2-cyclohexylcarbamate

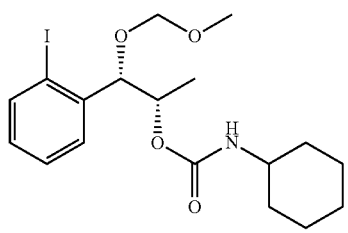 [SMILES: COCO[C@@H](c1ccccc1I)[C@H](C)OC(=O)NC1CCCCC1]

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.18~7.91 (m, 4H).

Example 26: Synthesis of 1-(2-iodophenyl)-(S)-1-methoxymethoxypropyl-(S)-2-cyclohexylcarbamate

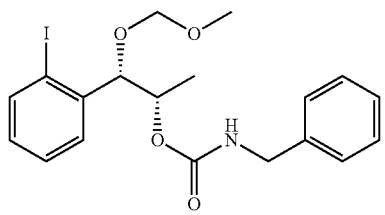 [SMILES: COCO[C@@H](c1ccccc1I)[C@H](C)OC(=O)NCc1ccccc1]

¹H NMR (400 MHz, CDCl₃) δ 1.37 (d, J=6.8 Hz, 3H), 3.30 (s, 3H), 4.20 (m, 2H), 4.71 (d, J=6.8 Hz, 1H), 4.82~4.88 (m, 1H), 5.45 (s, 2H), 7.15~7.68 (m, 4H), 7.72~7.88 (m, 5H).

Example 27: Synthesis of 1-(2-iodophenyl)-(S)-1-methoxymethoxypropyl-(S)-2-bicyclo[2,2,1]heptanescarbamate

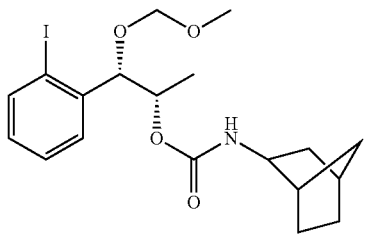 [SMILES: COCO[C@@H](c1ccccc1I)[C@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.15~7.68 (m, 4H), 7.37~7.88 (m, 5H).

Example 28: Synthesis of 1-(2-iodophenyl)-(S)-1-methoxymethoxybutyl-(S)-2-carbamate

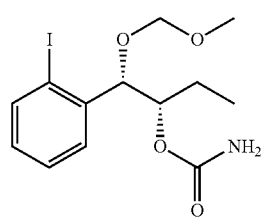 [SMILES: CC[C@H](OC(N)=O)[C@@H](OCOC)c1ccccc1I]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.82~4.88 (m, 1H), 5.45 (s, 2H), 7.26~7.70 (m, 4H).

Example 29: Synthesis of 1-(2-iodophenyl)-(S)-1-methoxymethoxybutyl-(S)-2-methylcarbamate

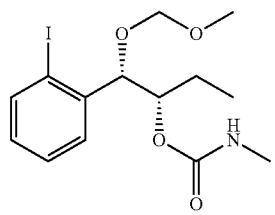 [SMILES: CC[C@H](OC(=O)NC)[C@@H](OCOC)c1ccccc1I]

¹H NMR (400 MHz, CDCl₃) δ 1.04 (t, J=7.6 Hz, 3H), 1.60~1.71 (m, 2H), 2.58 (s, 3H), 3.30 (s, 3H), 4.71 (d, J=6.8 Hz, 1H), 4.82~4.88 (m, 1H), 5.45 (s, 2H), 7.13~7.88 (m, 4H).

Example 30: Synthesis of 1-(2-iodophenyl)-(S)-1-methoxymethoxybutyl-(S)-2-propylcarbamate

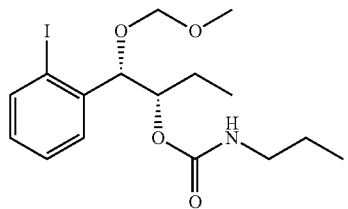 [SMILES: CCCNC(=O)O[C@@H](CC)[C@@H](OCOC)c1ccccc1I]

¹H NMR (400 MHz, CDCl₃) δ 0.90 (t, J=6.8 Hz, 3H), 1.04 (t, J=7.6 Hz, 3H), 1.58~1.71 (m, 4H), 3.18 (t, J=7.1 Hz, 2H), 3.30 (s, 3H), 4.71 (d, J=6.8 Hz, 1H), 4.82~4.88 (m, 1H), 5.45 (s, 2H), 7.14~7.89 (m, 4H).

Example 31: Synthesis of 1-(2-iodophenyl)-(S)-1-methoxymethoxybutyl-(S)-2-isopropylcarbamate

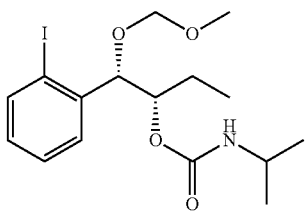 [SMILES: CC[C@H](OC(=O)NC(C)C)[C@@H](OCOC)c1ccccc1I]

¹H NMR (400 MHz, CDCl₃) δ 1.04 (t, J=7.6 Hz, 3H), 1.27 (d, J=6.8 Hz, 6H), 1.60~1.71 (m, 2H), 3.30 (s, 3H), 4.17 (m, 1H), 4.71 (d, J=6.8 Hz, 1H), 4.82~4.88 (m, 1H), 5.45 (s, 2H), 7.15~7.90 (m, 4H).

Example 32: Synthesis of 1-(2-iodophenyl)-(S)-1-methoxymethoxybutyl-(S)-2-cyclopropylcarbamate

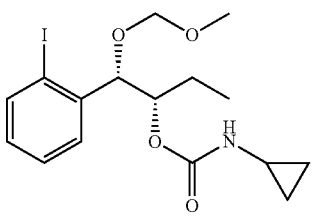 [SMILES: CC[C@H](OC(=O)NC1CC1)[C@@H](OCOC)c1ccccc1I]

¹H NMR (400 MHz, CDCl₃) δ 0.57 (m, 2H), 0.82 (m, 2H), 1.04 (t, J=7.6 Hz, 3H), 1.60~1.71 (m, 2H), 2.75 (m, 1H), 3.30 (s, 3H), 4.71 (d, J=6.8 Hz, 1H), 4.82~4.88 (m, 1H), 5.45 (s, 2H), 7.16~7.90 (m, 4H).

Example 33: Synthesis of 1-(2-iodophenyl)-(S)-1-methoxymethoxybutyl-(S)-2-cyclohexylcarbamate

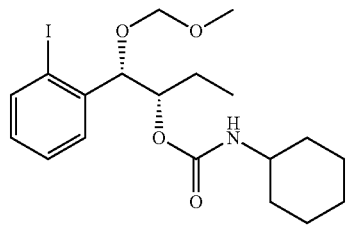 [SMILES: CC[C@H](OC(=O)NC1CCCCC1)[C@@H](OCOC)c1ccccc1I]

¹H NMR (400 MHz, CDCl₃) δ 1.04 (t, J=7.6 Hz, 3H), 1.11~1.21 (m, 4H), 1.47~1.49 (m, 4H), 1.60~1.71 (m, 2H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.14~7.87 (m, 4H).

Example 34: Synthesis of 1-(2-iodophenyl)-(S)-1-methoxymethoxybutyl-(S)-2-cyclohexylcarbamate

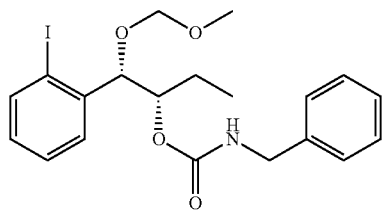 [SMILES: CC[C@H](OC(=O)NCc1ccccc1)[C@@H](OCOC)c1ccccc1I]

¹H NMR (400 MHz, CDCl₃) δ 1.04 (t, J=7.6 Hz, 3H), 1.60~1.71 (m, 2H), 3.30 (s, 3H), 4.20 (m, 2H), 4.71 (d, J=6.8 Hz, 1H), 4.82~4.88 (m, 1H), 5.45 (s, 2H), 7.14~7.19 (m, 4H), 7.37~7.88 (m, 5H).

Example 35: Synthesis of 1-(2-iodophenyl)-(S)-1-methoxymethoxybutyl-(S)-2-bicyclo[2,2,1]heptanes-carbamate

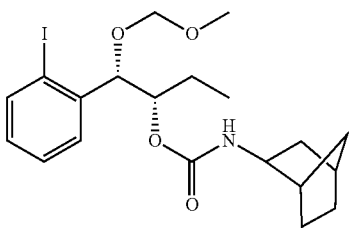 [SMILES: CC[C@H](OC(=O)NC1CC2CCC1C2)[C@@H](OCOC)c1ccccc1I]

¹H NMR (400 MHz, CDCl₃) δ 1.04 (t, J=7.6 Hz, 3H), 1.33~1.58 (m, 6H), 1.60~1.71 (m, 2H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.15~7.19 (m, 4H), 7.37~7.88 (m, 5H).

Example 36: Synthesis of 1-(2-iodophenyl)-(S)-1-methoxymethoxy-3-methyl-butyl-(S)-2-carbamate

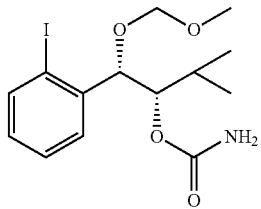 [SMILES: COCO[C@@H](c1ccccc1I)[C@@H](OC(N)=O)C(C)C]

$^1$H NMR (400 MHz, CDCl$_3$) δ 1.07 (d, J=7.6 Hz, 3H), 1.83~1.89 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 37: Synthesis of 1-(2-iodophenyl)-(S)-1-methoxymethoxy-3-methyl-butyl-(S)-2-methylcarbamate

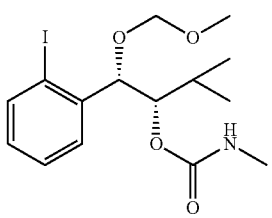 [SMILES: CNC(=O)O[C@@H](C(C)C)[C@@H](OCOC)c1ccccc1I]

$^1$H NMR (400 MHz, CDCl$_3$) δ 1.04 (d, J=7.6 Hz, 6H), 1.60~1.71 (m, 1H), 2.58 (s, 3H), 3.30 (s, 3H), 4.71 (d, J=6.8 Hz, 1H), 4.82~4.88 (m, 1H), 5.45 (s, 2H), 7.13~7.88 (m, 4H).

Example 38: Synthesis of 1-(2-iodophenyl)-(S)-1-methoxymethoxy-3-methyl-butyl-(S)-2-propylcarbamate

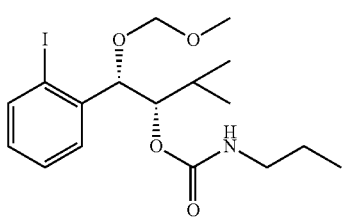 [SMILES: CCCNC(=O)O[C@@H](C(C)C)[C@@H](OCOC)c1ccccc1I]

$^1$H NMR (400 MHz, CDCl$_3$) δ 0.90 (t, J=6.8 Hz, 3H), 1.04 (d, J=7.6 Hz, 6H), 1.58~1.71 (m, 5H), 3.18 (t, J=7.1 Hz, 2H), 3.30 (s, 3H), 4.71 (d, J=6.8 Hz, 1H), 4.82~4.88 (m, 1H), 5.45 (s, 2H), 7.14~7.89 (m, 4H).

Example 39: Synthesis of 1-(2-iodophenyl)-(S)-1-methoxymethoxy-3-methyl-butyl-(S)-2-isopropyl-carbamate

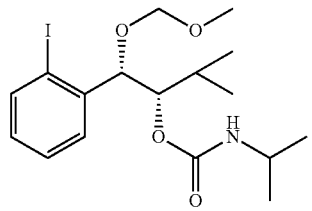 [SMILES: COCO[C@@H](c1ccccc1I)[C@@H](OC(=O)NC(C)C)C(C)C]

$^1$H NMR (400 MHz, CDCl$_3$) δ 1.04 (t, J=7.6 Hz, 6H), 1.27 (d, J=6.8 Hz, 6H), 1.60~1.71 (m, 1H), 3.30 (s, 3H), 4.17 (m, 1H), 4.71 (d, J=6.8 Hz, 1H), 4.82~4.88 (m, 1H), 5.45 (s, 2H), 7.15~7.90 (m, 4H).

Example 40: Synthesis of 1-(2-iodophenyl)-(S)-1-methoxymethoxy-3-methyl-butyl-(S)-2-cyclopropyl-carbamate

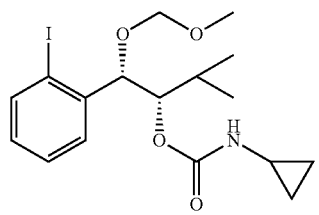 [SMILES: COCO[C@@H](c1ccccc1I)[C@@H](OC(=O)NC1CC1)C(C)C]

$^1$H NMR (400 MHz, CDCl$_3$) δ 0.57 (m, 2H), 0.82 (m, 2H), 1.04 (d, J=7.6 Hz, 6H), 1.60~1.71 (m, 1H), 2.75 (m, 1H), 3.30 (s, 3H), 4.71 (d, J=6.8 Hz, 1H), 4.82~4.88 (m, 1H), 5.45 (s, 2H), 7.16~7.90 (m, 4H).

Example 41: Synthesis of 1-(2-iodophenyl)-(S)-1-methoxymethoxy-3-methyl-butyl-(S)-2-cyclohexyl-carbamate

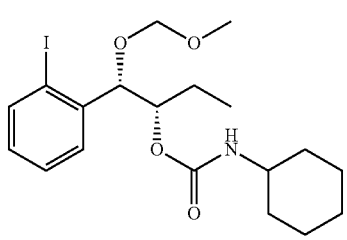 [SMILES: CC[C@H](OC(=O)NC1CCCCC1)[C@@H](OCOC)c1ccccc1I]

$^1$H NMR (400 MHz, CDCl$_3$) δ 1.04 (d, J=7.6 Hz, 6H), 1.11~1.21 (m, 4H), 1.47~1.49 (m, 4H), 1.74 (m, 2H), 1.84~1.90 (m, 1H), 3.30 (s, 3H), 3.54 (m, 1H), 4.71 (d, J=6.8 Hz, 1H), 4.82~4.88 (m, 1H), 5.45 (s, 2H), 7.14~7.87 (m, 4H).

Example 42: Synthesis of 1-(2-iodophenyl)-(S)-1-methoxymethoxy-3-methyl-butyl-(S)-2-cyclohexyl-carbamate

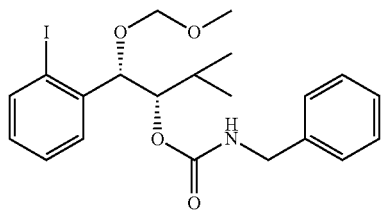 [SMILES: COCO[C@@H](c1ccccc1I)[C@@H](OC(=O)NCc1ccccc1)C(C)C]

$^1$H NMR (400 MHz, CDCl$_3$) δ 1.04 (d, J=7.6 Hz, 6H), 1.87~1.90 (m, 1H), 3.30 (s, 3H), 4.20 (m, 2H), 4.71 (d, J=6.8 Hz, 1H), 4.82~4.88 (m, 1H), 5.45 (s, 2H), 7.14~7.19 (m, 4H), 7.37~7.88 (m, 5H).

Example 43: Synthesis of 1-(2-iodophenyl)-(S)-1-methoxymethoxy-3-methyl-butyl-(S)-2-bicyclo[2,2,1]heptanescarbamate

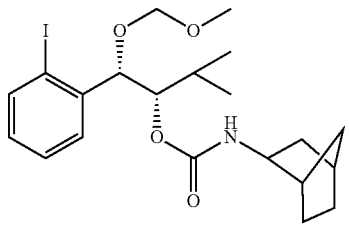 [SMILES: COCO[C@@H](c1ccccc1I)[C@@H](OC(=O)NC1CC2CCC1C2)C(C)C]

$^1$H NMR (400 MHz, CDCl$_3$) δ 1.04 (d, J=7.6 Hz, 6H), 1.33~1.58 (m, 6H), 1.75~1.88 (m, 2H), 1.88~1.93 (m, 1H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.15~7.19 (m, 4H), 7.37~7.88 (m, 5H).

Example 44: Synthesis of 1-(2-iodophenyl)-(S)-1-methoxymethoxyhexyl-(S)-2-carbamate

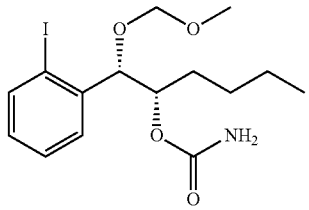

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8 Hz, 1H), 4.82~4.88 (m, 1H), 5.45 (s, 2H), 7.26~7.70 (m, 4H).

Example 45: Synthesis of 1-(2-iodophenyl)-(S)-1-methoxymethoxyhexyl-(S)-2-methylcarbamate

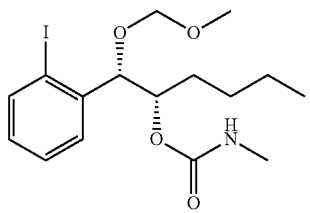 [SMILES: CCCC[C@H](OC(=O)NC)[C@@H](OCOC)c1ccccc1I]

$^1$H NMR (400 MHz, CDCl$_3$) δ 0.89 (t, J=7.2 Hz, 3H), 1.20~1.35 (m, 4H), 1.36~1.41 (m, 1H), 1.59~1.63 (m, 1H), 2.58 (s, 3H), 3.30 (s, 3H), 4.71 (d, J=6.8 Hz, 1H), 4.82~4.88 (m, 1H), 5.45 (s, 2H), 7.13~7.88 (m, 4H).

Example 46: Synthesis of 1-(2-iodophenyl)-(S)-1-methoxymethoxyhexyl-(S)-2-propylcarbamate

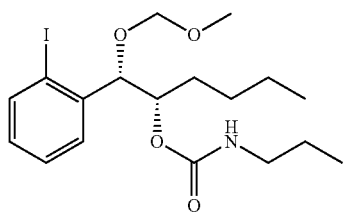 [SMILES: CCCC[C@H](OC(=O)NCCC)[C@@H](OCOC)c1ccccc1I]

$^1$H NMR (400 MHz, CDCl$_3$) δ 0.87 (t, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.30 (s, 3H), 4.71 (d, J=6.8 Hz, 1H), 4.82~4.88 (m, 1H), 5.45 (s, 2H), 7.14~7.89 (m, 4H).

Example 47: Synthesis of 1-(2-iodophenyl)-(S)-1-methoxymethoxyhexyl-(S)-2-isopropylcarbamate

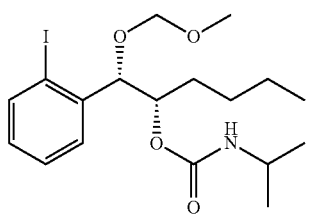 [SMILES: CCCC[C@H](OC(=O)NC(C)C)[C@@H](OCOC)c1ccccc1I]

$^1$H NMR (400 MHz, CDCl$_3$) δ 0.84 (t, J=7.6 Hz, 3H), 1.22~1.35 (m, 4H), 1.27 (d, J=6.8 Hz, 6H), 1.36~1.40 (m, 1H), 1.58~1.62 (m, 1H), 3.30 (s, 3H), 4.17 (m, 1H), 4.71 (d, J=6.8 Hz, 1H), 4.82~4.88 (m, 1H), 5.45 (s, 2H), 7.15~7.90 (m, 4H).

Example 48: Synthesis of 1-(2-iodophenyl)-(S)-1-methoxymethoxyhexyl-(S)-2-cyclopropylcarbamate

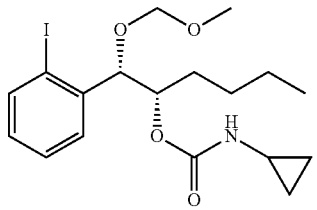 [SMILES: CCCC[C@H](OC(=O)NC1CC1)[C@@H](OCOC)c1ccccc1I]

¹H NMR (400 MHz, CDCl₃) δ 0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.30 (s, 3H), 4.71 (d, J=6.8 Hz, 1H), 4.82~4.88 (m, 1H), 5.45 (s, 2H), 7.16~7.90 (m, 4H).

Example 49: Synthesis of 1-(2-iodophenyl)-(S)-1-methoxymethoxyhexyl-(S)-2-cyclohexylcarbamate

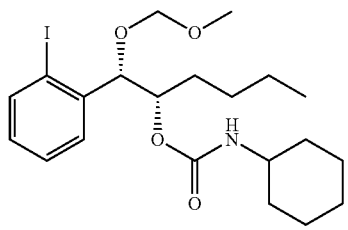 [SMILES: CCCC[C@H](OC(=O)NC1CCCCC1)[C@@H](OCOC)c1ccccc1I]

¹H NMR (400 MHz, CDCl₃) δ 0.98 (t, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.30 (s, 3H), 3.54 (m, 1H), 4.71 (d, J=6.8 Hz, 1H), 4.82~4.88 (m, 1H), 5.45 (s, 2H), 7.14~7.87 (m, 4H).

Example 50: Synthesis of 1-(2-iodophenyl)-(S)-1-methoxymethoxyhexyl-(S)-2-cyclohexylcarbamate

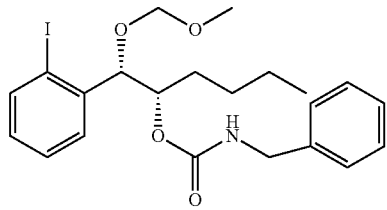 [SMILES: CCCC[C@H](OC(=O)NCc1ccccc1)[C@@H](OCOC)c1ccccc1I]

¹H NMR (400 MHz, CDCl₃) δ 0.94 (t, J=7.6 Hz, 3H), 1.26~1.33 (m, 4H), 1.51~1.55 (m, 2H), 3.30 (s, 3H), 4.20 (m, 2H), 4.71 (d, J=6.8 Hz, 1H), 4.82~4.88 (m, 1H), 5.45 (s, 2H), 7.14~7.19 (m, 4H), 7.37~7.88 (m, 5H).

Example 51: Synthesis of 1-(2-iodophenyl)-(S)-1-methoxymethoxyhexyl-(S)-2-bicyclo[2,2,1]heptan-escarbamate

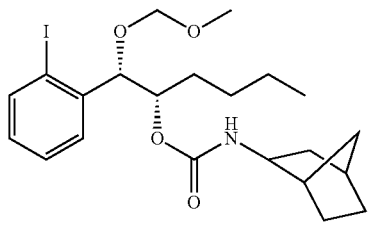 [SMILES: CCCC[C@H](OC(=O)NC1CC2CCC1C2)[C@@H](OCOC)c1ccccc1I]

¹H NMR (400 MHz, CDCl₃) δ 0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.15~7.19 (m, 4H), 7.37~7.88 (m, 5H).

Example 52: Synthesis of 1-(3-iodophenyl)-(S)-1-methoxymethoxypropyl-(S)-2-carbamate

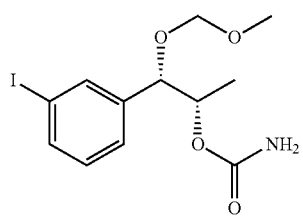 [SMILES: COCO[C@@H](c1cccc(I)c1)[C@H](C)OC(N)=O]

¹H NMR (400 MHz, CDCl₃) δ 1.16 (d, J=6.4 Hz, 3H), 3.39 (s, 3H), 4.54~4.63 (m, 6H), 5.04~5.10 (m, 1H), 7.09~7.73 (m, 4H).

Example 53: Synthesis of 1-(3-iodophenyl)-(S)-1-methoxymethoxybutyl-(S)-2-carbamate

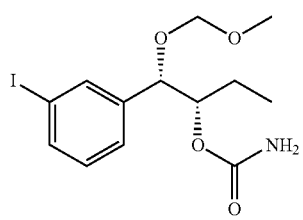 [SMILES: CC[C@H](OC(N)=O)[C@@H](OCOC)c1cccc(I)c1]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 6.96~7.57 (m, 4H).

Example 54: Synthesis of 1-(3-iodophenyl)-(S)-1-methoxymethoxy-3-methyl-butyl-(S)-2-carbamate

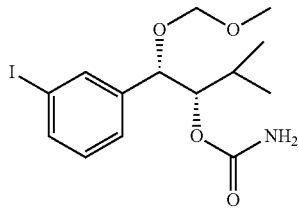 [SMILES: COCO[C@@H](c1cccc(I)c1)[C@@H](OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.00~7.58 (m, 4H).

Example 55: Synthesis of 1-(3-iodophenyl)-(S)-1-methoxymethoxyhexyl-(S)-2-carbamate

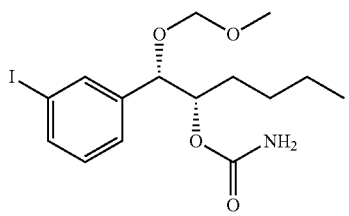 [SMILES: CCCC[C@H](OC(N)=O)[C@@H](OCOC)c1cccc(I)c1]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.01~7.59 (m, 4H).

Example 56: Synthesis of 1-(4-fluorophenyl)-(S)-1-methoxymethoxypropyl-(S)-2-carbamate

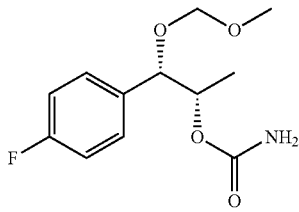 [SMILES: COCO[C@@H](c1ccc(F)cc1)[C@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 6.96~7.17 (m, 4H).

Example 57: Synthesis of 1-(4-fluorophenyl)-(S)-1-methoxymethoxybutyl-(S)-2-carbamate

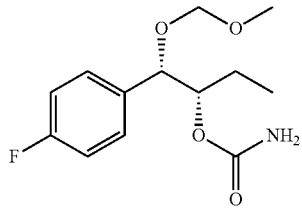 [SMILES: CC[C@H](OC(N)=O)[C@@H](OCOC)c1ccc(F)cc1]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 6.90~7.20 (m, 4H).

Example 58: Synthesis of 1-(4-fluorophenyl)-(S)-1-methoxymethoxy-3-methyl-butyl-(S)-2-carbamate

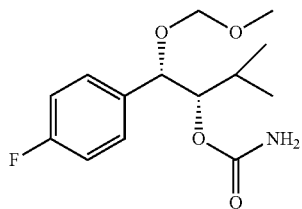 [SMILES: COCO[C@@H](c1ccc(F)cc1)[C@@H](OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 6.92~7.17 (m, 4H).

Example 59: Synthesis of 1-(4-fluorophenyl)-(S)-1-methoxymethoxyhexyl-(S)-2-carbamate

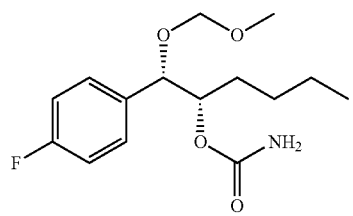 [SMILES: CCCC[C@H](OC(N)=O)[C@@H](OCOC)c1ccc(F)cc1]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 6.96~7.19 (m, 4H).

Example 60: Synthesis of 1-(2,4-dichlorophenyl)-(S)-1-methoxymethoxypropyl-(S)-2-carbamate

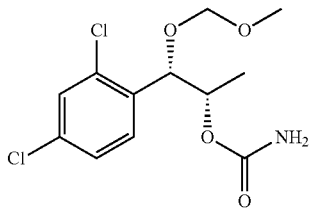 [SMILES: COCO[C@@H](c1ccc(Cl)cc1Cl)[C@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.24~7.30 (m, 2H), 7.73 (d, J=1.5 Hz, 1H).

Example 61: Synthesis of 1-(2,4-dichlorophenyl)-(S)-1-methoxymethoxybutyl-(S)-2-carbamate

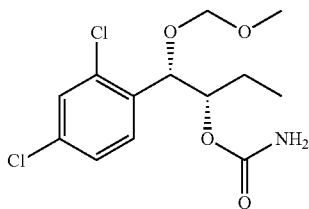 [SMILES: CC[C@H](OC(N)=O)[C@@H](OCOC)c1ccc(Cl)cc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 62: Synthesis of 1-(2,4-dichlorophenyl)-(S)-1-methoxymethoxy-3-methyl-butyl-(S)-2-carbamate

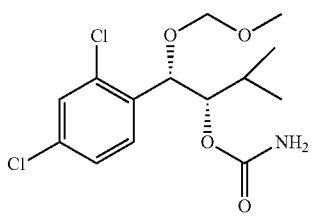 [SMILES: COCO[C@@H](c1ccc(Cl)cc1Cl)[C@@H](OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 63: Synthesis of 1-(2,4-dichlorophenyl)-(S)-1-methoxymethoxyhexyl-(S)-2-carbamate

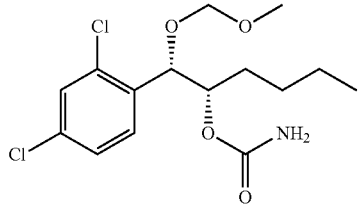

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 64: Synthesis of 1-(2,6-dichlorophenyl)-(S)-1-methoxymethoxypropyl-(S)-2-carbamate

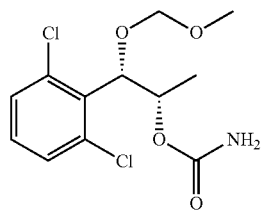

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.57~7.58 (m, 3H).

Example 65: Synthesis of 1-(2,6-dichlorophenyl)-(S)-1-methoxymethoxybutyl-(S)-2-carbamate

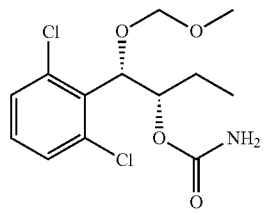

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.54~7.57 (m, 3H).

Example 66: Synthesis of 1-(2,6-dichlorophenyl)-(S)-1-methoxymethoxy-3-methyl-butyl-(S)-2-carbamate

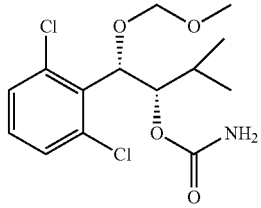

$^1$H NMR (400 MHz, CDCl$_3$) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.55~7.57 (m, 3H).

Example 67: Synthesis of 1-(2,4-dichlorophenyl)-(S)-1-methoxymethoxyhexyl-(S)-2-carbamate

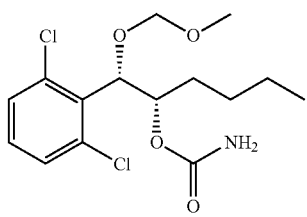

$^1$H NMR (400 MHz, CDCl$_3$) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.54~7.59 (m, 3H).

Example 68: Synthesis of 1-(2,3-dichlorophenyl)-(S)-1-methoxymethoxypropyl-(S)-2-carbamate

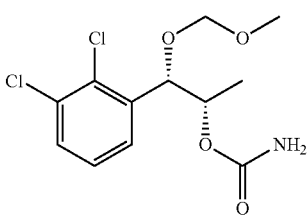 [SMILES: COCO[C@@H](c1cccc(Cl)c1Cl)[C@H](C)OC(N)=O]

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.01~7.14 (m, 3H).

Example 69: Synthesis of 1-(2-chlorophenyl)-(R)-1-methoxymethoxypropyl-(R)-2-carbamate

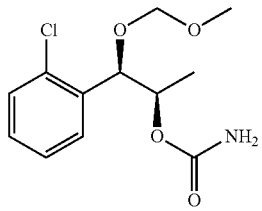 [SMILES: COCO[C@H](c1ccccc1Cl)[C@@H](C)OC(N)=O]

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.26~7.70 (m, 4H).

Example 70: Synthesis of 1-(2-chlorophenyl)-1-methoxymethoxypropyl-2-carbamate

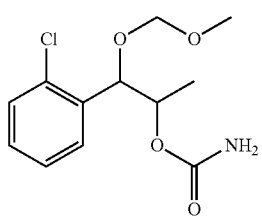 [SMILES: COCOC(c1ccccc1Cl)C(C)OC(N)=O]

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.26~7.70 (m, 4H).

Example 71: Synthesis of 1-(2-chlorophenyl)-(R)-1-methoxymethoxypropyl-(S)-2-carbamate

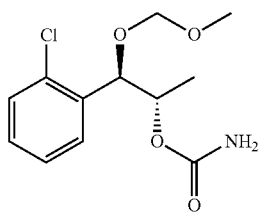 [SMILES: COCO[C@H](c1ccccc1Cl)[C@H](C)OC(N)=O]

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.26~7.70 (m, 4H).

Example 72: Synthesis of 1-(2-chlorophenyl)-(S)-1-methoxymethoxypropyl-(R)-2-carbamate

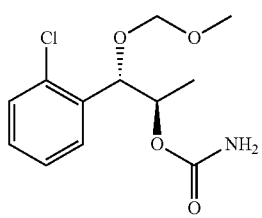 [SMILES: COCO[C@@H](c1ccccc1Cl)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.26~7.70 (m, 4H).

Example 73: Synthesis of 1-(2-chlorophenyl)-(R)-1-methoxymethoxybutyl-(R)-2-carbamate

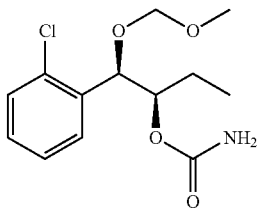

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 74: Synthesis of 1-(2-chlorophenyl)-1-methoxymethoxybutyl-2-carbamate

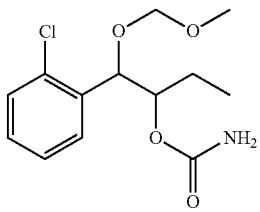 [SMILES: CCC(OC(N)=O)C(OCOC)c1ccccc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 75: Synthesis of 1-(2-chlorophenyl)-(R)-1-methoxymethoxy-3-methyl-butyl-(R)-2-carbamate

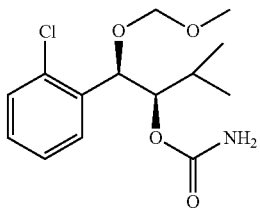 [SMILES: COCO[C@H](c1ccccc1Cl)[C@H](OC(N)=O)C(C)C]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 76: Synthesis of 1-(2-chlorophenyl)-1-methoxymethoxy-3-methyl-butyl-2-carbamate

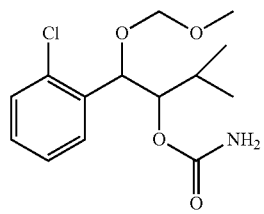

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 77: Synthesis of 1-(2-chlorophenyl)-(R)-1-methoxymethoxyhexyl-(R)-2-carbamate

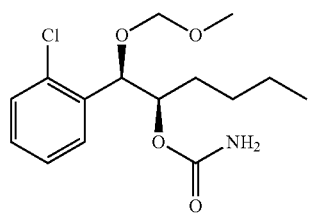 [SMILES: CCCC[C@@H](OC(N)=O)[C@H](OCOC)c1ccccc1Cl]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 78: Synthesis of 1-(2-chlorophenyl)-1-methoxymethoxyhexyl-2-carbamate

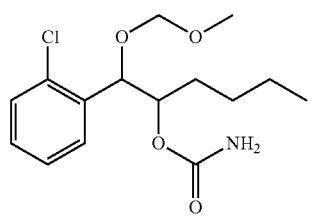 [SMILES: CCCCC(OC(N)=O)C(OCOC)c1ccccc1Cl]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H).

Example 79: Synthesis of 1-(2-chlorophenyl)-(R)-1-methoxymethoxypropyl-(R)-2-methylcarbamate

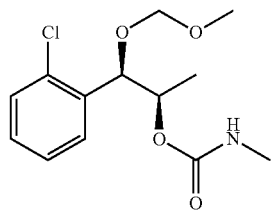 [SMILES: CNC(=O)O[C@H](C)[C@H](OCOC)c1ccccc1Cl]

¹H NMR (400 MHz, CDCl₃) δ 1.37 (d, J=6.8 Hz, 3H), 2.58 (s, 3H), 3.30 (s, 3H), 4.71 (d, J=6.8 Hz, 1H), 4.82~4.88 (m, 1H), 5.45 (s, 2H), 7.26~7.70 (m, 4H).

Example 80: Synthesis of 1-(2-chlorophenyl)-(R)-1-methoxymethoxypropyl-(R)-2-propylcarbamate

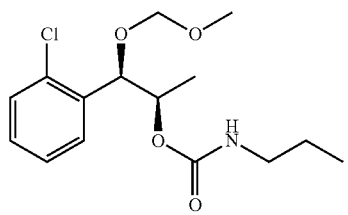 [SMILES: CCCNC(=O)O[C@H](C)[C@H](OCOC)c1ccccc1Cl]

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8 Hz, 1H), 4.82~4.88 (m, 1H), 5.45 (s, 2H), 7.26~7.70 (m, 4H).

Example 81: Synthesis of 1-(2-chlorophenyl)-(R)-1-methoxymethoxypropyl-(R)-2-isopropylcarbamate

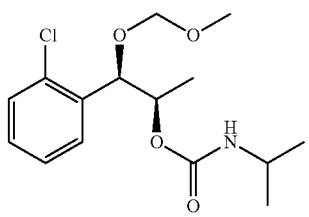 [SMILES: COCO[C@H](c1ccccc1Cl)[C@@H](C)OC(=O)NC(C)C]

¹H NMR (400 MHz, CDCl₃) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.26~7.70 (m, 4H).

Example 82: Synthesis of 1-(2-chlorophenyl)-(R)-1-methoxymethoxypropyl-(R)-2-cyclopropylcarbamate

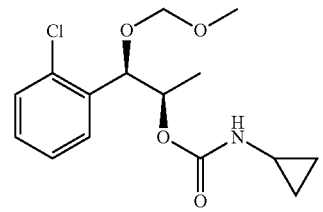 [SMILES: COCO[C@H](c1ccccc1Cl)[C@@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 83: Synthesis of 1-(2-chlorophenyl)-(R)-1-methoxymethoxypropyl-(R)-2-cyclohexylcarbamate

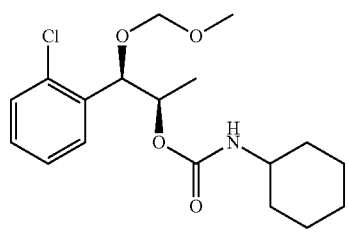 [SMILES: COCO[C@H](c1ccccc1Cl)[C@@H](C)OC(=O)NC1CCCCC1]

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.26~7.70 (m, 4H).

Example 84: Synthesis of 1-(2-chlorophenyl)-(R)-1-methoxymethoxypropyl-(R)-2-cyclohexylcarbamate

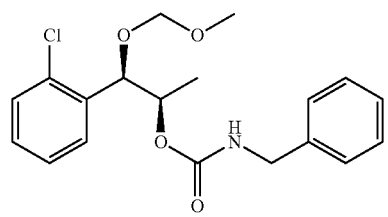 [SMILES: COCO[C@H](c1ccccc1Cl)[C@@H](C)OC(=O)NCc1ccccc1]

¹H NMR (400 MHz, CDCl₃) δ 1.37 (d, J=6.8 Hz, 3H), 3.30 (s, 3H), 4.20 (m, 2H), 4.71 (d, J=6.8 Hz, 1H), 4.82~4.88 (m, 1H), 5.45 (s, 2H), 7.13~7.19 (m, 4H), 7.37~7.88 (m, 5H).

Example 85: Synthesis of 1-(2-chlorophenyl)-(R)-1-methoxymethoxypropyl-(R)-2-bicyclo[2,2,1]heptan-escarbamate

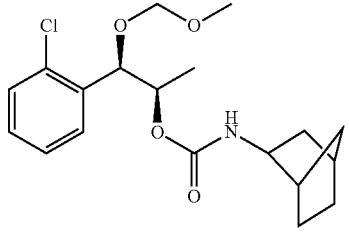 [SMILES: COCO[C@H](c1ccccc1Cl)[C@@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.13~7.19 (m, 4H), 7.37~7.88 (m, 5H).

Example 86: Synthesis of 1-(2-fluorophenyl)-(R)-1-methoxymethoxypropyl-(R)-2-carbamate

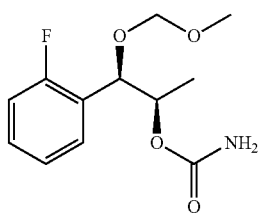

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.15~7.68 (m, 4H).

Example 87: Synthesis of 1-(4-fluorophenyl)-(R)-1-methoxymethoxypropyl-(R)-2-carbamate

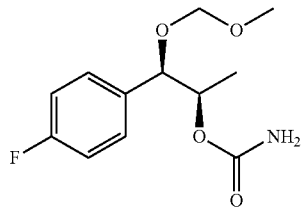 [SMILES: COCO[C@H](c1ccc(F)cc1)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 6.96~7.17 (m, 4H).

Example 88: Synthesis of 1-(4-fluorophenyl)-(R)-1-methoxymethoxybutyl-(R)-2-carbamate

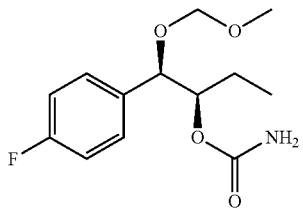 [SMILES: CC[C@@H](OC(N)=O)[C@H](OCOC)c1ccc(F)cc1]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 6.90~7.20 (m, 4H).

Example 89: Synthesis of 1-(4-fluorophenyl)-(R)-1-methoxymethoxy-3-methyl-butyl-(R)-2-carbamate

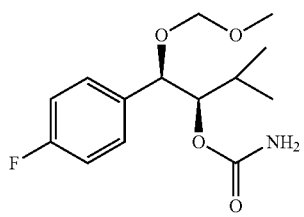 [SMILES: COCO[C@H](c1ccc(F)cc1)[C@H](OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 6.92~7.17 (m, 4H).

Example 90: Synthesis of 1-(4-fluorophenyl)-(R)-1-methoxymethoxyhexyl-(R)-2-carbamate

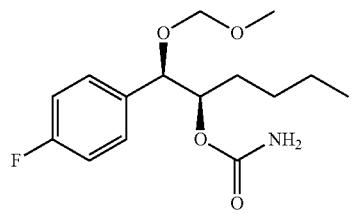

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 6.96~7.19 (m, 4H).

Example 91: Synthesis of 1-(2-iodophenyl)-(R)-1-methoxymethoxypropyl-(R)-2-carbamate

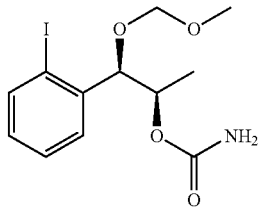

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.13~7.88 (m, 4H).

Example 92: Synthesis of 1-(2-iodophenyl)-(R)-1-methoxymethoxybutyl-(R)-2-carbamate

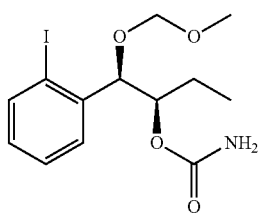

$^1$H NMR (400 MHz, CDCl$_3$) δ 1.04 (t, J=7.6 Hz, 3H), 1.60~1.71 (m, 2H), 3.30 (s, 3H), 4.71 (d, J=6.8 Hz, 1H), 4.82~4.88 (m, 1H), 5.45 (s, 2H), 7.26~7.70 (m, 4H).

Example 93: Synthesis of 1-(2-iodophenyl)-(R)-1-methoxymethoxy-3-methyl-butyl-(R)-2-carbamate

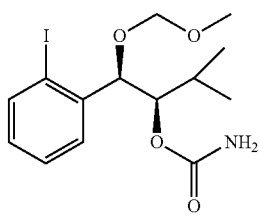 [SMILES: COCO[C@H](c1ccccc1I)[C@H](OC(N)=O)C(C)C]

$^1$H NMR (400 MHz, CDCl$_3$) δ 1.07 (d, J=7.6 Hz, 3H), 1.83~1.89 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 94: Synthesis of 1-(2-iodophenyl)-(R)-1-methoxymethoxyhexyl-(R)-2-carbamate

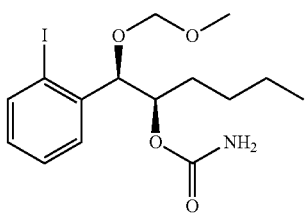 [SMILES: CCCC[C@@H](OC(N)=O)[C@H](OCOC)c1ccccc1I]

$^1$H NMR (400 MHz, CDCl$_3$) δ 0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8 Hz, 1H), 4.82~4.88 (m, 1H), 5.45 (s, 2H), 7.26~7.70 (m, 4H).

Example 95: Synthesis of 1-(3-iodophenyl)-(R)-1-methoxymethoxypropyl-(R)-2-carbamate

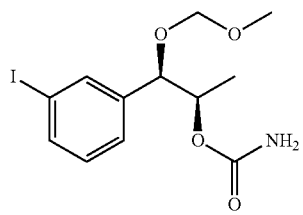 [SMILES: COCO[C@H](c1cccc(I)c1)[C@@H](C)OC(N)=O]

$^1$H NMR (400 MHz, CDCl$_3$) δ 1.16 (d, J=6.4 Hz, 3H), 3.39 (s, 3H), 4.54~4.63 (m, 6H), 5.04~5.10 (m, 1H), 7.09~7.73 (m, 4H).

Example 96: Synthesis of 1-(3-iodophenyl)-(R)-1-methoxymethoxybutyl-(R)-2-carbamate

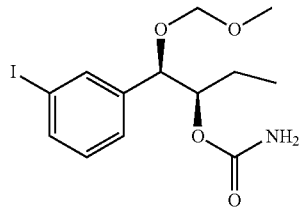 [SMILES: CC[C@@H](OC(N)=O)[C@H](OCOC)c1cccc(I)c1]

$^1$H NMR (400 MHz, CDCl$_3$) δ 1.04 (t, J=7.6 Hz, 3H), 1.60~1.71 (m, 2H), 3.30 (s, 3H), 4.71 (d, J=6.8 Hz, 1H), 4.82~4.88 (m, 1H), 5.45 (s, 2H), 7.26~7.70 (m, 4H).

Example 97: Synthesis of 1-(3-iodophenyl)-(R)-1-methoxymethoxy-3-methyl-butyl-(R)-2-carbamate

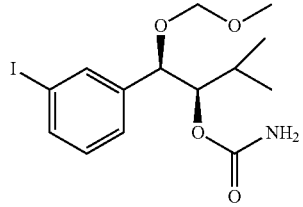 [SMILES: COCO[C@H](c1cccc(I)c1)[C@H](OC(N)=O)C(C)C]

$^1$H NMR (400 MHz, CDCl$_3$) δ 1.07 (d, J=7.6 Hz, 3H), 1.83~1.89 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 98: Synthesis of 1-(3-iodophenyl)-(R)-1-methoxymethoxyhexyl-(R)-2-carbamate

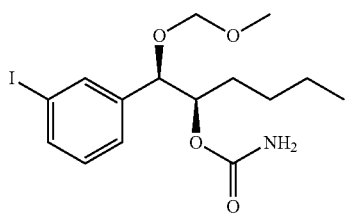 [SMILES: CCCC[C@@H](OC(N)=O)[C@H](OCOC)c1cccc(I)c1]

¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8 Hz, 1H), 4.82~4.88 (m, 1H), 5.45 (s, 2H), 7.26~7.70 (m, 4H).

Example 99: Synthesis of 1-(2-chlorophenyl)-(R)-1-methoxymethoxypropyl-(R)-2-methylcarbamate

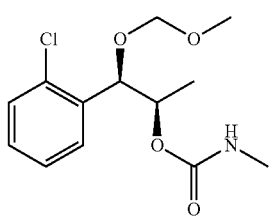 [SMILES: CNC(=O)O[C@H](C)[C@H](OCOC)c1ccccc1Cl]

¹H NMR (400 MHz, CDCl₃) δ 1.37 (d, J=6.8 Hz, 3H), 2.58 (s, 3H), 3.30 (s, 3H), 4.71 (d, J=6.8 Hz, 1H), 4.82~4.88 (m, 1H), 5.45 (s, 2H), 7.26~7.70 (m, 4H).

Example 100: Synthesis of 1-(2-chlorophenyl)-(R)-1-methoxymethoxypropyl-(R)-2-propylcarbamate

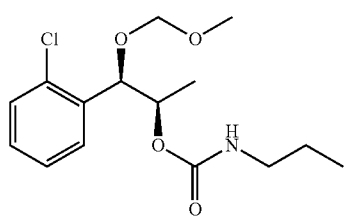 [SMILES: CCCNC(=O)O[C@H](C)[C@H](OCOC)c1ccccc1Cl]

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8 Hz, 1H), 4.82~4.88 (m, 1H), 5.45 (s, 2H), 7.26~7.70 (m, 4H).

Example 101: Synthesis of 1-(2-chlorophenyl)-(R)-1-methoxymethoxypropyl-(R)-2-isopropylcarbamate

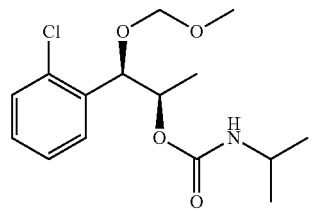 [SMILES: COCO[C@H](c1ccccc1Cl)[C@@H](C)OC(=O)NC(C)C]

¹H NMR (400 MHz, CDCl₃) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.26~7.70 (m, 4H).

Example 102: Synthesis of 1-(2-chlorophenyl)-(R)-1-methoxymethoxypropyl-(R)-2-cyclopropylcarbamate

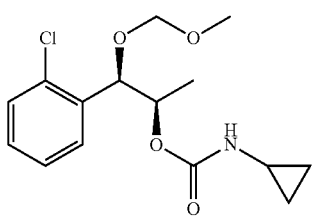 [SMILES: COCO[C@H](c1ccccc1Cl)[C@@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.26~7.70 (m, 4H).

Example 103: Synthesis of 1-(2-chlorophenyl)-(R)-1-methoxymethoxypropyl-(R)-2-cyclohexylcarbamate

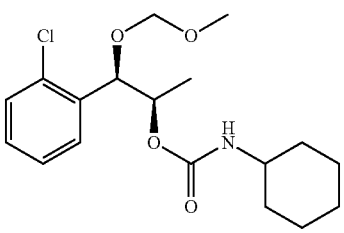 [SMILES: COCO[C@H](c1ccccc1Cl)[C@@H](C)OC(=O)NC1CCCCC1]

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.26~7.70 (m, 4H).

Example 104: Synthesis of 1-(2-chlorophenyl)-(R)-1-methoxymethoxypropyl-(R)-2-cyclohexylcarbamate

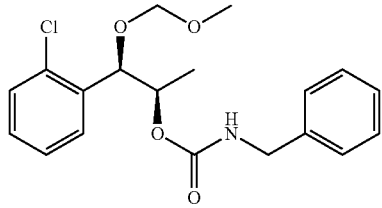 [SMILES: COCO[C@H](c1ccccc1Cl)[C@@H](C)OC(=O)NCc1ccccc1]

¹H NMR (400 MHz, CDCl₃) δ 1.37 (d, J=6.8 Hz, 3H), 3.30 (s, 3H), 4.20 (m, 2H), 4.71 (d, J=6.8 Hz, 1H), 4.82~4.88 (m, 1H), 5.45 (s, 2H), 7.13~7.19 (m, 4H), 7.37~7.88 (m, 5H).

Example 105: Synthesis of 1-(2-chlorophenyl)-(R)-1-methoxymethoxypropyl-(R)-2-bicyclo[2,2,1]heptanescarbamate

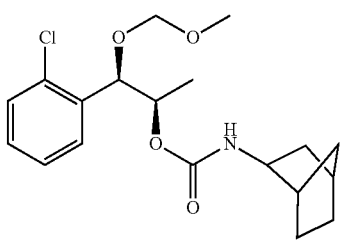 [SMILES: COCO[C@H](c1ccccc1Cl)[C@@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.30 (s, 3H), 3.53 (m, 1H), 4.71 (d, J=6.8 Hz, 1H), 4.82~4.88 (m, 1H), 5.45 (s, 2H), 7.13~7.19 (m, 4H), 7.37~7.88 (m, 5H).

Example 106: Synthesis of 1-(2,4-dichlorophenyl)-(R)-1-methoxymethoxypropyl-(R)-2-carbamate

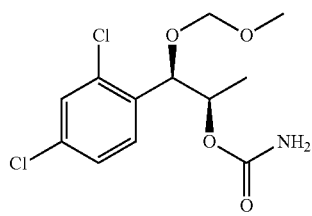 [SMILES: COCO[C@H](c1ccc(Cl)cc1Cl)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.24~7.30 (m, 2H), 7.73 (d, J=1.5 Hz, 1H).

Example 107: Synthesis of 1-(2,6-dichlorophenyl)-(R)-1-methoxymethoxypropyl-(R)-2-carbamate

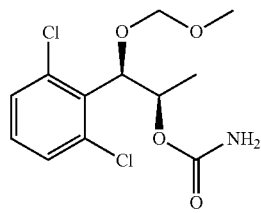 [SMILES: COCO[C@H](c1c(Cl)cccc1Cl)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.57~7.58 (m, 3H).

Example 108: Synthesis of 1-(2,3-dichlorophenyl)-(R)-1-methoxymethoxypropyl-(R)-2-carbamate

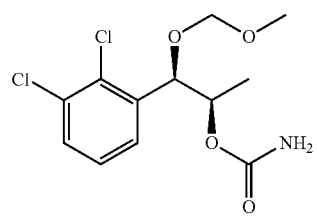 [SMILES: COCO[C@H](c1cccc(Cl)c1Cl)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.01~7.14 (m, 3H).

Example 109: Synthesis of 1-(2,4-dichlorophenyl)-(R)-1-methoxymethoxybutyl-(R)-2-carbamate

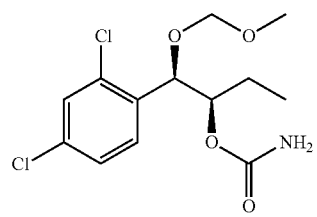 [SMILES: CC[C@@H](OC(N)=O)[C@H](OCOC)c1ccc(Cl)cc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 110: Synthesis of 1-(2,6-dichlorophenyl)-(R)-1-methoxymethoxybutyl-(R)-2-carbamate

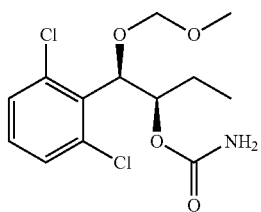 [SMILES: CC[C@@H](OC(N)=O)[C@H](OCOC)c1c(Cl)cccc1Cl]

$^1$H NMR (400 MHz, CDCl$_3$) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.54~7.57 (m, 3H).

Example 111: Synthesis of 1-(2,4-dichlorophenyl)-(R)-1-methoxymethoxy-3-methyl-butyl-(R)-2-carbamate

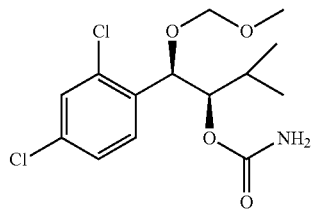 [SMILES: COCO[C@H](c1ccc(Cl)cc1Cl)[C@H](OC(N)=O)C(C)C]

$^1$H NMR (400 MHz, CDCl$_3$) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 112: Synthesis of 1-(2,6-dichlorophenyl)-(R)-1-methoxymethoxy-3-methyl-butyl-(R)-2-carbamate

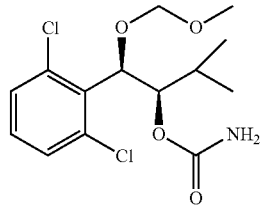 [SMILES: COCO[C@H](c1c(Cl)cccc1Cl)[C@H](OC(N)=O)C(C)C]

$^1$H NMR (400 MHz, CDCl$_3$) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.55~7.57 (m, 3H).

Example 113: Synthesis of 1-(2,4-dichlorophenyl)-(R)-1-methoxymethoxyhexyl-(R)-2-carbamate

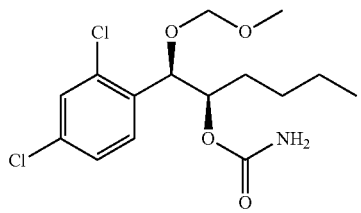 [SMILES: CCCC[C@@H](OC(N)=O)[C@H](OCOC)c1ccc(Cl)cc1Cl]

$^1$H NMR (400 MHz, CDCl$_3$) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 114: Synthesis of 1-(2,4-dichlorophenyl)-(R)-1-methoxymethoxyhexyl-(R)-2-carbamate

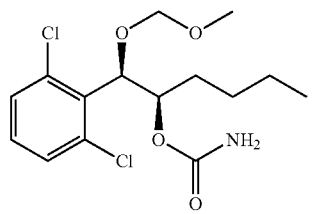 [SMILES: CCCC[C@@H](OC(N)=O)[C@H](OCOC)c1c(Cl)cccc1Cl]

$^1$H NMR (400 MHz, CDCl$_3$) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.54~7.59 (m, 3H).

Example 115: Synthesis of 1-(2,4-dichlorophenyl)-1-methoxymethoxypropyl-2-carbamate

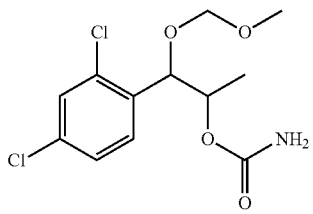

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.24~7.30 (m, 2H), 7.73 (d, J=1.5 Hz, 1H).

Example 116: Synthesis of 1-(2,6-dichlorophenyl)-1-methoxymethoxypropyl-2-carbamate

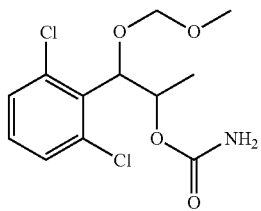 [SMILES: COCOC(c1c(Cl)cccc1Cl)C(C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.57~7.58 (m, 3H).

Example 117: Synthesis of 1-(2,3-dichlorophenyl)-1-methoxymethoxypropyl-2-carbamate

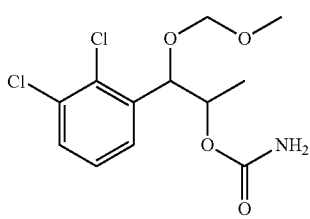 [SMILES: COCOC(c1cccc(Cl)c1Cl)C(C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.01~7.14 (m, 3H).

Example 118: Synthesis of 1-(2,4-dichlorophenyl)-1-methoxymethoxybutyl-2-carbamate

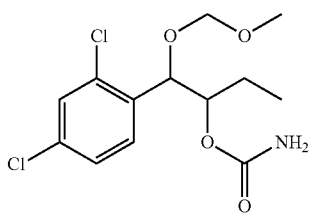 [SMILES: CCC(OC(N)=O)C(OCOC)c1ccc(Cl)cc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 119: Synthesis of 1-(2,6-dichlorophenyl)-1-methoxymethoxybutyl-2-carbamate

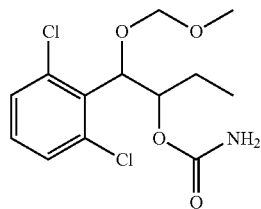 [SMILES: CCC(OC(N)=O)C(OCOC)c1c(Cl)cccc1Cl]

¹H NMR (400 MHz, CDCl₃) δ 1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.54~7.57 (m, 3H).

Example 120: Synthesis of 1-(2,4-dichlorophenyl)-1-methoxymethoxy-3-methyl-butyl-2-carbamate

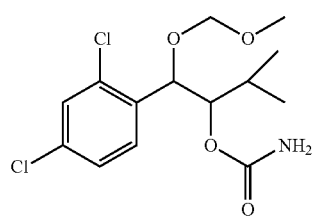 [SMILES: COCOC(c1ccc(Cl)cc1Cl)C(OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 121: Synthesis of 1-(2,6-dichlorophenyl)-1-methoxymethoxy-3-methyl-butyl-2-carbamate

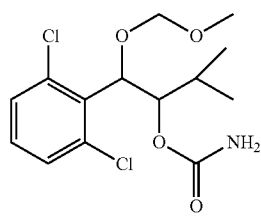 [SMILES: COCOC(c1c(Cl)cccc1Cl)C(OC(N)=O)C(C)C]

¹H NMR (400 MHz, CDCl₃) δ 1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.55~7.57 (m, 3H).

Example 122: Synthesis of 1-(2,4-dichlorophenyl)-1-methoxymethoxyhexyl-2-carbamate

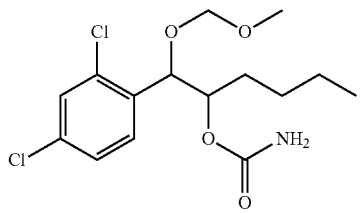 [SMILES: CCCCC(OC(N)=O)C(OCOC)c1ccc(Cl)cc1Cl]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H).

Example 123: Synthesis of 1-(2,4-dichlorophenyl)-1-methoxymethoxyhexyl-2-carbamate

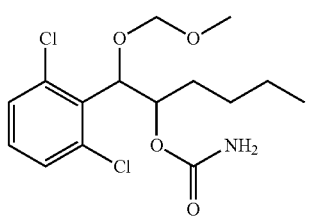 [SMILES: CCCCC(OC(N)=O)C(OCOC)c1c(Cl)cccc1Cl]

¹H NMR (400 MHz, CDCl₃) δ 0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 7.54~7.59 (m, 3H).

Example 124: Synthesis of 1-(2-chlorophenyl)-(S)-1-methoxypropyl-(S)-2-carbamate

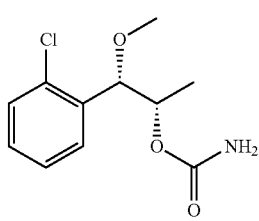 [SMILES: CO[C@@H](c1ccccc1Cl)[C@H](C)OC(N)=O]

1-(2-chlorophenyl)-1-hydorxyalkyl-2-alkylcarbamate (Preparation Example 103, 0.5 g), THF (Tetrahydrofuran), MeI (Methyliodide, 5 eq, 0.5 mL) and t-BuOH (Potassium tert-butoxide, 1.5 eq, 0.26 g) were put into a flask and stirred at the 0° C. When the reaction was completed, the obtained product was washed with 1 M HCl solution and EA (Ethylacetate). The separated organic layer was dehydrated with anhydrous MgSO₄ (Magnesium sulfate), filtrated, and concentrated under reduced pressure. The concentrated residue was purified by a silicagel aolumn chromatography, to obtain title compound.

¹H NMR (400 MHz, CDCl₃) δ 1.40 (d, J=6.0 Hz, 3H), 3.24 (s, 3H), 4.71 (d, J=6.4 Hz, 1H), 4.80~4.85 (m, 1H), 7.01 (br s, 1H), 7.07~7.20 (m, 4H).

According to the method described in Example 124, the following compounds of Examples 125 to 246 were prepared:

Example 125: Synthesis of 1-(2-chlorophenyl)-(S)-1-methoxypropyl-(S)-2-methylcarbamate

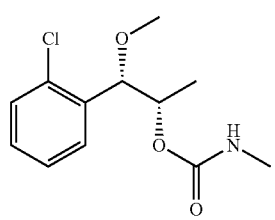 [SMILES: CNC(=O)O[C@@H](C)[C@@H](OC)c1ccccc1Cl]

¹H NMR (400 MHz, CDCl₃) δ 1.40 (d, J=6.0 Hz, 3H), 2.74 (s, 3H), 3.24 (s, 3H), 4.71 (d, J=6.4 Hz, 1H), 4.80~4.85 (m, 1H), 7.01 (br s, 1H), 7.07~7.20 (m, 4H).

Example 126: Synthesis of 1-(2-chlorophenyl)-(S)-1-methoxypropyl-(S)-2-propylcarbamate

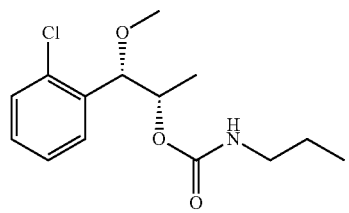 [SMILES: CCCNC(=O)O[C@@H](C)[C@@H](OC)c1ccccc1Cl]

¹H NMR (400 MHz, CDCl₃) δ 0.96 (t, J=6.4 Hz, 3H), 1.40 (d, J=6.0 Hz, 3H), 1.55~1.60 (m, 2H), 2.96 (t, J=6.0 Hz, 2H), 3.24 (s, 3H), 4.71 (d, J=6.0 Hz, 1H), 4.82~4.88 (m, 1H), 6.76 (br s, 2H), 7.07~7.21 (m, 4H).

Example 127: Synthesis of 1-(2-chlorophenyl)-(S)-1-methoxypropyl-(S)-2-isopropylcarbamate

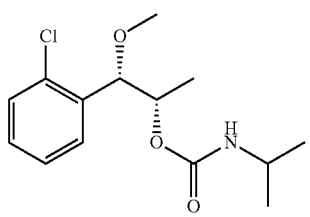

¹H NMR (400 MHz, CDCl₃) δ 1.15 (d, J=6.0 Hz, 3H), 1.35 (d, J=6.4 Hz, 3H), 1.50 (d, J=6.8 Hz, 3H), 3.24 (s, 3H), 3.75 (br s, 1H), 4.48 (br s, 1H), 4.50 (d, J=4.8 Hz, 1H), 5.09~5.20 (m, 1H), 7.07~7.20 (m, 4H).

Example 128: Synthesis of 1-(2-chlorophenyl)-(S)-1-methoxypropyl-(S)-2-cyclopropylcarbamate

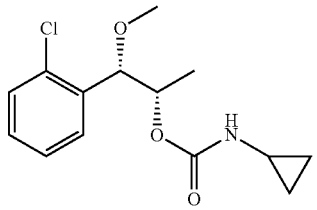

$^1$H NMR (400 MHz, CDCl$_3$) δ 0.30~0.34 (m, 2H), 0.54~0.58 (m, 2H), 1.30 (d, J=6.8 Hz, 3H), 2.55 (m, 1H), 3.24 (s, 3H), 4.55 (d, J=4.8 Hz, 1H), 4.90 (br m, 1H), 5.09~5.15 (br s, 1H), 7.06~7.21 (m, 4H).

Example 129: Synthesis of 1-(2-chlorophenyl)-(S)-1-methoxypropyl-(S)-2-cyclohexylcarbamate

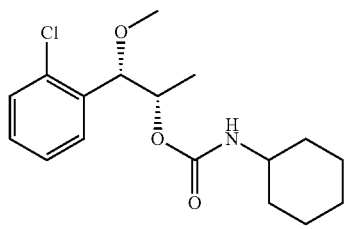 [SMILES: CO[C@@H](c1ccccc1Cl)[C@H](C)OC(=O)NC1CCCCC1]

$^1$H NMR (400 MHz, CDCl$_3$) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.26~7.70 (m, 4H).

Example 130: Synthesis of 1-(2-chlorophenyl)-(S)-1-methoxypropyl-(S)-2-cyclohexylcarbamate

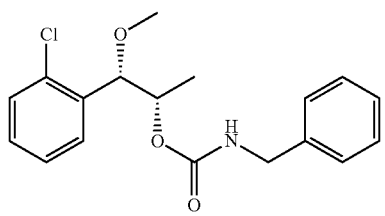

$^1$H NMR (400 MHz, CDCl$_3$) δ 1.40 (d, J=6.8 Hz, 3H), 3.24 (s, 3H), 4.20 (m, 2H), 4.71 (d, J=6.8 Hz, 1H), 4.82~4.88 (m, 1H), 7.13~7.19 (m, 4H), 7.32~7.46 (m, 5H).

Example 131: Synthesis of 1-(2-chlorophenyl)-(S)-1-methoxypropyl-(S)-2-bicyclo[2,2,1]heptanescarbamate

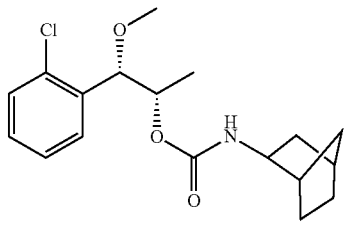 [SMILES: CO[C@@H](c1ccccc1Cl)[C@H](C)OC(=O)NC1CC2CCC1C2]

$^1$H NMR (400 MHz, CDCl$_3$) δ 1.40 (d, J=6.4 Hz, 3H), 1.44~1.50 (m, 7H), 1.70~1.73 (m, 1H), 2.03~2.07 (m, 1H), 3.24 (s, 3H), 3.50~3.55 (m, 2H), 4.71 (d, J=6.4 Hz, 1H), 4.80~4.87 (m, 1H), 7.07~7.19 (m, 4H).

Example 132: Synthesis of 1-(2-chlorophenyl)-(S)-1-methoxybutyl-(S)-2-carbamate

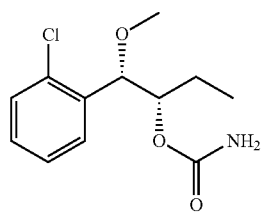 [SMILES: CC[C@H](OC(N)=O)[C@@H](OC)c1ccccc1Cl]

$^1$H NMR (400 MHz, CDCl$_3$) δ 1.04 (t, J=7.6 Hz, 3H), 1.60~1.71 (m, 2H), 3.22 (s, 3H), 4.71 (d, J=6.8 Hz, 1H), 4.73 (br s, 2H), 4.82~4.88 (m, 1H), 7.26~7.70 (m, 4H).

Example 133: Synthesis of 1-(2-chlorophenyl)-(S)-1-methoxy-3-methyl-butyl-(S)-2-carbamate

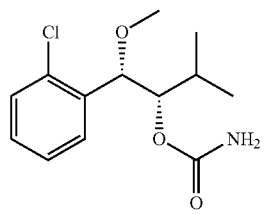 [SMILES: CO[C@@H](c1ccccc1Cl)[C@@H](OC(N)=O)C(C)C]

$^1$H NMR (400 MHz, CDCl$_3$) δ 1.07 (t, J=7.6 Hz, 6H), 1.83~1.89 (m, 1H), 3.26 (s, 3H), 4.71 (d, J=6.8 Hz, 1H), 4.73 (br s, 2H), 4.82~4.88 (m, 1H), 7.26~7.70 (m, 4H).

Example 134: Synthesis of 1-(2-chlorophenyl)-(S)-1-methoxyhexyl-(S)-2-carbamate

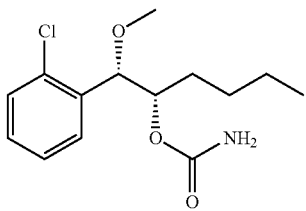 [SMILES: CCCC[C@H](OC(N)=O)[C@@H](OC)c1ccccc1Cl]

$^1$H NMR (400 MHz, CDCl$_3$) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 7.26~7.70 (m, 4H).

Example 135: Synthesis of 1-(2-fluorophenyl)-(S)-1-methoxypropyl-(S)-2-carbamate

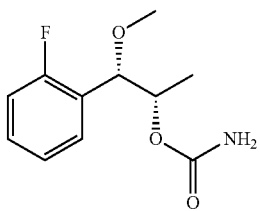

$^1$H NMR (400 MHz, CDCl$_3$) δ 1.37 (d, J=6.8 Hz, 3H), 3.23 (s, 3H), 4.71 (d, J=6.8 Hz, 1H), 4.82~4.88 (m, 1H), 7.15~7.68 (m, 4H).

Example 136: Synthesis of 1-(2-fluorophenyl)-(S)-1-methoxypropyl-(S)-2-methylcarbamate

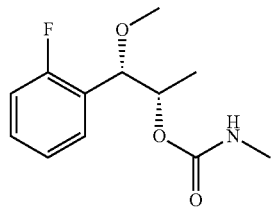

$^1$H NMR (400 MHz, CDCl$_3$) δ 1.37 (d, J=6.8 Hz, 3H), 2.58 (s, 3H), 3.24 (s, 3H), 4.71 (d, J=6.8 Hz, 1H), 4.82~4.88 (m, 1H), 7.15~7.68 (m, 4H).

Example 137: Synthesis of 1-(2-fluorophenyl)-(S)-1-methoxypropyl-(S)-2-propylcarbamate

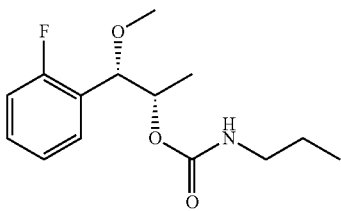

$^1$H NMR (400 MHz, CDCl$_3$) δ 0.90 (t, J=6.8 Hz, 3H), 1.37 (d, J=6.8 Hz, 3H), 1.60 (m, 2H), 3.18 (t, J=7.1 Hz, 2H), 3.22 (s, 3H), 4.71 (d, J=6.8 Hz, 1H), 4.82~4.88 (m, 1H), 7.15~7.68 (m, 4H).

Example 138: Synthesis of 1-(2-fluorophenyl)-(S)-1-methoxypropyl-(S)-2-isopropylcarbamate

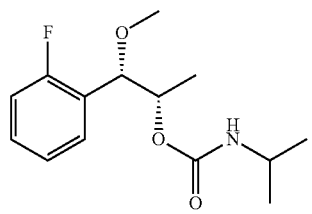 [SMILES: CO[C@@H](c1ccccc1F)[C@H](C)OC(=O)NC(C)C]

$^1$H NMR (400 MHz, CDCl$_3$) δ 1.27 (d, J=6.8 Hz, 6H), 1.37 (d, J=6.8 Hz, 3H), 3.25 (s, 3H), 4.17 (m, 1H), 4.71 (d, J=6.8 Hz, 1H), 4.82~4.88 (m, 1H), 7.15~7.69 (m, 4H).

Example 139: Synthesis of 1-(2-fluorophenyl)-(S)-1-methoxypropyl-(S)-2-cyclopropylcarbamate

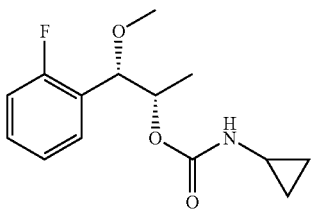 [SMILES: CO[C@@H](c1ccccc1F)[C@H](C)OC(=O)NC1CC1]

$^1$H NMR (400 MHz, CDCl$_3$) δ 0.57 (m, 2H), 0.82 (m, 2H), 1.37 (d, J=6.8 Hz, 3H), 2.75 (m, 1H), 3.24 (s, 3H), 4.71 (d, J=6.8 Hz, 1H), 4.82~4.88 (m, 1H), 7.16~7.70 (m, 4H).

Example 140: Synthesis of 1-(2-fluorophenyl)-(S)-1-methoxypropyl-(S)-2-cyclohexylcarbamate

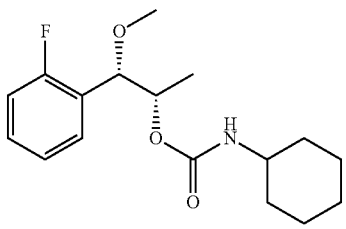

$^1$H NMR (400 MHz, CDCl$_3$) δ 1.11~1.21 (m, 4H), 1.37 (d, J=6.8 Hz, 3H), 1.47~1.49 (m, 4H), 1.74 (m, 2H), 3.26 (s, 3H), 3.54 (m, 1H), 4.71 (d, J=6.8 Hz, 1H), 4.82~4.88 (m, 1H), 7.15~7.66 (m, 4H).

Example 141: Synthesis of 1-(2-fluorophenyl)-(S)-1-methoxymethoxypropyl-(S)-2-cyclohexylcarbamate

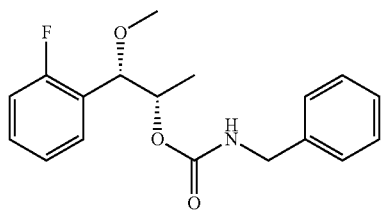

¹H NMR (400 MHz, CDCl₃) δ 1.37 (d, J=6.8 Hz, 3H), 3.24 (s, 3H), 4.20 (m, 2H), 4.71 (d, J=6.8 Hz, 1H), 4.82~4.88 (m, 1H), 7.15~7.68 (m, 4H), 7.72~7.88 (m, 5H).

Example 142: Synthesis of 1-(2fluorophenyl)-(S)-1-methoxypropyl-(S)-2-bicyclo[2,2,1]heptanescarbamate

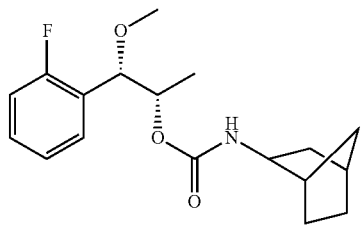 [SMILES: CO[C@@H](c1ccccc1F)[C@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.23 (s, 3H), 3.53 (m, 1H), 4.71 (d, J=6.8 Hz, 1H), 4.82~4.88 (m, 1H), 7.15~7.68 (m, 4H), 7.37~7.88 (m, 5H).

Example 143: Synthesis of 1-(2-iodophenyl)-(S)-1-methoxypropyl-(S)-2-carbamate

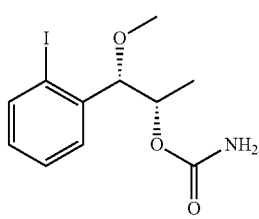 [SMILES: CO[C@@H](c1ccccc1I)[C@H](C)OC(N)=O]

¹H NMR (400 MHz, CDCl₃) δ 1.37 (d, J=6.8 Hz, 3H), 3.21 (s, 3H), 4.71 (d, J=6.8 Hz, 1H), 4.82~4.88 (m, 1H), 7.13~7.88 (m, 4H).

Example 144: Synthesis of 1-(2-iodophenyl)-(S)-1-methoxypropyl-(S)-2-methylcarbamate

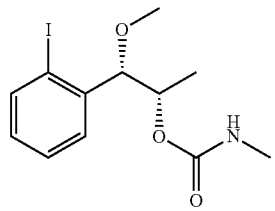 [SMILES: CNC(=O)O[C@@H](C)[C@@H](OC)c1ccccc1I]

¹H NMR (400 MHz, CDCl₃) δ 1.37 (d, J=6.8 Hz, 3H), 2.58 (s, 3H), 3.24 (s, 3H), 4.71 (d, J=6.8 Hz, 1H), 4.82~4.88 (m, 1H), 7.13~7.90 (m, 4H).

Example 145: Synthesis of 1-(2-iodophenyl)-(S)-1-methoxypropyl-(S)-2-propylcarbamate

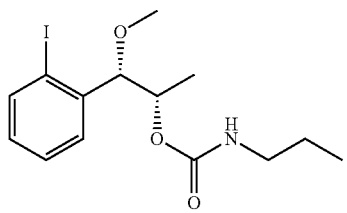 [SMILES: CCCNC(=O)O[C@@H](C)[C@@H](OC)c1ccccc1I]

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.24 (s, 3H), 4.71 (d, J=6.8 Hz, 1H), 4.82~4.88 (m, 1H), 7.14~7.87 (m, 4H).

Example 146: Synthesis of 1-(2-iodophenyl)-(S)-1-methoxypropyl-(S)-2-isopropylcarbamate

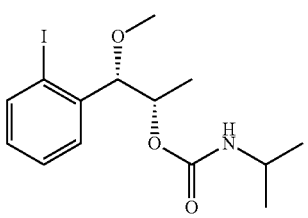 [SMILES: CO[C@@H](c1ccccc1I)[C@H](C)OC(=O)NC(C)C]

¹H NMR (400 MHz, CDCl₃) δ 1.27 (d, J=6.8 Hz, 6H), 1.37 (d, J=6.8 Hz, 3H), 3.30 (s, 3H), 4.17 (m, 1H), 4.71 (d, J=6.8 Hz, 1H), 4.82~4.88 (m, 1H), 5.45 (s, 2H), 7.15~7.89 (m, 4H).

Example 147: Synthesis of 1-(2-iodophenyl)-(S)-1-methoxypropyl-(S)-2-cyclopropylcarbamate

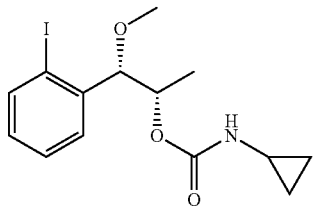

¹H NMR (400 MHz, CDCl₃) δ 0.57 (m, 2H), 0.82 (m, 2H), 1.37 (d, J=6.8 Hz, 3H), 2.75 (m, 1H), 3.30 (s, 3H), 4.71 (d, J=6.8 Hz, 1H), 4.82~4.88 (m, 1H), 5.45 (s, 2H), 7.16~7.87 (m, 4H).

Example 148: Synthesis of 1-(2-iodophenyl)-(S)-1-methoxypropyl-(S)-2-cyclohexylcarbamate

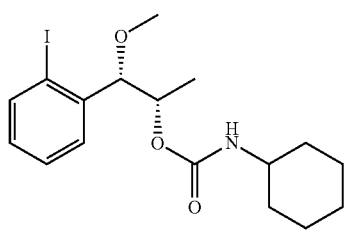

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8 Hz, 1H), 4.82~4.88 (m, 1H), 5.45 (s, 2H), 7.18~7.91 (m, 4H).

Example 149: Synthesis of 1-(2-iodophenyl)-(S)-1-methoxypropyl-(S)-2-cyclohexylcarbamate

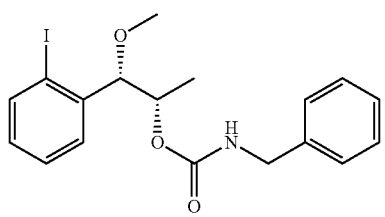

¹H NMR (400 MHz, CDCl₃) δ 1.37 (d, J=6.8 Hz, 3H), 3.24 (s, 3H), 4.20 (m, 2H), 4.71 (d, J=6.8 Hz, 1H), 4.82~4.88 (m, 1H), 7.15~7.68 (m, 4H), 7.72~7.88 (m, 5H).

Example 150: Synthesis of 1-(2-iodophenyl)-(S)-1-methoxypropyl-(S)-2-bicyclo[2,2,1]heptanescarbamate

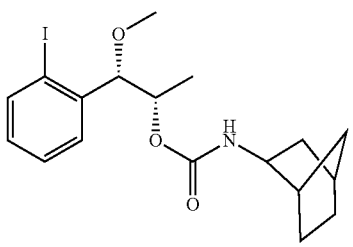 [SMILES: CO[C@@H](c1ccccc1I)[C@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.22 (s, 3H), 3.53 (m, 1H), 4.71 (d, J=6.8 Hz, 1H), 4.82~4.88 (m, 1H), 7.15~7.68 (m, 4H), 7.37~7.88 (m, 5H).

Example 151: Synthesis of 1-(2-iodophenyl)-(S)-1-methoxybutyl-(S)-2-carbamate

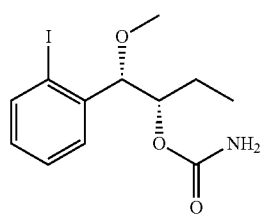 [SMILES: CC[C@H](OC(N)=O)[C@@H](OC)c1ccccc1I]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.82~4.88 (m, 1H), 7.26~7.70 (m, 4H).

Example 152: Synthesis of 1-(2-iodophenyl)-(S)-1-methoxybutyl-(S)-2-methylcarbamate

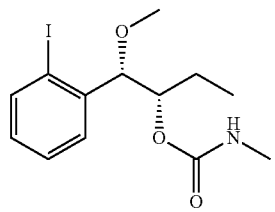 [SMILES: CC[C@H](OC(=O)NC)[C@@H](OC)c1ccccc1I]

¹H NMR (400 MHz, CDCl₃) δ 1.04 (t, J=7.6 Hz, 3H), 1.60~1.71 (m, 2H), 2.58 (s, 3H), 3.23 (s, 3H), 4.71 (d, J=6.8 Hz, 1H), 4.82~4.88 (m, 1H), 7.13~7.88 (m, 4H).

Example 153: Synthesis of 1-(2-iodophenyl)-(S)-1-methoxybutyl-(S)-2-propylcarbamate

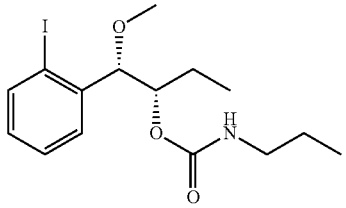 [SMILES: CCCNC(=O)O[C@@H](CC)[C@@H](OC)c1ccccc1I]

¹H NMR (400 MHz, CDCl₃) δ 0.90 (t, J=6.8 Hz, 3H), 1.04 (t, J=7.6 Hz, 3H), 1.58~1.71 (m, 4H), 3.18 (t, J=7.1 Hz, 2H), 3.22 (s, 3H), 4.71 (d, J=6.8 Hz, 1H), 4.82~4.88 (m, 1H), 7.14~7.89 (m, 4H).

Example 154: Synthesis of 1-(2-iodophenyl)-(S)-1-methoxybutyl-(S)-2-isopropylcarbamate

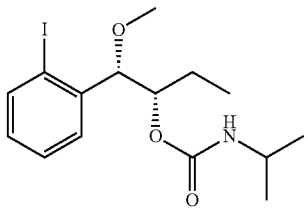 [SMILES: CC[C@H](OC(=O)NC(C)C)[C@@H](OC)c1ccccc1I]

¹H NMR (400 MHz, CDCl₃) δ 1.04 (t, J=7.6 Hz, 3H), 1.27 (d, J=6.8 Hz, 6H), 1.60~1.71 (m, 2H), 3.23 (s, 3H), 4.17 (m, 1H), 4.71 (d, J=6.8 Hz, 1H), 4.82~4.88 (m, 1H), 7.15~7.90 (m, 4H).

Example 155: Synthesis of 1-(2-iodophenyl)-(S)-1-methoxybutyl-(S)-2-cyclopropylcarbamate

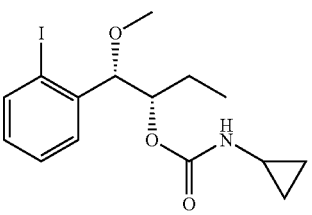 [SMILES: CC[C@H](OC(=O)NC1CC1)[C@@H](OC)c1ccccc1I]

¹H NMR (400 MHz, CDCl₃) δ 0.57 (m, 2H), 0.82 (m, 2H), 1.04 (t, J=7.6 Hz, 3H), 1.60~1.71 (m, 2H), 2.75 (m, 1H), 3.24 (s, 3H), 4.71 (d, J=6.8 Hz, 1H), 4.82~4.88 (m, 1H), 7.16~7.90 (m, 4H).

Example 156: Synthesis of 1-(2-iodophenyl)-(S)-1-methoxybutyl-(S)-2-cyclohexylcarbamate

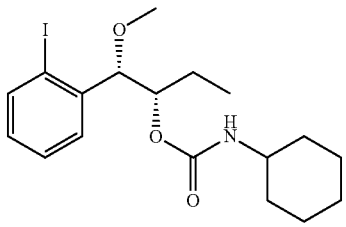 [SMILES: CC[C@H](OC(=O)NC1CCCCC1)[C@@H](OC)c1ccccc1I]

¹H NMR (400 MHz, CDCl₃) δ 1.04 (t, J=7.6 Hz, 3H), 1.11~1.21 (m, 4H), 1.47~1.49 (m, 4H), 1.60~1.71 (m, 2H), 1.74 (m, 2H), 3.23 (s, 3H), 3.54 (m, 1H), 4.71 (d, J=6.8 Hz, 1H), 4.82~4.88 (m, 1H), 7.14~7.87 (m, 4H).

Example 157: Synthesis of 1-(2-iodophenyl)-(S)-1-methoxybutyl-(S)-2-cyclohexylcarbamate

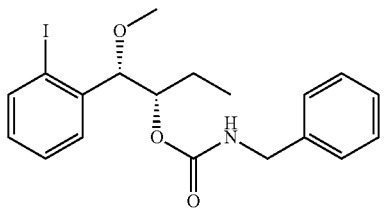

¹H NMR (400 MHz, CDCl₃) δ 1.04 (t, J=7.6 Hz, 3H), 1.60~1.71 (m, 2H), 3.23 (s, 3H), 4.20 (m, 2H), 4.71 (d, J=6.8 Hz, 1H), 4.82~4.88 (m, 1H), 7.14~7.19 (m, 4H), 7.37~7.88 (m, 5H).

Example 158: Synthesis of 1-(2-iodophenyl)-(S)-1-methoxybutyl-(S)-2-bicyclo[2,2,1]heptanescarbamate

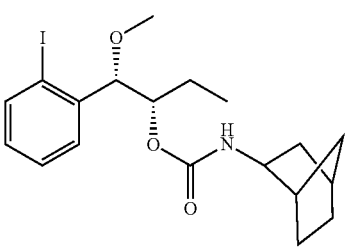 [SMILES: CC[C@H](OC(=O)NC1CC2CCC1C2)[C@@H](OC)c1ccccc1I]

¹H NMR (400 MHz, CDCl₃) δ 1.04 (t, J=7.6 Hz, 3H), 1.33~1.58 (m, 6H), 1.60~1.71 (m, 2H), 1.75~1.88 (m, 2H), 2.06~2.13 (m, 2H), 3.24 (s, 3H), 3.53 (m, 1H), 4.71 (d, J=6.8 Hz, 1H), 4.82~4.88 (m, 1H), 7.15~7.19 (m, 4H), 7.37~7.88 (m, 5H).

Example 159: Synthesis of 1-(2-iodophenyl)-(S)-1-methoxy-3-methyl-butyl-(S)-2-carbamate

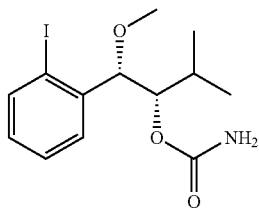 [SMILES: CO[C@@H](c1ccccc1I)[C@@H](OC(N)=O)C(C)C]

$^1$H NMR (400 MHz, CDCl$_3$) δ 1.07 (d, J=7.6 Hz, 3H), 1.83~1.89 (m, 1H), 3.23 (s, 3H), 4.71 (d, J=6.8 Hz, 1H), 4.82~4.88 (m, 1H), 7.26~7.70 (m, 4H).

Example 160: Synthesis of 1-(2-iodophenyl)-(S)-1-methoxy-3-methyl-butyl-(S)-2-methylcarbamate

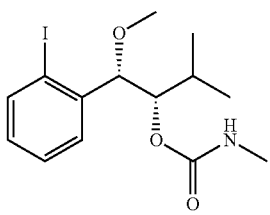 [SMILES: CNC(=O)O[C@@H](C(C)C)[C@@H](OC)c1ccccc1I]

$^1$H NMR (400 MHz, CDCl$_3$) δ 1.04 (d, J=7.6 Hz, 6H), 1.60~1.71 (m, 1H), 2.58 (s, 3H), 3.24 (s, 3H), 4.71 (d, J=6.8 Hz, 1H), 4.82~4.88 (m, 1H), 7.13~7.88 (m, 4H).

Example 161: Synthesis of 1-(2-iodophenyl)-(S)-1-methoxy-3-methyl-butyl-(S)-2-propylcarbamate

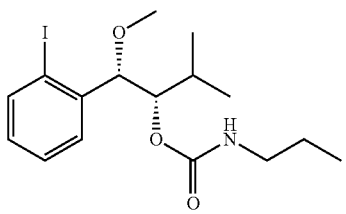 [SMILES: CCCNC(=O)O[C@@H](C(C)C)[C@@H](OC)c1ccccc1I]

$^1$H NMR (400 MHz, CDCl$_3$) δ 0.90 (t, J=6.8 Hz, 3H), 1.04 (d, J=7.6 Hz, 6H), 1.58~1.71 (m, 5H), 3.18 (t, J=7.1 Hz, 2H), 3.23 (s, 3H), 4.71 (d, J=6.8 Hz, 1H), 4.82~4.88 (m, 1H), 7.14~7.89 (m, 4H).

Example 162: Synthesis of 1-(2-iodophenyl)-(S)-1-methoxy-3-methyl-butyl-(S)-2-isopropylcarbamate

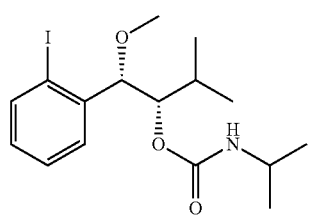 [SMILES: CO[C@@H](c1ccccc1I)[C@@H](OC(=O)NC(C)C)C(C)C]

$^1$H NMR (400 MHz, CDCl$_3$) δ 1.04 (t, J=7.6 Hz, 6H), 1.27 (d, J=6.8 Hz, 6H), 1.60~1.71 (m, 1H), 3.24 (s, 3H), 4.17 (m, 1H), 4.71 (d, J=6.8 Hz, 1H), 4.82~4.88 (m, 1H), 7.15~7.90 (m, 4H).

Example 163: Synthesis of 1-(2-iodophenyl)-(S)-1-methoxy-3-methyl-butyl-(S)-2-cyclopropylcarbamate

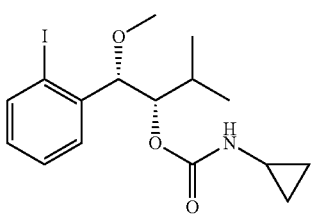 [SMILES: CO[C@@H](c1ccccc1I)[C@@H](OC(=O)NC1CC1)C(C)C]

$^1$H NMR (400 MHz, CDCl$_3$) δ 0.57 (m, 2H), 0.82 (m, 2H), 1.04 (d, J=7.6 Hz, 6H), 1.60~1.71 (m, 1H), 2.75 (m, 1H), 3.24 (s, 3H), 4.71 (d, J=6.8 Hz, 1H), 4.82~4.88 (m, 1H), 7.16~7.90 (m, 4H).

Example 164: Synthesis of 1-(2-iodophenyl)-(S)-1-methoxy-3-methyl-butyl-(S)-2-cyclohexylcarbamate

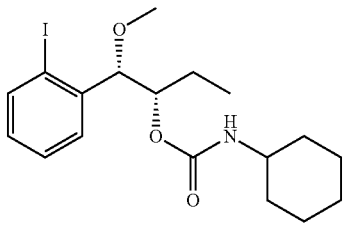 [SMILES: CC[C@H](OC(=O)NC1CCCCC1)[C@@H](OC)c1ccccc1I]

$^1$H NMR (400 MHz, CDCl$_3$) δ 1.04 (d, J=7.6 Hz, 6H), 1.11~1.21 (m, 4H), 1.47~1.49 (m, 4H), 1.74 (m, 2H), 1.84~1.90 (m, 1H), 3.23 (s, 3H), 3.54 (m, 1H), 4.71 (d, J=6.8 Hz, 1H), 4.82~4.88 (m, 1H), 7.14~7.87 (m, 4H).

Example 165: Synthesis of 1-(2-iodophenyl)-(S)-1-methoxy-3-methyl-butyl-(S)-2-cyclohexylcarbamate

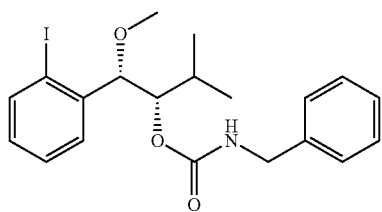 [SMILES: CO[C@@H](c1ccccc1I)[C@@H](OC(=O)NCc1ccccc1)C(C)C]

¹H NMR (400 MHz, CDCl₃) δ 1.04 (d, J=7.6 Hz, 6H), 1.87~1.90 (m, 1H), 3.24 (s, 3H), 4.20 (m, 2H), 4.71 (d, J=6.8 Hz, 1H), 4.82~4.88 (m, 1H), 7.14~7.19 (m, 4H), 7.37~7.88 (m, 5H).

Example 166: Synthesis of 1-(2-iodophenyl)-(S)-1-methoxy-3-methyl-butyl-(S)-2-bicyclo[2,2,1]heptan-escarbamate

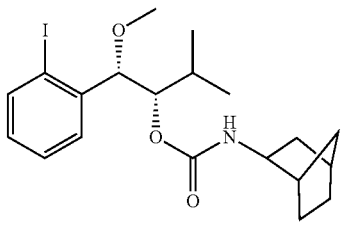 [SMILES: CO[C@@H](c1ccccc1I)[C@@H](OC(=O)NC1CC2CCC1C2)C(C)C]

¹H NMR (400 MHz, CDCl₃) δ 1.04 (d, J=7.6 Hz, 6H), 1.33~1.58 (m, 6H), 1.75~1.88 (m, 2H), 1.88~1.93 (m, 1H), 2.06~2.13 (m, 2H), 3.22 (s, 3H), 3.53 (m, 1H), 4.71 (d, J=6.8 Hz, 1H), 4.82~4.88 (m, 1H), 7.15~7.19 (m, 4H), 7.37~7.88 (m, 5H).

Example 167: Synthesis of 1-(2-iodophenyl)-(S)-1-methoxyhexyl-(S)-2-carbamate

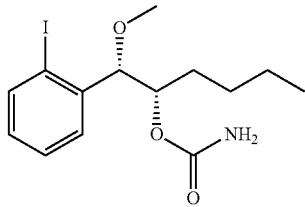 [SMILES: CCCC[C@H](OC(N)=O)[C@@H](OC)c1ccccc1I]

¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.23 (s, 3H), 4.47 (br s, 2H), 4.71 (d, J=6.8 Hz, 1H), 4.82~4.88 (m, 1H), 7.26~7.70 (m, 4H).

Example 168: Synthesis of 1-(2-iodophenyl)-(S)-1-methoxyhexyl-(S)-2-methylcarbamate

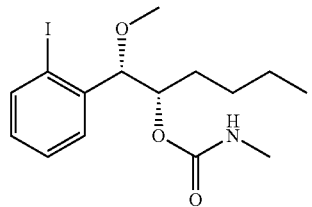 [SMILES: CCCC[C@H](OC(=O)NC)[C@@H](OC)c1ccccc1I]

¹H NMR (400 MHz, CDCl₃) δ 0.89 (t, J=7.2 Hz, 3H), 1.20~1.35 (m, 4H), 1.36~1.41 (m, 1H), 1.59~1.63 (m, 1H), 2.58 (s, 3H), 3.23 (s, 3H), 4.71 (d, J=6.8 Hz, 1H), 4.82~4.88 (m, 1H), 7.13~7.88 (m, 4H).

Example 169: Synthesis of 1-(2-iodophenyl)-(S)-1-methoxyhexyl-(S)-2-propylcarbamate

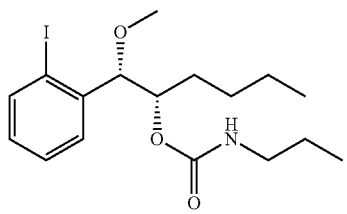 [SMILES: CCCC[C@H](OC(=O)NCCC)[C@@H](OC)c1ccccc1I]

¹H NMR (400 MHz, CDCl₃) δ 0.87 (t, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.24 (s, 3H), 4.71 (d, J=6.8 Hz, 1H), 4.82~4.88 (m, 1H), 7.14~7.89 (m, 4H).

Example 170: Synthesis of 1-(2-iodophenyl)-(S)-1-methoxyhexyl-(S)-2-isopropylcarbamate

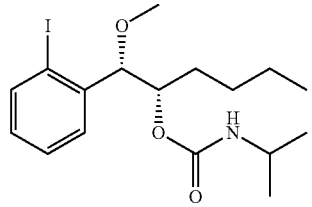 [SMILES: CCCC[C@H](OC(=O)NC(C)C)[C@@H](OC)c1ccccc1I]

¹H NMR (400 MHz, CDCl₃) δ 0.84 (t, J=7.6 Hz, 3H), 1.22~1.35 (m, 4H), 1.27 (d, J=6.8 Hz, 6H), 1.36~1.40 (m, 1H), 1.58~1.62 (m, 1H), 3.23 (s, 3H), 4.17 (m, 1H), 4.71 (d, J=6.8 Hz, 1H), 4.82~4.88 (m, 1H), 7.15~7.90 (m, 4H).

Example 171: Synthesis of 1-(2-iodophenyl)-(S)-1-methoxyhexyl-(S)-2-cyclopropylcarbamate

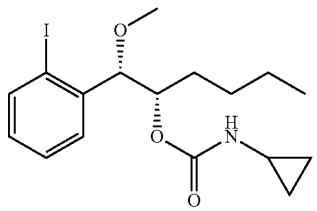 [SMILES: CCCC[C@H](OC(=O)NC1CC1)[C@@H](OC)c1ccccc1I]

$^1$H NMR (400 MHz, CDCl$_3$) δ 0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.23 (s, 3H), 4.71 (d, J=6.8 Hz, 1H), 4.82~4.88 (m, 1H), 7.16~7.90 (m, 4H).

Example 172: Synthesis of 1-(2-iodophenyl)-(S)-1-methoxyhexyl-(S)-2-cyclohexylcarbamate

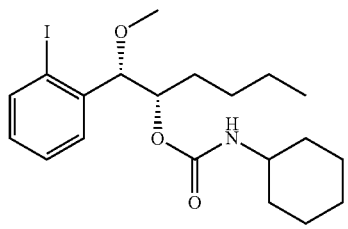 [SMILES: CCCC[C@H](OC(=O)NC1CCCCC1)[C@@H](OC)c1ccccc1I]

$^1$H NMR (400 MHz, CDCl$_3$) δ 0.98 (t, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.23 (s, 3H), 3.54 (m, 1H), 4.71 (d, J=6.8 Hz, 1H), 4.82~4.88 (m, 1H), 7.14~7.87 (m, 4H).

Example 173: Synthesis of 1-(2-iodophenyl)-(S)-1-methoxyhexyl-(S)-2-cyclohexylcarbamate

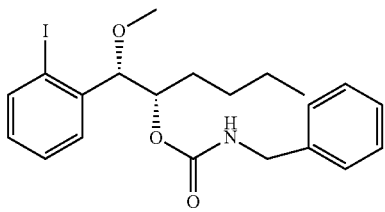 [SMILES: CCCC[C@H](OC(=O)NCc1ccccc1)[C@@H](OC)c1ccccc1I]

$^1$H NMR (400 MHz, CDCl$_3$) δ 0.94 (t, J=7.6 Hz, 3H), 1.26~1.33 (m, 4H), 1.51~1.55 (m, 2H), 3.23 (s, 3H), 4.20 (m, 2H), 4.71 (d, J=6.8 Hz, 1H), 4.82~4.88 (m, 1H), 7.14~7.19 (m, 4H), 7.37~7.88 (m, 5H).

Example 174: Synthesis of 1-(2-iodophenyl)-(S)-1-methoxyhexyl-(S)-2-bicyclo[2,2,1]heptanescarbamate

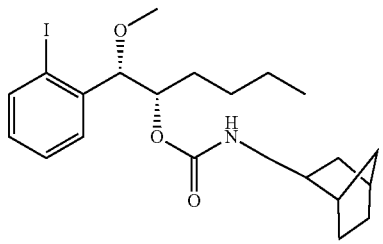 [SMILES: CCCC[C@H](OC(=O)NCC1CC2CCC1C2)[C@@H](OC)c1ccccc1I]

$^1$H NMR (400 MHz, CDCl$_3$) δ 0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.24 (s, 3H), 3.53 (m, 1H), 4.71 (d, J=6.8 Hz, 1H), 4.82~4.88 (m, 1H), 7.15~7.19 (m, 4H), 7.37~7.88 (m, 5H).

Example 175: Synthesis of 1-(3-iodophenyl)-(S)-1-methoxypropyl-(S)-2-carbamate

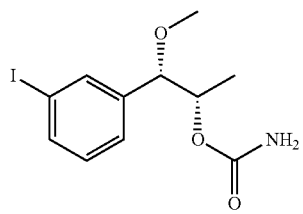 [SMILES: CO[C@@H](c1cccc(I)c1)[C@H](C)OC(N)=O]

$^1$H NMR (400 MHz, CDCl$_3$) δ 1.16 (d, J=6.4 Hz, 3H), 3.24 (s, 3H), 4.54~4.63 (m, 4H), 5.04~5.10 (m, 1H), 7.09~7.73 (m, 4H).

Example 176: Synthesis of 1-(3-iodophenyl)-(S)-1-methoxybutyl-(S)-2-carbamate

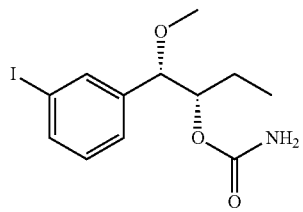 [SMILES: CC[C@H](OC(N)=O)[C@@H](OC)c1cccc(I)c1]

$^1$H NMR (400 MHz, CDCl$_3$) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 6.96~7.57 (m, 4H).

Example 177: Synthesis of 1-(3-iodophenyl)-(S)-1-methoxy-3-methyl-butyl-(S)-2-carbamate

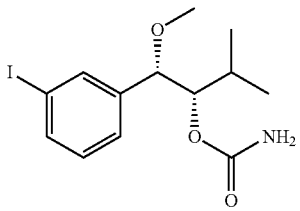 [SMILES: CO[C@@H](c1cccc(I)c1)[C@@H](OC(N)=O)C(C)C]

$^1$H NMR (400 MHz, CDCl$_3$) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.00~7.58 (m, 4H).

Example 178: Synthesis of 1-(3-iodophenyl)-(S)-1-methoxyhexyl-(S)-2-carbamate

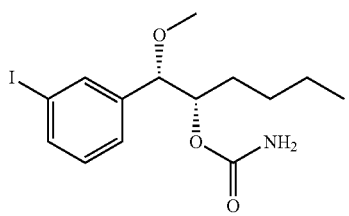 [SMILES: CCCC[C@H](OC(N)=O)[C@@H](OC)c1cccc(I)c1]

$^1$H NMR (400 MHz, CDCl$_3$) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 7.01~7.59 (m, 4H).

Example 179: Synthesis of 1-(4-fluorophenyl)-(S)-1-methoxypropyl-(S)-2-carbamate

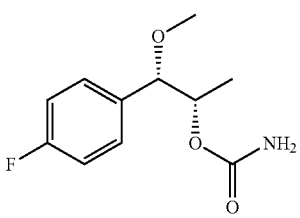 [SMILES: CO[C@@H](c1ccc(F)cc1)[C@H](C)OC(N)=O]

$^1$H NMR (400 MHz, CDCl$_3$) δ 1.37 (d, J=6.8 Hz, 3H), 3.23 (s, 3H), 4.71 (d, J=6.8 Hz, 1H), 4.82~4.88 (m, 1H), 6.96~7.17 (m, 4H).

Example 180: Synthesis of 1-(4-fluorophenyl)-(S)-1-methoxybutyl-(S)-2-carbamate

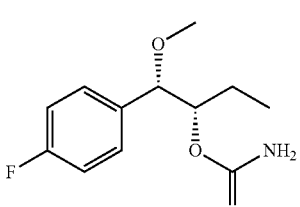

$^1$H NMR (400 MHz, CDCl$_3$) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 6.90~7.20 (m, 4H).

Example 181: Synthesis of 1-(4-fluorophenyl)-(S)-1-methoxy-3-methyl-butyl-(S)-2-carbamate

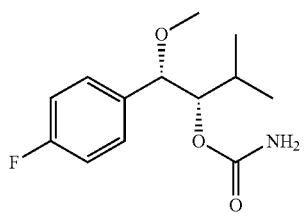 [SMILES: CO[C@@H](c1ccc(F)cc1)[C@@H](OC(N)=O)C(C)C]

$^1$H NMR (400 MHz, CDCl$_3$) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 6.92~7.17 (m, 4H).

Example 182: Synthesis of 1-(4-fluorophenyl)-(S)-1-methoxyhexyl-(S)-2-carbamate

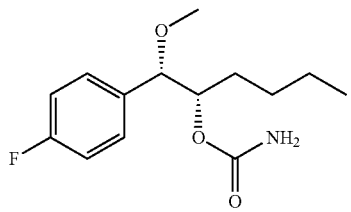 [SMILES: CCCC[C@H](OC(N)=O)[C@@H](OC)c1ccc(F)cc1]

$^1$H NMR (400 MHz, CDCl$_3$) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 6.96~7.19 (m, 4H).

Example 183: Synthesis of 1-(2,4-dichlorophenyl)-(S)-1-methoxypropyl-(S)-2-carbamate

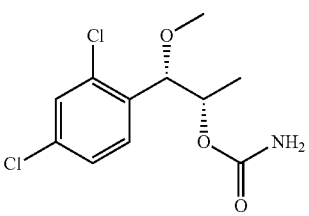

$^1$H NMR (400 MHz, CDCl$_3$) δ 1.37 (d, J=6.8 Hz, 3H), 3.24 (s, 3H), 4.71 (d, J=6.8 Hz, 1H), 4.82~4.88 (m, 1H), 7.24~7.30 (m, 2H), 7.73 (d, J=1.5 Hz, 1H).

Example 184: Synthesis of 1-(2,4-dichlorophenyl)-(S)-1-methoxybutyl-(S)-2-carbamate

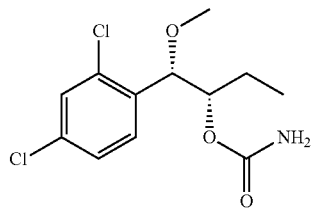

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 185: Synthesis of 1-(2,4-dichlorophenyl)-(S)-1-methoxy-3-methyl-butyl-(S)-2-carbamate

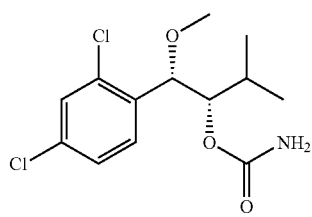

¹H NMR (400 MHz, CDCl₃) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 186: Synthesis of 1-(2,4-dichlorophenyl)-(S)-1-methoxyhexyl-(S)-2-carbamate

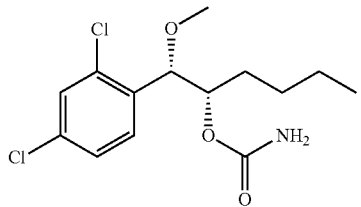

¹H NMR (400 MHz, CDCl₃) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 187: Synthesis of 1-(2,6-dichlorophenyl)-(S)-1-methoxypropyl-(S)-2-carbamate

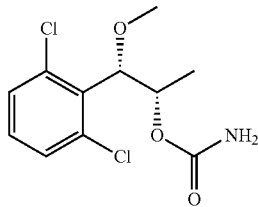 [SMILES: CO[C@@H](c1c(Cl)cccc1Cl)[C@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.57~7.58 (m, 3H).

Example 188: Synthesis of 1-(2,6-dichlorophenyl)-(S)-1-methoxybutyl-(S)-2-carbamate

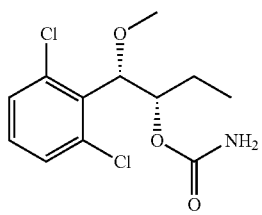 [SMILES: CC[C@H](OC(N)=O)[C@@H](OC)c1c(Cl)cccc1Cl]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.54~7.57 (m, 3H).

Example 189: Synthesis of 1-(2,6-dichlorophenyl)-(S)-1-methoxy-3-methyl-butyl-(S)-2-carbamate

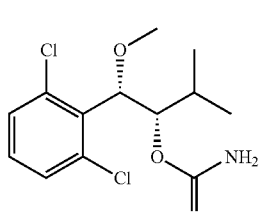

¹H NMR (400 MHz, CDCl₃) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.55~7.57 (m, 3H).

Example 190: Synthesis of 1-(2,4-dichlorophenyl)-(S)-1-methoxyhexyl-(S)-2-carbamate

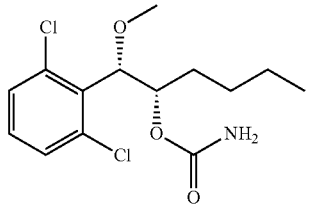 [SMILES: CCCC[C@H](OC(N)=O)[C@@H](OC)c1c(Cl)cccc1Cl]

¹H NMR (400 MHz, CDCl₃) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 7.54~7.59 (m, 3H).

Example 191: Synthesis of 1-(2,3-dichlorophenyl)-(S)-1-methoxypropyl-(S)-2-carbamate

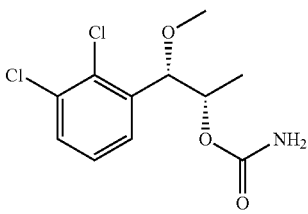 [SMILES: CO[C@@H](c1cccc(Cl)c1Cl)[C@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.01~7.14 (m, 3H).

Example 192: Synthesis of 1-(2-chlorophenyl)-(R)-1-methoxypropyl-(R)-2-carbamate

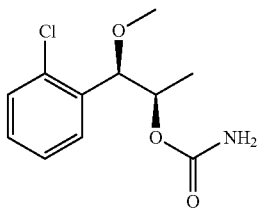 [SMILES: CO[C@H](c1ccccc1Cl)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.26~7.70 (m, 4H).

Example 193: Synthesis of 1-(2-chlorophenyl)-1-methoxypropyl-2-carbamate

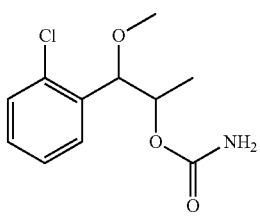 [SMILES: COC(c1ccccc1Cl)C(C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.26~7.70 (m, 4H).

Example 194: Synthesis of 1-(2-chlorophenyl)-(R)-1-methoxypropyl-(S)-2-carbamate

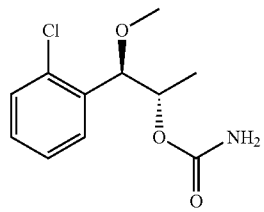 [SMILES: CO[C@H](c1ccccc1Cl)[C@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.26~7.70 (m, 4H).

Example 195: Synthesis of 1-(2-chlorophenyl)-(S)-1-methoxypropyl-(R)-2-carbamate

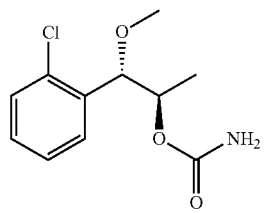 [SMILES: CO[C@@H](c1ccccc1Cl)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.26~7.70 (m, 4H).

Example 196: Synthesis of 1-(2-chlorophenyl)-(R)-1-methoxybutyl-(R)-2-carbamate

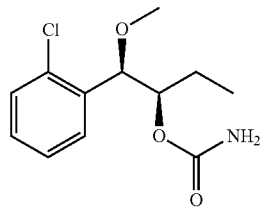 [SMILES: CC[C@@H](OC(N)=O)[C@H](OC)c1ccccc1Cl]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.26~7.70 (m, 4H).

Example 197: Synthesis of 1-(2-chlorophenyl)-1-methoxybutyl-2-carbamate

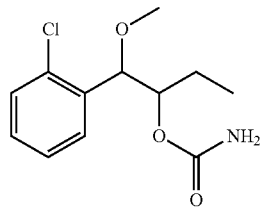 [SMILES: CCC(OC(N)=O)C(OC)c1ccccc1Cl]

$^1$H NMR (400 MHz, CDCl$_3$) δ 1.04 (t, J=7.6 Hz, 3H), 1.60~1.71 (m, 2H), 3.23 (s, 3H), 4.71 (d, J=6.8 Hz, 1H), 4.73 (br s, 2H), 4.82~4.88 (m, 1H), 7.26~7.70 (m, 4H).

Example 198: Synthesis of 1-(2-chlorophenyl)-(R)-1-methoxy-3-methyl-butyl-(R)-2-carbamate

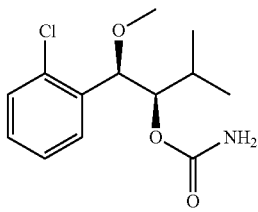 [SMILES: CO[C@H](c1ccccc1Cl)[C@H](OC(N)=O)C(C)C]

$^1$H NMR (400 MHz, CDCl$_3$) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.26~7.70 (m, 4H).

Example 199: Synthesis of 1-(2-chlorophenyl)-1-methoxy-3-methyl-butyl-2-carbamate

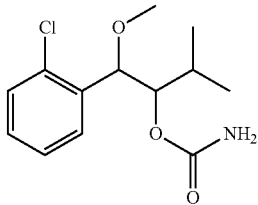 [SMILES: COC(c1ccccc1Cl)C(OC(N)=O)C(C)C]

$^1$H NMR (400 MHz, CDCl$_3$) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.26~7.70 (m, 4H).

Example 200: Synthesis of 1-(2-chlorophenyl)-(R)-1-methoxyhexyl-(R)-2-carbamate

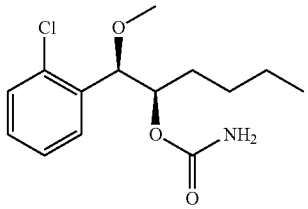

$^1$H NMR (400 MHz, CDCl$_3$) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.26~7.70 (m, 4H).

Example 201: Synthesis of 1-(2-chlorophenyl)-1-methoxyhexyl-2-carbamate

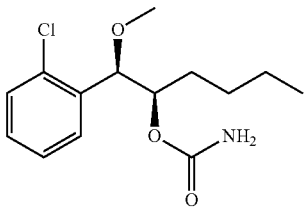 [SMILES: CCCC[C@@H](OC(N)=O)[C@H](OC)c1ccccc1Cl]

$^1$H NMR (400 MHz, CDCl$_3$) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.26~7.70 (m, 4H).

Example 202: Synthesis of 1-(2-chlorophenyl)-(R)-1-methoxypropyl-(R)-2-methylcarbamate

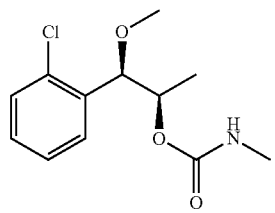 [SMILES: CNC(=O)O[C@H](C)[C@H](OC)c1ccccc1Cl]

$^1$H NMR (400 MHz, CDCl$_3$) δ 1.37 (d, J=6.8 Hz, 3H), 2.58 (s, 3H), 3.24 (s, 3H), 4.71 (d, J=6.8 Hz, 1H), 4.82~4.88 (m, 1H), 7.26~7.70 (m, 4H).

Example 203: Synthesis of 1-(2-chlorophenyl)-(R)-1-methoxypropyl-(R)-2-propylcarbamate

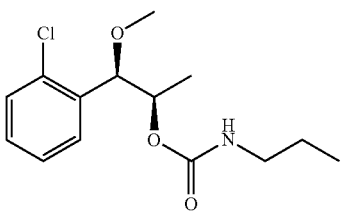 [SMILES: CCCNC(=O)O[C@H](C)[C@H](OC)c1ccccc1Cl]

$^1$H NMR (400 MHz, CDCl$_3$) δ 0.90 (t, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8 Hz, 1H), 4.82~4.88 (m, 1H), 7.26~7.70 (m, 4H).

Example 204: Synthesis of 1-(2-chlorophenyl)-(R)-
1-thoxypropyl-(R)-2-isopropylcarbamate

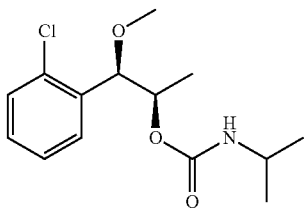 [SMILES: CO[C@H](c1ccccc1Cl)[C@@H](C)OC(=O)NC(C)C]

¹H NMR (400 MHz, CDCl₃) δ 1.27 (d, J=6.8 Hz, 6H), 1.37 (d, J=6.8 Hz, 3H), 3.23 (s, 3H), 4.17 (m, 1H), 4.71 (d, J=6.8 Hz, 1H), 4.82~4.88 (m, 1H), 7.26~7.70 (m, 4H).

Example 205: Synthesis of 1-(2-chlorophenyl)-(R)-
1-methoxypropyl-(R)-2-cyclopropylcarbamate

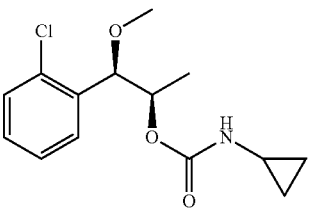 [SMILES: CO[C@H](c1ccccc1Cl)[C@@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.24 (s, 3H), 4.71 (d, J=6.8 Hz, 1H), 4.82~4.88 (m, 1H), 7.26~7.70 (m, 4H).

Example 206: Synthesis of 1-(2-chlorophenyl)-(R)-
1-methoxypropyl-(R)-2-cyclohexylcarbamate

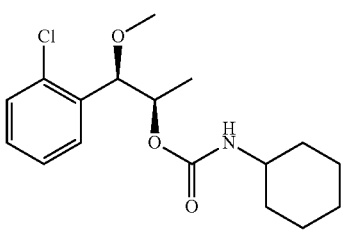 [SMILES: CO[C@H](c1ccccc1Cl)[C@@H](C)OC(=O)NC1CCCCC1]

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8 Hz, 1H), 4.82~4.88 (m, 1H), 7.26~7.70 (m, 4H).

Example 207: Synthesis of 1-(2-chlorophenyl)-(R)-
1-methoxypropyl-(R)-2-cyclohexylcarbamate

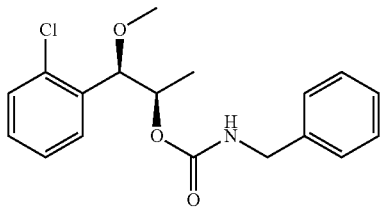 [SMILES: CO[C@H](c1ccccc1Cl)[C@@H](C)OC(=O)NCc1ccccc1]

¹H NMR (400 MHz, CDCl₃) δ 1.37 (d, J=6.8 Hz, 3H), 3.24 (s, 3H), 4.20 (m, 2H), 4.71 (d, J=6.8 Hz, 1H), 4.82~4.88 (m, 1H), 7.13~7.19 (m, 4H), 7.37~7.88 (m, 5H).

Example 208: Synthesis of 1-(2-chlorophenyl)-(R)-
1-methoxypropyl-(R)-2-bicyclo[2,2,1]heptanescar-
bamate

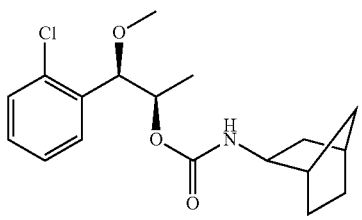 [SMILES: CO[C@H](c1ccccc1Cl)[C@@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.22 (s, 3H), 3.53 (m, 1H), 4.71 (d, J=6.8 Hz, 1H), 4.82~4.88 (m, 1H), 7.13~7.19 (m, 4H), 7.37~7.88 (m, 5H).

Example 209: Synthesis of 1-(2-fluorophenyl)-(R)-
1-methoxypropyl-(R)-2-carbamate

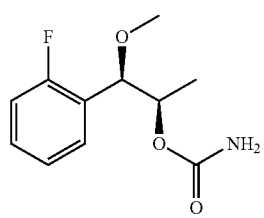 [SMILES: CO[C@H](c1ccccc1F)[C@@H](C)OC(N)=O]

¹H NMR (400 MHz, CDCl₃) δ 1.37 (d, J=6.8 Hz, 3H), 3.23 (s, 3H), 4.71 (d, J=6.8 Hz, 1H), 4.82~4.88 (m, 1H), 7.15~7.68 (m, 4H).

Example 210: Synthesis of 1-(4-fluorophenyl)-(R)-1-methoxypropyl-(R)-2-carbamate

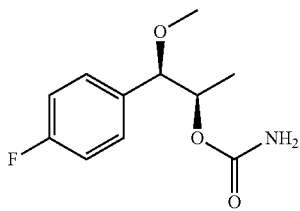 [SMILES: CO[C@H](c1ccc(F)cc1)[C@@H](C)OC(N)=O]

¹H NMR (400 MHz, CDCl₃) δ 1.37 (d, J=6.8 Hz, 3H), 3.23 (s, 3H), 4.71 (d, J=6.8 Hz, 1H), 4.82~4.88 (m, 1H), 6.96~7.17 (m, 4H).

Example 211: Synthesis of 1-(4-fluorophenyl)-(R)-1-methoxybutyl-(R)-2-carbamate

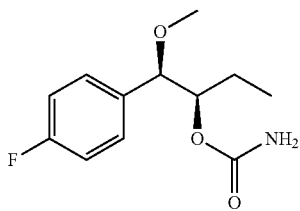 [SMILES: CC[C@@H](OC(N)=O)[C@H](OC)c1ccc(F)cc1]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 6.90~7.20 (m, 4H).

Example 212: Synthesis of 1-(4-fluorophenyl)-(R)-1-methoxy-3-methyl-butyl-(R)-2-carbamate

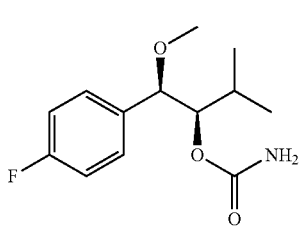 [SMILES: CO[C@H](c1ccc(F)cc1)[C@H](OC(N)=O)C(C)C]

¹H NMR (400 MHz, CDCl₃) δ 1.07 (t, J=7.6 Hz, 6H), 1.83~1.89 (m, 1H), 3.23 (s, 3H), 4.71 (d, J=6.8 Hz, 1H), 4.73 (br s, 2H), 4.82~4.88 (m, 1H), 6.92~7.17 (m, 4H).

Example 213: Synthesis of 1-(4-fluorophenyl)-(R)-1-methoxyhexyl-(R)-2-carbamate

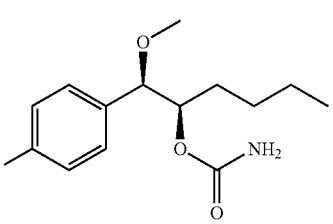

¹H NMR (400 MHz, CDCl₃) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 6.96~7.19 (m, 4H).

Example 214: Synthesis of 1-(2-iodophenyl)-(R)-1-methoxypropyl-(R)-2-carbamate

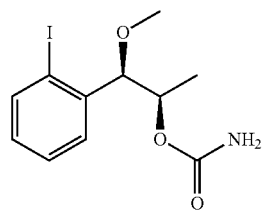 [SMILES: CO[C@H](c1ccccc1I)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.13~7.88 (m, 4H).

Example 215: Synthesis of 1-(2-iodophenyl)-(R)-1-methoxybutyl-(R)-2-carbamate

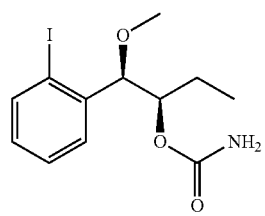 [SMILES: CC[C@@H](OC(N)=O)[C@H](OC)c1ccccc1I]

¹H NMR (400 MHz, CDCl₃) δ 1.04 (t, J=7.6 Hz, 3H), 1.60~1.71 (m, 2H), 3.23 (s, 3H), 4.71 (d, J=6.8 Hz, 1H), 4.82~4.88 (m, 1H), 7.26~7.70 (m, 4H).

Example 216: Synthesis of 1-(2-iodophenyl)-(R)-1-methoxy-3-methyl-butyl-(R)-2-carbamate

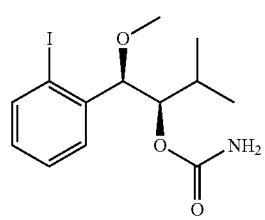 [SMILES: CO[C@H](c1ccccc1I)[C@H](OC(N)=O)C(C)C]

¹H NMR (400 MHz, CDCl₃) δ 1.07 (d, J=7.6 Hz, 3H), 1.83~1.89 (m, 1H), 3.24 (s, 3H), 4.71 (d, J=6.8 Hz, 1H), 4.82~4.88 (m, 1H), 7.26~7.70 (m, 4H).

Example 217: Synthesis of 1-(2-iodophenyl)-(R)-1-methoxyhexyl-(R)-2-carbamate

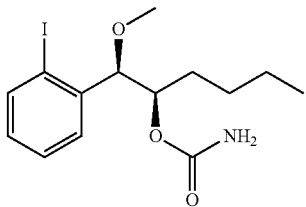 [SMILES: CCCC[C@@H](OC(N)=O)[C@H](OC)c1ccccc1I]

¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8 Hz, 1H), 4.82~4.88 (m, 1H), 5.45 (s, 2H), 7.26~7.70 (m, 4H).

Example 218: Synthesis of 1-(3-iodophenyl)-(R)-1-methoxypropyl-(R)-2-carbamate

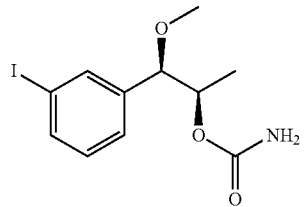 [SMILES: CO[C@H](c1cccc(I)c1)[C@@H](C)OC(N)=O]

¹H NMR (400 MHz, CDCl₃) δ 1.16 (d, J=6.4 Hz, 3H), 3.23 (s, 3H), 4.54~4.63 (m, 4H), 5.04~5.10 (m, 1H), 7.09~7.73 (m, 4H).

Example 219: Synthesis of 1-(3-iodophenyl)-(R)-1-methoxybutyl-(R)-2-carbamate

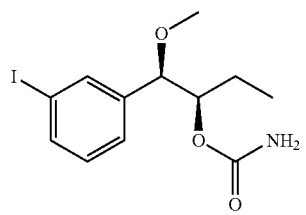 [SMILES: CC[C@@H](OC(N)=O)[C@H](OC)c1cccc(I)c1]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.82~4.88 (m, 1H), 7.26~7.70 (m, 4H).

Example 220: Synthesis of 1-(3-iodophenyl)-(R)-1-methoxy-3-methyl-butyl-(R)-2-carbamate

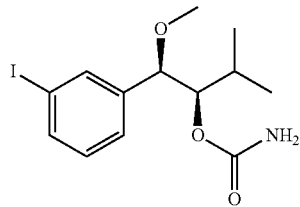 [SMILES: CO[C@H](c1cccc(I)c1)[C@H](OC(N)=O)C(C)C]

¹H NMR (400 MHz, CDCl₃) δ 1.07 (d, J=7.6 Hz, 3H), 1.83~1.89 (m, 1H), 3.24 (s, 3H), 4.71 (d, J=6.8 Hz, 1H), 4.82~4.88 (m, 1H), 7.26~7.70 (m, 4H).

Example 221: Synthesis of 1-(3-iodophenyl)-(R)-1-methoxyhexyl-(R)-2-carbamate

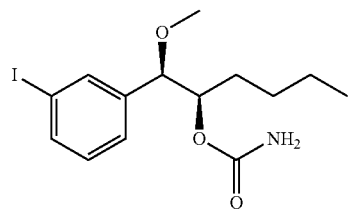 [SMILES: CCCC[C@@H](OC(N)=O)[C@H](OC)c1cccc(I)c1]

¹H NMR (400 MHz, CDCl₃) δ 0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8 Hz, 1H), 4.82~4.88 (m, 1H), 7.26~7.70 (m, 4H).

Example 222: Synthesis of 1-(2-chlorophenyl)-(R)-1-methoxypropyl-(R)-2-methylcarbamate

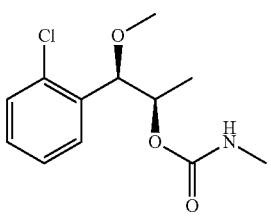 [SMILES: CNC(=O)O[C@H](C)[C@H](OC)c1ccccc1Cl]

¹H NMR (400 MHz, CDCl₃) δ 1.37 (d, J=6.8 Hz, 3H), 2.58 (s, 3H), 2.24 (s, 3H), 4.71 (d, J=6.8 Hz, 1H), 4.82~4.88 (m, 1H), 7.26~7.70 (m, 4H).

Example 223: Synthesis of 1-(2-chlorophenyl)-(R)-1-methoxypropyl-(R)-2-propylcarbamate

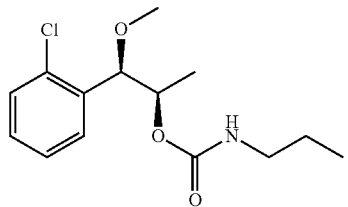 [SMILES: CCCNC(=O)O[C@H](C)[C@H](OC)c1ccccc1Cl]

¹H NMR (400 MHz, CDCl₃) δ 0.90 (t, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8 Hz, 1H), 4.82~4.88 (m, 1H), 7.26~7.70 (m, 4H).

Example 224: Synthesis of 1-(2-chlorophenyl)-(R)-1-methoxypropyl-(R)-2-isopropylcarbamate

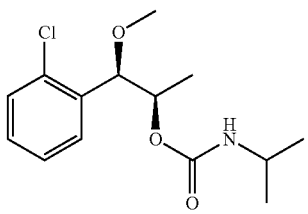 [SMILES: CO[C@H](c1ccccc1Cl)[C@@H](C)OC(=O)NC(C)C]

¹H NMR (400 MHz, CDCl₃) δ 1.27 (d, J=6.8 Hz, 6H), 1.37 (d, J=6.8 Hz, 3H), 3.24 (s, 3H), 4.17 (m, 1H), 4.71 (d, J=6.8 Hz, 1H), 4.82~4.88 (m, 1H), 7.26~7.70 (m, 4H).

Example 225: Synthesis of 1-(2-chlorophenyl)-(R)-1-methoxypropyl-(R)-2-cyclopropylcarbamate

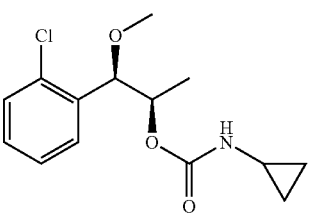 [SMILES: CO[C@H](c1ccccc1Cl)[C@@H](C)OC(=O)NC1CC1]

¹H NMR (400 MHz, CDCl₃) δ 0.57 (m, 2H), 0.82 (m, 2H), 1.37 (d, J=6.8 Hz, 3H), 2.75 (m, 1H), 3.24 (s, 3H), 4.71 (d, J=6.8 Hz, 1H), 4.82~4.88 (m, 1H), 7.26~7.70 (m, 4H).

Example 226: Synthesis of 1-(2-chlorophenyl)-(R)-1-methoxypropyl-(R)-2-cyclohexylcarbamate

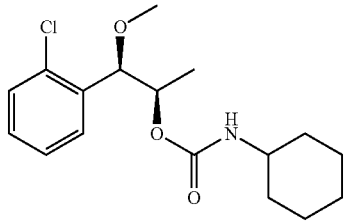 [SMILES: CO[C@H](c1ccccc1Cl)[C@@H](C)OC(=O)NC1CCCCC1]

¹H NMR (400 MHz, CDCl₃) δ 1.11~1.21 (m, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8 Hz, 1H), 4.82~4.88 (m, 1H), 7.26~7.70 (m, 4H).

Example 227: Synthesis of 1-(2-chlorophenyl)-(R)-1-methoxypropyl-(R)-2-cyclohexylcarbamate

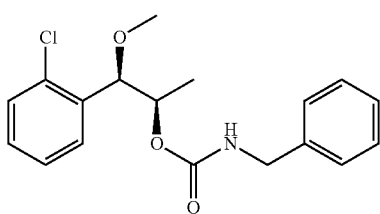 [SMILES: CO[C@H](c1ccccc1Cl)[C@@H](C)OC(=O)NCc1ccccc1]

¹H NMR (400 MHz, CDCl₃) δ 1.37 (d, J=6.8 Hz, 3H), 3.24 (s, 3H), 4.20 (m, 2H), 4.71 (d, J=6.8 Hz, 1H), 4.82~4.88 (m, 1H), 7.13~7.19 (m, 4H), 7.37~7.88 (m, 5H).

Example 228: Synthesis of 1-(2-chlorophenyl)-(R)-1-methoxypropyl-(R)-2-bicyclo[2,2,1]heptanescarbamate

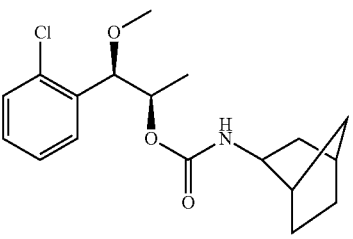 [SMILES: CO[C@H](c1ccccc1Cl)[C@@H](C)OC(=O)NC1CC2CCC1C2]

¹H NMR (400 MHz, CDCl₃) δ 1.33~1.58 (m, 9H), 1.75~1.88 (m, 2H), 2.06~2.13 (m, 2H), 3.24 (s, 3H), 3.53 (m, 1H), 4.71 (d, J=6.8 Hz, 1H), 4.82~4.88 (m, 1H), 7.13~7.19 (m, 4H), 7.37~7.88 (m, 5H).

Example 229: Synthesis of 1-(2,4-dichlorophenyl)-(R)-1-methoxypropyl-(R)-2-carbamate

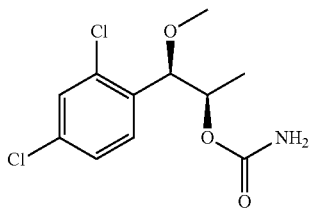 [SMILES: CO[C@H](c1ccc(Cl)cc1Cl)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.24~7.30 (m, 2H), 7.73 (d, J=1.5 Hz, 1H).

Example 230: Synthesis of 1-(2,6-dichlorophenyl)-(R)-1-methoxypropyl-(R)-2-carbamate

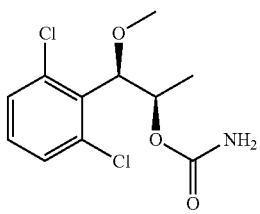 [SMILES: CO[C@H](c1c(Cl)cccc1Cl)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.57~7.58 (m, 3H).

Example 231: Synthesis of 1-(2,3-dichlorophenyl)-(R)-1-methoxypropyl-(R)-2-carbamate

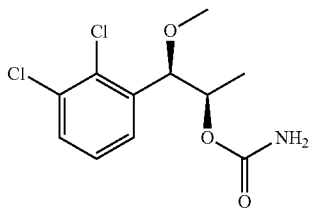 [SMILES: CO[C@H](c1cccc(Cl)c1Cl)[C@@H](C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.01~7.14 (m, 3H).

Example 232: Synthesis of 1-(2,4-dichlorophenyl)-(R)-1-methoxybutyl-(R)-2-carbamate

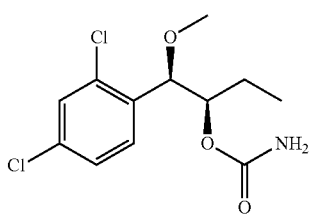 [SMILES: CC[C@@H](OC(N)=O)[C@H](OC)c1ccc(Cl)cc1Cl]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 233: Synthesis of 1-(2,6-dichlorophenyl)-(R)-1-methoxybutyl-(R)-2-carbamate

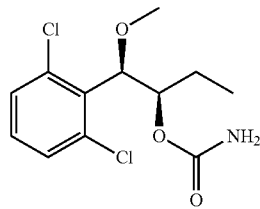 [SMILES: CC[C@@H](OC(N)=O)[C@H](OC)c1c(Cl)cccc1Cl]

¹H NMR (400 MHz, CDCl₃) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.54~7.57 (m, 3H).

Example 234: Synthesis of 1-(2,4-dichlorophenyl)-(R)-1-methoxy-3-methyl-butyl-(R)-2-carbamate

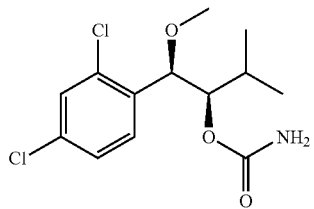 [SMILES: CO[C@H](c1ccc(Cl)cc1Cl)[C@H](OC(N)=O)C(C)C]

¹H NMR (400 MHz, CDCl₃) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 235: Synthesis of 1-(2,6-dichlorophenyl)-(R)-1-methoxy-3-methyl-butyl-(R)-2-carbamate

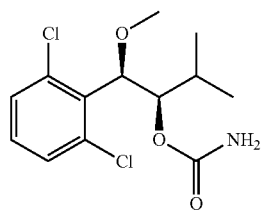 [SMILES: CO[C@H](c1c(Cl)cccc1Cl)[C@H](OC(N)=O)C(C)C]

¹H NMR (400 MHz, CDCl₃) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.55~7.57 (m, 3H).

Example 236: Synthesis of 1-(2,4-dichlorophenyl)-(R)-1-methoxyhexyl-(R)-2-carbamate

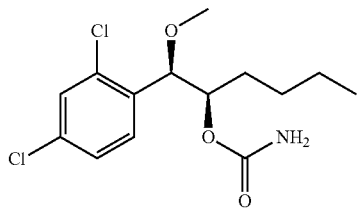 [SMILES: CCCC[C@@H](OC(N)=O)[C@H](OC)c1ccc(Cl)cc1Cl]

¹H NMR (400 MHz, CDCl₃) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 237: Synthesis of 1-(2,4-dichlorophenyl)-(R)-1-methoxyhexyl-(R)-2-carbamate

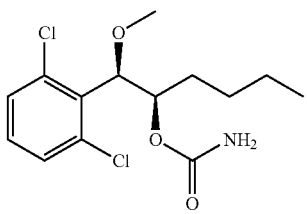 [SMILES: CCCC[C@@H](OC(N)=O)[C@H](OC)c1c(Cl)cccc1Cl]

¹H NMR (400 MHz, CDCl₃) δ 0.90 (t, J=7.6 Hz, 3H), 1.35~1.65 (m, 6H), 3.23 (s, 3H), 4.71 (d, J=6.8 Hz, 1H), 4.73 (br s, 2H), 4.82~4.88 (m, 1H), 7.54~7.59 (m, 3H).

Example 238: Synthesis of 1-(2,4-dichlorophenyl)-1-methoxypropyl-2-carbamate

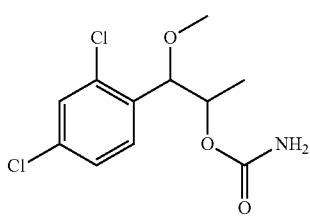 [SMILES: COC(c1ccc(Cl)cc1Cl)C(C)OC(N)=O]

¹H NMR (400 MHz, CDCl₃) δ 1.37 (d, J=6.8 Hz, 3H), 3.23 (s, 3H), 4.71 (d, J=6.8 Hz, 1H), 4.82~4.88 (m, 1H), 7.24~7.30 (m, 2H), 7.73 (d, J=1.5 Hz, 1H).

Example 239: Synthesis of 1-(2,6-dichlorophenyl)-1-methoxypropyl-2-carbamate

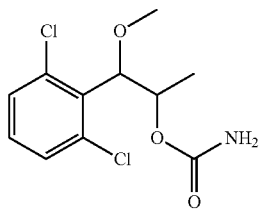 [SMILES: COC(c1c(Cl)cccc1Cl)C(C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.57~7.58 (m, 3H).

Example 240: Synthesis of 1-(2,3-dichlorophenyl)-1-methoxypropyl-2-carbamate

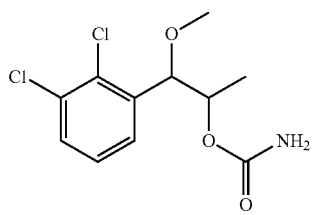 [SMILES: COC(c1cccc(Cl)c1Cl)C(C)OC(N)=O]

¹H NMR (400 MHz, CDCl₃) δ 1.37 (d, J=6.8 Hz, 3H), 3.24 (s, 3H), 4.71 (d, J=6.8 Hz, 1H), 4.82~4.88 (m, 1H), 7.01~7.14 (m, 3H).

Example 241: Synthesis of 1-(2,4-dichlorophenyl)-1-methoxybutyl-2-carbamate

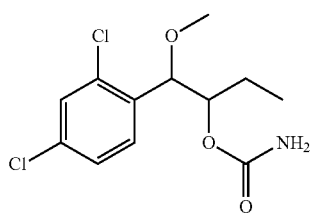 [SMILES: CCC(OC(N)=O)C(OC)c1ccc(Cl)cc1Cl]

¹H NMR (400 MHz, CDCl₃) δ 1.04 (t, J=7.6 Hz, 3H), 1.60~1.71 (m, 2H), 3.23 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 242: Synthesis of 1-(2,6-dichlorophenyl)-1-methoxybutyl-2-carbamate

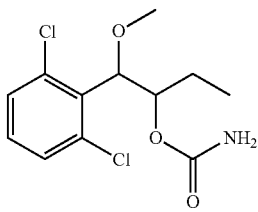 [SMILES: CCC(OC(N)=O)C(OC)c1c(Cl)cccc1Cl]

$^1$H NMR (400 MHz, CDCl$_3$) δ 1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 7.54~7.57 (m, 3H).

Example 243: Synthesis of 1-(2,4-dichlorophenyl)-1-methoxy-3-methyl-butyl-2-carbamate

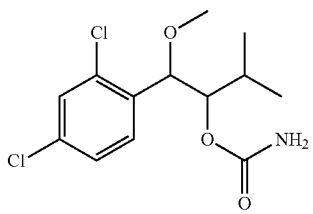 [SMILES: COC(c1ccc(Cl)cc1Cl)C(OC(N)=O)C(C)C]

$^1$H NMR (400 MHz, CDCl$_3$) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 244: Synthesis of 1-(2,6-dichlorophenyl)-1-methoxy-3-methyl-butyl-2-carbamate

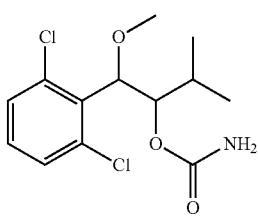 [SMILES: COC(c1c(Cl)cccc1Cl)C(OC(N)=O)C(C)C]

$^1$H NMR (400 MHz, CDCl$_3$) δ 1.07 (t, J=7.6 Hz, 6H), 1.83~1.89 (m, 1H), 3.24 (s, 3H), 4.71 (d, J=6.8 Hz, 1H), 4.73 (br s, 2H), 4.82~4.88 (m, 1H), 7.55~7.57 (m, 3H).

Example 245: Synthesis of 1-(2,4-dichlorophenyl)-1-methoxyhexyl-2-carbamate

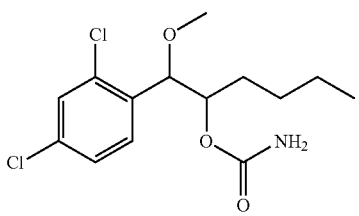 [SMILES: CCCCC(OC(N)=O)C(OC)c1ccc(Cl)cc1Cl]

$^1$H NMR (400 MHz, CDCl$_3$) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.24~7.30 (m, 2H), 7.73 (d, J=1.5 Hz, 1H).

Example 246: Synthesis of 1-(2,4-dichlorophenyl)-1-methoxyhexyl-2-carbamate

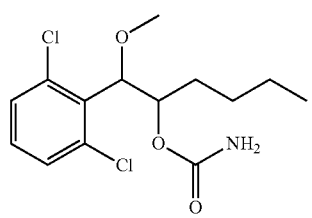 [SMILES: CCCCC(OC(N)=O)C(OC)c1c(Cl)cccc1Cl]

$^1$H NMR (400 MHz, CDCl$_3$) δ 0.90 (t, J=7.6 Hz, 3H), 1.35~1.65 (m, 6H), 3.24 (s, 3H), 4.71 (d, J=6.8 Hz, 1H), 4.73 (br s, 2H), 4.82~4.88 (m, 1H), 7.54~7.59 (m, 3H).

Example 247: Synthesis of 1-(2-chlorophenyl)-(S)-1-carbamoyloxypropyl-(S)-2-carbamate

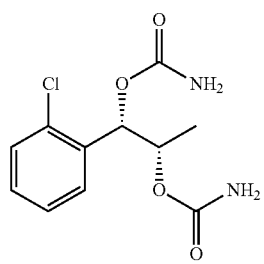 [SMILES: C[C@H](OC(N)=O)[C@@H](OC(N)=O)c1ccccc1Cl]

1-(2-chlorophenyl)-1-hydroxypropyl-1-carbamate (Preparation Example 103, 8 g), tetrahydrofuran (THF), and carbonyldiimidazole (CDI, 1.5 eq, 9.1 g) were put into a flask and stirred at the room temperature. After approximately 3 hours, ammonia solution (NH$_4$OH, 3 eq, 4.4 mL) was added thereto. When the reaction was completed, the obtained product was washed with 1 M HCl solution and ethylacetate (EA). The separated organic layer was dehydrated with anhydrous MgSO$_4$ (Magnesium sulfate), filtrated, and concentrated under reduced pressure. The concentrated residue was purified by a silica gel column chromatography, to obtain the title compound.

$^1$H NMR (400 MHz, DMSO-d$_6$) δ 1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H).

According to the method described in Example 247, the following compounds of Examples 248 to 295 were prepared:

Example 248: Synthesis of 1-(2-chlorophenyl)-(S)-1-carbamoyloxypropyl-(S)-2-methylcarbamate

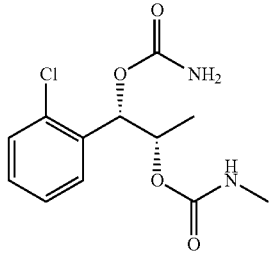 [SMILES: CNC(=O)O[C@@H](C)[C@@H](OC(N)=O)c1ccccc1Cl]

$^1$H NMR (400 MHz, CDCl$_3$) δ 1.40 (d, J=6.0 Hz, 3H), 2.74 (s, 3H), 4.71 (d, J=6.4 Hz, 1H), 4.80~4.85 (m, 1H), 6.30~6.90 (br s, 3H), 7.28~7.43 (m, 4H).

Example 249: Synthesis of 1-(2-chlorophenyl)-(S)-1-carbamoyloxypropyl-(S)-2-propylcarbamate

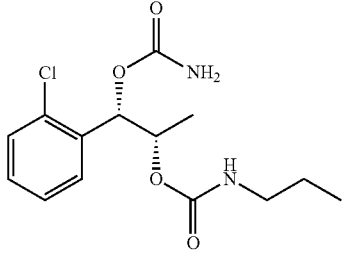 [SMILES: CCCNC(=O)O[C@@H](C)[C@@H](OC(N)=O)c1ccccc1Cl]

$^1$H NMR (400 MHz, CDCl$_3$) δ 0.96 (t, J=6.4 Hz, 3H), 1.40 (d, J=6.0 Hz, 3H), 1.55~1.60 (m, 2H), 2.96 (t, J=6.0 Hz, 2H), 4.71 (d, J=6.0 Hz, 1H), 4.82~4.88 (m, 1H), 6.76 (br s, 3H), 7.07~7.21 (m, 4H).

Example 250: Synthesis of 1-(2-chlorophenyl)-(R)-2-carbamoyloxypropyl-(R)-1-carbamate

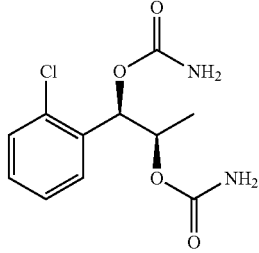 [SMILES: C[C@@H](OC(N)=O)[C@H](OC(N)=O)c1ccccc1Cl]

$^1$H NMR (400 MHz, DMSO-d$_6$) δ 1.12 (d, J=6.4 Hz, 3H), 4.97~5.04 (m, 1H), 5.92 (d, J=5.2 Hz, 1H), 6.25~6.83 (m, 4H), 7.30~7.44 (m, 4H).

Example 251: Synthesis of 1-(2-chlorophenyl)-2-carbamoyloxypropyl-1-carbamate

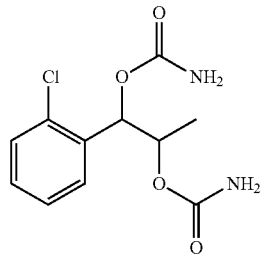 [SMILES: CC(OC(N)=O)C(OC(N)=O)c1ccccc1Cl]

$^1$H NMR (400 MHz, DMSO-d$_6$) δ 1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H).

Example 252: Synthesis of 1-(2-chlorophenyl)-(S)-1-carbamoyloxybutyl-(S)-2-carbamate

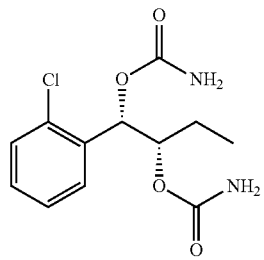 [SMILES: CC[C@H](OC(N)=O)[C@@H](OC(N)=O)c1ccccc1Cl]

$^1$H NMR (400 MHz, CDCl$_3$) δ 1.04 (t, J=7.6 Hz, 3H), 1.60~1.71 (m, 2H), 4.71 (d, J=6.8 Hz, 1H), 4.73 (br s, 2H), 5.82~5.88 (m, 1H), 7.26~7.70 (m, 4H).

Example 253: Synthesis of 1-(2-chlorophenyl)-(S)-1-carbamoyloxy-3-methyl-butyl-(S)-2-carbamate

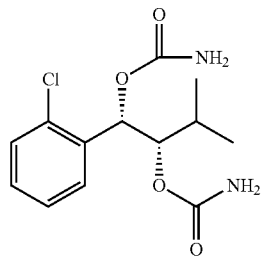 [SMILES: CC(C)[C@H](OC(N)=O)[C@@H](OC(N)=O)c1ccccc1Cl]

$^1$H NMR (400 MHz, CDCl$_3$) δ 1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.26~7.70 (m, 4H).

Example 254: Synthesis of 1-(2-chlorophenyl)-(S)-1-carbamoyloxyhexyl-(S)-2-carbamate

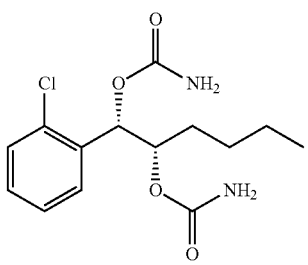 [SMILES: CCCC[C@H](OC(N)=O)[C@@H](OC(N)=O)c1ccccc1Cl]

$^1$H NMR (400 MHz, CDCl$_3$) δ 0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.26~7.70 (m, 4H).

Example 255: Synthesis of 1-(2-fluorophenyl)-(S)-1-carbamoyloxypropyl-(S)-2-carbamate

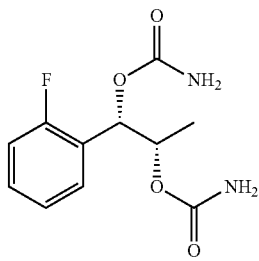

$^1$H NMR 400 MHz, DMSO-d$_6$) δ 1.37 (d, J=6.8 Hz, 3H), 4.71 (d, J=6.8 Hz, 1H), 5.82~5.88 (m, 1H), 7.15~7.68 (m, 4H).

Example 256: Synthesis of 1-(2-fluorophenyl)-(S)-1-carbamoyloxybutyl-(S)-2-carbamate

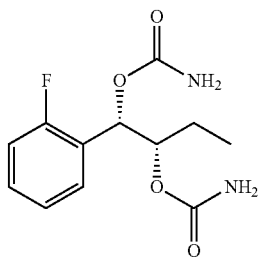

$^1$H NMR (400 MHz, CDCl$_3$) δ 1.02 (t, J=7.2 Hz, 3H), 1.60~1.71 (m, 2H), 4.71 (d, J=6.8 Hz, 1H), 4.73 (br s, 2H), 5.82~5.88 (m, 1H), 6.09~7.17 (m, 4H).

Example 257: Synthesis of 1-(2-fluorophenyl)-(S)-1-carbamoyloxy-3-methyl-butyl-(S)-2-carbamate

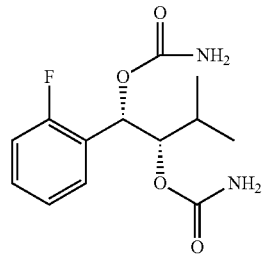 [SMILES: CC(C)[C@H](OC(N)=O)[C@@H](OC(N)=O)c1ccccc1F]

$^1$H NMR (400 MHz, CDCl$_3$) δ 1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.10~7.20 (m, 4H).

Example 258: Synthesis of 1-(2-fluorophenyl)-(S)-1-carbamoyloxyhexyl-(S)-2-carbamate

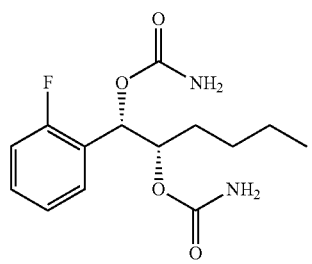 [SMILES: CCCC[C@H](OC(N)=O)[C@@H](OC(N)=O)c1ccccc1F]

$^1$H NMR (400 MHz, CDCl$_3$) δ 0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.16~7.69 (m, 4H).

Example 259: Synthesis of 1-(2-iodophenyl)-(S)-1-carbamoyloxypropyl-(S)-2-carbamate

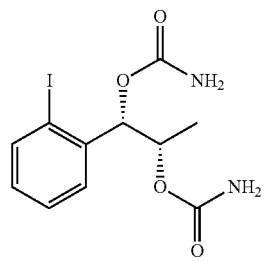 [SMILES: C[C@H](OC(N)=O)[C@@H](OC(N)=O)c1ccccc1I]

$^1$H NMR (400 MHz, DMSO-d$_6$) δ 1.37 (d, J=6.8 Hz, 3H), 4.71 (d, J=6.8 Hz, 1H), 4.82~4.88 (m, 1H), 7.13~7.88 (m, 4H).

Example 260: Synthesis of 1-(2-iodophenyl)-(S)-1-carbamoyloxybutyl-(S)-2-carbamate

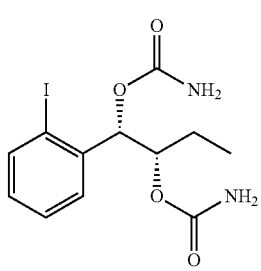 [SMILES: CC[C@H](OC(N)=O)[C@@H](OC(N)=O)c1ccccc1I]

¹H NMR (400 MHz, CDCl₃) δ 1.02 (t, J=7.2 Hz, 3H), 1.60~1.71 (m, 2H), 4.71 (d, J=6.8 Hz, 1H), 4.73 (br s, 2H), 5.82~5.88 (m, 1H), 6.96~7.57 (m, 4H).

Example 261: Synthesis of 1-(2-iodophenyl)-(S)-1-carbamoyloxy-3-methyl-butyl-(S)-2-carbamate

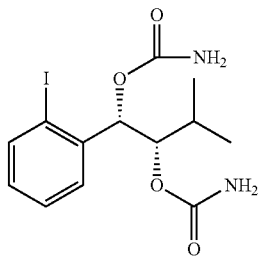 [SMILES: CC(C)[C@H](OC(N)=O)[C@@H](OC(N)=O)c1ccccc1I]

¹H NMR (400 MHz, CDCl₃) δ 1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.98~7.61 (m, 4H).

Example 262: Synthesis of 1-(2-iodophenyl)-(S)-1-carbamoyloxyhexyl-(S)-2-carbamate

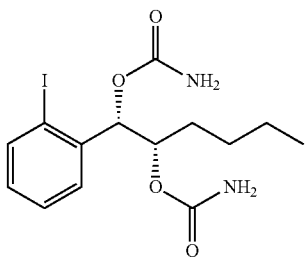

¹H NMR (400 MHz, CDCl₃) δ 0.90 (t, J=7.6 Hz, 3H), 1.35~1.65 (m, 6H), 4.71 (d, J=6.8 Hz, 1H), 4.73 (br s, 2H), 5.82~5.88 (m, 1H), 6.95~7.61 (m, 4H).

Example 263: Synthesis of 1-(2,4-dichlorophenyl)-(S)-1-carbamoyloxypropyl-(S)-2-carbamate

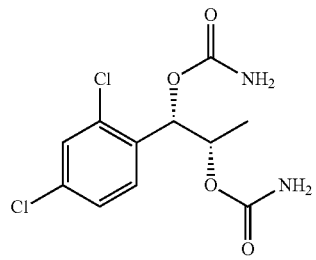 [SMILES: C[C@H](OC(N)=O)[C@@H](OC(N)=O)c1ccc(Cl)cc1Cl]

¹H NMR (400 MHz, DMSO-d₆) δ 1.37 (d, J=6.8 Hz, 3H), 4.71 (d, J=6.8 Hz, 1H), 4.82~4.88 (m, 1H), 7.07~7.21 (m, 3H).

Example 264: Synthesis of 1-(2,4-dichlorophenyl)-(S)-1-carbamoyloxybutyl-(S)-2-carbamate

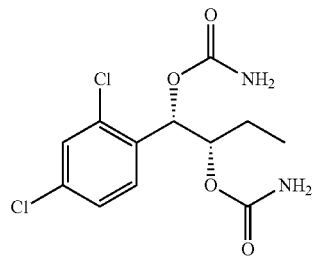 [SMILES: CC[C@H](OC(N)=O)[C@@H](OC(N)=O)c1ccc(Cl)cc1Cl]

¹H NMR (400 MHz, CDCl₃) δ 1.02 (t, J=7.2 Hz, 3H), 1.60~1.71 (m, 2H), 4.71 (d, J=6.8 Hz, 1H), 4.73 (br s, 2H), 5.82~5.88 (m, 1H), 7.05~7.19 (m, 3H).

Example 265: Synthesis of 1-(2,4-dichlorophenyl)-(S)-1-carbamoyloxy-3-methyl-butyl-(S)-2-carbamate

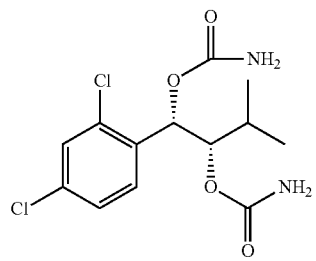 [SMILES: CC(C)[C@H](OC(N)=O)[C@@H](OC(N)=O)c1ccc(Cl)cc1Cl]

¹H NMR (400 MHz, CDCl₃) δ 1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.17 (m, 3H).

Example 266: Synthesis of 1-(2,4-dichlorophenyl)-(S)-1-carbamoyloxyhexyl-(S)-2-carbamate

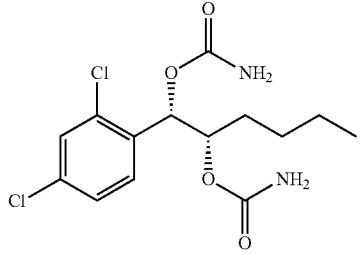 [SMILES: CCCC[C@H](OC(N)=O)[C@@H](OC(N)=O)c1ccc(Cl)cc1Cl]

$^1$H NMR (400 MHz, CDCl$_3$) δ 0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.08~7.22 (m, 3H).

Example 267: Synthesis of 1-(2,6-dichlorophenyl)-(S)-1-carbamoyloxypropyl-(S)-2-carbamate

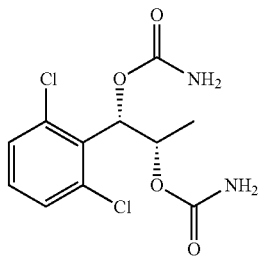 [SMILES: C[C@H](OC(N)=O)[C@@H](OC(N)=O)c1c(Cl)cccc1Cl]

$^1$H NMR (400 MHz, DMSO-d$_6$) δ 1.37 (d, J=6.8 Hz, 3H), 4.71 (d, J=6.8 Hz, 1H), 4.82~4.88 (m, 1H), 7.07~7.11 (m, 3H).

Example 268: Synthesis of 1-(2,6-dichlorophenyl)-(S)-1-carbamoyloxybutyl-(S)-2-carbamate

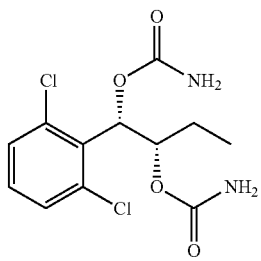 [SMILES: CC[C@H](OC(N)=O)[C@@H](OC(N)=O)c1c(Cl)cccc1Cl]

$^1$H NMR (400 MHz, CDCl$_3$) δ 1.02 (t, J=7.2 Hz, 3H), 1.60~1.71 (m, 2H), 4.71 (d, J=6.8 Hz, 1H), 4.73 (br s, 2H), 5.82~5.88 (m, 1H), 7.05~7.10 (m, 3H).

Example 269: Synthesis of 1-(2,6-dichlorophenyl)-(S)-1-carbamoyloxy-3-methyl-butyl-(S)-2-carbamate

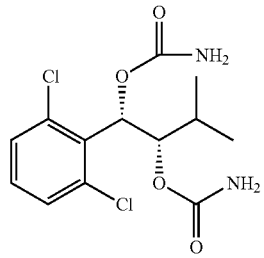 [SMILES: CC(C)[C@H](OC(N)=O)[C@@H](OC(N)=O)c1c(Cl)cccc1Cl]

$^1$H NMR (400 MHz, CDCl$_3$) δ 1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.08 (m, 3H).

Example 270: Synthesis of 1-(2,6-dichlorophenyl)-(S)-1-carbamoyloxyhexyl-(S)-2-carbamate

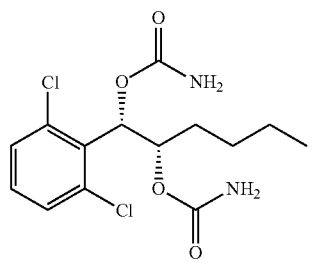 [SMILES: CCCC[C@H](OC(N)=O)[C@@H](OC(N)=O)c1c(Cl)cccc1Cl]

$^1$H NMR (400 MHz, CDCl$_3$) δ 0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.05~7.12 (m, 3H).

Example 271: Synthesis of 1-(2,6-difluorophenyl)-(S)-1-methoxymethoxypropyl-(S)-2-carbamate

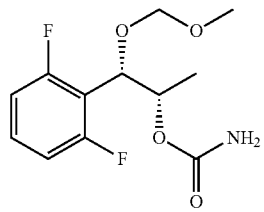 [SMILES: COCO[C@@H](c1c(F)cccc1F)[C@H](C)OC(N)=O]

$^1$H NMR (400 MHz, CDCl$_3$) δ 1.37 (d, J=6.8 Hz, 3H), 3.30 (s, 3H), 4.71 (d, J=6.8 Hz, 1H), 4.82~4.88 (m, 1H), 5.45 (s, 2H), 6.67~7.15 (m, 3H).

Example 272: Synthesis of 1-(2,5-dichlorophenyl)-(S)-1-methoxymethoxypropyl-(S)-2-carbamate

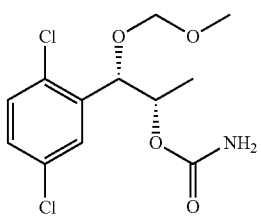 [SMILES: COCO[C@@H](c1cc(Cl)ccc1Cl)[C@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.13~7.26 (m, 3H).

Example 273: Synthesis of 1-(2,5-dichlorophenyl)-(R)-1-methoxymethoxypropyl-(R)-2-carbamate

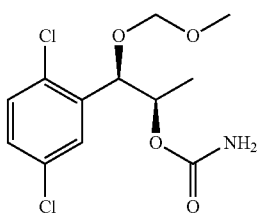 [SMILES: COCO[C@H](c1cc(Cl)ccc1Cl)[C@@H](C)OC(N)=O]

¹H NMR (400 MHz, CDCl₃) δ 1.37 (d, J=6.8 Hz, 3H), 3.30 (s, 3H), 4.71 (d, J=6.8 Hz, 1H), 4.82~4.88 (m, 1H), 5.45 (s, 2H), 7.13~7.26 (m, 3H).

Example 274: Synthesis of 1-(2-chlorophenyl)-(S)-2-methoxymethoxypropyl-(S)-1-carbamate

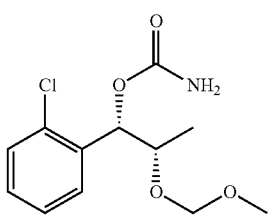 [SMILES: COCO[C@@H](C)[C@@H](OC(N)=O)c1ccccc1Cl]

¹H NMR (400 MHz, CDCl₃) δ 1.21 (d, J=6.8 Hz, 3H), 3.24 (s, 3H), 3.94~4.05 (m, 1H), 5.45 (s, 2H), 5.56 (d, J=6.8 Hz, 1H), 7.07~7.20 (m, 4H).

Example 275: Synthesis of 1-(2-chlorophenyl)-(S)-2-methoxypropyl-(S)-1-carbamate

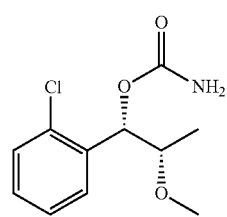 [SMILES: CO[C@@H](C)[C@@H](OC(N)=O)c1ccccc1Cl]

¹H NMR (400 MHz, CDCl₃) δ 1.23 (d, J=6.4 Hz, 3H), 3.22 (s, 3H), 3.99 (m, 1H), 5.52 (d, J=6.4 Hz, 1H), 7.07~7.21 (n, 4H).

Example 276: Synthesis of 1-(2-chlorophenyl)-(S)-1-methoxymethoxyethyl-2-carbamate

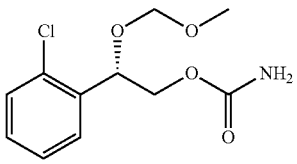 [SMILES: COCO[C@H](COC(N)=O)c1ccccc1Cl]

¹H NMR (400 MHz, DMSO-d₆) δ 3.30 (s, 3H), 4.71 (d, J=6.8 Hz, 1H), 4.82~4.88 (m, 1H), 5.45 (s, 2H), 7.26~7.70 (m, 4H).

Example 277: Synthesis of 1-(2-fluorophenyl)-(S)-1-methoxymethoxyethyl-2-carbamate

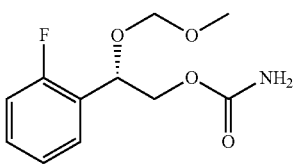

¹H NMR (400 MHz, CDCl₃) δ 3.30 (s, 3H), 4.71 (d, J=6.8 Hz, 1H), 4.82~4.88 (m, 1H), 5.45 (s, 2H), 7.26~7.70 (m, 4H).

Example 278: Synthesis of 1-(2-iodophenyl)-(S)-1-methoxymethoxyethyl-2-carbamate

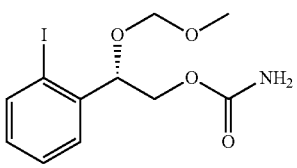 [SMILES: COCO[C@H](COC(N)=O)c1ccccc1I]

¹H NMR (400 MHz, DMSO-d₆) δ 3.26 (s, 3H), 3.94~4.09 (m, 1H), 4.47 (d, J=6.8 Hz, 1H), 4.60 (d, J=6.8 Hz, 1H), 4.97 (m, 1H), 6.55 (br 2H), 7.07~7.87 (m, 4H).

Example 279: Synthesis of 1-(2-chlorophenyl)-(S)-1-methoxyethyl-2-carbamate

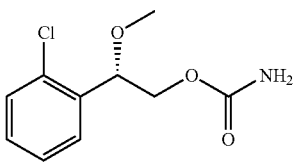

¹H NMR (400 MHz, DMSO-d₆) δ 3.27 (s, 3H), 4.71 (d, J=6.8 Hz, 1H), 4.82~4.88 (m, 1H), 6.47~6.63 (br 2H), 7.26~7.70 (m, 4H).

Example 280: Synthesis of 1-(2-fluorophenyl)-(S)-1-methoxyethyl-2-carbamate

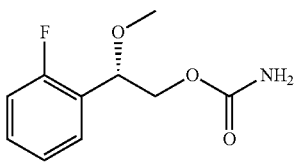

¹H NMR (400 MHz, DMSO-d₆) δ 3.29 (s, 3H), 4.71 (d, J=6.8 Hz, 1H), 4.82~4.88 (m, 1H), 7.26~7.70 (m, 4H).

Example 281: Synthesis of 1-(2-iodophenyl)-(S)-1-methoxyethyl-2-carbamate

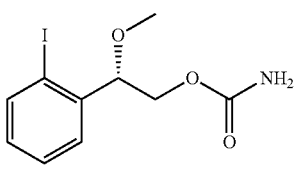

¹H NMR (400 MHz, DMSO-d₆) δ 3.28 (s, 3H), 3.94~4.09 (m, 1H), 4.97 (m, 1H), 7.07~7.87 (m, 4H).

Example 282: Synthesis of 1-(2-iodophenyl)-(S)-2-methoxymethoxypropyl-1-carbamate

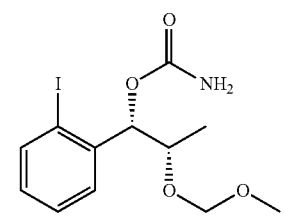 [SMILES: COCO[C@@H](C)[C@@H](OC(N)=O)c1ccccc1I]

¹H NMR (400 MHz, CDCl₃) δ 1.31 (d, J=9.6 Hz, 3H), 3.08 (s, 3H), 4.15~4.20 (m, 1H), 4.33 (d, J=6.8 Hz, 1H), 4.56 (d, J=7.2 Hz, 1H), 4.79 (br s, 2H), 5.88 (d, J=4.0 Hz, 1H), 6.98~7.02 (m, 1H), 7.33~7.42 (m, 2H), 7.85 (dd, J=0.8, 7.8 Hz, 1H).

Example 283: Synthesis of 1-(2-iodophenyl)-(S)-2-methoxypropyl-1-carbamate

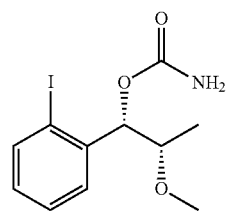 [SMILES: CO[C@@H](C)[C@@H](OC(N)=O)c1ccccc1I]

¹H NMR (400 MHz, CDCl₃) δ 1.29 (d, J=6.4 Hz, 3H), 3.29 (s, 3H), 4.56 (d, J=5.3 Hz, 1H), 4.55 (br s, 2H), 5.08~5.11 (m, 1H), 7.01~7.05 (m, 1H), 7.38~7.86 (m, 3H).

Example 284: Synthesis of 1-(2-fluorophenyl)-(S)-2-methoxymethoxypropyl-1-carbamate

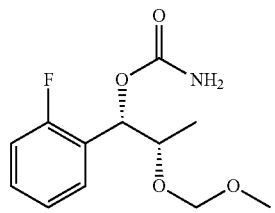

¹H NMR (400 MHz, CDCl₃) δ 1.19 (d, J=6.4 Hz, 3H), 3.15 (s, 3H), 4.03~4.18 (m, 1H), 4.49 (d, J=6.8 Hz, 1H), 4.61 (d, J=7.2 Hz, 1H), 4.81 (s, 2H), 5.95 (d, J=5.2 Hz, 1H), 7.00~7.43 (m, 4H).

Example 285: Synthesis of 1-(2-fluorophenyl)-(S)-2-methoxypropyl-(S)-1-carbamate

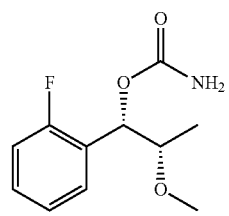 [SMILES: CO[C@@H](C)[C@@H](OC(N)=O)c1ccccc1F]

¹H NMR (400 MHz, CDCl₃) δ 1.18 (d, J=6.4 Hz, 3H), 3.30 (s, 3H), 3.99 (d, J=5.3 Hz, 1H), 4.65 (br s, 2H), 4.89~5.01 (m, 1H), 7.01~7.05 (m, 1H), 7.38~7.68 (m, 3H).

Example 286: Synthesis of 1-(2-chloro-6-fluorophenyl)-(S)-1-carbamoyloxypropyl-(S)-2-carbamate

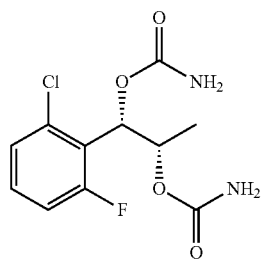 [SMILES: C[C@H](OC(N)=O)[C@@H](OC(N)=O)c1c(F)cccc1Cl]

¹H NMR (400 MHz, DMSO-d₆) δ 0.97 (d, J=6.4 Hz, 3H), 5.28~5.31 (m, 1H), 6.48 (d, J=8.4 Hz, 1H), 6.48~6.77 (br, 4H), 7.23~7.45 (m, 3H).

Example 287: Synthesis of 1-(2-chloro-6-fluorophenyl)-(R)-1-carbamoyloxypropyl-(R)-2-carbamate

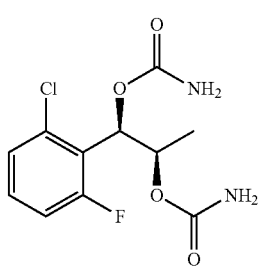 [SMILES: C[C@@H](OC(N)=O)[C@H](OC(N)=O)c1c(F)cccc1Cl]

¹H NMR (400 MHz, CDCl₃) δ 1.17 (d, J=6.4 Hz, 3H), 4.74 (br s, 4H), 5.52~5.60 (m, 1H), 6.29 (d, J=8.4 Hz, 1H), 7.00~7.05 (m, 1H), 7.22~7.23 (m, 2H).

Example 288: Synthesis of 1-(2-iodophenyl)-(R)-1-carbamoyloxypropyl-(R)-2-carbamate

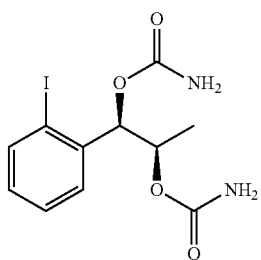 [SMILES: C[C@@H](OC(N)=O)[C@H](OC(N)=O)c1ccccc1I]

¹H NMR (400 MHz, DMSO-d₆) δ 1.15 (d, J=6.8 Hz, 3H), 4.96~5.00 (m, 1H), 5.72 (d, J=4.4 Hz, 1H), 6.43 (br s, 2H), 6.57 (br s, 1H), 6.79 (br s, 1H), 7.04~7.12 (m, 1H), 7.33~7.49 (m, 2H), 7.84 (d, J=8.0 Hz, 1H).

Example 289: Synthesis of 1-(2-fluorophenyl)-(R)-1-carbamoyloxypropyl-(R)-2-carbamate

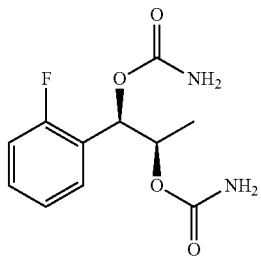

¹H NMR (400 MHz, DMSO-d₆) δ 1.06 (d, J=6.4 Hz, 3H), 4.95~5.01 (m, 1H), 5.80 (d, J=6.0 Hz, 1H), 6.50 (br s, 2H), 6.82 (br s, 2H), 7.17~7.24 (m, 2H), 7.34~7.37 (m, 2H).

Example 290: Synthesis of 1-(2,6-dichlorophenyl)-(R)-1-carbamoyloxypropyl-(R)-2-carbamate

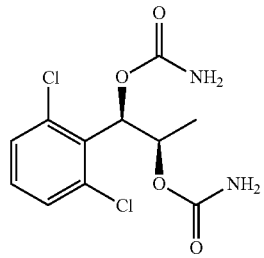 [SMILES: C[C@@H](OC(N)=O)[C@H](OC(N)=O)c1c(Cl)cccc1Cl]

¹H NMR (400 MHz, CDCl₃) δ 1.64 (d, J=6.4 Hz, 3H), 4.59 (br s, 2H), 4.86 (br s, 2H), 4.97~5.02 (m, 1H), 6.02 (d, J=8.0 Hz, 1H), 7.31~7.35 (m, 1H), 7.41~7.44 (m, 2H).

Example 291: Synthesis of 1-(2,4-difluorophenyl)-(R)-1-carbamoyloxypropyl-(R)-2-carbamate

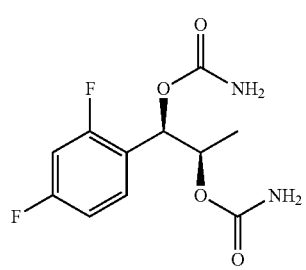 [SMILES: C[C@@H](OC(N)=O)[C@H](OC(N)=O)c1ccc(F)cc1F]

¹H NMR (400 MHz, CDCl₃) δ 1.18 (d, J=6.4 Hz, 3H), 4.65 (br s, 2H), 4.75 (br s, 2H), 5.17~5.24 (m, 1H), 5.95 (d, J=7.2 Hz, 1H), 6.81~6.93 (m, 2H), 7.36~7.42 (m, 1H).

Example 292: Synthesis of 1-(2,6-difluorophenyl)-(R)-1-carbamoyloxypropyl-(R)-2-carbamate

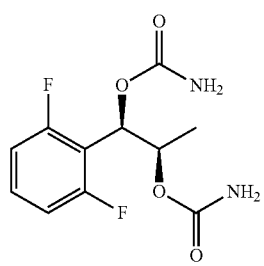 [SMILES: C[C@@H](OC(N)=O)[C@H](OC(N)=O)c1c(F)cccc1F]

¹H NMR (400 MHz, CDCl₃) δ 1.16 (d, J=6.8 Hz, 3H), 4.76 (br s, 4H), 5.44~5.48 (m, 1H), 6.10 (d, J=8.4 Hz, 1H), 6.90~6.95 (m, 2H), 7.28~7.35 (m, 2H).

Example 293: Synthesis of 1-(2,5-difluorophenyl)-(R)-1-carbamoyloxypropyl-(R)-2-carbamate

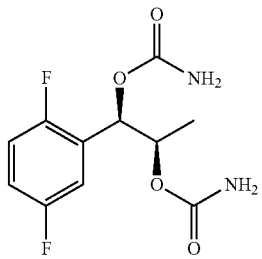 [SMILES: C[C@@H](OC(N)=O)[C@H](OC(N)=O)c1cc(F)ccc1F]

¹H NMR (400 MHz, CDCl₃) δ 1.23 (d, J=6.8 Hz, 3H), 4.64 (br s, 2H), 4.77 (br s, 2H), 5.15~5.22 (m, 1H), 5.97 (d, J=6.4 Hz, 1H), 6.98~7.07 (m, 2H), 7.08~7.13 (m, 1H).

Example 294: Synthesis of 1-(2-chlorophenyl)-(S)-1-carbamoyloxypropyl-(R)-2-carbamate

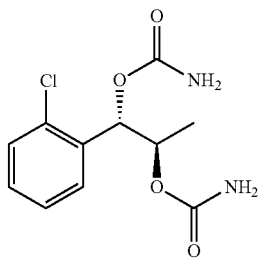 [SMILES: C[C@@H](OC(N)=O)[C@@H](OC(N)=O)c1ccccc1Cl]

¹H NMR (400 MHz, DMSO-d₆) δ 1.09 (d, J=6.8 Hz, 3H), 4.95~5.01 (m, 1H), 5.95 (d, J=3.6 Hz, 1H), 6.53 (br s, 2H), 6.86 (br s, 2H), 7.32~7.42 (m, 2H), 7.44~7.47 (m, 2H).

Example 295: Synthesis of 1-(2-chlorophenyl)-(R)-1-carbamoyloxypropyl-(S)-2-carbamate

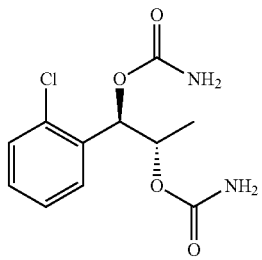 [SMILES: C[C@H](OC(N)=O)[C@H](OC(N)=O)c1ccccc1Cl]

¹H NMR (400 MHz, DMSO-d₆) δ 1.09 (d, J=6.4 Hz, 3H), 4.95~5.01 (m, 1H), 5.95 (d, J=3.6 Hz, 1H), 6.47 (br s, 2H), 6.82 (br s, 2H), 7.32~7.41 (m, 2H), 7.44~7.47 (m, 2H).

Biological Experimental Example 1: Preparation of Parkinson's Disease Animal Model C57BL/6 mice (n=61) were purchased from Samtako bio korea Co. Ltd (Osan, Korea.) Mice were housed in the room which offers 12 hours light/dark cycle with a temperature of 20~22° C.

All mice were separated into groups with enough food and sterilized water. All experiments and animal care were approved by the Institutional Animal Care and Use Committee of Chonnam National University (Korea).

Mice were randomly divided into four groups:
Group 1: vehicle control mice,
Group 2: Compound of Example 124—treated mice,
Group 3: rotenone treated mice,
Group 4: Compound of Example 124—rotenone treated mice.

Rotenone was suspended in 0.5% Carboxymethyl cellulose (CMC) sodium salt. Compound of Example 124 were dissolved in Tween 80. 0.5% CMC and Rotenone (30 mg/kg) were administered orally, the compound of Example 124 (40 mg/kg) was injected intraperitoneally (IP) once a day for 35 days (5 weeks).

Biological Experimental Example 2: Confirmation of the Effect of Improving Movement Abnormality by the Compound of Example 124

In the present invention, in order to confirm whether the compound of Example 124 (compound 124) improves the motor abnormalities found in rotenone-induced Parkinson's disease model mice, rota-rod test, pole test, and foot printing assay test were performed.

2-1: Rota-Rod Test

Rotarod test was performed using the Parkinson's disease model mice of Biological Experiment Example 1 as follows. Mice were tested for one day on the accelerating rota-rod (B.S Techno lab Inc, Seoul, Korea) [Shiotsuki, H., et al., *A rotarod test for evaluation of motor skill learning*. J Neurosci Methods, 2010. 189(2): p. 180-5.]. The speed of the rotation was set to accelerate constantly from a minimum speed of 0 rpm to a maximum speed of 49 rpm. Five trials were performed with animals and each trial lasted for 3 min. Latency to fall from the rotating apparatus was recorded through the camera. Analysis was conducted through the display from the apparatus, indicating parameters such as distance and running time.

As a result of the rota-rod test, as shown in FIG. 1(A), all 4 groups showed similar retention time on rota-rod apparatus showing no difference.

2-2: Pole Test

Pole test was performed using the Parkinson's disease model mice of Biological Experiment Example 1 as follows. A wood pole that is 40 cm long was set up in the center of the arena full of sawdust. Pole was wrapped with polyethylene vinyl to avoid slippering during the test. Each trial was recorded through the camera locating in front of the pole. The time mice turned upside down (head down) and the time it completely climbs down the pole was measured through a recorded video file manually by using the software Boris. Results from manually counted files were scored and presented.

As a result of the pole test, as shown in FIG. 1(B-C), the Rotenone-injected group spent a long time climbing down the pole from the top and gained a higher score compared to the wild-type vehicle group in the pole test. And these disabilities were slightly attenuated by the compound of Example 124 but not significantly.

2-3: Foot Printing Assay

Foot printing assay was performed using the Parkinson's disease model mice of Biological Experiment Example 1 as follows. Mice paws were dipped with non-toxic water paints (forelimbs in green and hind limbs in blue). Mice were placed in the corner of the enclosed maze with white paper lined through the maze and allowed to walk along the maze freely. [Heck, D. H., et al., *Analysis of cerebellar function in Ube3a-deficient mice reveals novel genotype-specific behaviors.* Hum Mol Genet, 2008. 17(14): p. 2181-9.] Fore limb-stride length and hind limb-stride length were measured using ImageJ (NIH).

As a result of the pole test, as shown in FIG. 2(A-C), Stride lengths of both forepaw and hind paw were decreased by rotenone injection but ameliorated by the compound of Example 124.

Although injection of rotenone for 5 weeks is not enough to show significant motor dysfunction, these results suggest that the compound of Example 124 has an effect on alleviating motor disabilities.

Biological Experimental Example 3: Confirmation of the Effect of Preventing Rotenone-Induced Dopaminergic Neuron Loss in the Striatum by the Compound of Example 124

3-1: Brain Tissue Preparation and Immunohistochemistry

Dopaminergic neuron loss has been implicated in motor dysfunction in Parkinson's disease. In the present invention, stained the striatum with Tyrosine hydroxylase (TH) antibody to check out whether compound of Example 124 prevents the TH+ neuron cell death by rotenone.

Specifically, mice of Biological Experiment Example 1 were anesthetized with sevoflurane and perfused with PBS (phosphate-buffered saline). After perfusion, dissected the left hemisphere of the brain from the mice and fixed the right hemisphere brain with 4% PFA for 1 day [Shin, S. J., et al., *Jowiseungchungtang Inhibits Amyloid-beta Aggregation and Amyloid-beta-Mediated Pathology in 5XFADMice*. Int J Mol Sci, 2018. 19(12).]. The frozen brain was sectioned in the coronal way (30 μm thick) using a cryostat (Leica CM3000, Leica Microsystems, Nussloch, Germany). Sections were stored at deep freezer (−70° C.) until the immunohistochemistry analysis starts.

In all immunofluorescence labeling procedures, rinsed off the brain sections and blocked the tissues with cold PBST (0.1% Triton X-100 in PBS) containing 5% BSA and 5% goat serum at room temperature. Brain sections were blocked with cold PBST (0.1% Triton X-100 in PBS) containing 5% BSA and 5% goat serum at room temperature. Primary antibody, including rabbit anti-tyrosine hydroxylase (TH) antibody (1:5000) was prepared.

Sections were incubated with TH antibody for 3 days. After washing three times for 10 min with PBS, the brain sections were incubated with the secondary antibody (goat Alexa Fluor® 568 conjugated anti-rabbit antibody (1:2000) at 4° C. overnight. The brain tissues were mounted with Fluoromount-G (Southern Biotech, AL, USA).

All the images were taken using a fluorescence microscope (Leica DM LB2). To determine the loss of TH positive neurons and the prevention effect of the compound of Example 124 in the striatum, TH+ neurons were counted by using a cell counter plugin from ImageJ software (NIH).

Immunofluorescence images were analyzed using one-way ANOVA and post hoc analysis using Tukey's post hoc test (GraphPad Prism). All data were presented as means±SEM. All p values <0.05 were considered statistically significant.

As shown in FIG. 3(A-B), immunohistochemistry results demonstrated that TH+ cell death was occurred by rotenone and this death was significantly blocked by the compound of Example 124.

3-2: Western Blotting

Whole ventral midbrain was homogenized with RIPA buffer containing 1% Triton X 100, 0.5% deoxycholic acid, 0.2% SDS, 150 mM NaCl, 2 mM EDTA, protease inhibitors (PMSF, Aprotinin, NaF, $Na_3VO_4$). The homogenate was centrifuged at 13,000 rpm for 30 min on a rotator and the supernatant was used [Vergara, C., et al., *Amyloid-beta pathology enhances pathological fibrillary tau seeding induced by Alzheimer PHF in vivo*. Acta Neuropathol, 2019. 137(3): p. 397-412.]. Proteins were separated using SDS-PAGE with a concentration gradient of 8-20% SDS gels and transferred onto PVDF membranes (Immobilon P membrane, Millipore). Membranes blocked in 5% skim milk in TBST (Tris-Buffered saline-Tween®20) and immunolabeled with primary antibody, rabbit anti-tyrosine hydroxylase (TH) antibody (1:5000)). Blots were developed with a chemiluminescence reagent (AbFrontier).

Western blot data were analyzed using a t-test(1-tailed t-test). All data were presented as means±SEM. All p values <0.05 were considered statistically significant.

As shown in FIG. 3(C-D), western blotting results demonstrated that tyrosine hydroxylase (TH) expression was increased by the compound of Example 124 in the ventral mid brain protein. This result indicates that the compound of Example 124 has a prevention effect on dopaminergic neuron loss in Parkinson's disease.

Biological Experimental Example 4: Confirmation of the Effect of Regulating Posttranslational Modification of Tau Protein and α-Tubulin by the Compound of Example 124

As tau pathology is found in Parkinson's disease patients, In the present invention focused on changes in the phosphorylation level of the microtubule-associated protein, tau.

Western blotting was performed in the same manner as in Biological Experimental Example 3-2, and the primary antibodies, including anti-phosphor-tau rabbit-polyclonal antibody (p-Ser262, 1:3000, Invitrogen), and anti-Acetyl-alpha tubulin rabbit-monoclonal antibody (1:3000, CST) were used.

As shown in FIG. 4(A-C), in the present invention, using phosphorylated tau antibody (p-Tau s262), found Tau to be hyperphosphorylated at Ser262 in the rotenone-vehicle mice group. And phosphorylation of tau protein was decreased in the compound of Example 124-rotenone-treated group compared to that in the rotenone-vehicle mice group but not significantly.

The present invention also evaluated α-tubulin acetylation levels, since posttranslational modification is a marker for stable microtubules. Compound of Example 124 promoted an increase in α-tubulin acetylation levels in the compound of Example 124-rotenone-treated group. Although the differences between groups were not significant, it indicates that the compound of Example 124 may contribute to microtubule stability.

Biological Experimental Example 5: Confirmation of the Effect of Repressing Rotenone-Induced Formation of p-α-Synuclein Inclusions in Cell Bodies of TH+ Neurons by the Compound of Example 124

Fibrillar aggregates called Lewy body (LB) formation is another pathological feature found in Parkinson's disease and is mainly caused by oligomerization of conformationally and post-translationally modified α-synuclein.

In the present invention, stained the brain tissue with Tyrosine hydroxylase (TH) and Phosphorylated alpha-synuclein (s129) to investigate the effect of the compound of Example 124 on the formation of α-synuclein inclusion on cell bodies of TH+ neurons.

Immunohistochemistry was performed in the same manner as in Biological Experimental Example 3-1, and the primary antibodies, including rabbit anti-tyrosine hydroxylase (TH) antibody (1:5000), and mouse anti-phosphor-alpha synuclein (p-α-syn)antibody (1:3000) were used.

As shown in FIG. 5(A-B), the compound of Example 124 dramatically decreased the accumulation of α-synuclein in the soma. This data suggests that the compound of Example 124 might suppress the formation of Lewy bodies by inhibiting p-α-Syn accumulation.

Biological Experimental Example 6: Confirmation of the Effect of Regulating the Activities of Astrocytes and Microglia by the Compound of Example 124

Reactive astrocytes and microglia are found in Parkinson's disease animal models, suggesting the involvement of neuroinflammation in Parkinson's disease pathogenesis.

To determine whether the compound of Example 124 affects regulating the activities of Rotenone-induced reactive astrocyte and microglia, in the present invention, obtained images of brain tissues stained with GFAP (Astrocyte marker) and Iba-1(microglia marker) antibodies. Through acquired images analyzed the activation level of astrocytes and microglia respectively by measuring fluorescent intensity.

Immunohistochemistry was performed in the same manner as in Biological Experimental Example 3-1, and the primary antibodies, including rabbit anti-Iba-1(1:3000) antibody, and rabbit anti-GFAP (1:3000) antibody were used.

All the images were taken using a fluorescence microscope (Leica DM LB2). Three coronal sections of the similar level of the striatum of the brain of each animal group were used to analyze the activation level of astrocytes and microglia. The signal intensity of GFAP and Iba-1 was measured in the chosen fields of the equal area using Image J.

As shown in FIG. 6(A-B), astrocytes, and microglia were activated by rotenone but attenuated by the compound of Example 124 administration. Furthermore, as shown in FIG. 6(C-D), the efficacy of the compound of Example 124 was more dramatic and obvious in microglia than in astrocytes. These results suggest that the compound of Example 124 prevented the activation of astrocytes and microglia, alleviating the neurotoxicity that occurred by the immune process.

Biological Experimental Example 7: Confirmation of the Effect of Reducing the Amyloid-Beta Precursor Protein (APP) in Alzheimer's Disease In Vitro Model by the Compound of Example 124

7-1: Preparation of Alzheimer's Disease In Vitro Model

In the present invention, the amyloid-beta precursor protein (APP) reduction effect of the compound of Example 124 in an In Vitro model of Alzheimer's disease (AD) was confirmed.

SH-SY5Y, a human neuroblastoma cell line, was used, and when the pcDNA3-APPswe vector was transfected, these cells generate an AD-inducing APP.

SH-SY5Y cells were incubated in DMEM with 10% FBS and 1% penicillin/streptomycin. 500,000 cells/well was plated in a 6 well plate and transfected 24 h later.

Cells were transfected with pcDNA3-APPswe or pcDNA3 vectors using Lipofectamine 2000 (Invitrogen). After 4 h incubation, the transfection mixture (Lipofectamine+Vector) was replaced with 10% FBS in DMEM. compound of Example 124 (100 uM) or vehicle was treated in 20 h after transfection.

7-2: Western Blotting

Cells were harvested 24 h after the compound of Example 124 treatments. Cells were washed twice with ice-cold PBS and lysed in RIPA buffer (1% Triton X-100, 0.5% deoxycholic acid, 0.2% SDS, 150 mM sodium chloride, 2 mM EDTA) with 1 mM PMSF, 2 ug/ml aprotinin, 10 ug/ml leupeptin, and 10 mM sodium fluoride.

The lysate was passed several times through a 26½-gauge syringe needle and centrifuged at 16,200*g for 20 min. The supernatant was quantified with the Bradford assay. 30 ug of protein samples, separated by SDS-PAGE, were transferred to the PVDF membrane. After overnight incubation with primary antibody (Aβ, 6e10, Covance, 1:3000), the membrane was incubated with HRP-conjugated secondary antibody.

As shown in FIG. 7(A-B), it was confirmed through West blot that the amount of APP protein decreased by the compound of Example 124 treatment. These results suggest that the compound of Example 124 reduced APP production in In Vitro model of Alzheimer's disease.

Biological Experimental Example 8: Confirmation of the Effect of Reducing the Amyloid-Beta (Aβ) in Primary Cultured Neurons by the Compound of Example 124

8-1: Primary Culture of Cortical Neurons

Primary cortical neurons were harvested from the E12-14 embryo. Briefly, isolated cortices were incubated for 20 min at 37° C. in HBSS with 0.25% trypsin-EDTA, 0.1% DNase I. The cortices were dissociated by trituration in NBA media (Neurobasal medium with 2% B27, 2 mM 1-glutamine, and 1% penicillin/streptomycin). Cells were plated in poly-D-lysine coated 24-well plates at 50,000 cells/well. After 3 days of culture, Amyloid-beta and compound of Example 124 (4 uM) were treated.

8-2: Immunofluorescence

Cortical neurons were fixed for 15 min at room temperature with 4% paraformaldehyde and 4% sucrose in PBS solution. Fixed neurons were incubated with blocking buffer (3% goat serum, 3% BSA in PBS-T (0.15% Triton-X100)) for 30 min at room temperature. After labeling with a primary antibody, cells were incubated with Alexa Fluor 488- or 568-conjugated secondary antibody. Aβ (6e10, Covance, 1:3000) and NeuN (ab177487, Abcam, 1:2000) were used as primary antibody.

As shown in FIG. 8, it was confirmed that the amount of amyloid-beta decreased when amyloid-beta and compound of Example 124 were treated together. These results suggest that the compound of Example 124 reduced the amyloid-beta in the In Vitro model of Alzheimer's disease.

Biological Experimental Example 9: Confirmation of the Effect of Reducing the Amyloid-Beta (Aβ) in In Vivo by the Compound of Example 124

Amyloid-beta (Aβ) is a substance that is naturally produced and degraded In Vivo. Therefore, in the present invention, it was attempted to determine whether Amyloid-beta production was reduced in the compound of Example 124-treated mice.

C57BL/6 mice were purchased from Samtako bio Korea Co. Ltd (Osan, Korea.) Mice were housed in the room which offers a 12 hours light/dark cycle with a temperature of 20~22° C. All experiments and animal care were approved by the Institutional Animal Care and Use Committee of Chonnam National University (Korea).

Mice were divided into a vehicle mice group and a drug-treated group, and then the vehicle (30% PEG400) or compound of Example 124 was orally administered for 6 weeks.

Mice were anesthetized with sevoflurane and perfused with PBS. After perfusion, the right hemisphere brain was fixed with 4% paraformaldehyde for one day. The frozen brains were sectioned at 30 um thickness. The tissue sections were blocked with 3% Goat serum and 3% BSA in cold PBS-T (0.15% Tx-100) for 30 min. Sections were then stained using anti-Aβ (ab5078p, millipore) 1:3000 in PBS. After 3 days of primary antibody labeling, sections were incubated with an Alexa Fluor 568 conjugated secondary antibody for 1 day. For each mouse, 8-10 tissue sections were quantified, and the Aβ intensity was measure at 15 choroid plexus cells. The measurement was done using Image J software.

As shown in FIG. 9, it was confirmed that the amount of endogenous amyloid-beta was reduced in the compound of Example 124-treated mice compared to the vehicle mice.

Through the above results, it was confirmed that the compound of Example 124 of the present invention has an amyloid-beta reduction effect In Vivo.

What is claimed is:

1. A method for treating Parkinson's disease or Alzheimer's disease, comprising administering, to a subject in need thereof, a pharmaceutically effective amount of a phenyl alkyl carbamate compound represented by the following formula 1 or pharmaceutically acceptable salt thereof as an active ingredient:

[Chemical Formula 1]

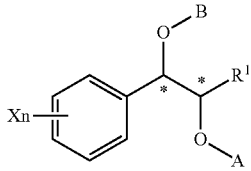

Wherein,
X is a halogen,
n means the number of substituent X and an integer from 1 to 5, wherein X is the same or different each other, when n is 2 or larger,
R1 is a hydrogen or linear or branched $C_1$-$C_4$ alkyl group,
A is selected from the group consisting of allyl, a $C_1$-$C_{19}$ linear or branched alkyl group, a $C_2$-$C_8$ alkoxy alky ether group and a carbamoyl derivative represented by

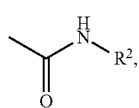

B is selected from the group consisting of an allyl, a $C_1$-$C_{19}$ linear or branched alkyl group, a $C_2$-$C_8$ alkoxy alky ether group and a carbamoyl derivative represented by

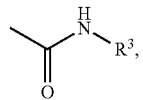

and
R² and R³ may be the same as or different from each other, and independently selected from the group consisting of hydrogen, a linear or branched alkyl group of $C_1$-$C_4$, a cycloalkyl group of $C_3$-$C_8$, and benzyl group.

2. The method according to claim 1, wherein A is a carbamoyl group, B is $C_1$-$C_{19}$ linear or branched alkyl group or a $C_2$-$C_8$ alkoxy alky ether group.

3. The method according to claim 1, wherein B is a carbamoyl group, A is $C_1$-$C_{19}$ linear or branched alkyl group or a $C_2$-$C_8$ alkoxy alky ether group.

4. The method according to claim 1, wherein the substituents of A and B are carbamoyl group at the same time.

5. The method according to claim 1, wherein the $C_2$-$C_8$ alkoxy alky ether group is methoxymethyl (MOM), methoxyethoxymethyl (MEM), tetrahydropyranyl (THP), benzyloxymethyl (BOM), methylthiomethyl (MTM), trimethylsilylethoxymethyl (SEM) or ethoxyethyl (EE) group.

6. The method according to claim 1, wherein the $C_1$-$C_{19}$ linear or branched alkyl group in the substituents A and B is a linear or branched $C_1$-$C_6$ lower aliphatic alkyl, a $C_3$-$C_{19}$ cycloaliphatic ring and a $C_6$-$C_{18}$ aromatic group which may be substituted with at least one selected from the group consisting of hydrogen, $C_1$-$C_6$ lower alkyl ad $C_1$-$C_6$ alkoxy group.

7. The method according to claim 1, wherein X is chlorine, fluorine, iodine, or bromine; n is 1 or 2; and R² and R³ are the same as or different from each other, and independently selected from the group consisting of hydrogen, methyl group, propyl group, isopropyl group, cyclopropyl group, cyclohexyl group, bicycloheptane group, and benzyl group.

8. The method according to claim 1, wherein the phenyl alkyl carbamate compound is selected from the group consisting of:
1-(2-chlorophenyl)-1-carbamoyloxypropyl-2-carbamate,
1-(2-chlorophenyl)-1-carbamoyloxypropyl-2-N-methyl-carbamate,
1-(2-chlorophenyl)-1-carbamoyloxypropyl-2-N-propyl-carbamate
1-(2-chlorophenyl)-1-carbamoyloxybutyl-2-carbamate,
1-(2-chlorophenyl)-1-carbamoyloxy-3-methyl-butyl-2-carbamate,
1-(2-chlorophenyl)-1-carbamoyloxyhexyl-2-carbamate,
1-(2-iodophenyl)-1-carbamoyloxypropyl-2-carbamate,
1-(2-iodophenyl)-1-carbamoyloxybutyl-2-carbamate,
1-(2-iodophenyl)-1-carbamoyloxy-3-methyl-butyl-2-carbamate,
1-(2-iodophenyl)-1-carbamoyloxyhexyl-2-carbamate,
1-(2-fluorophenyl)-1-carbamoyloxypropyl-2-carbamate,
1-(2-fluorophenyl)-1-carbamoyloxybutyl-2-carbamate,
1-(2-fluorophenyl)-1-carbamoyloxy-3-methyl-butyl-2-carbamate,
1-(2-fluorophenyl)-1-carbamoyloxyhexyl-2-carbamate,
1-(2,4-dichlorophenyl)-1-carbamoyloxypropyl-2-carbamate,
1-(2,4-dichlorophenyl)-1-carbamoyloxybutyl-2-carbamate,
1-(2,4-dichlorophenyl)-1-carbamoyloxy-3-methyl-butyl-2-carbamate, 1-(2,4-dichlorophenyl)-1-carbamoyloxyhexyl-2-carbamate,
1-(2,6-dichlorophenyl)-1-carbamoyloxypropyl-2-carbamate,
1-(2,6-dichlorophenyl)-1-carbamoyloxybutyl-2-carbamate,
1-(2,6-dichlorophenyl)-1-carbamoyloxy-3-methyl-butyl-2-carbamate,
1-(2,6-dichlorophenyl)-1-carbamoyloxyhexyl-2-carbamate,
1-(2,4-difluorophenyl)-1-carbamoyloxypropyl-2-carbamate
1-(2,5-difluorophenyl)-1-carbamoyloxypropyl-2-carbamate
1-(2,6-difluorophenyl)-1-carbamoyloxypropyl-2-carbamate
1-(2-chloro-6-fluorophenyl)-1-carbamoyloxypropyl-2-carbamate
1-(2-chlorophenyl)-1-(methoxy)-ethyl-2-carbamate,
1-(2-fluorophenyl)-1-(methoxy)-ethyl-2-carbamate,
1-(2-iodophenyl)-1-(methoxy)-ethyl-2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate
1-(2-iodophenyl)-1-(methoxy)-butyl-2-carbamate,
1-(2-iodophenyl)-1-(methoxy)-butyl-2-N-methylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-propyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate, 1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate, 1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate,
1-(2-chlorophenyl)-2-(methoxy)-propyl-1-carbamate,
1-(2-fluorophenyl)-2-(methoxymethoxy)-propyl-1-carbamate,
1-(2-fluorophenyl)-2-(methoxy)-propyl-1-carbamate
1-(2-iodophenyl)-2-(methoxymethoxy)-propyl-1-carbamate, and
1-(2-iodophenyl)-2-(methoxy)-propyl-1-carbamate.

9. The method according to claim 1, wherein the phenyl carbamate compound is in the form of racemate, enantiomer, diastereomer, a mixture of enantiomers, or a mixture of diastereomers of the compound.

10. The method according to claim 9, wherein the phenyl alkyl carbamate compound is selected from the group consisting of:
1-(2-chlorophenyl)-(S)-1-carbamoyloxypropyl-(S)-2-carbamate,
1-(2-chlorophenyl)-(S)-1-carbamoyl oxypropyl-(S)-2-N-methylcarbamate,
1-(2-chlorophenyl)-(S)-1-carbamoyl oxypropyl-(S)-2-N-propylcarbamate
1-(2-chlorophenyl)-(S)-1-carbamoyloxybutyl-(S)-2-carbamate,
1-(2-chlorophenyl)-(S)-1-carbamoyloxy-3-methyl-butyl-(S)-2-carbamate,
1-(2-chlorophenyl)-(S)-1-carbamoyloxyhexyl-(S)-2-carbamate,
1-(2-iodophenyl)-(S)-1-carbamoyloxypropyl-(S)-2-carbamate,
1-(2-iodophenyl)-(S)-1-carbamoyloxybutyl-(S)-2-carbamate,
1-(2-iodophenyl)-(S)-1-carbamoyloxy-3-methyl-butyl-(S)-2-carbamate,
1-(2-iodophenyl)-(S)-1-carbamoyloxyhexyl-(S)-2-carbamate,
1-(2-fluorophenyl)-(S)-1-carbamoyloxypropyl-(S)-2-carbamate,
1-(2-fluorophenyl)-(S)-1-carbamoyloxybutyl-(S)-2-carbamate,
1-(2-fluorophenyl)-(S)-1-carbamoyloxy-3-methyl-butyl-(S)-2-carbamate,
1-(2-fluorophenyl)-(S)-1-carbamoyloxyhexyl-(S)-2-carbamate,
1-(2,4-di chlorophenyl)-(S)-1-carbamoyloxypropyl-(S)-2-carbamate,
1-(2,4-di chlorophenyl)-(S)-1-carbamoyloxybutyl-(S)-2-carbamate,
1-(2,4-di chlorophenyl)-(S)-1-carbamoyloxy-3-methyl-butyl-2-carbamate,
1-(2,4-di chlorophenyl)-(S)-1-carbamoyloxyhexyl-(S)-2-carbamate,
1-(2,6-dichlorophenyl)-(S)-1-carbamoyloxypropyl-(S)-2-carbamate,
1-(2,6-dichlorophenyl)-(S)-1-carbamoyloxybutyl-(S)-2-carbamate,
1-(2,6-dichlorophenyl)-(S)-1-carbamoyloxy-3-methyl-butyl-(S)-2-carbamate,
1-(2,6-dichlorophenyl)-(S)-1-carbamoyloxyhexyl-(S)-2-carbamate,
1-(2-chloro-6-fluorophenyl)-(S)-1-carbamoyloxypropyl-(S)-2-carbamate
1-(2-chlorophenyl)-(S)-1-(methoxy)-ethyl-2-carbamate,
1-(2-fluorophenyl)-(S)-1-(methoxy)-ethyl-2-carbamate,
1-(2-iodophenyl)-(S)-1-(methoxy)-ethyl-2-carbamate,
1-(2-iodophenyl)-(S)-1-(methoxy)-propyl-(S)-2-carbamate,
1-(2-iodophenyl)-(S)-1-(methoxy)-propyl-(S)-2-N-methylcarbamate,
1-(2-iodophenyl)-(S)-1-(methoxy)-propyl-(S)-2-N-propylcarbamate,
1-(2-iodophenyl)-(S)-1-(methoxy)-propyl-(S)-2-N-isopropylcarbamate,
1-(2-iodophenyl)-(S)-1-(methoxy)-propyl-(S)-2-N-cyclopropylcarbamate,
1-(2-iodophenyl)-(S)-1-(methoxy)-propyl-(S)-2-N-cyclohexylcarbamate,
1-(2-iodophenyl)-(S)-1-(methoxy)-propyl-(S)-2-N-benzylcarbamate,
1-(2-iodophenyl)-(S)-1-(methoxy)-propyl-(S)-2-N-bicyclo[2,2,1]heptanecarbamate
1-(2-iodophenyl)-(S)-1-(methoxy)-butyl(S)-2-carbamate,
1-(2-iodophenyl)-(S)-1-(methoxy)-butyl-(S)-2-N-methylcarbamate,
1-(2-iodophenyl)-(S)-1-(methoxy)-butyl-(S)-2-N-propylcarbamate,
1-(2-iodophenyl)-(S)-1-(methoxy)-butyl-(S)-2-N-isopropylcarbamate,
1-(2-iodophenyl)-(S)-1-(methoxy)-butyl-(S)-2-N-cyclopropylcarbamate,
1-(2-iodophenyl)-(S)-1-(methoxy)-butyl-(S)-2-N-cyclohexylcarbamate,
1-(2-iodophenyl)-(S)-1-(methoxy)-butyl-(S)-2-N-benzylcarbamate,
1-(2-iodophenyl)-(S)-1-(methoxy)-butyl-(S)-2-N-bicyclo[2,2,1]heptanecarbamate,
1-(2-iodophenyl)-(S)-1-(methoxy)3-methyl-butyl-(S)-2-carbamate,
1-(2-iodophenyl)-(S)-1-(methoxy)-3-methyl-butyl-(S)-2-N-methylcarbamate,
1-(2-iodophenyl)-(S)-1-(methoxy)-3-methyl-butyl-(S)-2-N-propylcarbamate,
1-(2-iodophenyl)-(S)-1-(methoxy)-3-methyl-butyl-(S)-2-N-isopropylcarbamate, 1-(2-iodophenyl)-(S)-1-(methoxy)-3-methyl-butyl-(S)-2-N-cyclopropylcarbamate,
1-(2-iodophenyl)-(S)-1-(methoxy)-3-methyl-butyl-(S)-2-N-cyclohexylcarbamate,
1-(2-iodophenyl)-(S)-1-(methoxy)-3-methyl-butyl-(S)-2-N-benzylcarbamate,
1-(2-iodophenyl)-(S)-1-(methoxy)-3-methyl-butyl-(S)-2-N-bicyclo[2,2,1]heptanecarbamate,
1-(2-iodophenyl)-(S)-1-(methoxy)-hexyl-(S)-2-carbamate,
1-(2-iodophenyl)-(S)-1-(methoxy)-hexyl-(S)-2-N-methylcarbamate,
1-(2-iodophenyl)-(S)-1-(methoxy)-hexyl-(S)-2-N-propylcarbamate,
1-(2-iodophenyl)-(S)-1-(methoxy)-hexyl-(S)-2-N-isopropylcarbamate,
1-(2-iodophenyl)-(S)-1-(methoxy)-hexyl-(S)-2-N-cyclopropylcarbamate,
1-(2-iodophenyl)-(S)-1-(methoxy)-hexyl-(S)-2-N-cyclohexylcarbamate,
1-(2-iodophenyl)-(S)-1-(methoxy)-hexyl-(S)-2-N-benzylcarbamate,
1-(2-iodophenyl)-(S)-1-(methoxy)-hexyl-(S)-2-N-bicyclo[2,2,1]heptanecarbamate,
1-(3-iodophenyl)-(S)-1-(methoxy)-propyl-(S)-2-carbamate,
1-(3-iodophenyl)-(S)-1-(methoxy)-butyl-(S)-2-carbamate,
1-(3-iodophenyl)-(S)-1-(methoxy)3-methyl-butyl-(S)-2-carbamate,
1-(3-iodophenyl)-(S)-1-(methoxy)-hexyl-(S)-2-carbamate,
1-(2-fluorophenyl)-(S)-1-(methoxy)-propyl-(S)-2-carbamate,
1-(2-fluorophenyl)-(S)-1-(methoxy)-propyl-(S)-2-N-methylcarbamate,
1-(2-fluorophenyl)-(S)-1-(methoxy)-propyl-(S)-2-N-propylcarbamate,
1-(2-fluorophenyl)-(S)-1-(methoxy)-propyl-(S)-2-N-isopropylcarbamate,
1-(2-fluorophenyl)-(S)-1-(methoxy)-propyl-(S)-2-N-cyclopropylcarbamate,
1-(2-fluorophenyl)-(S)-1-(methoxy)-propyl-(S)-2-N-cyclohexylcarbamate,
1-(2-fluorophenyl)-(S)-1-(methoxy)-propyl-(S)-2-N-benzylcarbamate,
1-(2-fluorophenyl)-(S)-1-(methoxy)-propyl-(S)-2-N-bicyclo[2,2,1]heptanecarbamate
1-(4-fluorophenyl)-(S)-1-(methoxy)-propyl-(S)-2-carbamate,
1-(4-fluorophenyl)-(S)-1-(methoxy)-butyl-(S)-2-carbamate,
1-(4-fluorophenyl)-(S)-1-(methoxy)-3-methyl-butyl-(S)-2-carbamate,
1-(4-fluorophenyl)-(S)-1-(methoxy)-hexyl-(S)-2-carbamate,
1-(2-chlorophenyl)-(S)-1-(methoxy)-propyl-(S)-2-carbamate,
1-(2-chlorophenyl)-(S)-1-(methoxy)-propyl-(S)-2-N-methylcarbamate,
1-(2-chlorophenyl)-(S)-1-(methoxy)-propyl-(S)-2-N-propylcarbamate,
1-(2-chlorophenyl)-(S)-1-(methoxy)-propyl-(S)-2-N-isopropylcarbamate,
1-(2-chlorophenyl)-(S)-1-(methoxy)-propyl-(S)-2-N-cyclopropylcarbamate,
1-(2-chlorophenyl)-(S)-1-(methoxy)-propyl-(S)-2-N-cyclohexylcarbamate,
1-(2-chlorophenyl)-(S)-1-(methoxy)-propyl-(S)-2-N-benzylcarbamate,
1-(2-chlorophenyl)-(S)-1-(methoxy)-propyl-(S)-2-N-bicyclo[2,2,1]heptanecarbamate
1-(2-chlorophenyl)-(S)-1-(methoxy)-butyl-(S)-2-carbamate,
1-(2-chlorophenyl)-(S)-1-(methoxy)-3-methyl-butyl-(S)-2-carbamate,
1-(2-chlorophenyl)-(S)-1-(methoxy)-hexyl-(S)-2-carbamate,
1-(2,3-dichlorophenyl)-(S)-1-(methoxy)-propyl-(S)-2-carbamate,
1-(2,4-dichlorophenyl)-(S)-1-(methoxy)-propyl-(S)-2-carbamate,
1-(2,4-dichlorophenyl)-(S)-1-(methoxy)-butyl-(S)-2-carbamate,
1-(2,4-dichlorophenyl)-(S)-1-(methoxy)-3-methyl-butyl-(S)-2-carbamate,
1-(2,4-dichlorophenyl)-(S)-1-(methoxy)-hexyl-(S)-2-carbamate,
1-(2,6-dichlorophenyl)-(S)-1-(methoxy)-propyl-(S)-2-carbamate,
1-(2,6-dichlorophenyl)-(S)-1-(methoxy)-butyl-(S)-2-carbamate,
1-(2,6-dichlorophenyl)-(S)-1-(methoxy)-3-methyl-butyl-(S)-2-carbamate,
1-(2,6-dichlorophenyl)-(S)-1-(methoxy)-hexyl-(S)-2-carbamate,
1-(2-chlorophenyl)-(S)-1-(methoxymethoxy)-ethyl-(S)-2-carbamate,
1-(2-fluorophenyl)-(S)-1-(methoxymethoxy)-ethyl-(S)-2-carbamate,
1-(2-iodophenyl)-(S)-1-(methoxymethoxy)-ethyl-(S)-2-carbamate,
1-(2-chlorophenyl)-(S)-1-(methoxymethoxy)-propyl-(S)-2-carbamate,
1-(2-chlorophenyl)-(S)-1-(methoxymethoxy)-propyl-(S)-2-N-methylcarbamate,
1-(2-chlorophenyl)-(S)-1-(methoxymethoxy)-propyl-(S)-2-N-propylcarbamate,
1-(2-chlorophenyl)-(S)-1-(methoxymethoxy)-propyl-(S)-2-N-isopropylcarbamate,
1-(2-chlorophenyl)-(S)-1-(methoxymethoxy)-propyl-(S)-2-N-cyclopropylcarbamate,
1-(2-chlorophenyl)-(S)-1-(methoxymethoxy)-propyl-(S)-2-N-cyclohexylcarbamate,
1-(2-chlorophenyl)-(S)-1-(methoxymethoxy)-propyl-2-N-benzylcarbamate,
1-(2-chlorophenyl)-(S)-1-(methoxymethoxy)-propyl-2-N-bicyclo[2,2,1]heptanecarbamate
1-(2-chlorophenyl)-(S)-1-(methoxymethoxy)-butyl-(S)-2-carbamate,
1-(2-chlorophenyl)-(S)-1-(methoxymethoxy)-3-methyl-butyl-(S)-2-carbamate,
1-(2-chlorophenyl)-(S)-1-(methoxymethoxy)-hexyl-(S)-2-carbamate,
1-(2,3-dichlorophenyl)-(S)-1-(methoxymethoxy)-propyl-(S)-2-carbamate,
1-(2,4-dichlorophenyl)-(S)-1-(methoxymethoxy)-propyl-(S)-2-carbamate,
1-(2,4-dichlorophenyl)-(S)-1-(methoxymethoxy)-butyl-(S)-2-carbamate,
1-(2,4-dichlorophenyl)-(S)-1-(methoxymethoxy)-3-methyl-butyl-(S)-2-carbamate, 1-(2,4-dichlorophenyl)-(S)-1-(methoxymethoxy)-hexyl-(S)-2-carbamate,
1-(2,5-dichlorophenyl)-(S)-1-(methoxymethoxy)-propyl-(S)-2-carbamate,
1-(2,6-dichlorophenyl)-(S)-1-(methoxymethoxy)-propyl-(S)--carbamate,
1-(2,6-dichlorophenyl)-(S)-1-(methoxymethoxy)-butyl-(S)-2-carbamate,
1-(2,6-dichlorophenyl)-(S)-1-(methoxymethoxy)-3-methyl-butyl-(S)-2-carbamate,
1-(2,6-dichlorophenyl)-(S)-1-(methoxymethoxy)-hexyl-(S)-2-carbamate,
1-(2-fluorophenyl)-(S)-1-(methoxymethoxy)-propyl-(S)-2-carbamate,
1-(2-fluorophenyl)-(S)-1-(methoxymethoxy)-propyl-(S)-2-N-methylcarbamate,
1-(2-fluorophenyl)-(S)-1-(methoxymethoxy)-propyl-(S)-2-N-propylcarbamate,
1-(2-fluorophenyl)-(S)-1-(methoxymethoxy)-propyl-(S)-2-N-isopropylcarbamate,
1-(2-fluorophenyl)-(S)-1-(methoxymethoxy)-propyl-(S)-2-N-cyclopropylcarbamate,
1-(2-fluorophenyl)-(S)-1-(methoxymethoxy)-propyl-(S)-2-N-cyclohexylcarbamate,
1-(2-fluorophenyl)-(S)-1-(methoxymethoxy)-propyl-(S)-2-N-benzylcarbamate,
1-(2-fluorophenyl)-(S)-1-(methoxymethoxy)-propyl-(S)-2-N-bicyclo[2,2,1]heptanecarbamate
1-(2-fluorophenyl)-(S)-1-(methoxymethoxy)-butyl-(S)-2-carbamate,
1-(2-fluorophenyl)-(S)-1-(methoxymethoxy)-3-methyl-butyl-(S)-2-carbamate,
1-(2-fluorophenyl)-(S)-1-(methoxymethoxy)-hexyl-(S)-2-carbamate,
1-(4-fluorophenyl)-(S)-1-(methoxymethoxy)-propyl-(S)-2-carbamate,
1-(4-fluorophenyl)-(S)-1-(methoxymethoxy)-butyl-(S)-2-carbamate,
1-(4-fluorophenyl)-(S)-1-(methoxymethoxy)-3-methyl-butyl-(S)-2-carbamate,
1-(4-fluorophenyl)-(S)-1-(methoxymethoxy)-hexyl-(S)-2-carbamate,
1-(2,6-difluorophenyl)-(S)-1-(methoxymethoxy)-propyl-(S)-2-carbamate,
1-(2-iodophenyl)-(S)-1-(methoxymethoxy)-propyl-(S)-2-carbamate,
1-(2-iodophenyl)-(S)-1-(methoxymethoxy)-propyl-(S)-2-N-methylcarbamate,
1-(2-iodophenyl)-(S)-1-(methoxymethoxy)-propyl-(S)-2-N-propylcarbamate,
1-(2-iodophenyl)-(S)-1-(methoxymethoxy)-propyl-(S)-2-N-isopropylcarbamate,
1-(2-iodophenyl)-(S)-1-(methoxymethoxy)-propyl-(S)-2-N-cyclopropylcarbamate,
1-(2-iodophenyl)-(S)-1-(methoxymethoxy)-propyl-(S)-2-N-cyclohexylcarbamate,
1-(2-iodophenyl)-(S)-1-(methoxymethoxy)-propyl-(S)-2-N-benzylcarbamate,
1-(2-iodophenyl)-(S)-1-(methoxymethoxy)-propyl-2-N-bicyclo[2,2,1]heptanecarbamate
1-(2-iodophenyl)-(S)-1-(methoxymethoxy)-butyl-(S)-2-carbamate,
1-(2-iodophenyl)-(S)-1-(methoxymethoxy)-butyl-(S)-2-N-methylcarbamate,
1-(2-iodophenyl)-(S)-1-(methoxymethoxy)-butyl-(S)-2-N-propylcarbamate,
1-(2-iodophenyl)-(S)-1-(methoxymethoxy)-butyl-(S)-2-N-isopropylcarbamate,
1-(2-iodophenyl)-(S)-1-(methoxymethoxy)-butyl-(S)-2-N-cyclopropylcarbamate,
1-(2-iodophenyl)-(S)-1-(methoxymethoxy)-butyl-(S)-2-N-cyclohexylcarbamate,
1-(2-iodophenyl)-(S)-1-(methoxymethoxy)-butyl-(S)-2-N-benzylcarbamate,
1-(2-iodophenyl)-(S)-1-(methoxymethoxy)-butyl-(S)-2-N-bicyclo[2,2,1]heptanecarbamate
1-(2-iodophenyl)-(S)-1-(methoxymethoxy)-3-methyl-butyl-(S)-2-carbamate,
1-(2-iodophenyl)-(S)-1-(methoxymethoxy)-3-methyl-butyl-(S)-2-N-methylcarbamate,
1-(2-iodophenyl)-(S)-1-(methoxymethoxy)-3-methyl-butyl-(S)-2-N-propylcarbamate,
1-(2-iodophenyl)-(S)-1-(methoxymethoxy)-3-methyl-butyl-(S)-2-N-isopropylcarbamate,
1-(2-iodophenyl)-(S)-1-(methoxymethoxy)-3-methyl-butyl-(S)-2-N-cyclopropylcarbamate,
1-(2-iodophenyl)-(S)-1-(methoxymethoxy)-3-methyl-butyl-(S)-2-N-cyclohexylcarbamate,
1-(2-iodophenyl)-(S)-1-(methoxymethoxy)-3-methyl-butyl-(S)-2-N-benzylcarbamate,
1-(2-iodophenyl)-(S)-1-(methoxymethoxy)-3-methyl-butyl-(S)-2-N-bicyclo[2,2,1]heptanecarbamate,
1-(2-iodophenyl)-(S)-1-(methoxymethoxy)-hexyl-2-carbamate,
1-(2-iodophenyl)-(S)-1-(methoxymethoxy)-hexyl-(S)-2-N-methylcarbamate,
1-(2-iodophenyl)-(S)-1-(methoxymethoxy)-hexyl-(S)-2-N-propylcarbamate,
1-(2-iodophenyl)-(S)-1-(methoxymethoxy)-hexyl-(S)-2-N-isopropylcarbamate,
1-(2-iodophenyl)-(S)-1-(methoxymethoxy)-hexyl-(S)-2-N-cyclopropylcarbamate,
1-(2-iodophenyl)-(S)-1-(methoxymethoxy)-hexyl-(S)-2-N-cyclohexylcarbamate,
1-(2-iodophenyl)-(S)-1-(methoxymethoxy)-hexyl-(S)-2-N-benzylcarbamate,
1-(2-iodophenyl)-(S)-1-(methoxymethoxy)-hexyl-(S)-2-N-bicyclo[2,2,1]heptanecarbamate
1-(3-iodophenyl)-(S)-1-(methoxymethoxy)-propyl-(S)-2-carbamate,
1-(3-iodophenyl)-(S)-1-(methoxymethoxy)-butyl-(S)-2-carbamate,
1-(3-iodophenyl)-(S)-1-(methoxymethoxy)-3-methyl-butyl-(S)-2-carbamate,
1-(3-iodophenyl)-(S)-1-(methoxymethoxy)-hexyl-(S)-2-carbamate,
1-(2-chlorophenyl)-(S)-2-(methoxymethoxy)-propyl-(S)-1-carbamate,
1-(2-chlorophenyl)-(S)-2-(methoxy)-propyl-(S)-1-carbamate,
1-(2-fluorophenyl)-(S)-2-(methoxymethoxy)-propyl-(S)-1-carbamate,
1-(2-fluorophenyl)-(S)-2-(methoxy)-propyl-(S)-1-carbamate
1-(2-iodophenyl)-(S)-2-(methoxymethoxy)-propyl-(S)-1-carbamate,
1-(2-iodophenyl)-(S)-2-(methoxy)-propyl-(S)-1-carbamate
1-(2-chlorophenyl)-(R)-1-carbamoyloxypropyl-(R)-2-carbamate,
1-(2-iodophenyl)-(R)-1-carbamoyloxypropyl-(R)-2-carbamate, 1-(2-fluorophenyl)-(R)-1-carbamoyloxypropyl-(R)-2-carbamate,
1-(2,4-dichlorophenyl)-(R)-1-carbamoyloxypropyl-(R)-2-carbamate,
1-(2,6-dichlorophenyl)-(R)-1-carbamoyloxypropyl-(R)-2-carbamate,
1-(2,4-difluorophenyl)-(R)-1-carbamoyloxypropyl(R)-2-carbamate
1-(2,5-difluorophenyl)-(R)-1-carbamoyloxypropyl-(R)-2-carbamate
1-(2,6-difluorophenyl)-(R)-1-carbamoyloxypropyl-(R)-2-carbamate
1-(2-chloro-6-fluorophenyl)-(R)-1-carbamoyloxypropyl-(R)-2-carbamate
1-(2-iodophenyl)-(R)-1-(methoxy)-propyl-(R)-2-carbamate,
1-(2-iodophenyl)-(R)-1-(methoxy)-butyl(R)-2-carbamate,
1-(2-iodophenyl)-(R)-1-(methoxy)3-methyl-butyl-(R)-2-carbamate,
1-(2-iodophenyl)-(R)-1-(methoxy)-hexyl-(R)-2-carbamate,
1-(3-iodophenyl)-(R)-1-(methoxy)-propyl-(R)-2-carbamate,
1-(3-iodophenyl)-(R)-1-(methoxy)-butyl-(R)-2-carbamate,
1-(3-iodophenyl)-(R)-1-(methoxy)3-methyl-butyl-(R)-2-carbamate,
1-(3-iodophenyl)-(R)-1-(methoxy)-hexyl-(R)-2-carbamate,
1-(2-fluorophenyl)-(R)-1-(methoxy)-propyl-(R)-2-carbamate,
1-(4-fluorophenyl)-(R)-1-(methoxy)-propyl-(R)-2-carbamate,
1-(4-fluorophenyl)-(R)-1-(methoxy)-butyl-(R)-2-carbamate,
1-(4-fluorophenyl)-(R)-1-(methoxy)-3-methyl-butyl-(R)-2-carbamate,
1-(4-fluorophenyl)-(R)-1-(methoxy)-hexyl-(R)-2-carbamate,
1-(2-chlorophenyl)-(R)-1-(methoxy)-propyl-(R)-2-carbamate,
1-(2-chlorophenyl)-(R)-1-(methoxy)-propyl-(R)-2-N-methylcarbamate,
1-(2-chlorophenyl)-(R)-1-(methoxy)-propyl-(R)-2-N-propylcarbamate,
1-(2-chlorophenyl)-(R)-1-(methoxy)-propyl-(R)-2-N-isopropylcarbamate,
1-(2-chlorophenyl)-(R)-1-(methoxy)-propyl-(R)-2-N-cyclopropylcarbamate,
1-(2-chlorophenyl)-(R)-1-(methoxy)-propyl-(R)-2-N-cyclohexylcarbamate,
1-(2-chlorophenyl)-(R)-1-(methoxy)-propyl-(R)-2-N-benzylcarbamate,
1-(2-chlorophenyl)-(R)-1-(methoxy)-propyl-(R)-2-N-bicyclo[2,2,1]heptanecarbamate
1-(2-chlorophenyl)-(R)-1-(methoxy)-butyl-(R)-2-carbamate,
1-(2-chlorophenyl)-(R)-1-(methoxy)-3-methyl-butyl-(R)-2-carbamate,
1-(2-chlorophenyl)-(R)-1-(methoxy)-hexyl-(R)-2-carbamate,
1-(2,3-dichlorophenyl)-(R)-1-(methoxy)-propyl-(R)-2-carbamate,
1-(2,4-dichlorophenyl)-(R)-1-(methoxy)-propyl-(R)-2-carbamate,
1-(2,4-dichlorophenyl)-(R)-1-(methoxy)-butyl(R)-2-carbamate,
1-(2,4-dichlorophenyl)-(R)-1-(methoxy)-3-methyl-butyl-(R)-2-carbamate,
1-(2,4-dichlorophenyl)-(R)-1-(methoxy)-hexyl-(R)-2-carbamate,
1-(2,6-dichlorophenyl)-(R)-1-(methoxy)-propyl-(R)-2-carbamate,
1-(2,6-dichlorophenyl)-(R)-1-(methoxy)-butyl-(R)-2-carbamate,
1-(2,6-dichlorophenyl)-(R)-1-(methoxy)-3-methyl-butyl-(R)-2-carbamate,
1-(2,6-dichlorophenyl)-(R)-1-(methoxy)-hexyl-(R)-2-carbamate,
1-(2-chlorophenyl)-(R)-1-(methoxymethoxy)-ethyl-(R)-2-carbamate,
1-(2-fluorophenyl)-(R)-1-(methoxymethoxy)-ethyl-(R)-2-carbamate,
1-(2-iodophenyl)-(R)-1-(methoxymethoxy)-ethyl-(R)-2-carbamate,
1-(2-chlorophenyl)-(R)-1-(methoxymethoxy)-propyl-(R)-2-carbamate,
1-(2-chlorophenyl)-(R)-1-(methoxymethoxy)-propyl-(R)-2-N-methylcarbamate,
1-(2-chlorophenyl)-(R)-1-(methoxymethoxy)-propyl-(R)-2-N-propylcarbamate,
1-(2-chlorophenyl)-(R)-1-(methoxymethoxy)-propyl-(R)-2-N-isopropylcarbamate,
1-(2-chlorophenyl)-(R)-1-(methoxymethoxy)-propyl-(R)-2-N-cyclopropylcarbamate,
1-(2-chlorophenyl)-(R)-1-(methoxymethoxy)-propyl-(R)-2-N-cyclohexylcarbamate,
1-(2-chlorophenyl)-(R)-1-(methoxymethoxy)-propyl-(R)-2-N-benzylcarbamate,
1-(2-chlorophenyl)-(R)-1-(methoxymethoxy)-propyl-(R)-2-N-bicyclo[2,2,1]heptanecarbamate
1-(2-chlorophenyl)-(R)-1-(methoxymethoxy)-butyl-(R)-2-carbamate,
1-(2-chlorophenyl)-(R)-1-(methoxymethoxy)-3-methyl-butyl-(R)-2-carbamate,
1-(2-chlorophenyl)-(R)-1-(methoxymethoxy)-hexyl-(R)-2-carbamate,
1-(2,3-dichlorophenyl)-(R)-1-(methoxymethoxy)-propyl-(R)-2-carbamate,
1-(2,4-dichlorophenyl)-(R)-1-(methoxymethoxy)-propyl-(R)-2-carbamate,
1-(2,4-dichlorophenyl)-(R)-1-(methoxymethoxy)-butyl-(R)-2-carbamate,
1-(2,4-dichlorophenyl)-(R)-1-(methoxymethoxy)-3-methyl-butyl-(R)-2-carbamate,
1-(2,4-dichlorophenyl)-(R)-1-(methoxymethoxy)-hexyl-(R)-2-carbamate,
1-(2,5-dichlorophenyl)-(R)-1-(methoxymethoxy)-propyl-(R)-2-carbamate,
1-(2,6-dichlorophenyl)-(R)-1-(methoxymethoxy)-propyl-(R)--carbamate,
1-(2,6-dichlorophenyl)-(R)-1-(methoxymethoxy)-butyl-(R)-2-carbamate,
1-(2,6-dichlorophenyl)-(R)-1-(methoxymethoxy)-3-methyl-butyl-(R)-2-carbamate,
1-(2,6-dichlorophenyl)-(R)-1-(methoxymethoxy)-hexyl-(R)-2-carbamate,
1-(2-fluorophenyl)-(R)-1-(methoxymethoxy)-propyl-(R)-2-carbamate,
1-(4-fluorophenyl)-(R)-1-(methoxymethoxy)-propyl-(R)-2-carbamate, 1-(4-fluorophenyl)-(R)-1-(methoxymethoxy)-butyl-(R)-2-carbamate,
1-(4-fluorophenyl)-(R)-1-(methoxymethoxy)-3-methyl-butyl-(R)-2-carbamate,
1-(4-fluorophenyl)-(R)-1-(methoxymethoxy)-hexyl-(R)-2-carbamate,
1-(2-iodophenyl)-(R)-1-(methoxymethoxy)-propyl-(R)-2-carbamate,
1-(2-iodophenyl)-(R)-1-(methoxymethoxy)-butyl-(R)-2-carbamate,
1-(2-iodophenyl)-(R)-1-(methoxymethoxy)-3-methyl-butyl-(R)-2-carbamate,
1-(2-iodophenyl)-(R)-1-(methoxymethoxy)-hexyl-(R)-2-carbamate,
1-(3-iodophenyl)-(R)-1-(methoxymethoxy)-propyl-(R)-2-carbamate,
1-(3-iodophenyl)-(R)-1-(methoxymethoxy)-butyl-(R)-2-carbamate,
1-(3-iodophenyl)-(R)-1-(methoxymethoxy)-3-methyl-butyl-(R)-2-carbamate,
1-(3-iodophenyl)-(R)-1-(methoxymethoxy)-hexyl-(R)-2-carbamate,
1-(2-chlorophenyl)-(S)-1-carbamoyloxypropyl-(R)-2-carbamate,
1-(2-chlorophenyl)-(R)-1-carbamoyloxypropyl-(S)-2-carbamate,
1-(2-chlorophenyl)-(S)-1-(methoxy)-propyl-(R)-2-carbamate,
1-(2-chlorophenyl)-(R)-1-(methoxy)-propyl-(S)-2-carbamate,
1-(2-chlorophenyl)-(S)-1-(methoxymethoxy)-propyl-(R)-2-carbamate, and
1-(2-chlorophenyl)-(R)-1-(methoxymethoxy)-propyl-(S)-2-carbamate.

11. A method for treating dopamine neurons loss or a disease caused by dopamine neurons loss, comprising administering a pharmaceutically effective amount of a phenyl alkyl carbamate compound represented by the following formula 1 or pharmaceutically acceptable salt thereof as an active ingredient to a subject in need thereof:

[Chemical Formula 1]

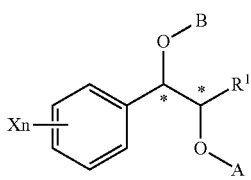

wherein
X is a halogen,
n means the number of substituent X and an integer from 1 to 5, wherein X is the same or different each other, when n is 2 or larger,
R1 is a hydrogen or linear or branched $C_1$-$C_4$ alkyl group,
A is selected from the group consisting of allyl, a $C_1$-$C_{19}$ linear or branched alkyl group, a $C_2$-$C_8$ alkoxy alky ether group and a carbamoyl derivative represented by

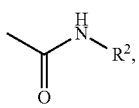

B is selected from the group consisting of an allyl, a $C_1$-$C_{19}$ linear or branched alkyl group, a $C_2$-$C_8$ alkoxy alky ether group and a carbamoyl derivative represented by

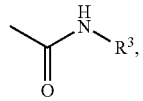

and
R² and R³ may be the same as or different from each other, and independently selected from the group consisting of hydrogen, a linear or branched alkyl group of $C_1$-$C_4$, a cycloalkyl group of $C_3$-$C_8$, and benzyl group.

12. A method for alleviating an activation of astrocytes and glial, or alleviating a neurotoxicity occurred by immune process comprising administering a pharmaceutically effective amount of a phenyl alkyl carbamate compound represented by the following formula 1 or pharmaceutically acceptable salt thereof as an active ingredient to a subject in need thereof:

[Chemical Formula 1]

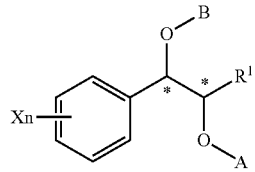

wherein
X is a halogen,
n means the number of substituent X and an integer from 1 to 5, wherein X is the same or different each other, when n is 2 or larger,
R1 is a hydrogen or linear or branched $C_1$-$C_4$ alkyl group,
A is selected from the group consisting of allyl, a $C_1$-$C_{19}$ linear or branched alkyl group, a $C_2$-$C_8$ alkoxy alky ether group and a carbamoyl derivative represented by

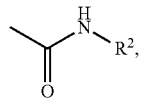

B is selected from the group consisting of an allyl, a $C_1$-$C_{19}$ linear or branched alkyl group, a $C_2$-$C_8$ alkoxy alky ether group and a carbamoyl derivative represented by

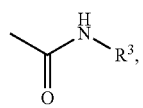

and
R² and R³ may be the same as or different from each other, and independently selected from the group consisting of hydrogen, a linear or branched alkyl group of $C_1$-$C_4$, a cycloalkyl group of $C_3$-$C_8$, and benzyl group.

13. A method for treating α-synucleinopathy or a disease associated with the presence of α-synuclein aggregates comprising administering a pharmaceutically effective amount of a phenyl alkyl carbamate compound represented by the following formula 1 or pharmaceutically acceptable salt thereof as an active ingredient to a subject in need thereof:

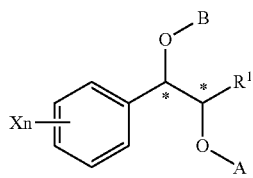

[Chemical Formula 1]

wherein
X is a halogen,
n means the number of substituent X and an integer from 1 to 5, wherein X is the same or different each other, when n is 2 or larger,
R1 is a hydrogen or linear or branched $C_1$-$C_4$ alkyl group,
A is selected from the group consisting of allyl, a $C_1$-$C_{19}$ linear or branched alkyl group, a $C_2$-$C_8$ alkoxy alky ether group and a carbamoyl derivative represented by

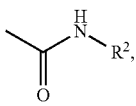

B is selected from the group consisting of an allyl, a $C_1$-$C_{19}$ linear or branched alkyl group, a $C_2$-$C_8$ alkoxy alky ether group and a carbamoyl derivative represented by

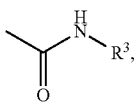

and
$R^2$ and $R^3$ may be the same as or different from each other, and independently selected from the group consisting of hydrogen, a linear or branched alkyl group of $C_1$-$C_4$, a cycloalkyl group of $C_3$-$C_8$, and benzyl group.

14. A method for treating a disease associated with overexpression of amyloid-beta precursor protein or amyloid-beta, comprising administering a pharmaceutically effective amount of a phenyl alkyl carbamate compound represented by the following formula 1 or pharmaceutically acceptable salt thereof as an active ingredient to a subject in need thereof:

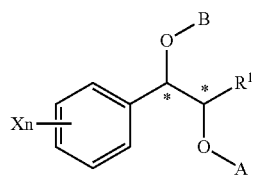

[Chemical Formula 1]

wherein,
X is a halogen,
n means the number of substituent X and an integer from 1 to 5, wherein X is the same or different each other, when n is 2 or larger,
R1 is a hydrogen or linear or branched $C_1$-$C_4$ alkyl group,
A is selected from the group consisting of allyl, a $C_1$-$C_{19}$ linear or branched alkyl group, a $C_2$-$C_8$ alkoxy alky ether group and a carbamoyl derivative represented by

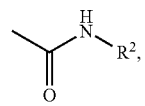

B is selected from the group consisting of an allyl, a $C_1$-$C_{19}$ linear or branched alkyl group, a $C_2$-$C_8$ alkoxy alky ether group and a carbamoyl derivative represented by

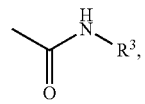

and
$R^2$ and $R^3$ may be the same as or different from each other, and independently selected from the group consisting of hydrogen, a linear or branched alkyl group of $C_1$-$C_4$, a cycloalkyl group of $C_3$-$C_8$, and benzyl group.

* * * * *